US007786071B2

(12) United States Patent
Tawfik et al.

(10) Patent No.: US 7,786,071 B2
(45) Date of Patent: Aug. 31, 2010

(54) PON POLYPEPTIDES POLYNUCLEOTIDES ENCODING SAME AND COMPOSITIONS AND METHODS UTILIZING SAME

(75) Inventors: Dan S. Tawfik, Jerusalem (IL); Amir Aharoni, Tel Aviv (IL); Leonid Gaydukov, Rehovot (IL); Joel L. Sussman, Rehovot (IL); Israel Silman, Rehovot (IL)

(73) Assignee: Yeda Research And Development Co. Ltd., Rehovot (IL)

( * ) Notice: Subject to any disclaimer, the term of this patent is extended or adjusted under 35 U.S.C. 154(b) by 423 days.

(21) Appl. No.: 10/547,771

(22) PCT Filed: Mar. 4, 2004

(86) PCT No.: PCT/IL2004/000216

§ 371 (c)(1),
(2), (4) Date: Feb. 28, 2006

(87) PCT Pub. No.: WO2004/078991

PCT Pub. Date: Sep. 16, 2004

(65) Prior Publication Data

US 2006/0205933 A1    Sep. 14, 2006

Related U.S. Application Data

(60) Provisional application No. 60/451,267, filed on Mar. 4, 2003, provisional application No. 60/512,925, filed on Oct. 22, 2003.

(51) Int. Cl.
*C12N 9/00* (2006.01)
*C12N 9/14* (2006.01)
*C12N 9/16* (2006.01)

(52) U.S. Cl. .......................... 514/2; 435/195; 435/196; 435/183; 514/12

(58) Field of Classification Search ........................ None
See application file for complete search history.

(56) References Cited

FOREIGN PATENT DOCUMENTS

WO    WO 01/90336    11/2001

OTHER PUBLICATIONS

Josse et al., The active site of human paraoxonase (PON1), J Appl Toxicol. Dec. 2001;21, Suppl 1:S7-11.*
Josse et al. "Identification of Residues Essential for Human Paraoxonase (PON1) Arylesterase/Organophosphatase Activities", Biochemistry, 38(9): 2816-2825, 1999.
Bessette et al. "Efficient Folding of Proteins With Multiple Disulfide Bonds in the *Escherichia coli* Cytoplasm", Proc. Natl. Acad. Sci. USA, 96(24): 13703-13708, 1999.
Brushia et al. "Baculovirus-Mediated Expression and Purification of Human Serum Paraoxonase 1A", Journal of Lipid Research, 42: 951-958, 2001.
Hammarström et al. "Rapid Screening for Improved Solubility of Small Human Proteins Produced as Fusion Proteins in *Escherichia coli*", Protein Science, 11: 313-321, 2002.
Josse et al. "Oligomeric States of the Detergent-Solubilized Human Serum Paraoxonase (PON1)", The Journal of Biological Chemistry, 277(36): 33386-33397, 2002.
Kuo et al. "Calcium Binding by Human and Rabbit Serum Paraoxonases. Structural Stability and Enzymatic Activity", Drug Metabolism and Disposition, 26(7): 653-660, 1998.
Maxwell et al. "A Simple In Vivo Assay for Increased Protein Solubility", Protein Science, 8: 1908-1911, 1999.
Sun et al. "Expression and Stabilization of Galactose Oxidase in *Escherichia coli* by Directed Evolution", Protein Engineering, 14(9): 699-704, 2001.
Waldo "Genetic Screens and Directed Evolution for Protein Solubility", Current Opinion in Chemical Biology, 7: 33-38, 2003.
Aharoni et al. "Directed Evolution of Mammalian Paraoxonases PON1 and PON3 for Bacterial Expression and Catalytic Specialization", Proc. Natl. Acad. Sci. USA, 101(2): 482-487, 2004.
Aharoni et al. "Synthetic Construct Paraoxonase PON1 Variant G1A5 Gene, Partial Cds", Database EMBL [Online], Retrieved From EBI Accession No. EMBL, Database Accession No. AY499188, 2004.
Aharoni et al. "Synthetic Construct Paraoxonase PON1 Variant G1C4 Gene, Partial Cds", Database EMBL [Online], Retrieved From EBI Accession No. EMBL, Database Accession No. AY499189, 2004.
Aharoni et al. "Synthetic Construct Paraoxonase PON1 Variant G2D6 Gene, Partial Cds", Database EMBL [Online], Retrieved From EBI Accession No. EMBL, Database Accession No. AY499190, 2004.
Aharoni et al. "Synthetic Construct Paraoxonase PON1 Variant G2E6 Gene, Partial Cds", Database EMBL [Online}, Retrieved From EBI Accession No. EMBL, Database Accession No. AY499191, 2004.
Aharoni et al. "Synthetic Construct Paraoxonase PON1 Variant G3C9 Gene, Partial Cds", Database EMBL [Online], Retrieved From EBI Accession No. EMBL, Database Accession No. AY499193, 2004.
Aharoni et al. "Synthetic Construct Paraoxonase PON1 Variant G3H8 Gene, Partial Cds", Database EMBL [Online], Retrieved From EBI Accession No. EMBL, Database Accession No. AY499192, 2004.
Aharoni et al. "Synthetic Construct Paraoxonase PON3 Variant G1A7 Gene, Partial Cds", Database EMBL [Online}, Retrieved From EBI Accession No. EMBL, Database Accession No. AY499194, 2004.
Aharoni et al. "Synthetic Construct Paraoxonase PON3 Variant G1B11 Gen, Partial Cds", Database Accession No. AY499195, 2004.
Aharoni et al. "Synthetic Construct Paraoxonase PON3 Variant G2C2 Gene, Partial Cds", Database EMBL [Online], Retrieved From EBI Accession No. EMBL, Database Accession No. AY499196, 2004.

(Continued)

*Primary Examiner*—David J Steadman
*Assistant Examiner*—Alexander D Kim

(57) ABSTRACT

Isolated polynucleotides and polypeptides encoded therefrom are provided. These include mutated PON enzymes with increased, modified or substantially the same substrate specificity as compared to respective wild-type PON. Also provided are kits and methods using these enzymes.

2 Claims, 75 Drawing Sheets

OTHER PUBLICATIONS

Aharoni et al. "Synthetic Construct Paraoxonase PON3 Variant G3A5 Gene, Partila Cds", Database EMBL [Online], Retrieved From EBI Accession No. EMBL, Database Accession No. AY499197, 2004.

Aharoni et al. "Synthetic Construct Paraoxonase PON3 Variant G3G3 Gene, Partial Cds", Database EMBL [Online], Retrieved From EBI Accession No. EMBL, Database Accession No. AY499198, 2004.

Aharoni et al. "Synthetic Construct Paraoxonase PON3 Variant G3H9 Gene, Partial Cds", Database EMBL [Online], Retrieved From EBI Accession No. EMBL, Database Accession No. AY499199, 2004.

Mackness et al. "Paraoxonase and Coronary Heart Disease", Atherosclerosis Supplements, 3: 49-55, 2002.

Communication Pursuant to Article 94(3) EPC Dated Mar. 13, 2009 From the European Patent Office Re.: Application No. 04717208.5.

Communication Pursuant to Article 94(3) EPC Dated Mar. 31, 2008 From the European Patent Office Re.: Application No. 04717208.5.

Office Action Dated Apr. 16, 2009 From the Israeli Patent Office Re.: Application No. 170623 and Its Translation Into English.

Supplementary European Search Report Dated Jul. 11, 2007 From the European Patent Office Re.: Application No. 04717208.5.

* cited by examiner

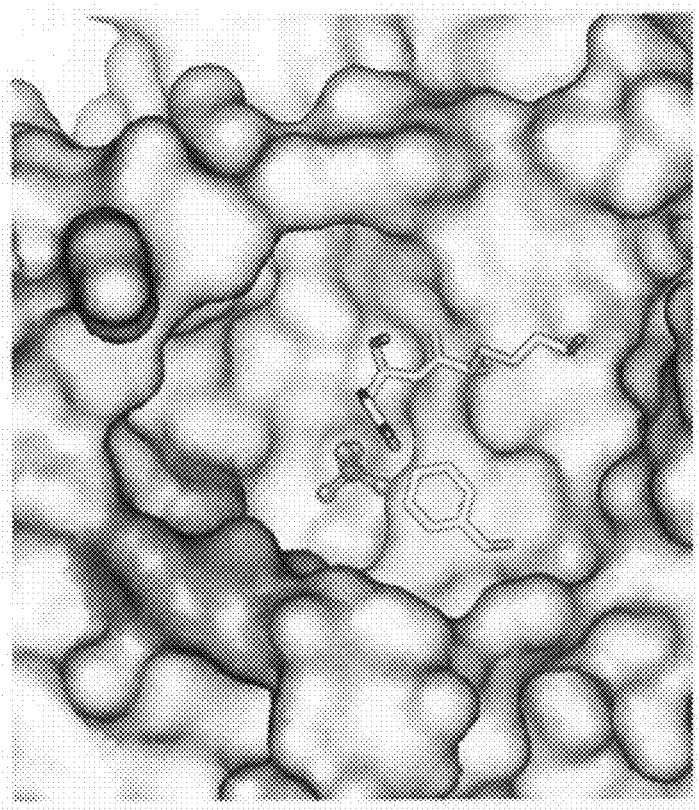
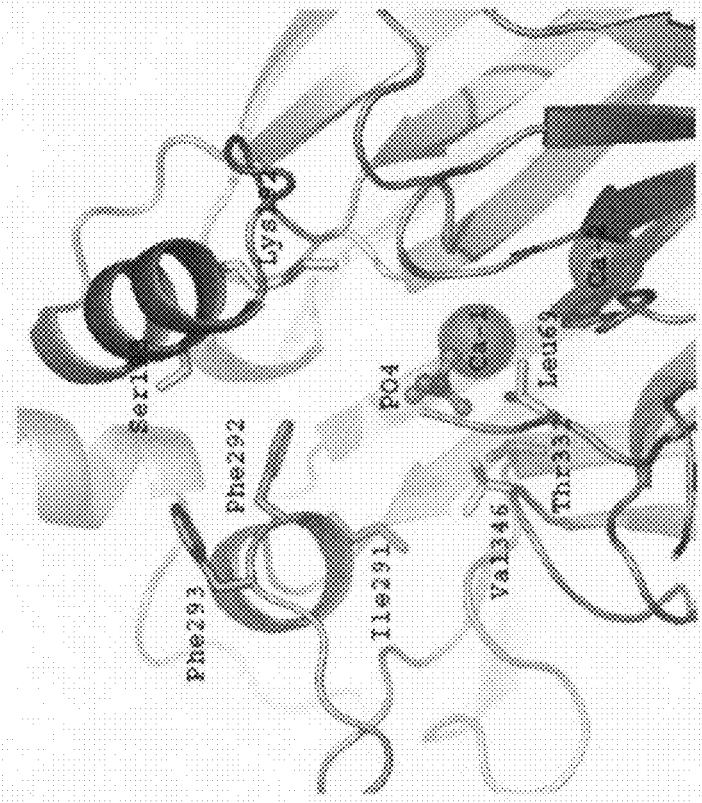
Fig. 18b
Fig. 18a

```
HEADER        ----                                    XX-XXX-XX   xxxx
COMPND                                                                           ---
REMARK   3
REMARK   3 REFINEMENT.
REMARK   3   PROGRAM     : REFMAC 5.1.24
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :    2.20
REMARK   3   RESOLUTION RANGE LOW  (ANGSTROMS) :   20.00
REMARK   3   DATA CUTOFF            (SIGMA(F)) :   NONE
REMARK   3   COMPLETENESS FOR RANGE        (%) :   99.74
REMARK   3   NUMBER OF REFLECTIONS             :   33505
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE     (WORKING + TEST SET) : 0.18666
REMARK   3   R VALUE            (WORKING SET) : 0.18503
REMARK   3   FREE R VALUE                     : 0.21704
REMARK   3   FREE R VALUE TEST SET SIZE   (%) : 5.0
REMARK   3   FREE R VALUE TEST SET COUNT      : 1767
REMARK   3
REMARK   3  FIT IN THE HIGHEST RESOLUTION BIN.
REMARK   3   TOTAL NUMBER OF BINS USED           :       20
REMARK   3   BIN RESOLUTION RANGE HIGH           :    2.200
REMARK   3   BIN RESOLUTION RANGE LOW            :    2.256
REMARK   3   REFLECTION IN BIN    (WORKING SET) :     2347
REMARK   3   BIN R VALUE          (WORKING SET) :    0.291
REMARK   3   BIN FREE R VALUE SET COUNT106      :
REMARK   3   BIN FREE R VALUE                    :    0.319
REMARK   3
REMARK   3  NUMBER OF NON-HYDROGEN ATOMS USED IN REFINEMENT.
REMARK   3   ALL ATOMS                :    2756
REMARK   3
REMARK   3  B VALUES.
REMARK   3   FROM WILSON PLOT)           A**2) : NULL
REMARK   3   MEAN B VALUE      (OVERALL, A**2) :  38.485
REMARK   3   OVERALL ANISOTROPIC B VALUE.
REMARK   3    B11 (A**2) :    -0.56
REMARK   3    B22 (A**2) :    -0.56
REMARK   3    B33 (A**2) :     1.13
REMARK   3    B12 (A**20.00      : (
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                    (A):   0.145
REMARK   3   ESU BASED ON FREE R VALUE)              A):   0.139
REMARK   3   ESU BASED ON MAXIMUM LIKELIHOOD         (A):   0.106
REMARK   3   ESU FOR B VALUES BASED ON MAXIMUM LIKELIHOOD (A**2):   4.256
REMARK   3
REMARK   3 CORRELATION COEFFICIENTS.
REMARK   3   CORRELATION COEFFICIENT FO-FC      :   0.960
REMARK   3   CORRELATION COEFFICIENT FO-FC FREE :   0.947
REMARK   3
REMARK   3  RMS DEVIATIONS FROM IDEAL VALUES        COUNT    RMS    WEIGHT
REMARK   3   BOND LENGTHS REFINED ATOMS       (A):  2705 ; 0.025 ; 0.021
REMARK   3   BOND ANGLES REFINED ATOMS   (DEGREES):  3685 ; 2.048 ; 1.951
```

Fig. 26

```
REMARK   3    TORSION ANGLES, PERIOD 1   (DEGREES):   330 ; 7.737 ; 5.000
REMARK   3    CHIRAL-CENTER RESTRAINTS        (A**3):  417 ; 0.168 ; 0.200
REMARK   3    GENERAL PLANES REFINED ATOMS)       A): 2057 ; 0.009 ; 0.020
REMARK   3    NON-BONDED CONTACTS REFINED ATOMS (A):  1063 ; 0.224 ; 0.200
REMARK   3    H-BOND (X...Y) REFINED ATOMS      (A):   115 ; 0.163 ; 0.200
REMARK   3    POTENTIAL METAL-ION REFINED ATOMS (A):     7 ; 0.131 ; 0.200
REMARK   3    SYMMETRY VDW REFINED ATOMS        (A):    13 ; 0.198 ; 0.200
REMARK   3    SYMMETRY H-BOND REFINED ATOMS     (A):     4 ; 0.102 ; 0.200
REMARK   3
REMARK   3   ISOTROPIC THERMAL FACTOR RESTRAINTS.   COUNT   RMS    WEIGHT
REMARK   3    MAIN-CHAIN BOND REFINED ATOMS   (A**2): 1655 ; 1.091 ; 1.500
REMARK   3    MAIN-CHAIN ANGLE REFINED ATOMS  (A**2): 2694 ; 1.872 ; 2.000
REMARK   3    SIDE-CHAIN BOND REFINED ATOMS   (A**2): 1050 ; 3.059 ; 3.000
REMARK   3    SIDE-CHAIN ANGLE REFINED ATOMS  (A**2):  991 ; 44.500 ; 521.
REMARK   3
REMARK   3  NCS RESTRAINTS STATISTICS
REMARK   3   NUMBER OF NCS GROUPS : NULL
REMARK   3
REMARK   3
REMARK   3  TLS DETAILS
REMARK   3   NUMBER OF TLS GROUPS  :    1
REMARK   3
REMARK   3   TLS GROUP :    1
REMARK   3    NUMBER OF COMPONENTS GROUP :    1
REMARK   3    COMPONENTS           C SSSEQI    TO   C SSSEQI
REMARK   3    RESIDUE RANGE :          -1             -1
REMARK   3    ORIGIN FOR THE GROUP (A):   8.3288  28.6493  21.4479
REMARK   3    T TENSOR
REMARK   3      T11:   0.0067 T22:   0.1081
REMARK   3      T33:   0.0487 T12:   0.0061
REMARK   3      T13:   0.0168 T23:   0.0414
REMARK   3    L TENSOR
REMARK   3      L11:   3.5916 L22:   2.2014
REMARK   3      L33:   3.4673 L12:   0.6914
REMARK   3      L13:  -1.5993 L23:  -0.1237
REMARK   3    S TENSOR
REMARK   3      S11:  -0.0701 S12:  -0.0679 S13:  -0.2068
REMARK   3      S21:   0.0903 S22:  -0.0402 S23:  -0.1588
REMARK   3      S31:   0.1729 S32:   0.1134 S33:   0.1103
REMARK   3
REMARK   3
REMARK   3  BULK SOLVENT MODELLING.
REMARK   3   METHOD USED : BABINET MODEL WITH MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS: NULL
REMARK   3
LINK         TYR A  71                     ASP A  80                 gap
CRYST1   98.440   98.440  139.170  90.00  90.00  90.00 P43212
SCALE1      0.010158  0.000000  0.000000        0.00000
SCALE2      0.000000  0.010158  0.000000        0.00000
SCALE3      0.000000  0.000000  0.007185        0.00000
ATOM      1  N   LEU A  16      20.229  -7.374  21.763  1.00 48.03           N
ATOM      2  CA  LEU A  16      21.538  -6.888  21.246  1.00 48.15           C
ATOM      3  CB  LEU A  16      22.372  -8.036  20.623  1.00 48.06           C
ATOM      4  CG  LEU A  16      21.874  -9.103  19.613  1.00 48.10           C
ATOM      5  CD1 LEU A          47.53  1.00 18.185  8.816- 22.390        16  C
ATOM      6  CD2 LEU A  16      22.242 -10.553  20.029  1.00 46.02           C
```

Fig. 26 (Cont.)

| ATOM | 7 | C | LEU | A | 16 | 21.322 | -5.735 | 20.266 | 1.00 | 48.37 | | | C |
|---|---|---|---|---|---|---|---|---|---|---|---|---|---|
| ATOM | 8 | O | LEU | A | 16 | 21.935 | -5 | | 48.40 | 1.00 | 19.197 | 694.0 | |
| ATOM | 9 | N | PHE | A | 17 | 20.453 | -4.796 | 20.639 | 1.00 | 48.56 | | | N |
| ATOM | 10 | CA | PHE | A | 17 | 20.144 | -3.665 | 19.760 | 1.00 | 49.17 | | | C |
| ATOM | 11 | CB | PHE | A | 17 | 18.662 | -3.649 | 19.324 | 1.00 | 49.00 | | | C |
| ATOM | 12 | CG | PHE | A | 17 | 17.687 | -3.278 | 20.412 | 1.00 | 49.31 | | | C |
| ATOM | 13 | CD1 | PHE | A | 17 | 17.171 | -1.970 | 20.497 | 1.00 | 50.66 | | | C |
| ATOM | 14 | CE1 | PHE | A | 17 | 16.227 | -1.622 | 21.503 | 1.00 | 51.30 | | | C |
| ATOM | 15 | CZ | PHE | A | 17 | 15.800 | -2.602 | 22.430 | 1.00 | 48.27 | | | C |
| ATOM | 16 | CE2 | PHE | A | 17 | 16.308 | -3.892 | 22.338 | 1.00 | 49.43 | | | C |
| ATOM | 17 | CD2 | PHE | A | 17 | 17.244 | -4.230 | 21.327 | 1.00 | 48.64 | | | C |
| ATOM | 18 | C | PHE | A | 17 | 20.736 | -2.267 | 20.124 | 1.00 | 49.78 | | | C |
| ATOM | 19 | O | PHE | A | 17 | 20.227 | -1.492 | 20.950 | 1.00 | 48.86 | | | O |
| ATOM | 20 | N | ASP | A | 18 | 21.861 | -2.007 | 19.455 | 1.00 | 50.85 | | | N |
| ATOM | 21 | CA | ASP | A | 18 | 22.558 | | 51.34 | 1.00 | 19.411 | 0.728- | | C |
| ATOM | 22 | CB | ASP | A | 18 | 23.818 | -0.856 | 18.506 | 1.00 | 51.42 | | | C |
| ATOM | 23 | CG | ASP | A | 18 | 25.093 | -1.310 | 19.264 | 1.00 | 51.79 | | | C |
| ATOM | 24 | OD1 | ASP | A | 18 | 25.506 | -0.571 | 20.196 | 1.00 | | | 52.10 | O |
| ATOM | 25 | OD2 | ASP | A | 18 | 25.767 | -2.354 | 18.971 | 1.00 | 49.88 | | | O |
| ATOM | 26 | C | ASP | A | 18 | 21.645 | 0.300 | 18.767 | 1.00 | 51.75 | | | C |
| ATOM | 27 | O | ASP | A | 18 | 22.123 | 1.378 | 18.368 | 1.00 | 52.40 | | | O |
| ATOM | 28 | N | ARG | A | 19 | 20.352 | -0.025 | 18.626 | 1.00 | 51.75 | | | N |
| ATOM | 29 | CA | ARG | A | 19 | 19.421 | 0.843 | 17.858 | 1.00 | 51.60 | | | C |
| ATOM | 30 | CB | ARG | A | 19 | 18.166 | 0.079 | 17.386 | 1.00 | 52.00 | | | C |
| ATOM | 31 | CG | ARG | A | 19 | 18.395 | -0.781 | 16.113 | 1.00 | 53.24 | | | C |
| ATOM | 32 | CD | ARG | A | 19 | 19.048 | -0.003 | 14.924 | 1.00 | 54.03 | | | C |
| ATOM | 33 | NE | ARG | A | 19 | 20.422 | -0.455 | 14.632 | 1.00 | 53.37 | | | N |
| ATOM | 34 | CZ | ARG | A | 19 | 21.433 | | 52.80 | 1.00 | 14.225 | 0.337 | | C |
| ATOM | 35 | NH1 | ARG | A | 19 | 21.257 | 1.653 | 14.043 | 1.00 | 50.30 | | | N |
| ATOM | 36 | NH2 | ARG | A | 19 | 22.628 | -0.201 | 13.994 | 1.00 | 51.17 | | | N |
| ATOM | 37 | C | ARG | A | 19 | 19.034 | 2.078 | 18.627 | | | 50.83 | 1.00 | C |
| ATOM | 38 | O | ARG | A | 19 | 18.849 | 3.153 | 18.037 | 1.00 | 50.62 | | | O |
| ATOM | 39 | N | GLN | A | 20 | 18.914 | 1.876 | 19.944 | 1.00 | 50.23 | | | N |
| ATOM | 40 | CA | GLN | A | 20 | 18.723 | 2.914 | 20.967 | 1.00 | 49.45 | | | C |
| ATOM | 41 | CB | GLN | A | 20 | 18.600 | 2.261 | 22.355 | 1.00 | 49.61 | | | C |
| ATOM | 42 | CG | GLN | A | 20 | 17.816 | 3.082 | 23.342 | 1.00 | 48.43 | | | C |
| ATOM | 43 | CD | GLN | A | 20 | 16.490 | 3.493 | 22.739 | 1.00 | 50.00 | | | C |
| ATOM | 44 | OE1 | GLN | A | 20 | 15.796 | 2.626 | 22.170 | 1.00 | 50.23 | | | O |
| ATOM | 45 | NE2 | GLN | A | 20 | 16.141 | 4.808 | 22.813 | 1.00 | 41.99 | | | N |
| ATOM | 46 | C | GLN | A | 20 | 19.835 | 3.976 | 21.023 | 1.00 | 49.06 | | | C |
| ATOM | 47 | O | GLN | A | 20 | 19 | | 48.53 | 1.00 | 21.172 | 5.178 | 546.0 | |
| ATOM | 48 | N | LYS | A | 21 | 21.090 | 3.502 | 20.957 | 1.00 | 48.65 | | | N |
| ATOM | 49 | CA | LYS | A | 21 | 22.272 | 4.361 | 20.927 | 1.00 | 47.93 | | | C |
| ATOM | 50 | CB | LYS | A | 21 | 23.565 | 3.555 | 21.137 | | | 47.74 | 1.00 | C |
| ATOM | 51 | CG | LYS | A | 21 | 23.830 | 3.230 | 22.625 | 1.00 | 47.47 | | | C |
| ATOM | 52 | CD | LYS | A | 21 | 24.805 | 2.065 | 22.814 | 1.00 | 46.97 | | | C |
| ATOM | 53 | CE | LYS | A | 21 | 24.621 | 1.374 | 24.183 | 1.00 | 46.00 | | | C |
| ATOM | 54 | NZ | LYS | A | 21 | 24.730 | -0.084 | 24.047 | 1.00 | 39.99 | | | N |
| ATOM | 55 | C | LYS | A | 21 | 22.323 | 5.172 | 19.635 | 1.00 | 47.48 | | | C |
| ATOM | 56 | O | LYS | A | 21 | 22.510 | 6.389 | 19.690 | 1.00 | 47.27 | | | O |
| ATOM | 57 | N | SER | A | 22 | 22.120 | 4.514 | 18.491 | 1.00 | 46.59 | | | N |
| ATOM | 58 | CA | SER | A | 22 | 22.122 | 5.210 | 17.201 | 1.00 | 46.04 | | | C |
| ATOM | 59 | CB | SER | A | 22 | 22.266 | 4.216 | 16.053 | 1.00 | 46.54 | | | C |
| ATOM | 60 | OG | SER | A | 22 | | 47.25 | 1.00 | 15.301 | 4.164 | 21.070 | | O |
| ATOM | 61 | C | SER | A | 22 | 20.895 | 6.120 | 16.966 | 1.00 | 45.39 | | | C |
| ATOM | 62 | O | SER | A | 22 | 20.981 | 7.112 | 16.242 | 1.00 | 45.07 | | | O |
| ATOM | 63 | N | SER | A | 23 | 19.757 | 5.767 | 17 | | | 44.20 | 1.00 | 556.N |
| ATOM | 64 | CA | SER | A | 23 | 18.571 | 6.608 | 17.481 | 1.00 | 42.87 | | | C |
| ATOM | 65 | CB | SER | A | 23 | 17.354 | 5.764 | 17.813 | 1.00 | 42.54 | | | C |
| ATOM | 66 | OG | SER | A | 23 | 16.206 | 6.541 | 17.796 | 1.00 | 44.03 | | | O |
| ATOM | 67 | C | SER | A | 23 | 18.728 | 7.852 | 18.398 | 1.00 | 42.19 | | | C |

Fig. 26 (Cont.)

| | | | | | | | | | |
|---|---|---|---|---|---|---|---|---|---|
| ATOM | 68 | O | SER A | 23 | 18.415 | 8.974 | 18.017 | 1.00 40.34 | O |
| ATOM | 69 | N | PHE A | 24 | 19.304 | 7.640 | 19.577 | 1.00 42.24 | N |
| ATOM | 70 | CA | PHE A | 24 | 19.677 | 8.734 | 20.473 | 1.00 42.54 | C |
| ATOM | 71 | CB | PHE A | 24 | 20.299 | 8.171 | 21.767 | 1.00 43.00 | C |
| ATOM | 72 | CG | PHE A | 24 | 20.490 | 9.211 | 22.842 | 1.00 45.48 | C |
| ATOM | 73 | CD1 | PHE A | 24 | | 47.44 1.00 | 23.682 | 9.575 19.422 | C |
| ATOM | 74 | CE1 | PHE A | 24 | 19.594 | 10.544 | 24.675 | 1.00 47.86 | C |
| ATOM | 75 | CZ | PHE A | 24 | 20.836 | 11.182 | 24.817 | 1.00 46.62 | C |
| ATOM | 76 | CE2 | PHE A | 24 | 21.904 | 10.829 | | 46.69 1.00 23.979 | C |
| ATOM | 77 | CD2 | PHE A | 24 | 21.727 | 9.849 | 23.002 | 1.00 46.52 | C |
| ATOM | 78 | C | PHE A | 24 | 20.678 | 9.701 | 19.828 | 1.00 41.94 | C |
| ATOM | 79 | O | PHE A | 24 | 20.515 | 10.913 | 19.936 | 1.00 42.08 | O |
| ATOM | 80 | N | GLN A | 25 | 21.722 | 9.160 | 19.188 | 1.00 40.91 | N |
| ATOM | 81 | CA | GLN A | 25 | 22.750 | 9.998 | 18.587 | 1.00 41.05 | C |
| ATOM | 82 | CB | GLN A | 25 | 23.983 | 9.212 | 18.146 | 1.00 40.83 | C |
| ATOM | 83 | CG | GLN A | 25 | 24.560 | 8.428 | 19.327 | 1.00 44.31 | C |
| ATOM | 84 | CD | GLN A | 25 | 26.059 | 8.516 | 19.471 | 1.00 46.68 | C |
| ATOM | 85 | OE1 | GLN A | 25 | 26.793 | 7.859 | 18.745 | 1.00 44.53 | O |
| ATOM | 86 | NE2 | GLN A | 25 | | 48.05 1.00 | 20.427 | 9.324 26.517 | N |
| ATOM | 87 | C | GLN A | 25 | 22.235 | 10.922 | 17.484 | 1.00 40.08 | C |
| ATOM | 88 | O | GLN A | 25 | 22.698 | 12.066 | 17.363 | 1.00 39.62 | O |
| ATOM | 89 | N | THR A | 26 | 21.275 | 10.430 | | 38.61 1.00 16.708 | N |
| ATOM | 90 | CA | THR A | 26 | 20.662 | 11.281 | 15.720 | 1.00 37.75 | C |
| ATOM | 91 | CB | THR A | 26 | 20.251 | 10.482 | 14.434 | 1.00 38.34 | C |
| ATOM | 92 | OG1 | THR A | 26 | 18.866 | 10.655 | 14.160 | 1.00 40 | 31.O |
| ATOM | 93 | CG2 | THR A | 26 | 20.353 | 9.033 | 14.607 | 1.00 38.26 | C |
| ATOM | 94 | C | THR A | 26 | 19.599 | 12.288 | 16.289 | 1.00 36.93 | C |
| ATOM | 95 | O | THR A | 26 | 19.625 | 13.461 | 15.927 | 1.00 36.82 | O |
| ATOM | 96 | N | ARG A | 27 | 18.716 | 11.871 | 17.207 | 1.00 35.17 | N |
| ATOM | 97 | CA | ARG A | 27 | 17.769 | 12.825 | 17.814 | 1.00 34.64 | C |
| ATOM | 98 | CB | ARG A | 27 | 16.822 | 12.140 | 18.811 | 1.00 33.43 | C |
| ATOM | 99 | CG | ARG A | | 34.40 1.00 | 18.260 | 10.882 | 16.145 | 27 C |
| ATOM | 100 | CD | ARG A | 27 | 15.507 | 10.006 | 19.341 | 1.00 34.32 | C |
| ATOM | 101 | NE | ARG A | 27 | 14.569 | 10.800 | 20.161 | 1.00 34.94 | N |
| ATOM | 102 | CZ | ARG A | 27 | 14.412 | 10.675 | | 34.58 1.00 21.484 | C |
| ATOM | 103 | NH1 | ARG A | 27 | 15.095 | 9.786 | 22.173 | 1.00 32.32 | N |
| ATOM | 104 | NH2 | ARG A | 27 | 13.526 | 11.430 | 22.122 | 1.00 34.47 | N |
| ATOM | 105 | C | ARG A | 27 | 18.476 | 14.018 | 18.467 | 1.00 | 33.78 C |
| ATOM | 106 | O | ARG A | 27 | 18.122 | 15.169 | 18.256 | 1.00 32.49 | O |
| ATOM | 107 | N | PHE A | 28 | 19.477 | 13.711 | 19.268 | 1.00 33.94 | N |
| ATOM | 108 | CA | PHE A | 28 | 20.269 | 14.717 | 19.973 | 1.00 35.08 | C |
| ATOM | 109 | CB | PHE A | 28 | 20.737 | 14.079 | 21.309 | 1.00 35.86 | C |
| ATOM | 110 | CG | PHE A | 28 | 19.613 | 13.973 | 22.310 | 1.00 37.70 | C |
| ATOM | 111 | CD1 | PHE A | 28 | 19.309 | 15.040 | 23.121 | 1.00 37.60 | C |
| ATOM | 112 | CE1 | PHE A | 28 | 18.224 | 14.972 | 24.014 | 1.00 38.07 | C |
| ATOM | 113 | CZ | PHE A | 28 | 17.434 | 13.852 | 24.060 | 1.00 33.97 | C |
| ATOM | 114 | CE2 | PHE A | 28 | 17.708 | 12.779 | 23.214 | 1.00 38.17 | C |
| ATOM | 115 | CD2 | PHE A | 28 | 18.779 | | 39.12 1.00 | 22.336 12.846 | C |
| ATOM | 116 | C | PHE A | 28 | 21.437 | 15.352 | 19.146 | 1.00 35.18 | C |
| ATOM | 117 | O | PHE A | 28 | 22.110 | 16.280 | 19.616 | 1.00 34.98 | O |
| ATOM | 118 | N | ASN A | 29 | 21.653 | 14.854 | 17.925 | 1 | 35.26 00.N |
| ATOM | 119 | CA | ASN A | 29 | 22.555 | 15.493 | 16.973 | 1.00 36.26 | C |
| ATOM | 120 | CB | ASN A | 29 | 21.982 | 16.908 | 16.672 | 1.00 35.95 | C |
| ATOM | 121 | CG | ASN A | 29 | 21.635 | 17.137 | 15.185 | 1.00 37.34 | C |
| ATOM | 122 | OD1 | ASN A | 29 | 21.466 | 16.201 | 14.378 | 1.00 37.30 | O |
| ATOM | 123 | ND2 | ASN A | 29 | 21.529 | 18.413 | 14.823 | 1.00 34.10 | N |
| ATOM | 124 | C | ASN A | 29 | 23.924 | 15.584 | 17.654 | 1.00 36.07 | C |
| ATOM | 125 | O | ASN A | 29 | 24.514 | 16.653 | 17.751 | 1.00 37.33 | O |
| ATOM | 126 | N | VAL A | 30 | 24.423 | 14.468 | 18.160 | 1.00 36.93 | N |
| ATOM | 127 | CA | VAL A | 30 | 25.428 | 14.513 | 19.231 | 1.00 37.82 | C |
| ATOM | 128 | CB | VAL A | 30 | 25 | | 38.05 1.00 | 19.947 13.127 | 558.C |

Fig. 26 (Cont.)

```
ATOM   129  CG1 VAL A  30      24.249  12.748  20.690  1.00 35.55           C
ATOM   130  CG2 VAL A  30      25.950  12.105  18.953  1.00 37.94           C
ATOM   131  C   VAL A  30      26.830  15.047  18.829       39.14 1.00      C
ATOM   132  O   VAL A  30      27.593  15.572  19.676  1.00 39.06           O
ATOM   133  N   HIS A  31      27.170  14.938  17.550  1.00 39.88           N
ATOM   134  CA  HIS A  31      28.452  15.469  17.148  1.00 41.80           C
ATOM   135  CB  HIS A  31      29.302  14.400  16.429  1.00 42.41           C
ATOM   136  CG  HIS A  31      29.573  13.175  17.256  1.00 44.50           C
ATOM   137  ND1 HIS A  31      30.397  13.187  18.366  1.00 47.02           N
ATOM   138  CE1 HIS A  31      30.453  11.969  18.891  1.00 47.31           C
ATOM   139  NE2 HIS A  31      29.682  11.170  18.172  1.00 47.94           N
ATOM   140  CD2 HIS A  31      29.119  11.899  17.142  1.00 46.89           C
ATOM   141  C   HIS A  31             42.57 1.00  16.322  16.772  28.364    C
ATOM   142  O   HIS A  31      29.409  17.239  15.923  1.00 42.18           O
ATOM   143  N   ARG A  32      27.163  17.341  16.070  1.00 42.84           N
ATOM   144  CA  ARG A  32      27.066  18.586  15       43.73 1.00  262.C
ATOM   145  CB  ARG A  32      25.608  19.031  14.833  1.00 44.10           C
ATOM   146  CG  ARG A  32      25.670  19.652  13.352  1.00 46.44           C
ATOM   147  CD  ARG A  32      24.440  19.646  12.439  1.00 48.91           C
ATOM   148  NE  ARG A  32      23.627  20.866  12.638  1.00 58.32           N
ATOM   149  CZ  ARG A  32      23.807  22.123  12.090  1.00 58.66           C
ATOM   150  NH1 ARG A  32      24.762  22.401  11.235  1.00 57.63           N
ATOM   151  NH2 ARG A  32      22.984  23.122  12.408  1.00 57.81           N
ATOM   152  C   ARG A  32      27.857  19.769  15.821  1.00 42.89           C
ATOM   153  O   ARG A  32      27.940  20.001  17.035  1.00 41.88           O
ATOM   154  N   GLU A  33             42.73 1.00  14.886  20.498  28.444    N
ATOM   155  CA  GLU A  33      29.270  21.681  15.156  1.00 42.85           C
ATOM   156  CB  GLU A  33      30.759  21.386  14.867  1.00 42.85           C
ATOM   157  CG  GLU A  33      31.455  20.562          46.08 1.00   15.941  C
ATOM   158  CD  GLU A  33      31.795  21.392  17.192  1.00 51.50           C
ATOM   159  OE1 GLU A  33      30.853  21.825  17.908  1.00 52.59           O
ATOM   160  OE2 GLU A  33      33.005  21.626  17.465  1.00 53.12           O
ATOM   161  C   GLU A  33      28.736  22.783  14.251  1.00 41.50           C
ATOM   162  O   GLU A  33      28.503  22.549  13.054  1.00 41.54           O
ATOM   163  N   VAL A  34      28.501  23.965  14.819  1.00 40.12           N
ATOM   164  CA  VAL A  34      27.857  25.046  14.080  1.00 37.78           C
ATOM   165  CB  VAL A  34      27.345  26.176  15.007  1.00 39.12           C
ATOM   166  CG1 VAL A  34      26.163  26.807  14.385  1.00 39.33           C
ATOM   167  CG2 VAL A  34             39.27 1.00  16.359  25.616  26.891    C
ATOM   168  C   VAL A  34      28.730  25.657  13.015  1.00 35.66           C
ATOM   169  O   VAL A  34      29.930  25.905  13.234  1.00 35.36           O
ATOM   170  N   THR A  35      28.160  25.849          33.70 1.00   11.835  N
ATOM   171  CA  THR A  35      28.854  26.681  10.823  1.00 33.15           C
ATOM   172  CB  THR A  35      28.505  26.258   9.342  1.00 32.88           C
ATOM   173  OG1 THR A  35      28.983  24.924   9.125  1.00 32         35.O
ATOM   174  CG2 THR A  35      29.254  27.214   8.238  1.00 27.35           C
ATOM   175  C   THR A  35      28.385  28.108  11.100  1.00 32.81           C
ATOM   176  O   THR A  35      27.185  28.368  10.959  1.00 33.94           O
ATOM   177  N   PRO A  36      29.264  28.986  11.576  1.00 31.78           N
ATOM   178  CA  PRO A  36      28.848  30.369  11.850  1.00 32.49           C
ATOM   179  CB  PRO A  36      30.103  31.049  12.435  1.00 32.26           C
ATOM   180  CG  PRO A         33.26 1.00  12.098  30.137  31.261      36    C
ATOM   181  CD  PRO A  36      30.691  28.738  11.872  1.00 32.51           C
ATOM   182  C   PRO A  36      28.290  31.133  10.586  1.00 32.63           C
ATOM   183  O   PRO A  36      28.753  31              31.81 1.00   9.470  009.O
ATOM   184  N   VAL A  37      27.230  31.878  10.825  1.00 32.30           N
ATOM   185  CA  VAL A  37      26.715  32.821   9.882  1.00 33.56           C
ATOM   186  CB  VAL A  37      25.340  32.318   9.285  1.00            34.80 C
ATOM   187  CG1 VAL A  37      24.754  33.467   8.439  1.00 37.90           C
ATOM   188  CG2 VAL A  37      25.565  31.092   8.368  1.00 33.76           C
ATOM   189  C   VAL A  37      26.565  34.149  10.626  1.00 32.02           C
```

Fig. 26 (Cont.)

| | | | | | | | | | | |
|---|---|---|---|---|---|---|---|---|---|---|
| ATOM | 190 | O | VAL | A | 37 | 25.800 | 34.253 | 11.566 | 1.00 33.52 | O |
| ATOM | 191 | N | GLU | A | 38 | 27.209 | 35.164 | 10.152 | 1.00 32.79 | N |
| ATOM | 192 | CA | GLU | A | 38 | 27.328 | 36.438 | 10.862 | 1.00 35.75 | C |
| ATOM | 193 | CB | GLU | A | 38 | 28.775 | 36.965 | 10.746 | 1.00 35.31 | C |
| ATOM | 194 | CG | GLU | A | 38 | 29.846 | 36.061 | 11.355 | 1.00 36.88 | C |
| ATOM | 195 | CD | GLU | A | 38 | 31.222 | 36.478 | 10.861 | 1.00 45.68 | C |
| ATOM | 196 | OE1 | GLU | A | 38 | 31.579 | | 45.43 1.00 | 11.020 37.677 | O |
| ATOM | 197 | OE2 | GLU | A | 38 | 31.966 | 35.632 | 10.287 | 1.00 50.57 | O |
| ATOM | 198 | C | GLU | A | 38 | 26.359 | 37.540 | 10.391 | 1.00 36.81 | C |
| ATOM | 199 | O | GLU | A | 38 | 25.943 | 37.558 | 9.212 | 1 37.04 00.0 | O |
| ATOM | 200 | N | LEU | A | 39 | 26.018 | 38.447 | 11.308 | 1.00 36.60 | N |
| ATOM | 201 | CA | LEU | A | 39 | 25.169 | 39.585 | 10.983 | 1.00 38.33 | C |
| ATOM | 202 | CB | LEU | A | 39 | 23.812 | 39.539 | 11.675 | 1.00 36.34 | C |
| ATOM | 203 | CG | LEU | A | 39 | 22.842 | 38.552 | 11.042 | 1.00 37.89 | C |
| ATOM | 204 | CD1 | LEU | A | 39 | 21.602 | 38.351 | 11.873 | 1.00 38.23 | C |
| ATOM | 205 | CD2 | LEU | A | 39 | 22.483 | 38.792 | 9.542 | 1.00 37.73 | C |
| ATOM | 206 | C | LEU | A | 39 | 25.902 | 40.824 | 11.395 | 1.00 40.33 | C |
| ATOM | 207 | O | LEU | A | 39 | 26.716 | 40.780 | 12.324 | 1.00 40.11 | O |
| ATOM | 208 | N | PRO | A | 40 | 25.615 | 41.952 | 10.727 | 1.00 41.55 | N |
| ATOM | 209 | CA | PRO | A | 40 | 26.216 | | 41.09 1.00 | 11.155 43.239 | C |
| ATOM | 210 | CB | PRO | A | 40 | 26.130 | 44.132 | 9.890 | 1.00 40.23 | C |
| ATOM | 211 | CG | PRO | A | 40 | 24.996 | 43.474 | 8.974 | 1.00 40.72 | C |
| ATOM | 212 | CD | PRO | A | 40 | 24.666 | 42.104 | 9.597 | 40.91 1.00 | C |
| ATOM | 213 | C | PRO | A | 40 | 25.419 | 43.830 | 12.353 | 1.00 41.26 | C |
| ATOM | 214 | O | PRO | A | 40 | 24.152 | 43.595 | 12.566 | 1.00 43.02 | O |
| ATOM | 215 | N | ASN | A | 41 | 26.159 | 44.527 | 13.187 | 1.00 40.27 | N |
| ATOM | 216 | CA | ASN | A | 41 | 25.578 | 45.252 | 14.292 | 1.00 41.60 | C |
| ATOM | 217 | CB | ASN | A | 41 | 24.755 | 46.423 | 13.738 | 1.00 43.44 | C |
| ATOM | 218 | CG | ASN | A | 41 | 24.764 | 47.671 | 14.660 | 1.00 48.67 | C |
| ATOM | 219 | OD1 | ASN | A | 41 | 25.799 | 48.348 | 14.818 | 1.00 52.00 | O |
| ATOM | 220 | ND2 | ASN | A | 41 | 23.589 | 48.000 | 15.235 | 1.00 50.53 | N |
| ATOM | 221 | C | ASN | A | 41 | 24.751 | 44.369 | 15.288 | 1.00 40.42 | C |
| ATOM | 222 | O | ASN | A | 41 | 23.603 | | 41.11 1.00 | 15.577 44.639 | O |
| ATOM | 223 | N | CYS | A | 42 | 25.341 | 43.316 | 15.810 | 1.00 38.02 | N |
| ATOM | 224 | CA | CYS | A | 42 | 24.658 | 42.549 | 16.827 | 1.00 37.95 | C |
| ATOM | 225 | CB | CYS | A | 42 | 25.114 | 41.118 | 16.739 | 37.78 1.00 | C |
| ATOM | 226 | SG | CYS | A | 42 | 24.327 | 40.365 | 15.308 | 1.00 43.83 | S |
| ATOM | 227 | C | CYS | A | 42 | 24.969 | 43.138 | 18.172 | 1.00 36.52 | C |
| ATOM | 228 | O | CYS | A | 42 | 26.124 | 43.367 | 18.467 | 1.00 37.85 | O |
| ATOM | 229 | N | ASN | A | 43 | 23.950 | 43.438 | 18.971 | 1.00 35.14 | N |
| ATOM | 230 | CA | ASN | A | 43 | 24.154 | 43.948 | 20.336 | 1.00 33.81 | C |
| ATOM | 231 | CB | ASN | A | 43 | 23.731 | 45.419 | 20.461 | 1.00 34.41 | C |
| ATOM | 232 | CG | ASN | A | 43 | 24.507 | 46.319 | 19.522 | 1.00 34.30 | C |
| ATOM | 233 | OD1 | ASN | A | 43 | 23.941 | 46.939 | 18.636 | 1.00 35.48 | O |
| ATOM | 234 | ND2 | ASN | A | 43 | 25.818 | 46.348 | 19.683 | 1.00 33.63 | N |
| ATOM | 235 | C | ASN | A | 43 | | 33.42 1.00 | 21.276 | 43.128 23.318 | C |
| ATOM | 236 | O | ASN | A | 43 | 22.142 | 42.856 | 21.003 | 1.00 31.56 | O |
| ATOM | 237 | N | LEU | A | 44 | 23.938 | 42.721 | 22.372 | 1.00 33.76 | N |
| ATOM | 238 | CA | LEU | A | 44 | 23.228 | 42.044 | 23.445 | 34.03 1.00 | C |
| ATOM | 239 | CB | LEU | A | 44 | 24.192 | 41.510 | 24.512 | 1.00 34.02 | C |
| ATOM | 240 | CG | LEU | A | 44 | 24.999 | 40.309 | 23.965 | 1.00 36.01 | C |
| ATOM | 241 | CD1 | LEU | A | 44 | 26.328 | 40.156 | 24.781 | 1.00 35.88 | C |
| ATOM | 242 | CD2 | LEU | A | 44 | 24.173 | 38.985 | 23.794 | 1.00 31.36 | C |
| ATOM | 243 | C | LEU | A | 44 | 22.261 | 43.035 | 24.045 | 1.00 33.85 | C |
| ATOM | 244 | O | LEU | A | 44 | 22.566 | 44.197 | 24.175 | 1.00 32.52 | O |
| ATOM | 245 | N | VAL | A | 45 | 21.070 | 42.559 | 24.348 | 1.00 34.08 | N |
| ATOM | 246 | CA | VAL | A | 45 | 20.078 | 43.421 | 24.917 | 1.00 35.36 | C |
| ATOM | 247 | CB | VAL | A | 45 | 18.642 | 42.852 | 24.648 | 1.00 35.04 | C |
| ATOM | 248 | CG1 | VAL | A | 45 | | 33.42 1.00 | 25.305 | 43.709 17.654 | C |
| ATOM | 249 | CG2 | VAL | A | 45 | 18.360 | 42.765 | 23.119 | 1.00 34.45 | C |
| ATOM | 250 | C | VAL | A | 45 | 20.330 | 43.686 | 26.429 | 1.00 36.38 | C |

Fig. 26 (Cont.)

| | | | | | | | | | | |
|---|---|---|---|---|---|---|---|---|---|---|
| ATOM | 251 | O | VAL | A | 45 | 20.172 | 42.801 | | 36.59 1.00 | 27.287 | O |
| ATOM | 252 | N | LYS | A | 46 | 20.674 | 44.927 | 26.752 | 1.00 37.39 | | N |
| ATOM | 253 | CA | LYS | A | 46 | 20.825 | 45.345 | 28.138 | 1.00 38.09 | | C |
| ATOM | 254 | CB | LYS | A | 46 | 21.018 | 46.851 | 28.165 | 1.00 39.12 | | C |
| ATOM | 255 | CG | LYS | A | 46 | 21.747 | 47.447 | 29.352 | 1.00 43.04 | | C |
| ATOM | 256 | CD | LYS | A | 46 | 22.744 | 48.499 | 28.768 | 1.00 50.53 | | C |
| ATOM | 257 | CE | LYS | A | 46 | 22.939 | 48.297 | 27.195 | 1.00 48.21 | | C |
| ATOM | 258 | NZ | LYS | A | 46 | 24.221 | 48.860 | 26.630 | 1.00 47.64 | | N |
| ATOM | 259 | C | LYS | A | 46 | 19.596 | 44.982 | 28.976 | 1.00 38.22 | | C |
| ATOM | 260 | O | LYS | A | 46 | 18.443 | 45.368 | 28.646 | 1.00 38.43 | | O |
| ATOM | 261 | N | GLY | A | | 38.07 1.00 | 30.069 | 44.257 | 19.855 | 47 | N |
| ATOM | 262 | CA | GLY | A | 47 | 18.809 | 43.881 | 31.022 | 1.00 37.70 | | C |
| ATOM | 263 | C | GLY | A | 47 | 18.242 | 42.474 | 30.886 | 1.00 38.75 | | C |
| ATOM | 264 | O | GLY | A | 47 | 17.309 | 42 | | 40.30 1.00 | 31.612 | 102.O |
| ATOM | 265 | N | ILE | A | 48 | 18.728 | 41.687 | 29.929 | 1.00 37.62 | | N |
| ATOM | 266 | CA | ILE | A | 48 | 18.219 | 40.321 | 29.800 | 1.00 36.52 | | C |
| ATOM | 267 | CB | ILE | A | 48 | 17.646 | 40.087 | 28.393 | 1.00 35.98 | | C |
| ATOM | 268 | CG1 | ILE | A | 48 | 16.552 | 41.132 | 28.118 | 1.00 35.58 | | C |
| ATOM | 269 | CD1 | ILE | A | 48 | 15.634 | 40.760 | 26.954 | 1.00 37.20 | | C |
| ATOM | 270 | CG2 | ILE | A | 48 | 17.184 | 38.602 | 28.196 | 1.00 33.42 | | C |
| ATOM | 271 | C | ILE | A | 48 | 19.351 | 39.372 | 30.121 | 1.00 37.25 | | C |
| ATOM | 272 | O | ILE | A | 48 | 20.344 | 39.294 | 29.352 | 1.00 36.71 | | O |
| ATOM | 273 | N | ASP | A | 49 | 19.271 | 38.727 | 31.292 | 1.00 37.85 | | N |
| ATOM | 274 | CA | ASP | A | 49 | 20.357 | 37.826 | 31.686 | 1.00 39.99 | | C |
| ATOM | 275 | CB | ASP | A | 49 | 21.291 | 38.460 | 32.704 | 1.00 40.77 | | C |
| ATOM | 276 | CG | ASP | A | 49 | 22.022 | 39.620 | 32.103 | 1.00 46.27 | | C |
| ATOM | 277 | OD1 | ASP | A | 49 | 23.055 | | 49.10 1.00 | 31.385 | 39.404 | O |
| ATOM | 278 | OD2 | ASP | A | 49 | 21.560 | 40.778 | 32.208 | 1.00 51.18 | | O |
| ATOM | 279 | C | ASP | A | 49 | 19.925 | 36.477 | 32.144 | 1.00 39.79 | | C |
| ATOM | 280 | O | ASP | A | 49 | 20.786 | 35.639 | 32.392 | 1.00 | 40.81 | O |
| ATOM | 281 | N | ASN | A | 50 | 18.609 | 36.278 | 32.227 | 1.00 39.81 | | N |
| ATOM | 282 | CA | ASN | A | 50 | 18.017 | 35.073 | 32.811 | 1.00 39.57 | | C |
| ATOM | 283 | CB | ASN | A | 50 | 17.421 | 35.415 | 34.179 | 1.00 40.04 | | C |
| ATOM | 284 | CG | ASN | A | 50 | 18.508 | 35.538 | 35.244 | 1.00 46.75 | | C |
| ATOM | 285 | OD1 | ASN | A | 50 | 18.756 | 34.583 | 35.962 | 1.00 52.04 | | O |
| ATOM | 286 | ND2 | ASN | A | 50 | 19.226 | 36.674 | 35.279 | 1.00 45.67 | | N |
| ATOM | 287 | C | ASN | A | 50 | 16.977 | 34.475 | 31.886 | 1.00 38.33 | | C |
| ATOM | 288 | O | ASN | A | 50 | 15.993 | 33.866 | 32.335 | 1.00 37.99 | | O |
| ATOM | 289 | N | GLY | A | 51 | 17.180 | 34.682 | 30.591 | 1.00 36.70 | | N |
| ATOM | 290 | CA | GLY | A | 51 | 16.463 | | 35.87 1.00 | 29.575 | 33.944 | C |
| ATOM | 291 | C | GLY | A | 51 | 15.481 | 34.869 | 28.892 | 1.00 36.19 | | C |
| ATOM | 292 | O | GLY | A | 51 | 15.095 | 35.926 | 29.455 | 1.00 34.76 | | O |
| ATOM | 293 | N | SER | A | 52 | 15.054 | 34.415 | 27.722 | | 33.57 1.00 | N |
| ATOM | 294 | CA | SER | A | 52 | 14.182 | 35.161 | 26.838 | 1.00 35.00 | | C |
| ATOM | 295 | CB | SER | A | 52 | 14.985 | 36.214 | 25.995 | 1.00 34.00 | | C |
| ATOM | 296 | OG | SER | A | 52 | 16.239 | 35.693 | 25.541 | 1.00 33.23 | | O |
| ATOM | 297 | C | SER | A | 52 | 13.563 | 34.106 | 25.945 | 1.00 35.67 | | C |
| ATOM | 298 | O | SER | A | 52 | 13.634 | 34.219 | 24.720 | 1.00 34.71 | | O |
| ATOM | 299 | N | GLU | A | 53 | 13.008 | 33.050 | 26.574 | 1.00 35.64 | | N |
| ATOM | 300 | CA | GLU | A | 53 | 12.706 | 31.832 | 25.828 | 1.00 35.43 | | C |
| ATOM | 301 | CB | GLU | A | 53 | 12.179 | 30.713 | 26.749 | 1.00 37.07 | | C |
| ATOM | 302 | CG | GLU | A | 53 | 12.300 | 29.284 | 26.120 | 1.00 38.97 | | C |
| ATOM | 303 | CD | GLU | A | 53 | 11 | | 45.33 1.00 | 25.240 | 28.838 | 098.C |
| ATOM | 304 | OE1 | GLU | A | 53 | 10.011 | 29.546 | 25.240 | 1.00 44.51 | | O |
| ATOM | 305 | OE2 | GLU | A | 53 | 11.216 | 27.751 | 24.546 | 1.00 42.02 | | O |
| ATOM | 306 | C | GLU | A | 53 | 11.712 | 32.037 | 24.703 | | 35.71 1.00 | C |
| ATOM | 307 | O | GLU | A | 53 | 11.770 | 31.332 | 23.671 | 1.00 35.46 | | O |
| ATOM | 308 | N | ASP | A | 54 | 10.720 | 32.905 | 24.899 | 1.00 35.35 | | N |
| ATOM | 309 | CA | ASP | A | 54 | 9.783 | 33.136 | 23.808 | 1.00 35.51 | | C |
| ATOM | 310 | CB | ASP | A | 54 | 8.442 | 32.431 | 24.001 | 1.00 34.20 | | C |
| ATOM | 311 | CG | ASP | A | 54 | 7.738 | 32.171 | 22.652 | 1.00 38.43 | | C |

Fig. 26 (Cont.)

| ATOM | 312 | OD1 | ASP | A | 54 | 8.339 | 32.416 | 21.539 | 1.00 | 39.84 | | | O |
|---|---|---|---|---|---|---|---|---|---|---|---|---|---|
| ATOM | 313 | OD2 | ASP | A | 54 | 6.555 | 31.804 | 22.545 | 1.00 | 37.47 | | | O |
| ATOM | 314 | C | ASP | A | 54 | 9.566 | 34.624 | 23.677 | 1.00 | 36.04 | | | C |
| ATOM | 315 | O | ASP | A | 54 | 9.756 | 35.394 | 24.633 | 1.00 | 34.50 | | | O |
| ATOM | 316 | N | LEU | A | 55 | | 36.48 | 1.00 | 22.516 | 35.029 | 9.111 | | N |
| ATOM | 317 | CA | LEU | A | 55 | 8.847 | 36.447 | 22.352 | 1.00 | 38.06 | | | C |
| ATOM | 318 | CB | LEU | A | 55 | 10.121 | 37.238 | 22.028 | 1.00 | 37.42 | | | C |
| ATOM | 319 | CG | LEU | A | 55 | 10.993 | 36.817 | 20 | | 39.53 | 1.00 | 889. | C |
| ATOM | 320 | CD1 | LEU | A | 55 | 10.636 | 37.664 | 19.628 | 1.00 | 38.52 | | | C |
| ATOM | 321 | CD2 | LEU | A | 55 | 12.423 | 37.147 | 21.329 | 1.00 | 40.87 | | | C |
| ATOM | 322 | C | LEU | A | 55 | 7.852 | 36.562 | 21.227 | 1.00 | 38.25 | | | C |
| ATOM | 323 | O | LEU | A | 55 | 7.719 | 35.646 | 20.440 | 1.00 | 38.70 | | | O |
| ATOM | 324 | N | GLU | A | 56 | 7.143 | 37.679 | 21.170 | 1.00 | 38.51 | | | N |
| ATOM | 325 | CA | GLU | A | 56 | 6.216 | 37.921 | 20.072 | 1.00 | 37.64 | | | C |
| ATOM | 326 | CB | GLU | A | 56 | 4.788 | 37.391 | 20.415 | 1.00 | 39.63 | | | C |
| ATOM | 327 | CG | GLU | A | 56 | 3.898 | 37.485 | 19.158 | 1.00 | 40.53 | | | C |
| ATOM | 328 | CD | GLU | A | 56 | 2.759 | 36.533 | 19.208 | 1.00 | 41.85 | | | C |
| ATOM | 329 | OE1 | GLU | A | 56 | | 46.69 | 1.00 | 18.887 | 36.927 | 1.636 | | O |
| ATOM | 330 | OE2 | GLU | A | 56 | 2.991 | 35.371 | 19.544 | 1.00 | 43.01 | | | O |
| ATOM | 331 | C | GLU | A | 56 | 6.182 | 39.432 | 19.857 | 1.00 | 37.78 | | | C |
| ATOM | 332 | O | GLU | A | 56 | 6.102 | 40.226 | | 37.75 | 1.00 | 20.810 | | O |
| ATOM | 333 | N | ILE | A | 57 | 6.275 | 39.831 | 18.596 | 1.00 | 37.29 | | | N |
| ATOM | 334 | CA | ILE | A | 57 | 6.202 | 41.211 | 18.239 | 1.00 | 36.87 | | | C |
| ATOM | 335 | CB | ILE | A | 57 | 7.282 | 41.469 | 17.163 | 1.00 | 36.67 | | | C |
| ATOM | 336 | CG1 | ILE | A | 57 | 8.634 | 40.949 | 17.677 | 1.00 | 35.29 | | | C |
| ATOM | 337 | CD1 | ILE | A | 57 | 9.887 | 41.067 | 16.616 | 1.00 | 33.23 | | | C |
| ATOM | 338 | CG2 | ILE | A | 57 | 7.283 | 42.981 | 16.834 | 1.00 | 35.45 | | | C |
| ATOM | 339 | C | ILE | A | 57 | 4.804 | 41.576 | 17.701 | 1.00 | 37.83 | | | C |
| ATOM | 340 | O | ILE | A | 57 | 4.299 | 40.870 | 16.822 | 1.00 | 38.53 | | | O |
| ATOM | 341 | N | LEU | A | 58 | 4.150 | 42.619 | 18.230 | 1.00 | 36.71 | | | N |
| ATOM | 342 | CA | LEU | A | 58 | | 36.75 | 1.00 | 17.640 | 43.051 | 2.859 | | C |
| ATOM | 343 | CB | LEU | A | 58 | 2.186 | 44.041 | 18.563 | 1.00 | 35.11 | | | C |
| ATOM | 344 | CG | LEU | A | 58 | 1.823 | 43.540 | 19.993 | 1.00 | 37.90 | | | C |
| ATOM | 345 | CD1 | LEU | A | 58 | 1.173 | 44.586 | | 33.13 | 1.00 | 20.784 | | C |
| ATOM | 346 | CD2 | LEU | A | 58 | 0.928 | 42.323 | 19.917 | 1.00 | 36.93 | | | C |
| ATOM | 347 | C | LEU | A | 58 | 3.125 | 43.778 | 16.272 | 1.00 | 37.80 | | | C |
| ATOM | 348 | O | LEU | A | 58 | 4.255 | 44.204 | 16.045 | 1.00 | 37 | | 07. | O |
| ATOM | 349 | N | PRO | A | 59 | 2.127 | 43.925 | 15.393 | 1.00 | 38.36 | | | N |
| ATOM | 350 | CA | PRO | A | 59 | 2.228 | 44.863 | 14.230 | 1.00 | 38.96 | | | C |
| ATOM | 351 | CB | PRO | A | 59 | 0.754 | 44.991 | 13.698 | 1.00 | 38.17 | | | C |
| ATOM | 352 | CG | PRO | A | 59 | 0.096 | 43.630 | 14.082 | 1.00 | 39.12 | | | C |
| ATOM | 353 | CD | PRO | A | 59 | 0.825 | 43.208 | 15.425 | 1.00 | 39.91 | | | C |
| ATOM | 354 | C | PRO | A | 59 | 2.683 | 46.287 | 14.615 | 1.00 | 37.80 | | | C |
| ATOM | 355 | O | PRO | A | | | 38.08 | 1.00 | 13.814 | 46.853 | 3.334 | 59 | O |
| ATOM | 356 | N | ASN | A | 60 | 2.359 | 46.856 | 15.768 | 1.00 | 36.68 | | | N |
| ATOM | 357 | CA | ASN | A | 60 | 2.843 | 48.213 | 16.039 | 1.00 | 35.74 | | | C |
| ATOM | 358 | CB | ASN | A | 60 | 1.953 | 48.972 | | 35.95 | 1.00 | 17.080 | | C |
| ATOM | 359 | CG | ASN | A | 60 | 1.945 | 48.265 | 18.481 | 1.00 | 39.11 | | | C |
| ATOM | 360 | OD1 | ASN | A | 60 | 2.713 | 47.314 | 18.702 | 1.00 | 32.54 | | | O |
| ATOM | 361 | ND2 | ASN | A | 60 | 1.044 | 48.688 | 19.388 | 1.00 | | | 37.73 | N |
| ATOM | 362 | C | ASN | A | 60 | 4.302 | 48.223 | 16.481 | 1.00 | 35.51 | | | C |
| ATOM | 363 | O | ASN | A | 60 | 4.805 | 49.266 | 16.806 | 1.00 | 35.95 | | | O |
| ATOM | 364 | N | GLY | A | 61 | 4.978 | 47.065 | 16.532 | 1.00 | 35.97 | | | N |
| ATOM | 365 | CA | GLY | A | 61 | 6.375 | 47.046 | 16.931 | 1.00 | 35.62 | | | C |
| ATOM | 366 | C | GLY | A | 61 | 6.688 | 46.830 | 18.420 | 1.00 | 34.98 | | | C |
| ATOM | 367 | O | GLY | A | 61 | 7.863 | 46.742 | 18.804 | 1.00 | 32.71 | | | O |
| ATOM | 368 | N | LEU | A | 62 | 5.660 | 46.745 | 19.258 | 1.00 | 34.79 | | | N |
| ATOM | 369 | CA | LEU | A | 62 | 5.855 | 46.329 | 20.680 | 1.00 | 35.23 | | | C |
| ATOM | 370 | CB | LEU | A | 62 | 4.614 | 46.660 | 21.561 | 1.00 | 34.59 | | | C |
| ATOM | 371 | CG | LEU | A | 62 | 4.222 | | 35.76 | 1.00 | 21.709 | 48.143 | | C |
| ATOM | 372 | CD1 | LEU | A | 62 | 3.048 | 48.340 | 22.655 | 1.00 | 32.43 | | | C |

Fig. 26 (Cont.)

| | | | | | | | | | | |
|---|---|---|---|---|---|---|---|---|---|---|
| ATOM | 373 | CD2 | LEU A | 62 | 5.414 | 48.997 | 22.156 | 1.00 | 34.98 | C |
| ATOM | 374 | C | LEU A | 62 | 6.198 | 44.819 | 20.748 | 1 | 34.64 00. | C |
| ATOM | 375 | O | LEU A | 62 | 5.500 | 43.977 | 20.163 | 1.00 | 36.80 | O |
| ATOM | 376 | N | ALA A | 63 | 7.268 | 44.477 | 21.440 | 1.00 | 34.10 | N |
| ATOM | 377 | CA | ALA A | 63 | 7.649 | 43.073 | 21.611 | 1.00 | 34.95 | C |
| ATOM | 378 | CB | ALA A | 63 | 9.139 | 42.825 | 21.132 | 1.00 | 33.37 | C |
| ATOM | 379 | C | ALA A | 63 | 7.504 | 42.633 | 23.075 | 1.00 | 34.16 | C |
| ATOM | 380 | O | ALA A | 63 | 7.988 | 43.312 | 23.966 | 1.00 | 34.79 | O |
| ATOM | 381 | N | PHE A | 64 | 6.905 | 41.466 | 23.283 | 1.00 | 34.36 | N |
| ATOM | 382 | CA | PHE A | 64 | 6.760 | 40.875 | 24.618 | 1.00 | 36.24 | C |
| ATOM | 383 | CB | PHE A | 64 | 5.388 | 40.221 | 24.754 | 1.00 | 36.32 | C |
| ATOM | 384 | CG | PHE A | 64 | 4 | 40.80 1.00 | 24.804 | 41.207 | 250. | C |
| ATOM | 385 | CD1 | PHE A | 64 | 3.918 | 41.849 | 26.013 | 1.00 | 37.80 | C |
| ATOM | 386 | CE1 | PHE A | 64 | 2.870 | 42.746 | 26.068 | 1.00 | 40.81 | C |
| ATOM | 387 | CZ | PHE A | 64 | 2.096 | 43.011 | 24.953 | | 41.28 1.00 | C |
| ATOM | 388 | CE2 | PHE A | 64 | 2.403 | 42.401 | 23.741 | 1.00 | 45.84 | C |
| ATOM | 389 | CD2 | PHE A | 64 | 3.490 | 41.489 | 23.661 | 1.00 | 42.25 | C |
| ATOM | 390 | C | PHE A | 64 | 7.771 | 39.765 | 24.680 | 1.00 | 34.84 | C |
| ATOM | 391 | O | PHE A | 64 | 7.933 | 39.076 | 23.675 | 1.00 | 34.61 | O |
| ATOM | 392 | N | ILE A | 65 | 8.418 | 39.590 | 25.824 | 1.00 | 33.62 | N |
| ATOM | 393 | CA | ILE A | 65 | 9.404 | 38.527 | 25.999 | 1.00 | 34.39 | C |
| ATOM | 394 | CB | ILE A | 65 | 10.801 | 39.185 | 26.008 | 1.00 | 34.90 | C |
| ATOM | 395 | CG1 | ILE A | 65 | 11.041 | 40.043 | 24.742 | 1.00 | 34.12 | C |
| ATOM | 396 | CD1 | ILE A | 65 | 12.195 | 40.924 | 24.927 | 1.00 | 32.55 | C |
| ATOM | 397 | CG2 | ILE A | 65 | | 33.43 1.00 | 26.281 | 38.185 | 11.943 | C |
| ATOM | 398 | C | ILE A | 65 | 9.182 | 37.813 | 27.328 | 1.00 | 35.34 | C |
| ATOM | 399 | O | ILE A | 65 | 9.141 | 38.473 | 28.358 | 1.00 | 36.38 | O |
| ATOM | 400 | N | SER A | 66 | 9.082 | 36.487 | 27 | | 35.61 1.00 | 360.N |
| ATOM | 401 | CA | SER A | 66 | 9.017 | 35.834 | 28.656 | 1.00 | 35.06 | C |
| ATOM | 402 | CB | SER A | 66 | 8.269 | 34.513 | 28.574 | 1.00 | 36.04 | C |
| ATOM | 403 | OG | SER A | 66 | 8.952 | 33.709 | 27.691 | 1.00 | 39.18 | O |
| ATOM | 404 | C | SER A | 66 | 10.454 | 35.577 | 29.102 | 1.00 | 35.97 | C |
| ATOM | 405 | O | SER A | 66 | 11.314 | 35.316 | 28.285 | 1.00 | 36.45 | O |
| ATOM | 406 | N | SER A | 67 | 10.707 | 35.628 | 30.393 | 1.00 | 34.80 | N |
| ATOM | 407 | CA | SER A | 67 | 12.005 | 35.473 | 30.879 | 1.00 | 36.50 | C |
| ATOM | 408 | CB | SER A | 67 | 12.720 | 36.855 | 30.910 | 1.00 | 37.35 | C |
| ATOM | 409 | OG | SER A | 67 | 12.223 | 37.624 | 31.976 | 1.00 | 43.15 | O |
| ATOM | 410 | C | SER A | 67 | | 36.01 1.00 | 32.244 | 34.858 | 12.003 | C |
| ATOM | 411 | O | SER A | 67 | 11.022 | 34.893 | 32.963 | 1.00 | 34.71 | O |
| ATOM | 412 | N | GLY A | 68 | 13.171 | 34.367 | 32.635 | 1.00 | 37.65 | N |
| ATOM | 413 | CA | GLY A | 68 | 13.355 | 33.873 | | 39.88 1.00 | 33.994 | C |
| ATOM | 414 | C | GLY A | 68 | 12.804 | 32.476 | 34.132 | 1.00 | 41.21 | C |
| ATOM | 415 | O | GLY A | 68 | 12.499 | 32.057 | 35.242 | 1.00 | 42.04 | O |
| ATOM | 416 | N | LEU A | 69 | 12.675 | 31.757 | 33.019 | 1.00 | 41.72 | N |
| ATOM | 417 | CA | LEU A | 69 | 12.261 | 30.354 | 33.090 | 1.00 | 43.42 | C |
| ATOM | 418 | CB | LEU A | 69 | 12.095 | 29.752 | 31.676 | 1.00 | 42.75 | C |
| ATOM | 419 | CG | LEU A | 69 | 11.608 | 28.292 | 31.565 | 1.00 | 43.34 | C |
| ATOM | 420 | CD1 | LEU A | 69 | 10.100 | 28.023 | 32.027 | 1.00 | 39.91 | C |
| ATOM | 421 | CD2 | LEU A | 69 | 11.797 | 27.853 | 30.124 | 1.00 | 44.52 | C |
| ATOM | 422 | C | LEU A | 69 | 13.168 | 29.453 | 33.983 | 1.00 | 44.35 | C |
| ATOM | 423 | O | LEU A | 69 | | 42.92 1.00 | 33.835 | 29.458 | 14.378 | O |
| ATOM | 424 | N | LYS A | 70 | 12.548 | 28.699 | 34.903 | 1.00 | 46.34 | N |
| ATOM | 425 | CA | LYS A | 70 | 13.185 | 27.551 | 35.560 | 1.00 | 50.33 | C |
| ATOM | 426 | CB | LYS A | 70 | 13.116 | 27.648 | | 50.44 1.00 | 37.065 | C |
| ATOM | 427 | CG | LYS A | 70 | 13.855 | 28.824 | 37.621 | 1.00 | 54.87 | C |
| ATOM | 428 | CD | LYS A | 70 | 12.902 | 29.721 | 38.380 | 1.00 | 58.02 | C |
| ATOM | 429 | CE | LYS A | 70 | 13.486 | 31.127 | 38.524 | 1.00 | 59 | 44.C |
| ATOM | 430 | NZ | LYS A | 70 | 13.821 | 31.200 | 40.002 | 1.00 | 59.29 | N |
| ATOM | 431 | C | LYS A | 70 | 12.544 | 26.186 | 35.160 | 1.00 | 52.65 | C |
| ATOM | 432 | O | LYS A | 70 | 11.271 | 25.977 | 35.139 | 1.00 | 50.49 | O |
| ATOM | 433 | N | TYR A | 71 | 13.474 | 25.271 | 34.853 | 1.00 | 55.39 | N |

Fig. 26 (Cont.)

```
ATOM   434  CA   TYR A  71      13.231  23.850  34.517  1.00 56.92           C
ATOM   435  CB   TYR A  71      14.572  23.221  33.982  1.00 57.50           C
ATOM   436  CG   TYR A          62.72 1.00  35.019  23.255  15.787      71   C
ATOM   437  CD1  TYR A  71      15.758  22.444  36.212  1.00 63.02           C
ATOM   438  CE1  TYR A  71      16.817  22.438  37.172  1.00 64.48           C
ATOM   439  CZ   TYR A  71      17.941  23      65.14 1.00  36.946    237.C
ATOM   440  OH   TYR A  71      18.939  23.189  37.896  1.00 63.37           O
ATOM   441  CE2  TYR A  71      18.037  24.058  35.763  1.00 66.39           C
ATOM   442  CD2  TYR A  71      16.949  24.071  34.799  1.00            63.42 C
ATOM   443  C    TYR A  71      12.678  23.089  35.770  1.00 56.66           C
ATOM   444  O    TYR A  71      13.145  23.288  36.912  1.00 55.16           O
ATOM   445  N    ASP A  80      18.307  36.478  43.053  1.00 61.40           N
ATOM   446  CA   ASP A  80      16.901  36.225  43.410  1.00 61.37           C
ATOM   447  CB   ASP A  80      16.585  36.896  44.761  1.00 61.28           C
ATOM   448  CG   ASP A  80      16.126  35.905  45.824  1.00 61.41           C
ATOM   449  OD1  ASP A  80      15.259  35.041  45.520  1.00 60.57           O
ATOM   450  OD2  ASP A  80      16.585  35.923  46.997  1.00 61.17           O
ATOM   451  C    ASP A  80      15.922  36.752  42.318  1.00 61.48           C
ATOM   452  O    ASP A  80      15.137          62.12 1.00    42.612  37.685 O
ATOM   453  N    LYS A  81      15.958  36.149  41.104  1.00 60.17           N
ATOM   454  CA   LYS A  81      15.363  36.718  39.862  1.00 58.70           C
ATOM   455  CB   LYS A  81      16.446  36.970  38.762  1             59.06 00.C
ATOM   456  CG   LYS A  81      17.757  36.072  38.847  1.00 59.89           C
ATOM   457  CD   LYS A  81      18.909  36.731  39.652  1.00 60.76           C
ATOM   458  CE   LYS A  81      20.358  36.331  39.176  1.00 62.31           C
ATOM   459  NZ   LYS A  81      20.816  36.999  37.853  1.00 60.80           N
ATOM   460  C    LYS A  81      14.128  35.961  39.290  1.00 57.17           C
ATOM   461  O    LYS A  81      14.238  34.884  38.647  1.00 57.87           O
ATOM   462  N    SER A  82      12.952  36.550  39.515  1.00 53.97           N
ATOM   463  CA   SER A  82      11.666  35.948  39.189  1.00 50.30           C
ATOM   464  CB   SER A  82      10.556  36.847  39.696  1.00 50.65           C
ATOM   465  OG   SER A  82      11.098          50.79 1.00    40.648  37.688 O
ATOM   466  C    SER A  82      11.379  35.704  37.709  1.00 47.88           C
ATOM   467  O    SER A  82      12.064  36.240  36.791  1.00 48.19           O
ATOM   468  N    GLY A  83      10.337  34.911  37.483          43.71 1.00   N
ATOM   469  CA   GLY A  83       9.741  34.859  36.173  1.00 41.45           C
ATOM   470  C    GLY A  83       9.145  36.249  35.929  1.00 39.73           C
ATOM   471  O    GLY A  83       8.571  36.865  36.851  1.00 37.58           O
ATOM   472  N    LYS A  84       9.319  36.766  34.713  1.00 37.76           N
ATOM   473  CA   LYS A  84       8.663  38.032  34.361  1.00 38.30           C
ATOM   474  CB   LYS A  84       9.403  39.263  34.923  1.00 38.98           C
ATOM   475  CG   LYS A  84      10.816  39.346  34.462  1.00 43.83           C
ATOM   476  CD   LYS A  84      11.676  40.343  35.257  1.00 44.31           C
ATOM   477  CE   LYS A  84      12.094  39.737  36.543  1.00 47.82           C
ATOM   478  NZ   LYS A  84      12.868          44.76 1.00    37.350  40.741 N
ATOM   479  C    LYS A  84       8.381  38.151  32.887  1.00 36.25           C
ATOM   480  O    LYS A  84       8.951  37.419  32.046  1.00 36.85           O
ATOM   481  N    ILE A  85       7.470  39.043  32.551          34.76 1.00   N
ATOM   482  CA   ILE A  85       7.275  39.383  31.144  1.00 33.39           C
ATOM   483  CB   ILE A  85       5.776  39.380  30.792  1.00 34.18           C
ATOM   484  CG1  ILE A  85       5.109  38.057  31.198  1.00 33.29           C
ATOM   485  CD1  ILE A  85       5.647  36.842  30.355  1.00 33.85           C
ATOM   486  CG2  ILE A  85       5.551  39.682  29.266  1.00 35.20           C
ATOM   487  C    ILE A  85       7.870  40.762  30.930  1.00 34.48           C
ATOM   488  O    ILE A  85       7.579  41.710  31.704  1.00 31.41           O
ATOM   489  N    LEU A  86       8.659  40.894  29.852  1.00 34.14           N
ATOM   490  CA   LEU A  86       9.365  42.137  29.528  1.00 34.32           C
ATOM   491  CB   LEU A  86          31.55 1.00  29.272  41.893  10.888        C
ATOM   492  CG   LEU A  86      11.654  41.074  30.313  1.00 36.32           C
ATOM   493  CD1  LEU A  86      13.089  40.767  29.832  1.00 36.82           C
ATOM   494  CD2  LEU A  86      11.763  41.825  31.640          32.85 1.00   C
```

| | | | | | | | | | |
|---|---|---|---|---|---|---|---|---|---|
| ATOM | 495 | C | LEU A | 86 | 8.767 | 42.704 | 28.263 | 1.00 34.55 | C |
| ATOM | 496 | O | LEU A | 86 | 8.267 | 41.954 | 27.446 | 1.00 35.10 | O |
| ATOM | 497 | N | LEU A | 87 | 8.904 | 44.018 | 28.074 | 1.00 34.40 | N |
| ATOM | 498 | CA | LEU A | 87 | 8.363 | 44.725 | 26.941 | 1.00 34.92 | C |
| ATOM | 499 | CB | LEU A | 87 | 7.368 | 45.771 | 27.387 | 1.00 35.47 | C |
| ATOM | 500 | CG | LEU A | 87 | 6.651 | 46.493 | 26.212 | 1.00 37.95 | C |
| ATOM | 501 | CD1 | LEU A | 87 | 5.700 | 45.533 | 25.418 | 1.00 35.22 | C |
| ATOM | 502 | CD2 | LEU A | 87 | 5.904 | 47.714 | 26.703 | 1.00 35.05 | C |
| ATOM | 503 | C | LEU A | 87 | 9.497 | 45.510 | 26.285 | 1.00 36.38 | C |
| ATOM | 504 | O | LEU A | | 34.97 1.00 | 26.963 | 46.213 | 10.236 | O |
| ATOM | 505 | N | MET A | 88 | 9.590 | 45.435 | 24.961 | 1.00 36.52 | N |
| ATOM | 506 | CA | MET A | 88 | 10.509 | 46.309 | 24.256 | 1.00 37.56 | C |
| ATOM | 507 | CB | MET A | 88 | 11.605 | 45.464 | | 38.06 1.00 23.590 | C |
| ATOM | 508 | CG | MET A | 88 | 12.809 | 45.157 | 24.447 | 1.00 39.38 | C |
| ATOM | 509 | SD | MET A | 88 | 13.930 | 43.972 | 23.523 | 1.00 41.13 | S |
| ATOM | 510 | CE | MET A | 88 | 14.926 | 45.064 | 22.630 | 1.00 36.63 | C |
| ATOM | 511 | C | MET A | 88 | 9.756 | 47.012 | 23.138 | 1.00 37.44 | C |
| ATOM | 512 | O | MET A | 88 | 9.019 | 46.353 | 22.398 | 1.00 37.94 | O |
| ATOM | 513 | N | ASP A | 89 | 10.004 | 48.296 | 22.948 | 1.00 36.32 | N |
| ATOM | 514 | CA | ASP A | 89 | 9.399 | 49.026 | 21.858 | 1.00 36.83 | C |
| ATOM | 515 | CB | ASP A | 89 | 9.003 | 50.446 | 22.317 | 1.00 36.38 | C |
| ATOM | 516 | CG | ASP A | 89 | 8.252 | 51.233 | 21.250 | 1.00 37.11 | C |
| ATOM | 517 | OD1 | ASP A | | 38.37 1.00 | 20.061 | 50.850 | 8.246 89 | O |
| ATOM | 518 | OD2 | ASP A | 89 | 7.648 | 52.288 | 21.498 | 1.00 42.32 | O |
| ATOM | 519 | C | ASP A | 89 | 10.426 | 49.098 | 20.711 | 1.00 36.70 | C |
| ATOM | 520 | O | ASP A | 89 | 11.375 | 49 | | 38.05 1.00 20.748 893. | O |
| ATOM | 521 | N | LEU A | 90 | 10.242 | 48.265 | 19.699 | 1.00 36.35 | N |
| ATOM | 522 | CA | LEU A | 90 | 11.235 | 48.095 | 18.656 | 1.00 35.31 | C |
| ATOM | 523 | CB | LEU A | 90 | 11.073 | 46.752 | 17.990 | 1.00 35.46 | C |
| ATOM | 524 | CG | LEU A | 90 | 11.240 | 45.448 | 18.800 | 1.00 34.32 | C |
| ATOM | 525 | CD1 | LEU A | 90 | 11.135 | 44.146 | 17.906 | 1.00 29.82 | C |
| ATOM | 526 | CD2 | LEU A | 90 | 12.541 | 45.451 | 19.618 | 1.00 31.59 | C |
| ATOM | 527 | C | LEU A | 90 | 11.174 | 49.231 | 17.615 | 1.00 36.97 | C |
| ATOM | 528 | O | LEU A | 90 | 11.994 | 49.238 | 16.699 | 1.00 36.95 | O |
| ATOM | 529 | N | ASN A | 91 | 10.258 | 50.212 | 17.773 | 1.00 36.99 | N |
| ATOM | 530 | CA | ASN A | 91 | 10.333 | 51.459 | 17.005 | 1.00 38.70 | C |
| ATOM | 531 | CB | ASN A | 91 | 8.987 | 52.186 | 16.890 | 1.00 37.08 | C |
| ATOM | 532 | CG | ASN A | 91 | 7.916 | 51.322 | 16.298 | 1.00 38.78 | C |
| ATOM | 533 | OD1 | ASN A | 91 | 6.978 | | 39.74 1.00 | 17.008 50.924 | O |
| ATOM | 534 | ND2 | ASN A | 91 | 8.060 | 50.954 | 15.013 | 1.00 34.37 | N |
| ATOM | 535 | C | ASN A | 91 | 11.388 | 52.423 | 17.569 | 1.00 40.81 | C |
| ATOM | 536 | O | ASN A | 91 | 11.781 | 53.378 | 16.894 | 1.00 40.02 | O |
| ATOM | 537 | N | GLU A | 92 | 11.859 | 52.199 | 18.800 | 1.00 42.98 | N |
| ATOM | 538 | CA | GLU A | 92 | 12.922 | 53.088 | 19.332 | 1.00 45.52 | C |
| ATOM | 539 | CB | GLU A | 92 | 13.034 | 52.914 | 20.840 | 1.00 45.36 | C |
| ATOM | 540 | CG | GLU A | 92 | 12.057 | 53.735 | 21.651 | 1.00 47.03 | C |
| ATOM | 541 | CD | GLU A | 92 | 11.814 | 53.097 | 23.003 | 1.00 51.90 | C |
| ATOM | 542 | OE1 | GLU A | 92 | 12.789 | 52.577 | 23.621 | 1.00 52.73 | O |
| ATOM | 543 | OE2 | GLU A | 92 | 10.633 | 53.070 | 23.447 | 1.00 55.53 | O |
| ATOM | 544 | C | GLU A | 92 | 14.277 | 52.773 | 18.698 | 1.00 46.51 | C |
| ATOM | 545 | O | GLU A | 92 | 14.544 | 51.615 | 18.368 | 1.00 48.06 | O |
| ATOM | 546 | N | LYS A | 93 | 15.172 | | 48.20 1.00 | 18.553 53.742 | N |
| ATOM | 547 | CA | LYS A | 93 | 16.441 | 53.371 | 17.912 | 1.00 49.26 | C |
| ATOM | 548 | CB | LYS A | 93 | 17.171 | 54.573 | 17.269 | 1.00 49.99 | C |
| ATOM | 549 | CG | LYS A | 93 | 17.036 | 54.545 | 15.688 | | 53.08 1.00 C |
| ATOM | 550 | CD | LYS A | 93 | 17.908 | 55.603 | 14.957 | 1.00 55.59 | C |
| ATOM | 551 | CE | LYS A | 93 | 17.305 | 56.034 | 13.593 | 1.00 55.06 | C |
| ATOM | 552 | NZ | LYS A | 93 | 17.400 | 57.532 | 13.438 | 1.00 53.03 | N |
| ATOM | 553 | C | LYS A | 93 | 17.347 | 52.442 | 18.770 | 1.00 49.26 | C |
| ATOM | 554 | O | LYS A | 93 | 18.015 | 51.541 | 18.212 | 1.00 49.65 | O |
| ATOM | 555 | N | GLU A | 94 | 17.334 | 52.635 | 20.102 | 1.00 48.09 | N |

Fig. 26 (Cont.)

| ATOM | 556 | CA | GLU | A | 94 | 18.024 | 51.739 | 21.054 | 1.00 | 47.70 | C |
|---|---|---|---|---|---|---|---|---|---|---|---|
| ATOM | 557 | CB | GLU | A | 94 | 18.977 | 52.515 | 22.010 | 1.00 | 48.56 | C |
| ATOM | 558 | CG | GLU | A | 94 | 19.995 | 53.500 | 21.411 | 1.00 | 53.12 | C |
| ATOM | 559 | CD | GLU | A | 94 | 21 | 55.54 1.00 | 20.772 | 52.775 | 180. | C |
| ATOM | 560 | OE1 | GLU | A | 94 | 21.039 | 51.547 | 20.432 | 1.00 | 56.98 | O |
| ATOM | 561 | OE2 | GLU | A | 94 | 22.231 | 53.423 | 20.615 | 1.00 | 53.13 | O |
| ATOM | 562 | C | GLU | A | 94 | 16.944 | 51.159 | 21.966 | | 46.61 1.00 | C |
| ATOM | 563 | O | GLU | A | 94 | 16.755 | 51.675 | 23.049 | 1.00 | 45.78 | O |
| ATOM | 564 | N | PRO | A | 95 | 16.203 | 50.130 | 21.569 | 1.00 | 46.18 | N |
| ATOM | 565 | CA | PRO | A | 95 | 15.087 | 49.669 | 22.429 | 1.00 | 45.54 | C |
| ATOM | 566 | CB | PRO | A | 95 | 14.494 | 48.502 | 21.655 | 1.00 | 44.41 | C |
| ATOM | 567 | CG | PRO | A | 95 | 14.958 | 48.739 | 20.271 | 1.00 | 46.28 | C |
| ATOM | 568 | CD | PRO | A | 95 | 16.310 | 49.365 | 20.320 | 1.00 | 45.75 | C |
| ATOM | 569 | C | PRO | A | 95 | 15.596 | 49.268 | 23.822 | 1.00 | 44.46 | C |
| ATOM | 570 | O | PRO | A | 95 | 16.649 | 48.659 | 23.944 | 1.00 | 45.48 | O |
| ATOM | 571 | N | ALA | A | 96 | 14.893 | 49.692 | 24.849 | 1.00 | 43.04 | N |
| ATOM | 572 | CA | ALA | A | 96 | 42.57 1.00 | 26.225 | 49.361 | 15.257 | | | C |
| ATOM | 573 | CB | ALA | A | 96 | 15.317 | 50.636 | 27.049 | 1.00 | 41.63 | C |
| ATOM | 574 | C | ALA | A | 96 | 14.164 | 48.430 | 26.741 | 1.00 | 41.25 | C |
| ATOM | 575 | O | ALA | A | 96 | 13.002 | 48.591 | 26 | | 41.30 1.00 371. | O |
| ATOM | 576 | N | VAL | A | 97 | 14.519 | 47.449 | 27.556 | 1.00 | 40.24 | N |
| ATOM | 577 | CA | VAL | A | 97 | 13.511 | 46.538 | 28.067 | 1.00 | 39.62 | C |
| ATOM | 578 | CB | VAL | A | 97 | 14.086 | 45.179 | 28.435 | 1.00 | 39.87 | C |
| ATOM | 579 | CG1 | VAL | A | 97 | 14.722 | 44.539 | 27.229 | 1.00 | 41.61 | C |
| ATOM | 580 | CG2 | VAL | A | 97 | 15.089 | 45.338 | 29.493 | 1.00 | 41.75 | C |
| ATOM | 581 | C | VAL | A | 97 | 12.857 | 47.091 | 29.304 | 1.00 | 39.47 | C |
| ATOM | 582 | O | VAL | A | 97 | 13.489 | 47.774 | 30.120 | 1.00 | 38.78 | O |
| ATOM | 583 | N | SER | A | 98 | 11.583 | 46.823 | 29.488 | 1.00 | 38.59 | N |
| ATOM | 584 | CA | SER | A | 98 | 11.051 | 47.140 | 30.819 | 1.00 | 37.98 | C |
| ATOM | 585 | CB | SER | A | 98 | 37.84 1.00 | 30.819 | 48.475 | 10.300 | | | C |
| ATOM | 586 | OG | SER | A | 98 | 9.140 | 48.356 | 30.039 | 1.00 | 42.34 | O |
| ATOM | 587 | C | SER | A | 98 | 10.242 | 45.955 | 31.314 | 1.00 | 36.68 | C |
| ATOM | 588 | O | SER | A | 98 | 9.771 | 45.174 | | 35.99 1.00 | 30.494 | O |
| ATOM | 589 | N | GLU | A | 99 | 10.179 | 45.767 | 32.636 | 1.00 | 35.80 | N |
| ATOM | 590 | CA | GLU | A | 99 | 9.385 | 44.710 | 33.254 | 1.00 | 35.35 | C |
| ATOM | 591 | CB | GLU | A | 99 | 9.800 | 44.496 | 34.735 | 1.00 | 35.59 | C |
| ATOM | 592 | CG | GLU | A | 99 | 9.269 | 43.146 | 35.231 | 1.00 | 38.52 | C |
| ATOM | 593 | CD | GLU | A | 99 | 9.454 | 42.876 | 36.732 | 1.00 | 43.63 | C |
| ATOM | 594 | OE1 | GLU | A | 99 | 10.300 | 43.500 | 37.367 | 1.00 | 46.24 | O |
| ATOM | 595 | OE2 | GLU | A | 99 | 8.735 | 42.042 | 37.302 | 1.00 | 46.36 | O |
| ATOM | 596 | C | GLU | A | 99 | 7.924 | 45.124 | 33.255 | 1.00 | 34.86 | C |
| ATOM | 597 | O | GLU | A | 99 | 7.578 | 46.185 | 33.822 | 1.00 | 33.31 | O |
| ATOM | 598 | N | LEU | A | 100 | 33.58 1.00 | 32.709 | 44.292 | 7.045 | | | N |
| ATOM | 599 | CA | LEU | A | 100 | 5.611 | 44.619 | 32.837 | 1.00 | 34.16 | C |
| ATOM | 600 | CB | LEU | A | 100 | 4.763 | 43.911 | 31.767 | 1.00 | 32.59 | C |
| ATOM | 601 | CG | LEU | A | 100 | 5.104 | 44.269 | | 33.96 1.00 | 30.309 | C |
| ATOM | 602 | CD1 | LEU | A | 100 | 4.385 | 43.372 | 29.407 | 1.00 | 29.48 | C |
| ATOM | 603 | CD2 | LEU | A | 100 | 4.620 | 45.708 | 30.079 | 1.00 | 33.80 | C |
| ATOM | 604 | C | LEU | A | 100 | 5.105 | 44.240 | 34.265 | 1.00 | 35 52. | C |
| ATOM | 605 | O | LEU | A | 100 | 5.256 | 43.093 | 34.669 | 1.00 | 36.14 | O |
| ATOM | 606 | N | GLU | A | 101 | 4.466 | 45.161 | 34.984 | 1.00 | 34.84 | N |
| ATOM | 607 | CA | GLU | A | 101 | 3.809 | 44.797 | 36.243 | 1.00 | 36.35 | C |
| ATOM | 608 | CB | GLU | A | 101 | 3.471 | 46.073 | 37.052 | 1.00 | 35.16 | C |
| ATOM | 609 | CG | GLU | A | 101 | 3.032 | 45.771 | 38.478 | 1.00 | 41.64 | C |
| ATOM | 610 | CD | GLU | A | 101 | 2.559 | 47.010 | 39.230 | 1.00 | 47.12 | C |
| ATOM | 611 | OE1 | GLU | A | | 50.39 1.00 | 38.685 | 48.131 | 2.717 | | 101 | O |
| ATOM | 612 | OE2 | GLU | A | 101 | 2.041 | 46.873 | 40.367 | 1.00 | 51.14 | O |
| ATOM | 613 | C | GLU | A | 101 | 2.541 | 43.930 | 36.030 | 1.00 | 35.47 | C |
| ATOM | 614 | O | GLU | A | 101 | 1.670 | 44.261 | | 34.90 1.00 | 35.236 | O |
| ATOM | 615 | N | ILE | A | 102 | 2.443 | 42.811 | 36.737 | 1.00 | 35.99 | N |
| ATOM | 616 | CA | ILE | A | 102 | 1.204 | 42.026 | 36.755 | 1.00 | 35.51 | C |

Fig. 26 (Cont.)

| ATOM | 617 | CB | ILE A 102 | 1.494 | 40.550 | 36.985 | 1.00 | | 36.81 | C |
|------|-----|-----|-----------|-------|--------|--------|------|-----|-----|---|
| ATOM | 618 | CG1 | ILE A 102 | 2.274 | 39.987 | 35.794 | 1.00 | 35.62 | | C |
| ATOM | 619 | CD1 | ILE A 102 | 2.932 | 38.588 | 36.126 | 1.00 | 36.89 | | C |
| ATOM | 620 | CG2 | ILE A 102 | 0.198 | 39.760 | 37.102 | 1.00 | 36.67 | | C |
| ATOM | 621 | C | ILE A 102 | 0.245 | 42.540 | 37.810 | 1.00 | 34.21 | | C |
| ATOM | 622 | O | ILE A 102 | 0.591 | 42.588 | 38.962 | 1.00 | 33.87 | | O |
| ATOM | 623 | N | ILE A 103 | -0.939 | 42.971 | 37.395 | 1.00 | 33.27 | | N |
| ATOM | 624 | CA | ILE A 103 | -1.981 | 43.283 | 38.322 | 1.00 | 35.10 | | C |
| ATOM | 625 | CB | ILE A 103 | -2.473 | 44.781 | 38.177 | 1.00 | 37.45 | | C |
| ATOM | 626 | CG1 | ILE A 103 | -3.243 | 45.008 | 36.877 | 1.00 | 38.74 | | C |
| ATOM | 627 | CD1 | ILE A 103 | -4.187 | | 41.50 | 1.00 | 37.058 | 46.265 | C |
| ATOM | 628 | CG2 | ILE A 103 | -1.258 | 45.844 | 38.300 | 1.00 | 38.02 | | C |
| ATOM | 629 | C | ILE A 103 | -3.118 | 42.249 | 38.305 | 1.00 | 33.06 | | C |
| ATOM | 630 | O | ILE A 103 | -3.347 | 41.579 | 37.305 | 1 | | 33.10 00.0 | O |
| ATOM | 631 | N | GLY A 104 | -3.773 | 42.110 | 39.435 | 1.00 | 31.11 | | N |
| ATOM | 632 | CA | GLY A 104 | -4.912 | 41.232 | 39.614 | 1.00 | 29.92 | | C |
| ATOM | 633 | C | GLY A 104 | -4.726 | 40.492 | 40.918 | 1.00 | 29.68 | | C |
| ATOM | 634 | O | GLY A 104 | -3.598 | 40.379 | 41.383 | 1.00 | 31.45 | | O |
| ATOM | 635 | N | ASN A 105 | -5.794 | 39.977 | 41.518 | 1.00 | 27.53 | | N |
| ATOM | 636 | CA | ASN A 105 | -5.672 | 39.158 | 42.701 | 1.00 | 25.31 | | C |
| ATOM | 637 | CB | ASN A 105 | -6.582 | 39.710 | 43.760 | 1.00 | 24.19 | | C |
| ATOM | 638 | CG | ASN A 105 | -6.006 | 40.960 | 44.403 | 1.00 | 26.19 | | C |
| ATOM | 639 | OD1 | ASN A 105 | -4.840 | 40.992 | 44.785 | 1.00 | 22.38 | | O |
| ATOM | 640 | ND2 | ASN A 105 | -6 | | 22.10 | 1.00 | 44.557 | 41.984 839. | N |
| ATOM | 641 | C | ASN A 105 | -5.995 | 37.679 | 42.437 | 1.00 | 25.35 | | C |
| ATOM | 642 | O | ASN A 105 | -6.157 | 36.899 | 43.383 | 1.00 | 24.92 | | O |
| ATOM | 643 | N | THR A 106 | -6.104 | 37.307 | 41.170 | | | 25.36 1.00 | N |
| ATOM | 644 | CA | THR A 106 | -6.445 | 35.957 | 40.796 | 1.00 | 27.53 | | C |
| ATOM | 645 | CB | THR A 106 | -7.398 | 36.003 | 39.573 | 1.00 | 27.47 | | C |
| ATOM | 646 | OG1 | THR A 106 | -6.928 | 36.994 | 38.653 | 1.00 | 26.93 | | O |
| ATOM | 647 | CG2 | THR A 106 | -8.830 | 36.427 | 39.951 | 1.00 | 25.61 | | C |
| ATOM | 648 | C | THR A 106 | -5.190 | 35.072 | 40.416 | 1.00 | 29.67 | | C |
| ATOM | 649 | O | THR A 106 | -5.342 | 33.909 | 40.000 | 1.00 | 31.09 | | O |
| ATOM | 650 | N | LEU A 107 | -3.986 | 35.627 | 40.493 | 1.00 | 29.57 | | N |
| ATOM | 651 | CA | LEU A 107 | -2.759 | 34.939 | 40.091 | 1.00 | 29.85 | | C |
| ATOM | 652 | CB | LEU A 107 | -2.123 | 35.618 | 38.873 | 1.00 | 29.27 | | C |
| ATOM | 653 | CG | LEU A 107 | | 32.79 | 1.00 | 38.388 | 34.954 | 0.801- | C |
| ATOM | 654 | CD1 | LEU A 107 | -0.996 | 33.439 | 38.041 | 1.00 | 32.49 | | C |
| ATOM | 655 | CD2 | LEU A 107 | -0.180 | 35.617 | 37.168 | 1.00 | 30.28 | | C |
| ATOM | 656 | C | LEU A 107 | -1.756 | 35.016 | 41 | | 30.88 | 1.00 258. | C |
| ATOM | 657 | O | LEU A 107 | -1.577 | 36.085 | 41.883 | 1.00 | 29.93 | | O |
| ATOM | 658 | N | ASP A 108 | -1.105 | 33.903 | 41.575 | 1.00 | 32.69 | | N |
| ATOM | 659 | CA | ASP A 108 | 0.000 | 33.964 | 42.540 | 1.00 | 35.00 | | C |
| ATOM | 660 | CB | ASP A 108 | 0.160 | 32.578 | 43.184 | 1.00 | 35.45 | | C |
| ATOM | 661 | CG | ASP A 108 | 1.187 | 32.564 | 44.326 | 1.00 | 39.16 | | C |
| ATOM | 662 | OD1 | ASP A 108 | 1.993 | 33.509 | 44.543 | 1.00 | 38.47 | | O |
| ATOM | 663 | OD2 | ASP A 108 | 1.207 | 31.616 | 45.125 | 1.00 | 51.01 | | O |
| ATOM | 664 | C | ASP A 108 | 1.271 | 34.310 | 41.781 | 1.00 | 34.30 | | C |
| ATOM | 665 | O | ASP A 108 | 1.733 | 33.450 | 41.066 | 1.00 | 35.43 | | O |
| ATOM | 666 | N | ILE A 109 | | 35.53 | 1.00 | 41.855 | 35.518 | 1.794 | N |
| ATOM | 667 | CA | ILE A 109 | 2.987 | 35.867 | 41.049 | 1.00 | 40.59 | | C |
| ATOM | 668 | CB | ILE A 109 | 3.156 | 37.427 | 40.806 | 1.00 | 42.05 | | C |
| ATOM | 669 | CG1 | ILE A 109 | 3.508 | 38.123 | | | 45.49 | 1.00 42.125 | C |
| ATOM | 670 | CD1 | ILE A 109 | 4.475 | 39.370 | 42.008 | 1.00 | 55.33 | | C |
| ATOM | 671 | CG2 | ILE A 109 | 1.849 | 38.056 | 40.334 | 1.00 | 45.95 | | C |
| ATOM | 672 | C | ILE A 109 | 4.287 | 35.366 | 41.664 | 1.00 | 41.10 | | C |
| ATOM | 673 | O | ILE A 109 | 5.344 | 35.468 | 41.040 | 1.00 | 41.85 | | O |
| ATOM | 674 | N | SER A 110 | 4.253 | 34.883 | 42.900 | 1.00 | 41.63 | | N |
| ATOM | 675 | CA | SER A 110 | 5.517 | 34.477 | 43.539 | 1.00 | 42.28 | | C |
| ATOM | 676 | CB | SER A 110 | 5.398 | 34.373 | 45.081 | 1.00 | 42.13 | | C |
| ATOM | 677 | OG | SER A 110 | 4.611 | 33.254 | 45.465 | 1.00 | 39.85 | | O |

Fig. 26 (Cont.)

| ATOM | 678 | C | SER A 110 | 6.032 | 33.193 | 42.889 | 1.00 | 42.80 | | C |
|---|---|---|---|---|---|---|---|---|---|---|
| ATOM | 679 | O | SER A 110 | | 44.07 | 1.00 | 42.888 | 32.928 | 7.204 | O |
| ATOM | 680 | N | SER A 111 | 5.165 | 32.413 | 42.279 | 1.00 | 42.32 | | N |
| ATOM | 681 | CA | SER A 111 | 5.658 | 31.211 | 41.634 | 1.00 | 42.01 | | C |
| ATOM | 682 | CB | SER A 111 | 4.884 | 30.001 | | 41.91 | 1.00 | 42.180 | C |
| ATOM | 683 | OG | SER A 111 | 3.550 | 30.015 | 41.716 | 1.00 | 44.76 | | O |
| ATOM | 684 | C | SER A 111 | 5.640 | 31.308 | 40.067 | 1.00 | 40.11 | | C |
| ATOM | 685 | O | SER A 111 | 5.813 | 30.303 | 39.371 | 1.00 | 40 | 26.0 | |
| ATOM | 686 | N | PHE A 112 | 5.430 | 32.516 | 39.548 | 1.00 | 37.47 | | N |
| ATOM | 687 | CA | PHE A 112 | 5.245 | 32.736 | 38.132 | 1.00 | 34.77 | | C |
| ATOM | 688 | CB | PHE A 112 | 4.997 | 34.212 | 37.915 | 1.00 | 35.24 | | C |
| ATOM | 689 | CG | PHE A 112 | 4.615 | 34.572 | 36.513 | 1.00 | 34.60 | | C |
| ATOM | 690 | CD1 | PHE A 112 | 3.485 | 34.038 | 35.931 | 1.00 | 31.92 | | C |
| ATOM | 691 | CE1 | PHE A 112 | 3.098 | 34.417 | 34.601 | 1.00 | 34.37 | | C |
| ATOM | 692 | CZ | PHE A | 32.93 | 1.00 | 33.882 | 35.302 | 3.891 | 112 | C |
| ATOM | 693 | CE2 | PHE A 112 | 5.075 | 35.822 | 34.475 | 1.00 | 33.02 | | C |
| ATOM | 694 | CD2 | PHE A 112 | 5.420 | 35.470 | 35.761 | 1.00 | 33.43 | | C |
| ATOM | 695 | C | PHE A 112 | 6.528 | 32 | | 34.09 | 1.00 | 37.408 | 313.C |
| ATOM | 696 | O | PHE A 112 | 7.619 | 32.686 | 37.792 | 1.00 | 30.41 | | O |
| ATOM | 697 | N | ASN A 113 | 6.373 | 31.511 | 36.363 | 1.00 | 33.35 | | N |
| ATOM | 698 | CA | ASN A 113 | 7.516 | 30.836 | 35.764 | 1.00 | | 34.63 | C |
| ATOM | 699 | CB | ASN A 113 | 7.730 | 29.496 | 36.479 | 1.00 | 35.10 | | C |
| ATOM | 700 | CG | ASN A 113 | 8.949 | 28.763 | 35.962 | 1.00 | 38.00 | | C |
| ATOM | 701 | OD1 | ASN A 113 | 9.798 | 29.376 | 35.370 | 1.00 | 38.18 | | O |
| ATOM | 702 | ND2 | ASN A 113 | 9.005 | 27.442 | 36.136 | 1.00 | 33.49 | | N |
| ATOM | 703 | C | ASN A 113 | 7.210 | 30.667 | 34.276 | 1.00 | 34.12 | | C |
| ATOM | 704 | O | ASN A 113 | 6.783 | 29.596 | 33.848 | 1.00 | 34.15 | | O |
| ATOM | 705 | N | PRO A 114 | 7.361 | 31.746 | 33.500 | 1.00 | 33.35 | | N |
| ATOM | 706 | CA | PRO A 114 | 6.732 | 31.838 | 32.176 | 1.00 | 32.35 | | C |
| ATOM | 707 | CB | PRO A 114 | 6.665 | 33.373 | 31.891 | 1.00 | 32.32 | | C |
| ATOM | 708 | CG | PRO A 114 | 7.886 | | 32.10 | 1.00 | 32.765 | 34.012 | C |
| ATOM | 709 | CD | PRO A 114 | 8.142 | 32.947 | 33.880 | 1.00 | 33.30 | | C |
| ATOM | 710 | C | PRO A 114 | 7.559 | 31.116 | 31.100 | 1.00 | 34.37 | | C |
| ATOM | 711 | O | PRO A 114 | 8.777 | 31.113 | 31.218 | 1 | | 32.77 00.0 | |
| ATOM | 712 | N | HIS A 115 | 6.904 | 30.579 | 30.047 | 1.00 | 34.79 | | N |
| ATOM | 713 | CA | HIS A 115 | 7.549 | 29.748 | 29.008 | 1.00 | 34.40 | | C |
| ATOM | 714 | CB | HIS A 115 | 7.149 | 28.295 | 29.238 | 1.00 | 35.35 | | C |
| ATOM | 715 | CG | HIS A 115 | 7.972 | 27.265 | 28.505 | 1.00 | 40.54 | | C |
| ATOM | 716 | ND1 | HIS A 115 | 7.815 | 25.902 | 28.738 | 1.00 | 42.20 | | N |
| ATOM | 717 | CE1 | HIS A 115 | 8.669 | 25.224 | 27.965 | 1.00 | 44.64 | | C |
| ATOM | 718 | NE2 | HIS A 115 | 9.357 | 26.091 | 27.224 | 1.00 | 42.76 | | N |
| ATOM | 719 | CD2 | HIS A 115 | 8.936 | 27.377 | 27.531 | 1.00 | 41.10 | | C |
| ATOM | 720 | C | HIS A 115 | 7.066 | 30.282 | 27.647 | 1.00 | 34.52 | | C |
| ATOM | 721 | O | HIS A 115 | 7.312 | | 34.15 | 1.00 | 27.336 | 31.458 | O |
| ATOM | 722 | N | GLY A 116 | 6.360 | 29.499 | 26.833 | 1.00 | 35.08 | | N |
| ATOM | 723 | CA | GLY A 116 | 5.865 | 30.040 | 25.553 | 1.00 | 33.52 | | C |
| ATOM | 724 | C | GLY A 116 | 4.837 | 31.139 | 25.778 | | | 35.02 1.00 | C |
| ATOM | 725 | O | GLY A 116 | 4.156 | 31.180 | 26.832 | 1.00 | 37.19 | | O |
| ATOM | 726 | N | ILE A 117 | 4.615 | 31.976 | 24.781 | 1.00 | 35.16 | | N |
| ATOM | 727 | CA | ILE A 117 | 3.609 | 33.004 | 24.917 | 1.00 | 35.66 | | C |
| ATOM | 728 | CB | ILE A 117 | 4.214 | 34.357 | 25.336 | 1.00 | 36.17 | | C |
| ATOM | 729 | CG1 | ILE A 117 | 5.133 | 34.943 | 24.221 | 1.00 | 33.06 | | C |
| ATOM | 730 | CD1 | ILE A 117 | 5.677 | 36.352 | 24.525 | 1.00 | 32.42 | | C |
| ATOM | 731 | CG2 | ILE A 117 | 4.831 | 34.301 | 26.770 | 1.00 | 34.66 | | C |
| ATOM | 732 | C | ILE A 117 | 2.955 | 33.164 | 23.546 | 1.00 | 36.61 | | C |
| ATOM | 733 | O | ILE A 117 | 3.458 | 32.691 | 22.566 | 1.00 | 35.89 | | O |
| ATOM | 734 | N | SER A 118 | | 37.76 | 1.00 | 23.497 | 33.876 | 1.844 | N |
| ATOM | 735 | CA | SER A 118 | 1.196 | 34.218 | 22.213 | 1.00 | 37.42 | | C |
| ATOM | 736 | CB | SER A 118 | 0.311 | 33.048 | 21.762 | 1.00 | 35.65 | | C |
| ATOM | 737 | OG | SER A 118 | -0.184 | 33.246 | 20.454 | | | 35.15 1.00 | O |
| ATOM | 738 | C | SER A 118 | 0.357 | 35.451 | 22.506 | 1.00 | 37.99 | | C |

Fig. 26 (Cont.)

| | | | | | | | | | |
|---|---|---|---|---|---|---|---|---|---|
| ATOM | 739 | O | SER A 118 | 0.030 | 35.684 | 23.670 | 1.00 | 37.65 | O |
| ATOM | 740 | N | THR A 119 | -0.009 | 36.220 | 21.479 | 1.00 | 37.46 | N |
| ATOM | 741 | CA | THR A 119 | -0.961 | 37.282 | 21.668 | 1.00 | 36.93 | C |
| ATOM | 742 | CB | THR A 119 | -0.268 | 38.652 | 21.313 | 1.00 | 37.88 | C |
| ATOM | 743 | OG1 | THR A 119 | 0.217 | 38.628 | 19.965 | 1.00 | 39.42 | O |
| ATOM | 744 | CG2 | THR A 119 | 1.019 | 38.792 | 22.087 | 1.00 | 37.04 | C |
| ATOM | 745 | C | THR A 119 | -2.157 | 37.105 | 20.747 | 1.00 | 37.66 | C |
| ATOM | 746 | O | THR A 119 | -2.111 | 36.375 | 19.780 | 1.00 | 38.23 | O |
| ATOM | 747 | N | PHE A 120 | 35.66 1.00 | 21.021 | 37.803 | 3.226- | | N |
| ATOM | 748 | CA | PHE A 120 | -4.343 | 37.806 | 20.168 | 1.00 | 35.40 | C |
| ATOM | 749 | CB | PHE A 120 | -5.426 | 36.823 | 20.627 | 1.00 | 35.01 | C |
| ATOM | 750 | CG | PHE A 120 | -6.703 | 36.902 | 19.792 | | 35.19 1.00 | C |
| ATOM | 751 | CD1 | PHE A 120 | -6.761 | 36.319 | 18.518 | 1.00 | 35.66 | C |
| ATOM | 752 | CE1 | PHE A 120 | -7.973 | 36.436 | 17.714 | 1.00 | 38.85 | C |
| ATOM | 753 | CZ | PHE A 120 | -9.075 | 37.144 | 18.173 | 1.00 | 34.68 | C |
| ATOM | 754 | CE2 | PHE A 120 | -8.996 | 37.753 | 19.489 | 1.00 | 38.49 | C |
| ATOM | 755 | CD2 | PHE A 120 | -7.798 | 37.610 | 20.252 | 1.00 | 35.32 | C |
| ATOM | 756 | C | PHE A 120 | -4.852 | 39.234 | 20.307 | 1.00 | 36.18 | C |
| ATOM | 757 | O | PHE A 120 | -5.040 | 39.768 | 21.459 | 1.00 | 34.94 | O |
| ATOM | 758 | N | ILE A 121 | -5.131 | 39.837 | 19.166 | 1.00 | 36.24 | N |
| ATOM | 759 | CA | ILE A 121 | -5.720 | 41.195 | 19.148 | 1.00 | 38.13 | C |
| ATOM | 760 | CB | ILE A 121 | 35.98 1.00 | 18.159 | 42.075 | 4.935- | | C |
| ATOM | 761 | CG1 | ILE A 121 | -3.505 | 42.202 | 18.612 | 1.00 | 36.83 | C |
| ATOM | 762 | CD1 | ILE A 121 | -2.620 | 42.856 | 17.541 | 1.00 | 42.55 | C |
| ATOM | 763 | CG2 | ILE A 121 | -5.533 | 43.479 | | 36.95 1.00 | 18.063 | C |
| ATOM | 764 | C | ILE A 121 | -7.182 | 41.186 | 18.752 | 1.00 | 38.65 | C |
| ATOM | 765 | O | ILE A 121 | -7.467 | 40.917 | 17.605 | 1.00 | 39.16 | O |
| ATOM | 766 | N | ASP A 122 | -8.114 | 41.487 | 19.644 | 1.00 | 41.22 | N |
| ATOM | 767 | CA | ASP A 122 | -9.523 | 41.367 | 19.255 | 1.00 | 44.68 | C |
| ATOM | 768 | CB | ASP A 122 | -10.509 | 40.961 | 20.435 | 1.00 | 45.77 | C |
| ATOM | 769 | CG | ASP A 122 | -11.006 | 42.147 | 21.311 | 1.00 | 51.84 | C |
| ATOM | 770 | OD1 | ASP A 122 | -10.852 | 43.344 | 20.913 | 1.00 | 55.94 | O |
| ATOM | 771 | OD2 | ASP A 122 | -11.589 | 41.961 | 22.454 | 1.00 | 55.83 | O |
| ATOM | 772 | C | ASP A 122 | -10.038 | 42.471 | 18.284 | 1.00 | 46.17 | C |
| ATOM | 773 | O | ASP A 122 | 45.30 1.00 | 17.888 | 43.379 | 9.282- | | O |
| ATOM | 774 | N | ASP A 123 | -11.316 | 42.407 | 17.908 | 1.00 | 48.58 | N |
| ATOM | 775 | CA | ASP A 123 | -11.847 | 43.464 | 17.050 | 1.00 | 51.81 | C |
| ATOM | 776 | CB | ASP A 123 | -13.226 | 43 | 53.86 1.00 | 16.453 | 116. | C |
| ATOM | 777 | CG | ASP A 123 | -13.195 | 41.843 | 15.587 | 1.00 | 58.85 | C |
| ATOM | 778 | OD1 | ASP A 123 | -12.135 | 41.489 | 14.989 | 1.00 | 60.93 | O |
| ATOM | 779 | OD2 | ASP A 123 | -14.225 | 41.137 | 15.458 | 1.00 | 65.68 | O |
| ATOM | 780 | C | ASP A 123 | -11.889 | 44.873 | 17.659 | 1.00 | 51.86 | C |
| ATOM | 781 | O | ASP A 123 | -11.668 | 45.825 | 16.901 | 1.00 | 52.43 | O |
| ATOM | 782 | N | ASP A 124 | -12.186 | 45.050 | 18.966 | 1.00 | 50.90 | N |
| ATOM | 783 | CA | ASP A 124 | -12.041 | 46.420 | 19.519 | 1.00 | 49.91 | C |
| ATOM | 784 | CB | ASP A 124 | -12.926 | 46.734 | 20.718 | 1.00 | 50.65 | C |
| ATOM | 785 | CG | ASP A 124 | -13.029 | 45.605 | 21.722 | 1.00 | 54.59 | C |
| ATOM | 786 | OD1 | ASP A 124 | -12.024 | 44.888 | 22.021 | 1.00 | 56.71 | O |
| ATOM | 787 | OD2 | ASP A 124 | -14.126 | 45.409 | 22.316 | 1.00 | 59.29 | O |
| ATOM | 788 | C | ASP A 124 | -10.594 | 46.853 | 19.785 | 1.00 | 48.18 | C |
| ATOM | 789 | O | ASP A 124 | -10.334 | | 48.13 1.00 | 20.392 | 47.887 | O |
| ATOM | 790 | N | ASN A 125 | -9.650 | 46.056 | 19.316 | 1.00 | 45.93 | N |
| ATOM | 791 | CA | ASN A 125 | -8.253 | 46.391 | 19.476 | 1.00 | 44.21 | C |
| ATOM | 792 | CB | ASN A 125 | -8.072 | 47.857 | 19.155 | 1.00 | 44.91 | C |
| ATOM | 793 | CG | ASN A 125 | -7.343 | 48.050 | 17.864 | 1.00 | 49.51 | C |
| ATOM | 794 | OD1 | ASN A 125 | -6.238 | 47.489 | 17.648 | 1.00 | 55.43 | O |
| ATOM | 795 | ND2 | ASN A 125 | -7.932 | 48.858 | 16.981 | 1.00 | 51.42 | N |
| ATOM | 796 | C | ASN A 125 | -7.568 | 46.067 | 20.822 | 1.00 | 41.26 | C |
| ATOM | 797 | O | ASN A 125 | -6.391 | 46.382 | 20.975 | 1.00 | 39.94 | O |
| ATOM | 798 | N | THR A 126 | -8.303 | 45.504 | 21.780 | 1.00 | 38.03 | N |
| ATOM | 799 | CA | THR A 126 | -7.720 | 44.857 | 22.982 | 1.00 | 35.93 | C |

Fig. 26 (Cont.)

| | | | | | | | | | |
|---|---|---|---|---|---|---|---|---|---|
| ATOM | 800 | CB | THR A 126 | -8.827 | 44.152 | 23.760 | 1.00 | 35.95 | C |
| ATOM | 801 | OG1 | THR A 126 | -9.850 | 45.107 | 24.075 | 1.00 | 38.04 | O |
| ATOM | 802 | CG2 | THR A 126 | -8.330 | 36.23 | 1.00 | 25.136 | 43.678 | C |
| ATOM | 803 | C | THR A 126 | -6.675 | 43.816 | 22.596 | 1.00 | 33.88 | C |
| ATOM | 804 | O | THR A 126 | -6.894 | 43.035 | 21.687 | 1.00 | 32.94 | O |
| ATOM | 805 | N | VAL A 127 | -5.517 | 43.870 | 23.248 | | 32.63 1.00 | N |
| ATOM | 806 | CA | VAL A 127 | -4.445 | 42.938 | 23.082 | 1.00 | 31.65 | C |
| ATOM | 807 | CB | VAL A 127 | -3.061 | 43.658 | 23.057 | 1.00 | 33.18 | C |
| ATOM | 808 | CG1 | VAL A 127 | -1.939 | 42.620 | 23.000 | 1.00 | 30.17 | C |
| ATOM | 809 | CG2 | VAL A 127 | -2.966 | 44.668 | 21.923 | 1.00 | 31.19 | C |
| ATOM | 810 | C | VAL A 127 | -4.469 | 41.969 | 24.286 | 1.00 | 32.76 | C |
| ATOM | 811 | O | VAL A 127 | -4.346 | 42.396 | 25.430 | 1.00 | 31.99 | O |
| ATOM | 812 | N | TYR A 128 | -4.625 | 40.675 | 23.997 | 1.00 | 32.89 | N |
| ATOM | 813 | CA | TYR A 128 | -4.461 | 39.634 | 24.965 | 1.00 | 32.99 | C |
| ATOM | 814 | CB | TYR A 128 | -5.591 | 38.625 | 24.840 | 1.00 | 32.72 | C |
| ATOM | 815 | CG | TYR A 128 | -6 | 33.62 1.00 | 25.057 | 39.250 | 954. | C |
| ATOM | 816 | CD1 | TYR A 128 | -7.510 | 39.307 | 26.328 | 1.00 | 31.06 | C |
| ATOM | 817 | CE1 | TYR A 128 | -8.770 | 39.886 | 26.544 | 1.00 | 33.80 | C |
| ATOM | 818 | CZ | TYR A 128 | -9.466 | 40.444 | 25.484 | | 34.20 1.00 | C |
| ATOM | 819 | OH | TYR A 128 | -10.691 | 41.016 | 25.746 | 1.00 | 37.27 | O |
| ATOM | 820 | CE2 | TYR A 128 | -8.927 | 40.431 | 24.202 | 1.00 | 30.23 | C |
| ATOM | 821 | CD2 | TYR A 128 | -7.645 | 39.854 | 24.009 | 1.00 | 34.50 | C |
| ATOM | 822 | C | TYR A 128 | -3.114 | 38.970 | 24.853 | 1.00 | 34.41 | C |
| ATOM | 823 | O | TYR A 128 | -2.564 | 38.747 | 23.733 | 1.00 | 34.58 | O |
| ATOM | 824 | N | LEU A 129 | -2.548 | 38.697 | 26.034 | 1.00 | 34.32 | N |
| ATOM | 825 | CA | LEU A 129 | -1.309 | 37.936 | 26.160 | 1.00 | 33.21 | C |
| ATOM | 826 | CB | LEU A 129 | -0.286 | 38.742 | 26.949 | 1.00 | 32.48 | C |
| ATOM | 827 | CG | LEU A 129 | 1.049 | 37.998 | 27.099 | 1.00 | 33.76 | C |
| ATOM | 828 | CD1 | LEU A 129 | 32.79 1.00 | 25.765 | 37.886 | 1.828 | | C |
| ATOM | 829 | CD2 | LEU A 129 | 1.939 | 38.741 | 28.073 | 1.00 | 34.22 | C |
| ATOM | 830 | C | LEU A 129 | -1.602 | 36.616 | 26.839 | 1.00 | 33.42 | C |
| ATOM | 831 | O | LEU A 129 | -2.151 | 36.592 | 27 | | 33.82 1.00 922. | O |
| ATOM | 832 | N | LEU A 130 | -1.278 | 35.500 | 26.204 | 1.00 | 33.27 | N |
| ATOM | 833 | CA | LEU A 130 | -1.387 | 34.200 | 26.836 | 1.00 | 31.83 | C |
| ATOM | 834 | CB | LEU A 130 | -2.045 | 33.222 | 25.854 | 1.00 | 32.49 | C |
| ATOM | 835 | CG | LEU A 130 | -3.581 | 33.398 | 25.731 | 1.00 | 35.57 | C |
| ATOM | 836 | CD1 | LEU A 130 | -4.008 | 34.776 | 25.183 | 1.00 | 36.15 | C |
| ATOM | 837 | CD2 | LEU A 130 | -4.182 | 32.228 | 24.932 | 1.00 | 37.88 | C |
| ATOM | 838 | C | LEU A 130 | 0.025 | 33.711 | 27.155 | 1.00 | 33.29 | C |
| ATOM | 839 | O | LEU A 130 | 0.924 | 33.831 | 26.307 | 1.00 | 31.76 | O |
| ATOM | 840 | N | VAL A 131 | 0.225 | 33.160 | 28.374 | 1.00 | 32.73 | N |
| ATOM | 841 | CA | VAL A 131 | | 32.23 1.00 | 28.787 | 32.774 | 1.543 | C |
| ATOM | 842 | CB | VAL A 131 | 2.037 | 33.778 | 29.875 | 1.00 | 34.57 | C |
| ATOM | 843 | CG1 | VAL A 131 | 3.392 | 33.302 | 30.472 | 1.00 | 32.33 | C |
| ATOM | 844 | CG2 | VAL A 131 | 2.139 | 35.210 | | 30.01 1.00 | 29.333 | C |
| ATOM | 845 | C | VAL A 131 | 1.452 | 31.367 | 29.436 | 1.00 | 33.83 | C |
| ATOM | 846 | O | VAL A 131 | 0.650 | 31.139 | 30.368 | 1.00 | 33.16 | O |
| ATOM | 847 | N | VAL A 132 | 2.306 | 30.466 | 28.976 | 1.00 | 34.09 | N |
| ATOM | 848 | CA | VAL A 132 | 2.451 | 29.153 | 29.564 | 1.00 | 33.65 | C |
| ATOM | 849 | CB | VAL A 132 | 3.277 | 28.221 | 28.693 | 1.00 | 34.80 | C |
| ATOM | 850 | CG1 | VAL A 132 | 3.424 | 26.820 | 29.400 | 1.00 | 31.97 | C |
| ATOM | 851 | CG2 | VAL A 132 | 2.657 | 28.062 | 27.287 | 1.00 | 33.73 | C |
| ATOM | 852 | C | VAL A 132 | 3.195 | 29.360 | 30.873 | 1.00 | 33.60 | C |
| ATOM | 853 | O | VAL A 132 | 4.226 | 30.026 | 30.892 | 1.00 | 35.01 | O |
| ATOM | 854 | N | ASN A 133 | | 32.26 1.00 | 31.961 | 28.772 | 2.715 | N |
| ATOM | 855 | CA | ASN A 133 | 3.311 | 29.051 | 33.254 | 1.00 | 33.11 | C |
| ATOM | 856 | CB | ASN A 133 | 2.313 | 29.880 | 34.069 | 1.00 | 32.10 | C |
| ATOM | 857 | CG | ASN A 133 | 2.796 | 30.241 | | 32.62 1.00 | 35.432 | C |
| ATOM | 858 | OD1 | ASN A 133 | 4.018 | 30.344 | 35.684 | 1.00 | 32.92 | O |
| ATOM | 859 | ND2 | ASN A 133 | 1.833 | 30.520 | 36.349 | 1.00 | 28.55 | N |
| ATOM | 860 | C | ASN A 133 | 3.526 | 27.668 | 33.889 | 1.00 | 33 | 78.C |

Fig. 26 (Cont.)

| ATOM | 861 | O | ASN A 133 | 2.651 | 26.780 | 33.719 | 1.00 | 32.60 | | | O |
|------|-----|-----|-----------|-------|--------|--------|------|-------|---|---|---|
| ATOM | 862 | N | HIS A 134 | 4.649 | 27.502 | 34.614 | 1.00 | 33.19 | | | N |
| ATOM | 863 | CA | HIS A 134 | 4.977 | 26.226 | 35.279 | 1.00 | 34.40 | | | C |
| ATOM | 864 | CB | HIS A 134 | 6.241 | 25.520 | 34.697 | 1.00 | 34.57 | | | C |
| ATOM | 865 | CG | HIS A 134 | 6.141 | 25.184 | 33.227 | 1.00 | 38.24 | | | C |
| ATOM | 866 | ND1 | HIS A 134 | 5.237 | 24.265 | 32.729 | 1.00 | 37.71 | | | N |
| ATOM | 867 | CE1 | HIS A | 39.92 | 1.00 | 31.408 | 24.222 | 5.334 | | 134 | C |
| ATOM | 868 | NE2 | HIS A 134 | 6.313 | 25.032 | 31.030 | 1.00 | 39.32 | | | N |
| ATOM | 869 | CD2 | HIS A 134 | 6.839 | 25.639 | 32.150 | 1.00 | 39.79 | | | C |
| ATOM | 870 | C | HIS A 134 | 5.187 | 26.490 | | 36.28 | 1.00 | | 36.763 | C |
| ATOM | 871 | O | HIS A 134 | 6.314 | 26.467 | 37.218 | 1.00 | 35.71 | | | O |
| ATOM | 872 | N | PRO A 135 | 4.125 | 26.689 | 37.536 | 1.00 | 37.05 | | | N |
| ATOM | 873 | CA | PRO A 135 | 4.291 | 26.757 | 38.980 | 1.00 | | | 39.58 | C |
| ATOM | 874 | CB | PRO A 135 | 2.893 | 27.217 | 39.481 | 1.00 | 39.92 | | | C |
| ATOM | 875 | CG | PRO A 135 | 1.916 | 27.187 | 38.286 | 1.00 | 37.51 | | | C |
| ATOM | 876 | CD | PRO A 135 | 2.705 | 26.717 | 37.108 | 1.00 | 37.78 | | | C |
| ATOM | 877 | C | PRO A 135 | 4.584 | 25.317 | 39.467 | 1.00 | 41.85 | | | C |
| ATOM | 878 | O | PRO A 135 | 3.713 | 24.424 | 39.242 | 1.00 | 42.09 | | | O |
| ATOM | 879 | N | GLY A 136 | 5.745 | 25.072 | 40.101 | 1.00 | 43.05 | | | N |
| ATOM | 880 | CA | GLY A 136 | 6.122 | 23.699 | 40.506 | 1.00 | 43.42 | | | C |
| ATOM | 881 | C | GLY A 136 | 6.257 | 22.897 | 39.190 | 1.00 | 43.98 | | | C |
| ATOM | 882 | O | GLY A 136 | 6.674 | 23.479 | 38.180 | 1.00 | 42.58 | | | O |
| ATOM | 883 | N | SER A 137 | 5.846 | | 43.24 | 1.00 | 39.138 | | 21.618 | N |
| ATOM | 884 | CA | SER A 137 | 5.994 | 20.923 | 37.843 | 1.00 | 44.40 | | | C |
| ATOM | 885 | CB | SER A 137 | 6.724 | 19.612 | 38.029 | 1.00 | 43.91 | | | C |
| ATOM | 886 | OG | SER A 137 | 5.884 | 18.727 | 38.714 | 1 | | | 46.89 00.0 | |
| ATOM | 887 | C | SER A 137 | 4.712 | 20.767 | 36.951 | 1.00 | 44.20 | | | C |
| ATOM | 888 | O | SER A 137 | 4.702 | 20.050 | 35.931 | 1.00 | 44.90 | | | O |
| ATOM | 889 | N | SER A 138 | 3.651 | 21.452 | 37.342 | 1.00 | 43.51 | | | N |
| ATOM | 890 | CA | SER A 138 | 2.382 | 21.488 | 36.604 | 1.00 | 42.28 | | | C |
| ATOM | 891 | CB | SER A 138 | 1.296 | 21.825 | 37.651 | 1.00 | 42.59 | | | C |
| ATOM | 892 | OG | SER A 138 | 1.370 | 23.238 | 37.882 | 1.00 | 44.59 | | | O |
| ATOM | 893 | C | SER A 138 | 2.421 | 22.531 | 35.450 | 1.00 | 40.99 | | | C |
| ATOM | 894 | O | SER A 138 | 3.390 | 23.313 | 35.289 | 1.00 | 40.71 | | | O |
| ATOM | 895 | N | SER A 139 | 1.436 | 22.496 | 34.569 | 1.00 | 39.16 | | | N |
| ATOM | 896 | CA | SER A 139 | 1 | | 38.06 | 1.00 | 33.569 | 23.530 | 342. | C |
| ATOM | 897 | CB | SER A 139 | 1.355 | 22.936 | 32.134 | 1.00 | 38.56 | | | C |
| ATOM | 898 | OG | SER A 139 | 2.632 | 22.485 | 31.773 | 1.00 | 43.04 | | | O |
| ATOM | 899 | C | SER A 139 | 0.003 | 24.260 | 33.705 | | | 36.25 | 1.00 | C |
| ATOM | 900 | O | SER A 139 | -1.029 | 23.627 | 33.855 | 1.00 | 35.80 | | | O |
| ATOM | 901 | N | THR A 140 | 0.018 | 25.561 | 33.453 | 1.00 | 34.75 | | | N |
| ATOM | 902 | CA | THR A 140 | -1.195 | 26.291 | 33.196 | 1.00 | 34.44 | | | C |
| ATOM | 903 | CB | THR A 140 | -1.601 | 27.177 | 34.370 | 1.00 | 34.21 | | | C |
| ATOM | 904 | OG1 | THR A 140 | -0.576 | 28.184 | 34.446 | 1.00 | 33.39 | | | O |
| ATOM | 905 | CG2 | THR A 140 | -1.559 | 26.491 | 35.786 | 1.00 | 31.00 | | | C |
| ATOM | 906 | C | THR A 140 | -0.912 | 27.246 | 32.017 | 1.00 | 34.94 | | | C |
| ATOM | 907 | O | THR A 140 | 0.265 | 27.493 | 31.590 | 1.00 | 34.04 | | | O |
| ATOM | 908 | N | VAL A 141 | -1.992 | 27.828 | 31.518 | 1.00 | 33.00 | | | N |
| ATOM | 909 | CA | VAL A 141 | | 33.35 | 1.00 | 30.572 | 28.953 | 1.868- | | C |
| ATOM | 910 | CB | VAL A 141 | -2.507 | 28.579 | 29.216 | 1.00 | 33.38 | | | C |
| ATOM | 911 | CG1 | VAL A 141 | -2.444 | 29.737 | 28.267 | 1.00 | 33.20 | | | C |
| ATOM | 912 | CG2 | VAL A 141 | -1.775 | 27.351 | 28 | | 30.56 | 1.00 | 574. | C |
| ATOM | 913 | C | VAL A 141 | -2.568 | 30.152 | 31.242 | 1.00 | 34.34 | | | C |
| ATOM | 914 | O | VAL A 141 | -3.770 | 30.104 | 31.651 | 1.00 | 33.38 | | | O |
| ATOM | 915 | N | GLU A 142 | -1.828 | 31.221 | 31.387 | 1.00 | 35.13 | | | N |
| ATOM | 916 | CA | GLU A 142 | -2.365 | 32.459 | 32.027 | 1.00 | 33.99 | | | C |
| ATOM | 917 | CB | GLU A 142 | -1.288 | 33.083 | 32.904 | 1.00 | 34.14 | | | C |
| ATOM | 918 | CG | GLU A 142 | -0.613 | 32.106 | 33.895 | 1.00 | 31.32 | | | C |
| ATOM | 919 | CD | GLU A 142 | -1.521 | 31.592 | 35.007 | 1.00 | 35.87 | | | C |
| ATOM | 920 | OE1 | GLU A 142 | -2.711 | 32.030 | 35.076 | 1.00 | 37.80 | | | O |
| ATOM | 921 | OE2 | GLU A 142 | -1.039 | 30.730 | 35.874 | 1.00 | 34.52 | | | O |

Fig. 26 (Cont.)

| ATOM | 922 | C | GLU | A | 142 | | 34.71 | 1.00 | 30.975 | 33.445 | 2.766- | C |
|------|-----|-----|-----|---|-----|--------|--------|--------|--------|--------|--------|---|
| ATOM | 923 | O | GLU | A | 142 | -2.022 | 33.686 | 30.044 | 1.00 | 35.61 | | O |
| ATOM | 924 | N | VAL | A | 143 | -3.999 | 33.941 | 31.062 | 1.00 | 35.10 | | N |
| ATOM | 925 | CA | VAL | A | 143 | -4.490 | 34.940 | | 34.76 | 1.00 | 30.134 | C |
| ATOM | 926 | CB | VAL | A | 143 | -6.003 | 34.668 | 29.722 | 1.00 | 35.54 | | C |
| ATOM | 927 | CG1 | VAL | A | 143 | -6.440 | 35.618 | 28.580 | 1.00 | 33.38 | | C |
| ATOM | 928 | CG2 | VAL | A | 143 | -6.202 | 33.223 | 29.294 | 1.00 | 34.33 | | C |
| ATOM | 929 | C | VAL | A | 143 | -4.435 | 36.320 | 30.826 | 1.00 | 34.29 | | C |
| ATOM | 930 | O | VAL | A | 143 | -4.963 | 36.479 | 31.918 | 1.00 | 33.69 | | O |
| ATOM | 931 | N | PHE | A | 144 | -3.841 | 37.294 | 30.146 | 1.00 | 32.78 | | N |
| ATOM | 932 | CA | PHE | A | 144 | -3.709 | 38.659 | 30.608 | 1.00 | 32.99 | | C |
| ATOM | 933 | CB | PHE | A | 144 | -2.216 | 39.015 | 30.724 | 1.00 | 33.28 | | C |
| ATOM | 934 | CG | PHE | A | 144 | -1.430 | 38.182 | 31.734 | 1.00 | 34.27 | | C |
| ATOM | 935 | CD1 | PHE | A | 144 | | 30.92 | 1.00 | 33.084 | 38.527 | 1.412- | C |
| ATOM | 936 | CE1 | PHE | A | 144 | -0.646 | 37.802 | 33.993 | 1.00 | 29.79 | | C |
| ATOM | 937 | CZ | PHE | A | 144 | 0.094 | 36.698 | 33.574 | 1.00 | 29.58 | | C |
| ATOM | 938 | CE2 | PHE | A | 144 | 0.064 | 36.294 | | 30.18 | 1.00 | 32.214 | C |
| ATOM | 939 | CD2 | PHE | A | 144 | -0.698 | 37.048 | 31.310 | 1.00 | 32.12 | | C |
| ATOM | 940 | C | PHE | A | 144 | -4.266 | 39.606 | 29.531 | 1.00 | 33.15 | | C |
| ATOM | 941 | O | PHE | A | 144 | -4.157 | 39.329 | 28.332 | 1.00 | 34 | 14.0 | O |
| ATOM | 942 | N | LYS | A | 145 | -4.792 | 40.742 | 29.937 | 1.00 | 31.98 | | N |
| ATOM | 943 | CA | LYS | A | 145 | -5.005 | 41.844 | 29.027 | 1.00 | 31.75 | | C |
| ATOM | 944 | CB | LYS | A | 145 | -6.342 | 42.475 | 29.302 | 1.00 | 30.94 | | C |
| ATOM | 945 | CG | LYS | A | 145 | -6.523 | 43.803 | 28.585 | 1.00 | 35.59 | | C |
| ATOM | 946 | CD | LYS | A | 145 | -7.962 | 44.286 | 28.656 | 1.00 | 39.32 | | C |
| ATOM | 947 | CE | LYS | A | 145 | -8.083 | 45.321 | 29.741 | 1.00 | 49.25 | | C |
| ATOM | 948 | NZ | LYS | A | | 51.26 | 1.00 | 29.237 | 46.702 | 8.385- | 145 | N |
| ATOM | 949 | C | LYS | A | 145 | -3.864 | 42.886 | 29.120 | 1.00 | 31.38 | | C |
| ATOM | 950 | O | LYS | A | 145 | -3.475 | 43.320 | 30.194 | 1.00 | 30.89 | | O |
| ATOM | 951 | N | PHE | A | 146 | -3.296 | 43 | | 31.94 | 1.00 | 27.983 | 254.N |
| ATOM | 952 | CA | PHE | A | 146 | -2.266 | 44.265 | 27.947 | 1.00 | 34.03 | | C |
| ATOM | 953 | CB | PHE | A | 146 | -1.497 | 44.125 | 26.649 | 1.00 | 34.39 | | C |
| ATOM | 954 | CG | PHE | A | 146 | -0.404 | 45.140 | 26.487 | 1.00 | | 37.03 | C |
| ATOM | 955 | CD1 | PHE | A | 146 | 0.515 | 45.370 | 27.517 | 1.00 | 33.21 | | C |
| ATOM | 956 | CE1 | PHE | A | 146 | 1.542 | 46.246 | 27.371 | 1.00 | 34.67 | | C |
| ATOM | 957 | CZ | PHE | A | 146 | 1.674 | 46.978 | 26.200 | 1.00 | 35.72 | | C |
| ATOM | 958 | CE2 | PHE | A | 146 | 0.740 | 46.796 | 25.160 | 1.00 | 37.77 | | C |
| ATOM | 959 | CD2 | PHE | A | 146 | -0.305 | 45.887 | 25.311 | 1.00 | 37.01 | | C |
| ATOM | 960 | C | PHE | A | 146 | -2.833 | 45.701 | 28.103 | 1.00 | 34.66 | | C |
| ATOM | 961 | O | PHE | A | 146 | -3.707 | 46.107 | 27.345 | 1.00 | 34.08 | | O |
| ATOM | 962 | N | GLN | A | 147 | -2.400 | 46.425 | 29.139 | 1.00 | 36.08 | | N |
| ATOM | 963 | CA | GLN | A | 147 | -2.782 | 47.834 | 29.333 | 1.00 | 37.69 | | C |
| ATOM | 964 | CB | GLN | A | 147 | -3.209 | | 37.31 | 1.00 | 30.768 | 48.085 | C |
| ATOM | 965 | CG | GLN | A | 147 | -4.151 | 46.988 | 31.255 | 1.00 | 39.30 | | C |
| ATOM | 966 | CD | GLN | A | 147 | -4.781 | 47.300 | 32.616 | 1.00 | 42.61 | | C |
| ATOM | 967 | OE1 | GLN | A | 147 | -4.043 | 47.467 | 33.600 | 1 | | 42.46 | 00.O |
| ATOM | 968 | NE2 | GLN | A | 147 | -6.145 | 47.378 | 32.682 | 1.00 | 40.05 | | N |
| ATOM | 969 | C | GLN | A | 147 | -1.601 | 48.672 | 28.899 | 1.00 | 39.07 | | C |
| ATOM | 970 | O | GLN | A | 147 | -0.574 | 48.734 | 29.584 | 1.00 | 38.71 | | O |
| ATOM | 971 | N | GLU | A | 148 | -1.684 | 49.198 | 27.672 | 1.00 | 42.00 | | N |
| ATOM | 972 | CA | GLU | A | 148 | -0.495 | 49.761 | 27.009 | 1.00 | 43.96 | | C |
| ATOM | 973 | CB | GLU | A | 148 | -0.713 | 50.060 | 25.518 | 1.00 | 45.31 | | C |
| ATOM | 974 | CG | GLU | A | 148 | 0.539 | 50.768 | 24.931 | 1.00 | 48.40 | | C |
| ATOM | 975 | CD | GLU | A | 148 | 0.576 | 50.970 | 23.407 | 1.00 | 52.85 | | C |
| ATOM | 976 | OE1 | GLU | A | 148 | -0.350 | 50.549 | 22.666 | 1.00 | 53.14 | | O |
| ATOM | 977 | OE2 | GLU | A | 148 | 1.592 | | 54.51 | 1.00 | 22.945 | 51.565 | O |
| ATOM | 978 | C | GLU | A | 148 | 0.029 | 51.021 | 27.703 | 1.00 | 44.53 | | C |
| ATOM | 979 | O | GLU | A | 148 | 1.227 | 51.119 | 27.985 | 1.00 | 44.33 | | O |
| ATOM | 980 | N | GLU | A | 149 | -0.868 | 51.968 | 27.954 | | 45.05 | 1.00 | N |
| ATOM | 981 | CA | GLU | A | 149 | -0.534 | 53.195 | 28.664 | 1.00 | 47.14 | | C |
| ATOM | 982 | CB | GLU | A | 149 | -1.814 | 53.969 | 28.984 | 1.00 | 47.58 | | C |

Fig. 26 (Cont.)

```
ATOM    983  CG   GLU A 149     -2.354  54.850  27.880  1.00 51.99           C
ATOM    984  CD   GLU A 149     -2.781  56.222  28.421  1.00 57.90           C
ATOM    985  OE1  GLU A 149     -3.724  56.294  29.276  1.00 57.80           O
ATOM    986  OE2  GLU A 149     -2.159  57.235  28.002  1.00 57.48           O
ATOM    987  C    GLU A 149      0.191  52.953  30.002  1.00 47.07           C
ATOM    988  O    GLU A 149      1.170  53.637  30.324  1.00 46.78           O
ATOM    989  N    GLU A 150     -0.306  51.994  30.785  1.00 46.62           N
ATOM    990  CA   GLU A 150       46.17  1.00  32.122  51.791   0.226        C
ATOM    991  CB   GLU A 150     -0.826  51.238  33.061  1.00 45.87           C
ATOM    992  CG   GLU A 150     -1.982  52.200  33.311  1.00 50.09           C
ATOM    993  CD   GLU A 150     -3.146  51.949  32.347              53.62 1.00 C
ATOM    994  OE1  GLU A 150     -2.953  51.364  31.215  1.00 50.85           O
ATOM    995  OE2  GLU A 150     -4.258  52.363  32.737  1.00 55.00           O
ATOM    996  C    GLU A 150      1.404  50.848  32.097  1.00 45.63           C
ATOM    997  O    GLU A 150      2.088  50.752  33.105  1.00 46.21           O
ATOM    998  N    LYS A 151      1.613  50.136  30.980  1.00 43.75           N
ATOM    999  CA   LYS A 151      2.702  49.165  30.865  1.00 42.87           C
ATOM   1000  CB   LYS A 151      4.043  49.860  31.114  1.00 43.29           C
ATOM   1001  CG   LYS A 151      4.820  50.045  29.832  1.00 47.87           C
ATOM   1002  CD   LYS A 151      4.289  51.253  29.037  1.00 53.13           C
ATOM   1003  CE   LYS A 151       54.31  1.00  29.086  52.470   5.256        C
ATOM   1004  NZ   LYS A 151      6.587  51.997  28.573  1.00 55.30           N
ATOM   1005  C    LYS A 151      2.531  48.035  31.845  1.00 41.01           C
ATOM   1006  O    LYS A 151      3.422  47.739  32.646              41.40 1.00 O
ATOM   1007  N    SER A 152      1.360  47.426  31.810  1.00 38.97           N
ATOM   1008  CA   SER A 152      0.991  46.479  32.833  1.00 36.99           C
ATOM   1009  CB   SER A 152      0.282  47.209  34.008  1.00 37.06           C
ATOM   1010  OG   SER A 152     -1.048  47.537  33.646  1.00 37.77           O
ATOM   1011  C    SER A 152      0.141  45.380  32.191  1.00 36.06           C
ATOM   1012  O    SER A 152     -0.372  45.541  31.065  1.00 37.11           O
ATOM   1013  N    LEU A 153      0.060  44.233  32.846  1.00 33.52           N
ATOM   1014  CA   LEU A 153     -0.694  43.095  32.332  1.00 31.98           C
ATOM   1015  CB   LEU A 153      0.225  41.900  32.235  1.00 30.46           C
ATOM   1016  CG   LEU A 153       33.27  1.00  31.047  41.926   1.201        C
ATOM   1017  CD1  LEU A 153      2.244  40.792  31.250  1.00 31.59           C
ATOM   1018  CD2  LEU A 153      0.458  41.743  29.702  1.00 28.83           C
ATOM   1019  C    LEU A 153     -1.756  42.851              32.54 1.00  33.408 C
ATOM   1020  O    LEU A 153     -1.411  42.709  34.607  1.00 31.76           O
ATOM   1021  N    LEU A 154     -3.028  42.922  33.031  1.00 31.40           N
ATOM   1022  CA   LEU A 154     -4.116  42.628  33.983  1.00 30.33           C
ATOM   1023  CB   LEU A 154     -5.358  43.441  33.604  1.00 28.85           C
ATOM   1024  CG   LEU A 154     -6.675  42.995  34.258  1.00 32.41           C
ATOM   1025  CD1  LEU A 154     -6.648  43.056  35.851  1.00 30.17           C
ATOM   1026  CD2  LEU A 154     -7.936  43.769  33.724  1.00 33.37           C
ATOM   1027  C    LEU A 154     -4.405  41.113  33.843  1.00 29.14           C
ATOM   1028  O    LEU A 154     -4.704  40.650  32.733  1.00 28.63           O
ATOM   1029  N    HIS A 155       28.69  1.00  34.919  40.347   4.274-       N
ATOM   1030  CA   HIS A 155     -4.538  38.914  34.853  1.00 29.23           C
ATOM   1031  CB   HIS A 155     -4.021  38.186  36.069  1.00 30.89           C
ATOM   1032  CG   HIS A 155     -4.169  36         31.74 1.00  35.973  697.C
ATOM   1033  ND1  HIS A 155     -5.043  36.000  36.767  1.00 31.01           N
ATOM   1034  CE1  HIS A 155     -5.001  34.717  36.436  1.00 30.82           C
ATOM   1035  NE2  HIS A 155     -4.078  34.555  35.509  1.00 31.99           N
ATOM   1036  CD2  HIS A 155     -3.544  35.779  35.195  1.00 30.24           C
ATOM   1037  C    HIS A 155     -6.034  38.679  34.709  1.00 29.61           C
ATOM   1038  O    HIS A 155     -6.810  39.307  35.337  1.00 25.45           O
ATOM   1039  N    LEU A 156     -6.413  37.833  33.762  1.00 31.18           N
ATOM   1040  CA   LEU A 156     -7.835  37.550  33.565  1.00 31.32           C
ATOM   1041  CB   LEU A 156     -8.242  37.704  32.099  1.00 30.04           C
ATOM   1042  CG   LEU A 156     -8.073  39.184  31.676  1.00 33.80           C
ATOM   1043  CD1  LEU A 156     -8.395  39.265  30.176  1.00 35.69           C
```

Fig. 26 (Cont.)

| | | | | | | | | | |
|---|---|---|---|---|---|---|---|---|---|
| ATOM | 1044 | CD2 | LEU A 156 | -9.054 | 40.099 | 32.482 | 1.00 | 30.36 | C |
| ATOM | 1045 | C | LEU A 156 | -8.118 | | 32.01 | 1.00 | 34.040 | 36.161 C |
| ATOM | 1046 | O | LEU A 156 | -9.106 | 35.937 | 34.723 | 1.00 | 32.91 | O |
| ATOM | 1047 | N | LYS A 157 | -7.274 | 35.223 | 33.688 | 1.00 | 32.02 | N |
| ATOM | 1048 | CA | LYS A 157 | -7.569 | 33.874 | 34.069 | 1.00 | | 34.57 C |
| ATOM | 1049 | CB | LYS A 157 | -8.897 | 33.450 | 33.449 | 1.00 | 36.17 | C |
| ATOM | 1050 | CG | LYS A 157 | -8.944 | 32.420 | 32.398 | 1.00 | 37.38 | C |
| ATOM | 1051 | CD | LYS A 157 | -10.480 | 32.110 | 32.248 | 1.00 | 45.13 | C |
| ATOM | 1052 | CE | LYS A 157 | -10.838 | 30.631 | 32.199 | 1.00 | 43.29 | C |
| ATOM | 1053 | NZ | LYS A 157 | -11.977 | 30.413 | 33.111 | 1.00 | 40.66 | N |
| ATOM | 1054 | C | LYS A 157 | -6.467 | 32.846 | 33.913 | 1.00 | 33.46 | C |
| ATOM | 1055 | O | LYS A 157 | -5.509 | 33.049 | 33.178 | 1.00 | 34.54 | O |
| ATOM | 1056 | N | THR A 158 | -6.599 | 31.794 | 34.703 | 1.00 | 33.86 | N |
| ATOM | 1057 | CA | THR A 158 | -5.668 | 30.661 | 34.760 | 1.00 | 34.12 | C |
| ATOM | 1058 | CB | THR A 158 | -5.338 | | 33.79 | 1.00 | 36.292 | 30.376 C |
| ATOM | 1059 | OG1 | THR A 158 | -4.538 | 31.441 | 36.778 | 1.00 | 33.45 | O |
| ATOM | 1060 | CG2 | THR A 158 | -4.422 | 29.120 | 36.491 | 1.00 | 32.76 | C |
| ATOM | 1061 | C | THR A 158 | -6.407 | 29.457 | 34.179 | | 33.68 | 1.00 C |
| ATOM | 1062 | O | THR A 158 | -7.454 | 29.044 | 34.658 | 1.00 | 33.67 | O |
| ATOM | 1063 | N | ILE A 159 | -5.854 | 28.893 | 33.148 | 1.00 | 34.56 | N |
| ATOM | 1064 | CA | ILE A 159 | -6.403 | 27.700 | 32.505 | 1.00 | 34.28 | C |
| ATOM | 1065 | CB | ILE A 159 | -6.451 | 27.967 | 31.002 | 1.00 | 34.20 | C |
| ATOM | 1066 | CG1 | ILE A 159 | -7.533 | 29.040 | 30.739 | 1.00 | 35.19 | C |
| ATOM | 1067 | CD1 | ILE A 159 | -7.485 | 29.599 | 29.286 | 1.00 | 32.73 | C |
| ATOM | 1068 | CG2 | ILE A 159 | -6.713 | 26.664 | 30.204 | 1.00 | 28.67 | C |
| ATOM | 1069 | C | ILE A 159 | -5.545 | 26.475 | 32.779 | 1.00 | 34.90 | C |
| ATOM | 1070 | O | ILE A 159 | -4.341 | 26.518 | 32.578 | 1.00 | 34.74 | O |
| ATOM | 1071 | N | ARG A 160 | -6 | | 36.12 | 1.00 | 33.235 | 25.383 141.N |
| ATOM | 1072 | CA | ARG A 160 | -5.442 | 24.082 | 33.207 | 1.00 | 37.28 | C |
| ATOM | 1073 | CB | ARG A 160 | -4.956 | 23.587 | 34.574 | 1.00 | 39.03 | C |
| ATOM | 1074 | CG | ARG A 160 | -5.100 | 24.511 | 35.640 | | 44.21 | 1.00 C |
| ATOM | 1075 | CD | ARG A 160 | -5.469 | 23.891 | 36.978 | 1.00 | 47.10 | C |
| ATOM | 1076 | NE | ARG A 160 | -5.605 | 25.077 | 37.804 | 1.00 | 49.73 | N |
| ATOM | 1077 | CZ | ARG A 160 | -4.578 | 25.643 | 38.409 | 1.00 | 52.72 | C |
| ATOM | 1078 | NH1 | ARG A 160 | -3.392 | 25.043 | 38.354 | 1.00 | 47.56 | N |
| ATOM | 1079 | NH2 | ARG A 160 | -4.744 | 26.766 | 39.121 | 1.00 | 55.30 | N |
| ATOM | 1080 | C | ARG A 160 | -6.401 | 22.997 | 32.772 | 1.00 | 36.47 | C |
| ATOM | 1081 | O | ARG A 160 | -7.616 | 23.150 | 32.859 | 1.00 | 34.99 | O |
| ATOM | 1082 | N | HIS A 161 | -5.841 | 21.847 | 32.438 | 1.00 | 33.40 | N |
| ATOM | 1083 | CA | HIS A 161 | -6.661 | 20.847 | 31.836 | 1.00 | 33.03 | C |
| ATOM | 1084 | CB | HIS A 161 | | 31.64 | 1.00 | 30.388 | 21.242 | 7.106- C |
| ATOM | 1085 | CG | HIS A 161 | -8.336 | 20.504 | 29.933 | 1.00 | 33.60 | C |
| ATOM | 1086 | ND1 | HIS A 161 | -8.278 | 19.255 | 29.322 | 1.00 | 33.78 | N |
| ATOM | 1087 | CE1 | HIS A 161 | -9.506 | 18.819 | 29 | | 32.25 | 1.00 086.C |
| ATOM | 1088 | NE2 | HIS A 161 | -10.362 | 19.691 | 29.594 | 1.00 | 33.24 | N |
| ATOM | 1089 | CD2 | HIS A 161 | -9.660 | 20.770 | 30.113 | 1.00 | 30.87 | C |
| ATOM | 1090 | C | HIS A 161 | -5.839 | 19.588 | 31.848 | 1.00 | 32.89 | C |
| ATOM | 1091 | O | HIS A 161 | -4.603 | 19.602 | 31.720 | 1.00 | 33.71 | O |
| ATOM | 1092 | N | LYS A 162 | -6.527 | 18.495 | 31.960 | 1.00 | 33.49 | N |
| ATOM | 1093 | CA | LYS A 162 | -5.891 | 17.205 | 31.839 | 1.00 | 35.30 | C |
| ATOM | 1094 | CB | LYS A 162 | -6.935 | 16.142 | 32.197 | 1.00 | 36.18 | C |
| ATOM | 1095 | CG | LYS A 162 | -6.853 | 14.904 | 31.364 | 1.00 | 40.99 | C |
| ATOM | 1096 | CD | LYS A 162 | -8.092 | 14.020 | 31.518 | 1.00 | 48.68 | C |
| ATOM | 1097 | CE | LYS A 162 | | 53.51 | 1.00 | 31.059 | 12.570 | 7.733- C |
| ATOM | 1098 | NZ | LYS A 162 | -7.905 | 11.628 | 32.242 | 1.00 | 53.91 | N |
| ATOM | 1099 | C | LYS A 162 | -5.203 | 16.971 | 30.472 | 1.00 | 34.56 | C |
| ATOM | 1100 | O | LYS A 162 | -4.204 | 16.279 | | | 35.10 | 1.00 30.424 O |
| ATOM | 1101 | N | LEU A 163 | -5.697 | 17.587 | 29.396 | 1.00 | 34.41 | N |
| ATOM | 1102 | CA | LEU A 163 | -5.071 | 17.508 | 28.045 | 1.00 | 34.07 | C |
| ATOM | 1103 | CB | LEU A 163 | -6.149 | 17.582 | 26.942 | 1.00 | 32.01 | C |
| ATOM | 1104 | CG | LEU A 163 | -7.179 | 16.467 | 26.981 | 1.00 | 33.91 | C |

Fig. 26 (Cont.)

```
ATOM   1105  CD1  LEU A 163      -8.233   16.644   25.881  1.00 32.64           C
ATOM   1106  CD2  LEU A 163      -6.532   15.085   26.893  1.00 30.09           C
ATOM   1107  C    LEU A 163      -3.974   18.615   27.850  1.00 34.30           C
ATOM   1108  O    LEU A 163      -3.476   18.859   26.752  1.00 33.73           O
ATOM   1109  N    LEU A 164      -3.658   19.320   28.934  1.00 34.53           N
ATOM   1110  CA   LEU A 164           35.03 1.00  28.928   20.303   2.569-      C
ATOM   1111  CB   LEU A 164      -3.142   21.688   29.241  1.00 34.30           C
ATOM   1112  CG   LEU A 164      -4.057   22.311   28.170  1.00 35.07           C
ATOM   1113  CD1  LEU A 164      -4.621   23.701           31.74 1.00   28.663  C
ATOM   1114  CD2  LEU A 164      -3.278   22.421   26.851  1.00 31.41           C
ATOM   1115  C    LEU A 164      -1.566   19.905   30.029  1.00 35.23           C
ATOM   1116  O    LEU A 164      -1.302   20.707   30.943  1.00 35         12.O
ATOM   1117  N    PRO A 165      -1.056   18.670   29.968  1.00 34.95           N
ATOM   1118  CA   PRO A 165      -0.183   18.130   31.026  1.00 34.71           C
ATOM   1119  CB   PRO A 165      -0.060   16.632   30.651  1.00 34.55           C
ATOM   1120  CG   PRO A 165      -0.267   16.553   29.143  1.00 34.10           C
ATOM   1121  CD   PRO A 165      -1.258   17.681   28.876  1.00 35.74           C
ATOM   1122  C    PRO A 165       1.213   18.771   31.090  1.00 34.23           C
ATOM   1123  O    PRO A          33.56 1.00  32.194   18.994   1.704     165 O
ATOM   1124  N    SER A 166       1.785   19.126   29.950  1.00 33.21           N
ATOM   1125  CA   SER A 166       3.207   19.529   29.871  1.00 34.68           C
ATOM   1126  CB   SER A 166       4.103   18.289           34.52 1.00   29.695  C
ATOM   1127  OG   SER A 166       5.463   18.633   29.855  1.00 38.52           O
ATOM   1128  C    SER A 166       3.416   20.513   28.723  1.00 34.30           C
ATOM   1129  O    SER A 166       4.006   20.169   27.668  1.00          37.14 O
ATOM   1130  N    VAL A 167       2.932   21.741   28.917  1.00 33.58           N
ATOM   1131  CA   VAL A 167       2.704   22.646   27.808  1.00 33.08           C
ATOM   1132  CB   VAL A 167       1.579   23.674   28.135  1.00 33.48           C
ATOM   1133  CG1  VAL A 167       1.445   24.696   26.996  1.00 32.56           C
ATOM   1134  CG2  VAL A 167       0.209   22.999   28.502  1.00 29.00           C
ATOM   1135  C    VAL A 167       4.023   23.387   27.551  1.00 33.26           C
ATOM   1136  O    VAL A 167       4.744   23.754   28.481  1.00 32.66           O
ATOM   1137  N    ASN A 168       4.333   23.584   26.294  1.00 33.98           N
ATOM   1138  CA   ASN A 168       5.598   24.197   25.895  1.00 32.75           C
ATOM   1139  CB   ASN A 168       6.279            34.28 1.00  24.838   23.299  C
ATOM   1140  CG   ASN A 168       7.712   23.810   24.487  1.00 34.93           C
ATOM   1141  OD1  ASN A 168       7.846   24.894   23.900  1.00 36.68           O
ATOM   1142  ND2  ASN A 168       8.758   23.113   24.994  1            31.94 00.N
ATOM   1143  C    ASN A 168       5.298   25.550   25.247  1.00 34.00           C
ATOM   1144  O    ASN A 168       5.800   26.603   25.682  1.00 34.55           O
ATOM   1145  N    ASP A 169       4.438   25.547   24.226  1.00 32.85           N
ATOM   1146  CA   ASP A 169       4.055   26.804   23.600  1.00 33.69           C
ATOM   1147  CB   ASP A 169       4.903   27.082   22.367  1.00 31.39           C
ATOM   1148  CG   ASP A 169       4.921   28.607   22.004  1.00 37.35           C
ATOM   1149  OD1  ASP A 169       4.352   29.484   22.694  1.00 33.53           O
ATOM   1150  OD2  ASP A 169       5.448   29.052   21.008  1.00 35.57           O
ATOM   1151  C    ASP A 169       2.548   26.804   23.185  1.00 34.34           C
ATOM   1152  O    ASP A 169       1          33.47 1.00  23.137   25.732   955.O
ATOM   1153  N    ILE A 170       1.974   27.994   22.869  1.00 33.68           N
ATOM   1154  CA   ILE A 170       0.578   28.080   22.408  1.00 32.64           C
ATOM   1155  CB   ILE A 170      -0.511   28.410   23.542           34.15 1.00  C
ATOM   1156  CG1  ILE A 170      -0.590   29.902   23.876  1.00 32.84           C
ATOM   1157  CD1  ILE A 170       0.686   30.476   24.593  1.00 30.90           C
ATOM   1158  CG2  ILE A 170      -0.311   27.527   24.801  1.00 29.34           C
ATOM   1159  C    ILE A 170       0.502   29.067   21.259  1.00 34.06           C
ATOM   1160  O    ILE A 170       1.348   29.969   21.148  1.00 33.34           O
ATOM   1161  N    VAL A 171      -0.509   28.918   20.396  1.00 33.57           N
ATOM   1162  CA   VAL A 171      -0.803   30.016   19.512  1.00 33.79           C
ATOM   1163  CB   VAL A 171      -0.468   29.659   18.004  1.00 34.75           C
ATOM   1164  CG1  VAL A 171      -1.142   28.324   17.527  1.00 33.41           C
ATOM   1165  CG2  VAL A 171           33.55 1.00  17.143   30.760   0.935-      C
```

Fig. 26 (Cont.)

```
ATOM   1166  C    VAL A 171     -2.291  30.411  19.748  1.00 34.61           C
ATOM   1167  O    VAL A 171     -3.176  29.598  19.635  1.00 33.42           O
ATOM   1168  N    ALA A 172     -2.532  31.661  20           34.65 1.00   093.N
ATOM   1169  CA   ALA A 172     -3.866  32.130  20.409  1.00 34.53           C
ATOM   1170  CB   ALA A 172     -3.772  33.473  21.116  1.00 33.21           C
ATOM   1171  C    ALA A 172     -4.685  32.313  19.130  1.00 35.97           C
ATOM   1172  O    ALA A 172     -4.192  32.895  18.148  1.00 35.88           O
ATOM   1173  N    VAL A 173     -5.933  31.837  19.137  1.00 35.55           N
ATOM   1174  CA   VAL A 173     -6.845  32.131  18.037  1.00 36.82           C
ATOM   1175  CB   VAL A 173     -7.241  30.855  17.237  1.00 37.26           C
ATOM   1176  CG1  VAL A 173     -5.978  30.267  16.545  1.00 36.68           C
ATOM   1177  CG2  VAL A 173     -7.919  29.769  18.156  1.00 35.00           C
ATOM   1178  C    VAL A 173             37.12 1.00   18.579  32.842   8.082- C
ATOM   1179  O    VAL A 173     -9.059  32.988  17.879  1.00 37.60           O
ATOM   1180  N    GLY A 174     -8.011  33.330  19.824  1.00 36.94           N
ATOM   1181  CA   GLY A 174     -9.101  34.078           35.34 1.00   20.460 C
ATOM   1182  C    GLY A 174     -8.535  34.458  21.843  1.00 37.36           C
ATOM   1183  O    GLY A 174     -7.460  33.985  22.215  1.00 36.10           O
ATOM   1184  N    PRO A 175     -9.250  35.284  22.614  1.00 37.77           N
ATOM   1185  CA   PRO A 175     -8.833  35.663  23.976  1.00 37.78           C
ATOM   1186  CB   PRO A 175    -10.006  36.489  24.503  1.00 37.36           C
ATOM   1187  CG   PRO A 175    -10.836  36.807  23.368  1.00 38.55           C
ATOM   1188  CD   PRO A 175    -10.533  35.887  22.209  1.00 36.90           C
ATOM   1189  C    PRO A 175     -8.622  34.450  24.925  1.00 38.97           C
ATOM   1190  O    PRO A 175     -7.754  34.550  25.826  1.00 41.79           O
ATOM   1191  N    GLU A 176             37.43 1.00   24.721  33.323   9.307- N
ATOM   1192  CA   GLU A 176     -9.125  32.115  25.559  1.00 38.03           C
ATOM   1193  CB   GLU A 176    -10.288  31.983  26.608  1.00 38.87           C
ATOM   1194  CG   GLU A 176    -10.123  32.976           41.42 1.00   27.675 C
ATOM   1195  CD   GLU A 176    -11.255  33.044  28.679  1.00 51.60           C
ATOM   1196  OE1  GLU A 176    -12.175  32.138  28.695  1.00 43.41           O
ATOM   1197  OE2  GLU A 176    -11.134  34.054  29.489  1.00 53        44.0
ATOM   1198  C    GLU A 176     -9.283  30.897  24.716  1.00 38.03           C
ATOM   1199  O    GLU A 176     -9.929  29.963  25.163  1.00 38.43           O
ATOM   1200  N    HIS A 177     -8.821  30.941  23.474  1.00 38.07           N
ATOM   1201  CA   HIS A 177     -8.859  29.820  22.595  1.00 38.35           C
ATOM   1202  CB   HIS A 177     -9.847  30.127  21.471  1.00 39.71           C
ATOM   1203  CG   HIS A 177    -11.147  30.726  21.933  1.00 44.72           C
ATOM   1204  ND1  HIS A          48.89 1.00   22.674  31.906  11.219-      177 N
ATOM   1205  CE1  HIS A 177    -12.493  32.210  22.899  1.00 43.34           C
ATOM   1206  NE2  HIS A 177    -13.249  31.262  22.343  1.00 42.62           N
ATOM   1207  CD2  HIS A 177    -12.437  30           42.17 1.00   21.742  321.C
ATOM   1208  C    HIS A 177     -7.453  29.689  22.004  1.00 38.33           C
ATOM   1209  O    HIS A 177     -6.878  30.708  21.588  1.00 36.52           O
ATOM   1210  N    PHE A 178     -6.897  28.467  21.938  1.00       36.18 N
ATOM   1211  CA   PHE A 178     -5.505  28.356  21.493  1.00 36.06           C
ATOM   1212  CB   PHE A 178     -4.492  28.869  22.566  1.00 34.24           C
ATOM   1213  CG   PHE A 178     -4.651  28.218  23.924  1.00 34.87           C
ATOM   1214  CD1  PHE A 178     -3.998  27.015  24.215  1.00 31.96           C
ATOM   1215  CE1  PHE A 178     -4.086  26.440  25.483  1.00 30.70           C
ATOM   1216  CZ   PHE A 178     -4.951  27.029  26.471  1.00 36.03           C
ATOM   1217  CE2  PHE A 178     -5.617  28.246  26.174  1.00 33.08           C
ATOM   1218  CD2  PHE A 178     -5.451  28.819  24.905  1.00 33.43           C
ATOM   1219  C    PHE A 178     -5.222  26.941  21.134  1.00 35.50           C
ATOM   1220  O    PHE A 178     -5.904           37.17 1.00   21.631  26.053 O
ATOM   1221  N    TYR A 179     -4.233  26.729  20.286  1.00 33.98           N
ATOM   1222  CA   TYR A 179     -3.612  25.413  20.164  1.00 34.03           C
ATOM   1223  CB   TYR A 179     -3.179  25.153  18.717  1           34.72 00.C
ATOM   1224  CG   TYR A 179     -4.338  25.030  17.752  1.00 35.16           C
ATOM   1225  CD1  TYR A 179     -4.981  23.823  17.588  1.00 33.38           C
ATOM   1226  CE1  TYR A 179     -6.033  23.667  16.635  1.00 35.83           C
```

Fig. 26 (Cont.)

| | | | | | | | | | |
|---|---|---|---|---|---|---|---|---|---|
| ATOM | 1227 | CZ | TYR A 179 | -6.469 | 24.759 | 15.881 | 1.00 | 38.08 | C |
| ATOM | 1228 | OH | TYR A 179 | -7.519 | 24.591 | 14.994 | 1.00 | 42.96 | O |
| ATOM | 1229 | CE2 | TYR A 179 | -5.837 | 26.013 | 16.025 | 1.00 | 38.52 | C |
| ATOM | 1230 | CD2 | TYR A 179 | -4.769 | 26.138 | 16.971 | 1.00 | 35.03 | C |
| ATOM | 1231 | C | TYR A 179 | -2.378 | 25.369 | 21.060 | 1.00 | 33.89 | C |
| ATOM | 1232 | O | TYR A 179 | -1.610 | 26.305 | 21.111 | 1.00 | 33.88 | O |
| ATOM | 1233 | N | ALA A 180 | -2.180 | 34.70 1.00 | 21.763 | 24.262 | | N |
| ATOM | 1234 | CA | ALA A 180 | -1.052 | 24.128 | 22.674 | 1.00 | 34.91 | C |
| ATOM | 1235 | CB | ALA A 180 | -1.580 | 23.969 | 24.124 | 1.00 | 33.30 | C |
| ATOM | 1236 | C | ALA A 180 | -0.210 | 22.907 | 22.307 | | 35.04 1.00 | C |
| ATOM | 1237 | O | ALA A 180 | -0.760 | 21.802 | 22.098 | 1.00 | 34.78 | O |
| ATOM | 1238 | N | THR A 181 | 1.117 | 23.051 | 22.310 | 1.00 | 34.55 | N |
| ATOM | 1239 | CA | THR A 181 | 1.896 | 21.838 | 22.283 | 1.00 | 33.59 | C |
| ATOM | 1240 | CB | THR A 181 | 3.246 | 22.057 | 21.586 | 1.00 | 35.33 | C |
| ATOM | 1241 | OG1 | THR A 181 | 3.977 | 23.097 | 22.235 | 1.00 | 33.90 | O |
| ATOM | 1242 | CG2 | THR A 181 | 3.084 | 22.496 | 20.094 | 1.00 | 34.42 | C |
| ATOM | 1243 | C | THR A 181 | 2.156 | 21.337 | 23.685 | 1.00 | 34.01 | C |
| ATOM | 1244 | O | THR A 181 | 2.375 | 22.103 | 24.609 | 1.00 | 34.67 | O |
| ATOM | 1245 | N | ASN A 182 | 2.169 | 20.034 | 23.843 | 1.00 | 33.85 | N |
| ATOM | 1246 | CA | ASN A 182 | 34.84 1.00 | 25.055 | 19.440 | 2.681 | | C |
| ATOM | 1247 | CB | ASN A 182 | 1.696 | 18.391 | 25.614 | 1.00 | 32.92 | C |
| ATOM | 1248 | CG | ASN A 182 | 0.426 | 19.013 | 26.185 | 1.00 | 36.43 | C |
| ATOM | 1249 | OD1 | ASN A 182 | 0.459 | 19.600 | 27.294 | | 36.21 1.00 | O |
| ATOM | 1250 | ND2 | ASN A 182 | -0.710 | 18.890 | 25.444 | 1.00 | 32.77 | N |
| ATOM | 1251 | C | ASN A 182 | 3.992 | 18.727 | 24.668 | 1.00 | 35.26 | C |
| ATOM | 1252 | O | ASN A 182 | 3.992 | 17.821 | 23.803 | 1.00 | 36.02 | O |
| ATOM | 1253 | N | ASP A 183 | 5.090 | 19.096 | 25.317 | 1.00 | 35.56 | N |
| ATOM | 1254 | CA | ASP A 183 | 6.378 | 18.491 | 24.964 | 1.00 | 35.27 | C |
| ATOM | 1255 | CB | ASP A 183 | 7.546 | 19.402 | 25.295 | 1.00 | 35.00 | C |
| ATOM | 1256 | CG | ASP A 183 | 7.544 | 19.902 | 26.709 | 1.00 | 38.10 | C |
| ATOM | 1257 | OD1 | ASP A 183 | 7.077 | 19.194 | 27.659 | 1.00 | 37.92 | O |
| ATOM | 1258 | OD2 | ASP A 183 | 7.969 | 21.066 | 26.936 | 1.00 | 38.64 | O |
| ATOM | 1259 | C | ASP A 183 | 35.15 1.00 | 25.549 | 17.064 | 6.557 | | C |
| ATOM | 1260 | O | ASP A 183 | 7.470 | 16.365 | 25.201 | 1.00 | 35.27 | O |
| ATOM | 1261 | N | HIS A 184 | 5.682 | 16.642 | 26.449 | 1.00 | 33.77 | N |
| ATOM | 1262 | CA | HIS A 184 | 5.805 | 15.297 | 27.011 | | 33.82 1.00 | C |
| ATOM | 1263 | CB | HIS A 184 | 6.533 | 15.258 | 28.366 | 1.00 | 33.63 | C |
| ATOM | 1264 | CG | HIS A 184 | 7.995 | 15.568 | 28.307 | 1.00 | 35.59 | C |
| ATOM | 1265 | ND1 | HIS A 184 | 8.486 | 16.857 | 28.216 | 1.00 | 36.05 | N |
| ATOM | 1266 | CE1 | HIS A 184 | 9.813 | 16.824 | 28.226 | 1.00 | 37.00 | C |
| ATOM | 1267 | NE2 | HIS A 184 | 10.195 | 15.568 | 28.368 | 1.00 | 40.08 | N |
| ATOM | 1268 | CD2 | HIS A 184 | 9.079 | 14.765 | 28.437 | 1.00 | 38.43 | C |
| ATOM | 1269 | C | HIS A 184 | 4.408 | 14.847 | 27.286 | 1.00 | 33.44 | C |
| ATOM | 1270 | O | HIS A 184 | 3.513 | 15.658 | 27.405 | 1.00 | 32.58 | O |
| ATOM | 1271 | N | TYR A 185 | 4.222 | 13.550 | 27.458 | 1.00 | 34.15 | N |
| ATOM | 1272 | CA | TYR A 185 | 35.00 1.00 | 27.799 | 13.045 | 2.940 | | C |
| ATOM | 1273 | CB | TYR A 185 | 2.812 | 11.662 | 27.163 | 1.00 | 37.80 | C |
| ATOM | 1274 | CG | TYR A 185 | 1.622 | 10.872 | 27.649 | 1.00 | 39.78 | C |
| ATOM | 1275 | CD1 | TYR A 185 | 0.456 | 10.765 | | 42.61 1.00 | 26.865 | C |
| ATOM | 1276 | CE1 | TYR A 185 | -0.657 | 10.069 | 27.344 | 1.00 | 46.90 | C |
| ATOM | 1277 | CZ | TYR A 185 | -0.567 | 9.474 | 28.626 | 1.00 | 48.51 | C |
| ATOM | 1278 | OH | TYR A 185 | -1.599 | 8.743 | 29.161 | 1.00 | 52.21 | O |
| ATOM | 1279 | CE2 | TYR A 185 | 0.586 | 9.590 | 29.404 | 1.00 | 46.28 | C |
| ATOM | 1280 | CD2 | TYR A 185 | 1.645 | 10.286 | 28.920 | 1.00 | 42.69 | C |
| ATOM | 1281 | C | TYR A 185 | 2.851 | 13.022 | 29.333 | 1.00 | 35.70 | C |
| ATOM | 1282 | O | TYR A 185 | 1.791 | 13.273 | 29.911 | 1.00 | 35.70 | O |
| ATOM | 1283 | N | PHE A 186 | 3.957 | 12.735 | 30.011 | 1.00 | 36.34 | N |
| ATOM | 1284 | CA | PHE A 186 | 3.946 | 12.628 | 31.489 | 1.00 | 37.07 | C |
| ATOM | 1285 | CB | PHE A 186 | 36.46 1.00 | 31.945 | 11.588 | 4.958 | | C |
| ATOM | 1286 | CG | PHE A 186 | 4.531 | 10.176 | 31.676 | 1.00 | 38.39 | C |
| ATOM | 1287 | CD1 | PHE A 186 | 3.408 | 9.616 | 32.348 | 1.00 | 38.29 | C |

Fig. 26 (Cont.)

| | | | | | | | | | | |
|---|---|---|---|---|---|---|---|---|---|---|
| ATOM | 1288 | CE1 | PHE | A | 186 | 3.011 | 8 | 40.85 | 1.00 | 32.085 | 279.C |
| ATOM | 1289 | CZ | PHE | A | 186 | 3.736 | 7.507 | 31.163 | 1.00 | 38.09 | C |
| ATOM | 1290 | CE2 | PHE | A | 186 | 4.858 | 8.076 | 30.498 | 1.00 | 38.85 | C |
| ATOM | 1291 | CD2 | PHE | A | 186 | 5.251 | 9.383 | 30.772 | 1.00 | 36.55 | C |
| ATOM | 1292 | C | PHE | A | 186 | 4.197 | 13.959 | 32.221 | 1.00 | 37.87 | C |
| ATOM | 1293 | O | PHE | A | 186 | 4.800 | 14.866 | 31.697 | 1.00 | 39.13 | O |
| ATOM | 1294 | N | ILE | A | 187 | 3.723 | 14.089 | 33.442 | 1.00 | 40.18 | N |
| ATOM | 1295 | CA | ILE | A | 187 | 3.977 | 15.315 | 34.198 | 1.00 | 41.06 | C |
| ATOM | 1296 | CB | ILE | A | 187 | 2.730 | 15.717 | 34.965 | 1.00 | 41.74 | C |
| ATOM | 1297 | CG1 | ILE | A | 187 | 1.609 | 16.064 | 33.986 | 1.00 | 39.46 | C |
| ATOM | 1298 | CD1 | ILE | A | 187 | 0.227 | 15.890 | 34.625 | 1.00 | 37.47 | C |
| ATOM | 1299 | CG2 | ILE | A | 187 | 3.075 | 16.835 | 36.006 | 1.00 | 41.74 | C |
| ATOM | 1300 | C | ILE | A | 187 | 5.153 | 15.132 | 35.170 | 1.00 | 41.68 | C |
| ATOM | 1301 | O | ILE | A | 187 | 5.990 | | 42.19 | 1.00 | 35.314 | 16.025 O |
| ATOM | 1302 | N | ASP | A | 188 | 5.224 | 13.973 | 35.816 | 1.00 | 42.34 | N |
| ATOM | 1303 | CA | ASP | A | 188 | 6.272 | 13.734 | 36.803 | 1.00 | 43.99 | C |
| ATOM | 1304 | CB | ASP | A | 188 | 6.107 | 12.367 | 37.445 | 1.00 | | 43.99 C |
| ATOM | 1305 | CG | ASP | A | 188 | 7.166 | 12.103 | 38.498 | 1.00 | 46.71 | C |
| ATOM | 1306 | OD1 | ASP | A | 188 | 6.771 | 12.113 | 39.674 | 1.00 | 54.14 | O |
| ATOM | 1307 | OD2 | ASP | A | 188 | 8.395 | 11.890 | 38.288 | 1.00 | 46.00 | O |
| ATOM | 1308 | C | ASP | A | 188 | 7.669 | 13.854 | 36.152 | 1.00 | 44.28 | C |
| ATOM | 1309 | O | ASP | A | 188 | 7.903 | 13.274 | 35.100 | 1.00 | 44.24 | O |
| ATOM | 1310 | N | PRO | A | 189 | 8.579 | 14.619 | 36.756 | 1.00 | 44.93 | N |
| ATOM | 1311 | CA | PRO | A | 189 | 9.864 | 14.915 | 36.102 | 1.00 | 45.08 | C |
| ATOM | 1312 | CB | PRO | A | 189 | 10.533 | 15.903 | 37.071 | 1.00 | 45.61 | C |
| ATOM | 1313 | CG | PRO | A | 189 | 9.354 | 16.486 | 37.816 | 1.00 | 46.54 | C |
| ATOM | 1314 | CD | PRO | A | 189 | 8.478 | | 44.80 | 1.00 | 38.077 | 15.276 C |
| ATOM | 1315 | C | PRO | A | 189 | 10.725 | 13.657 | 35.875 | 1.00 | 43.88 | C |
| ATOM | 1316 | O | PRO | A | 189 | 11.359 | 13.568 | 34.824 | 1.00 | 44.54 | O |
| ATOM | 1317 | N | TYR | A | 190 | 10.719 | 12.705 | 36.788 | | 42.19 | 1.00 N |
| ATOM | 1318 | CA | TYR | A | 190 | 11.443 | 11.450 | 36.578 | 1.00 | 42.19 | C |
| ATOM | 1319 | CB | TYR | A | 190 | 11.381 | 10.565 | 37.831 | 1.00 | 42.69 | C |
| ATOM | 1320 | CG | TYR | A | 190 | 12.615 | 10.500 | 38.724 | 1.00 | 46.62 | C |
| ATOM | 1321 | CD1 | TYR | A | 190 | 13.892 | 10.953 | 38.315 | 1.00 | 51.01 | C |
| ATOM | 1322 | CE1 | TYR | A | 190 | 15.054 | 10.845 | 39.215 | 1.00 | 53.20 | C |
| ATOM | 1323 | CZ | TYR | A | 190 | 14.877 | 10.293 | 40.514 | 1.00 | 55.24 | C |
| ATOM | 1324 | OH | TYR | A | 190 | 15.910 | 10.121 | 41.462 | 1.00 | 56.77 | O |
| ATOM | 1325 | CE2 | TYR | A | 190 | 13.599 | 9.858 | 40.906 | 1.00 | 54.03 | C |
| ATOM | 1326 | CD2 | TYR | A | 190 | 12.497 | 9.954 | 40.016 | 1.00 | 52.80 | C |
| ATOM | 1327 | C | TYR | A | 190 | 10 | | 40.57 | 1.00 | 35.367 | 10.707 860.C |
| ATOM | 1328 | O | TYR | A | 190 | 11.596 | 10.319 | 34.452 | 1.00 | 40.37 | O |
| ATOM | 1329 | N | LEU | A | 191 | 9.540 | 10.544 | 35.350 | 1.00 | 38.75 | N |
| ATOM | 1330 | CA | LEU | A | 191 | 8.882 | 9.844 | 34.263 | | 38.05 | 1.00 C |
| ATOM | 1331 | CB | LEU | A | 191 | 7.372 | 9.674 | 34.534 | 1.00 | 38.10 | C |
| ATOM | 1332 | CG | LEU | A | 191 | 6.944 | 8.245 | 34.960 | 1.00 | 38.94 | C |
| ATOM | 1333 | CD1 | LEU | A | 191 | 7.911 | 7.627 | 35.957 | 1.00 | 37.28 | C |
| ATOM | 1334 | CD2 | LEU | A | 191 | 5.529 | 8.208 | 35.514 | 1.00 | 36.41 | C |
| ATOM | 1335 | C | LEU | A | 191 | 9.134 | 10.506 | 32.922 | 1.00 | 38.09 | C |
| ATOM | 1336 | O | LEU | A | 191 | 9.462 | 9.841 | 31.947 | 1.00 | 37.65 | O |
| ATOM | 1337 | N | LYS | A | 192 | 8.987 | 11.827 | 32.879 | 1.00 | 37.85 | N |
| ATOM | 1338 | CA | LYS | A | 192 | 9.101 | 12.518 | 31.633 | 1.00 | 39.20 | C |
| ATOM | 1339 | CB | LYS | A | 192 | 8.502 | 13.953 | 31.684 | 1.00 | 38.95 | C |
| ATOM | 1340 | CG | LYS | A | 192 | | 40.20 | 1.00 | 32.334 | 14.970 | 9.364 C |
| ATOM | 1341 | CD | LYS | A | 192 | 8.579 | 16.265 | 32.703 | 1.00 | 41.75 | C |
| ATOM | 1342 | CE | LYS | A | 192 | 7.792 | 16.872 | 31.595 | 1.00 | 37.21 | C |
| ATOM | 1343 | NZ | LYS | A | 192 | 7.452 | 18.283 | 31 | | 41.51 | 1.00 960.N |
| ATOM | 1344 | C | LYS | A | 192 | 10.539 | 12.441 | 31.109 | 1.00 | 39.66 | C |
| ATOM | 1345 | O | LYS | A | 192 | 10.753 | 12.355 | 29.908 | 1.00 | 39.59 | O |
| ATOM | 1346 | N | SER | A | 193 | 11.528 | 12.470 | 31.991 | 1.00 | 39.94 | N |
| ATOM | 1347 | CA | SER | A | 193 | 12.896 | 12.416 | 31.492 | 1.00 | 40.75 | C |
| ATOM | 1348 | CB | SER | A | 193 | 13.902 | 12.837 | 32.565 | 1.00 | 40.72 | C |

Fig. 26 (Cont.)

```
ATOM  1349  OG   SER A 193    14.899  11.855  32.701  1.00 43.71              O
ATOM  1350  C    SER A 193    13.179  11.009  30.907  1.00 40.75              C
ATOM  1351  O    SER A 193    13.764  10.890  29.823  1.00 41.25              O
ATOM  1352  N    TRP A 194    12.710   9.959  31.571  1.00 39.07              N
ATOM  1353  CA   TRP A 194          39.61 1.00   30.935   8.647   12.746      C
ATOM  1354  CB   TRP A 194    12.166   7.606  31.838  1.00 39.71              C
ATOM  1355  CG   TRP A 194    13.020   7.048  32.886  1.00 44.92              C
ATOM  1356  CD1  TRP A 194    12.974   7.351          47.60 1.00    34.222    C
ATOM  1357  NE1  TRP A 194    13.821   6.532  34.929  1.00 51.38              N
ATOM  1358  CE2  TRP A 194    14.433   5.659  34.061  1.00 51.80              C
ATOM  1359  CD2  TRP A 194    13.943   5.946  32.757  1.00 51.01              C
ATOM  1360  CE3  TRP A 194    14.415   5.169  31.667  1.00 50.56              C
ATOM  1361  CZ3  TRP A 194    15.348   4.175  31.906  1.00 49.13              C
ATOM  1362  CH2  TRP A 194    15.825   3.923  33.217  1.00 51.31              C
ATOM  1363  CZ2  TRP A 194    15.382   4.650  34.304  1.00 51.07              C
ATOM  1364  C    TRP A 194    11.953   8.572  29.629  1.00 38.30              C
ATOM  1365  O    TRP A 194    12.432   7.992  28.640  1.00 37.45              O
ATOM  1366  N    GLU A 195          37.39 1.00   29.642   9.108   10.728      N
ATOM  1367  CA   GLU A 195     9.895   9.158  28.435  1.00 37.90              C
ATOM  1368  CB   GLU A 195     8.594   9.978  28.672  1.00 37.28              C
ATOM  1369  CG   GLU A 195     7.931  10.528          35.53 1.00    27.420    C
ATOM  1370  CD   GLU A 195     6.738  11.470  27.677  1.00 34.81              C
ATOM  1371  OE1  GLU A 195     6.363  11.775  28.851  1.00 33.01              O
ATOM  1372  OE2  GLU A 195     6.159  11.943  26.674  1.00 31        80.0     O
ATOM  1373  C    GLU A 195    10.707   9.739  27.262  1.00 38.60              C
ATOM  1374  O    GLU A 195    10.698   9.202  26.146  1.00 38.88              O
ATOM  1375  N    MET A 196    11.427  10.824  27.515  1.00 39.25              N
ATOM  1376  CA   MET A 196    12.205  11.430  26.464  1.00 41.10              C
ATOM  1377  CB   MET A 196    12.699  12.810  26.881  1.00 42.06              C
ATOM  1378  CG   MET A 196    13.511  13.452  25.769  1.00 42.76              C
ATOM  1379  SD   MET A        51.57 1.00   26.381  14.916   14.339      196   S
ATOM  1380  CE   MET A 196    15.633  14.177  27.586  1.00 43.59              C
ATOM  1381  C    MET A 196    13.381  10.557  25.969  1.00 42.12              C
ATOM  1382  O    MET A 196    13.563  10.396          42.18 1.00    24.730    O
ATOM  1383  N    HIS A 197    14.150   9.996  26.925  1.00 42.21              N
ATOM  1384  CA   HIS A 197    15.345   9.205  26.636  1.00 43.42              C
ATOM  1385  CB   HIS A 197    16.099   8.812  27.939  1.00        44.39       C
ATOM  1386  CG   HIS A 197    16.927   9.925  28.518  1.00 47.16              C
ATOM  1387  ND1  HIS A 197    18.297   9.842  28.655  1.00 49.28              N
ATOM  1388  CE1  HIS A 197    18.752  10.966  29.181  1.00 49.10              C
ATOM  1389  NE2  HIS A 197    17.729  11.777  29.385  1.00 49.11              N
ATOM  1390  CD2  HIS A 197    16.577  11.152  28.976  1.00 48.23              C
ATOM  1391  C    HIS A 197    14.991   7.944  25.872  1.00 42.96              C
ATOM  1392  O    HIS A 197    15.797   7.442  25.122  1.00 42.13              O
ATOM  1393  N    LEU A 198    13.774   7.441  26.069  1.00 42.35              N
ATOM  1394  CA   LEU A 198    13.378   6.217  25.391  1.00 41.91              C
ATOM  1395  CB   LEU A 198    12.346          41.48 1.00    26.218   5.439    C
ATOM  1396  CG   LEU A 198    12.899   4.761  27.484  1.00 42.82              C
ATOM  1397  CD1  LEU A 198    11.775   4.214  28.373  1.00 42.85              C
ATOM  1398  CD2  LEU A 198    13.890   3.656  27.156  1                40.77 00.C
ATOM  1399  C    LEU A 198    12.864   6.481  23.969  1.00 41.23              C
ATOM  1400  O    LEU A 198    12.662   5.541  23.212  1.00 41.86              O
ATOM  1401  N    GLY A 199    12.640   7.745  23.615  1.00 40.03              N
ATOM  1402  CA   GLY A 199    12.053   8.094  22.322  1.00 38.77              C
ATOM  1403  C    GLY A 199    10.646   7.542  22.051  1.00 37.47              C
ATOM  1404  O    GLY A 199    10.292   7.253  20.903  1.00 36.49              O
ATOM  1405  N    LEU A 200     9.854   7.416  23.113  1.00 36.79              N
ATOM  1406  CA   LEU A 200     8.436   7.034  23.052  1.00 36.92              C
ATOM  1407  CB   LEU A 200     7.791   7.101  24.457  1.00 36.26              C
ATOM  1408  CG   LEU A 200     8              37.87 1.00   25.509   6.065  193.C
ATOM  1409  CD1  LEU A 200     7.385   6.228  26.845  1.00 38.91              C
```

Fig. 26 (Cont.)

| | | | | | | | | | |
|---|---|---|---|---|---|---|---|---|---|
| ATOM | 1410 | CD2 | LEU A 200 | 8.061 | 4.609 | 24.964 | 1.00 | 37.18 | C |
| ATOM | 1411 | C | LEU A 200 | 7.602 | 7.898 | 22.086 | | 36.88 1.00 | C |
| ATOM | 1412 | O | LEU A 200 | 6.682 | 7.374 | 21.459 | 1.00 | 38.03 | O |
| ATOM | 1413 | N | ALA A 201 | 7.895 | 9.206 | 21.988 | 1.00 | 36.42 | N |
| ATOM | 1414 | CA | ALA A 201 | 7.156 | 10.128 | 21.114 | 1.00 | 35.63 | C |
| ATOM | 1415 | CB | ALA A 201 | 7.490 | 9.874 | 19.599 | 1.00 | 35.48 | C |
| ATOM | 1416 | C | ALA A 201 | 5.642 | 10.081 | 21.353 | 1.00 | 35.21 | C |
| ATOM | 1417 | O | ALA A 201 | 4.881 | 9.818 | 20.441 | 1.00 | 34.83 | O |
| ATOM | 1418 | N | TRP A 202 | 5.218 | 10.330 | 22.600 | 1.00 | 36.17 | N |
| ATOM | 1419 | CA | TRP A 202 | 3.805 | 10.329 | 23.007 | 1.00 | 35.90 | C |
| ATOM | 1420 | CB | TRP A 202 | 3.647 | 9.587 | 24.313 | 1.00 | 35.09 | C |
| ATOM | 1421 | CG | TRP A 202 | | 36.25 1.00 | 24.224 | 8.116 | 3.761 | C |
| ATOM | 1422 | CD1 | TRP A 202 | 3.933 | 7.360 | 23.091 | 1.00 | 35.22 | C |
| ATOM | 1423 | NE1 | TRP A 202 | 3.976 | 6.027 | 23.421 | 1.00 | 30.37 | N |
| ATOM | 1424 | CE2 | TRP A 202 | 3.874 | 5.890 | 24 | | 34.24 1.00 | 777.C |
| ATOM | 1425 | CD2 | TRP A 202 | 3.725 | 7.187 | 25.323 | 1.00 | 33.98 | C |
| ATOM | 1426 | CE3 | TRP A 202 | 3.573 | 7.323 | 26.718 | 1.00 | 35.51 | C |
| ATOM | 1427 | CZ3 | TRP A 202 | 3.566 | 6.170 | 27.514 | 1.00 | 36.58 | C |
| ATOM | 1428 | CH2 | TRP A 202 | 3.715 | 4.884 | 26.937 | 1.00 | 36.85 | C |
| ATOM | 1429 | CZ2 | TRP A 202 | 3.863 | 4.719 | 25.575 | 1.00 | 36.13 | C |
| ATOM | 1430 | C | TRP A 202 | 3.330 | 11.755 | 23.256 | 1.00 | 36.55 | C |
| ATOM | 1431 | O | TRP A 202 | 2.251 | 11.973 | 23.807 | 1.00 | 37.44 | O |
| ATOM | 1432 | N | SER A 203 | 4.152 | 12.714 | 22.911 | 1.00 | 35.70 | N |
| ATOM | 1433 | CA | SER A 203 | 3.769 | 14.092 | 23.098 | 1.00 | 37.59 | C |
| ATOM | 1434 | CB | SER A 203 | | 37.00 1.00 | 23.098 | 14.968 | 5.039 | C |
| ATOM | 1435 | OG | SER A 203 | 5.070 | 15.767 | 21.982 | 1.00 | 38.93 | O |
| ATOM | 1436 | C | SER A 203 | 2.699 | 14.511 | 22.053 | 1.00 | 36.66 | C |
| ATOM | 1437 | O | SER A 203 | 2.579 | 13.907 | | 36.47 1.00 | 20.994 | O |
| ATOM | 1438 | N | PHE A 204 | 1.921 | 15.531 | 22.366 | 1.00 | 35.35 | N |
| ATOM | 1439 | CA | PHE A 204 | 0.746 | 15.814 | 21.550 | 1.00 | 36.01 | C |
| ATOM | 1440 | CB | PHE A 204 | -0.420 | 14.835 | 21.933 | 1.00 | 34.15 | C |
| ATOM | 1441 | CG | PHE A 204 | -0.892 | 14.996 | 23.336 | 1.00 | 35.45 | C |
| ATOM | 1442 | CD1 | PHE A 204 | -1.998 | 15.778 | 23.621 | 1.00 | 32.40 | C |
| ATOM | 1443 | CE1 | PHE A 204 | -2.444 | 15.959 | 24.957 | 1.00 | 31.73 | C |
| ATOM | 1444 | CZ | PHE A 204 | -1.792 | 15.314 | 26.033 | 1.00 | 34.00 | C |
| ATOM | 1445 | CE2 | PHE A 204 | -0.693 | 14.497 | 25.755 | 1.00 | 36.88 | C |
| ATOM | 1446 | CD2 | PHE A 204 | -0.217 | 14.371 | 24.412 | 1.00 | 37.67 | C |
| ATOM | 1447 | C | PHE A 204 | | 34.75 1.00 | 21.643 | 17.267 | 0.280 | C |
| ATOM | 1448 | O | PHE A 204 | 0.725 | 18.032 | 22.538 | 1.00 | 36.33 | O |
| ATOM | 1449 | N | VAL A 205 | -0.635 | 17.614 | 20.749 | 1.00 | 34.02 | N |
| ATOM | 1450 | CA | VAL A 205 | -1.121 | 18.985 | | 33.36 1.00 | 20.524 | C |
| ATOM | 1451 | CB | VAL A 205 | -0.925 | 19.335 | 19.104 | 1.00 | 32.87 | C |
| ATOM | 1452 | CG1 | VAL A 205 | -1.524 | 20.723 | 18.846 | 1.00 | 33.78 | C |
| ATOM | 1453 | CG2 | VAL A 205 | 0.581 | 19.360 | 18.805 | 1.00 | 35 | 25.C |
| ATOM | 1454 | C | VAL A 205 | -2.640 | 19.062 | 20.807 | 1.00 | 33.87 | C |
| ATOM | 1455 | O | VAL A 205 | -3.372 | 18.168 | 20.415 | 1.00 | 32.64 | O |
| ATOM | 1456 | N | THR A 206 | -3.073 | 20.106 | 21.549 | 1.00 | 34.41 | N |
| ATOM | 1457 | CA | THR A 206 | -4.426 | 20.200 | 22.122 | 1.00 | 34.15 | C |
| ATOM | 1458 | CB | THR A 206 | -4.322 | 20.220 | 23.649 | 1.00 | 33.81 | C |
| ATOM | 1459 | OG1 | THR A 206 | -3.923 | 18.928 | 24.072 | 1.00 | 35.89 | O |
| ATOM | 1460 | CG2 | THR A | | 31.04 1.00 | 24.332 | 20.341 | 5.678- | 206 C |
| ATOM | 1461 | C | THR A 206 | -4.974 | 21.529 | 21.636 | 1.00 | 33.88 | C |
| ATOM | 1462 | O | THR A 206 | -4.257 | 22.515 | 21.651 | 1.00 | 33.11 | O |
| ATOM | 1463 | N | TYR A 207 | -6.229 | 21 | | 33.18 1.00 | 21.207 | 522.N |
| ATOM | 1464 | CA | TYR A 207 | -6.984 | 22.722 | 20.902 | 1.00 | 32.30 | C |
| ATOM | 1465 | CB | TYR A 207 | -7.959 | 22.432 | 19.748 | 1.00 | 31.79 | C |
| ATOM | 1466 | CG | TYR A 207 | -8.966 | 23.565 | 19.620 | 1.00 | | 34.07 C |
| ATOM | 1467 | CD1 | TYR A 207 | -8.544 | 24.893 | 19.251 | 1.00 | 35.44 | C |
| ATOM | 1468 | CE1 | TYR A 207 | -9.472 | 25.964 | 19.197 | 1.00 | 35.03 | C |
| ATOM | 1469 | CZ | TYR A 207 | -10.806 | 25.686 | 19.416 | 1.00 | 39.56 | C |
| ATOM | 1470 | OH | TYR A 207 | -11.731 | 26.690 | 19.331 | 1.00 | 42.12 | O |

Fig. 26 (Cont.)

```
ATOM   1471  CE2 TYR A 207     -11.231  24.406  19.808  1.00 36.43           C
ATOM   1472  CD2 TYR A 207     -10.286  23.361  19.912  1.00 33.51           C
ATOM   1473  C   TYR A 207      -7.785  22.989  22.160  1.00 30.71           C
ATOM   1474  O   TYR A 207      -8.486  22.101  22.617  1.00 31.92           O
ATOM   1475  N   TYR A 208      -7.703  24.189  22.726  1.00 32.09           N
ATOM   1476  CA  TYR A 208      -8.431          32.10 1.00  23.968   24.523  C
ATOM   1477  CB  TYR A 208      -7.493  25.086  25.064  1.00 32.59           C
ATOM   1478  CG  TYR A 208      -8.293  25.529  26.307  1.00 32.32           C
ATOM   1479  CD1 TYR A 208      -8.567  24.641  27.360  1             31.65 00.C
ATOM   1480  CE1 TYR A 208      -9.395  25.014  28.470  1.00 31.66           C
ATOM   1481  CZ  TYR A 208      -9.915  26.291  28.462  1.00 35.28           C
ATOM   1482  OH  TYR A 208     -10.707  26.778  29.480  1.00 42.53           O
ATOM   1483  CE2 TYR A 208      -9.670  27.169  27.417  1.00 34.37           C
ATOM   1484  CD2 TYR A 208      -8.843  26.796  26.355  1.00 32.42           C
ATOM   1485  C   TYR A 208      -9.409  25.623  23.653  1.00 33.74           C
ATOM   1486  O   TYR A 208      -9.027  26.611  23.050  1.00 35.53           O
ATOM   1487  N   SER A 209     -10.666  25.493  24.052  1.00 34.12           N
ATOM   1488  CA  SER A 209     -11.575  26.635  24.041  1.00 34.18           C
ATOM   1489  CB  SER A 209     -12.385          32.98 1.00  22.728   26.638  C
ATOM   1490  OG  SER A 209     -13.343  25.606  22.742  1.00 32.66           O
ATOM   1491  C   SER A 209     -12.500  26.513  25.269  1.00 36.12           C
ATOM   1492  O   SER A 209     -12.624  25.425  25.834           35.32 1.00  O
ATOM   1493  N   PRO A 210     -13.196  27.588  25.681  1.00 38.21           N
ATOM   1494  CA  PRO A 210     -14.197  27.438  26.740  1.00 39.98           C
ATOM   1495  CB  PRO A 210     -14.984  28.788  26.719  1.00 40.45           C
ATOM   1496  CG  PRO A 210     -13.966  29.841  26.093  1.00 40.19           C
ATOM   1497  CD  PRO A 210     -13.115  28.980  25.170  1.00 39.38           C
ATOM   1498  C   PRO A 210     -15.172  26.258  26.397  1.00 40.69           C
ATOM   1499  O   PRO A 210     -15.499  25.437  27.262  1.00 41.13           O
ATOM   1500  N   ASN A 211     -15.627  26.165  25.155  1.00 39.29           N
ATOM   1501  CA  ASN A 211     -16.716  25.212  24.891  1.00 41.22           C
ATOM   1502  CB  ASN A 211     -17.585          40.75 1.00  23.679   25.681  C
ATOM   1503  CG  ASN A 211     -16.717  25.951  22.406  1.00 46.82           C
ATOM   1504  OD1 ASN A 211     -15.930  26.931  22.329  1.00 49.42           O
ATOM   1505  ND2 ASN A 211     -16.813  25.029  21.436           49.92 1.00  N
ATOM   1506  C   ASN A 211     -16.198  23.735  24.793  1.00 39.70           C
ATOM   1507  O   ASN A 211     -16.920  22.789  25.119  1.00 41.33           O
ATOM   1508  N   ASP A 212     -14.924  23.561  24.447  1.00 38.23           N
ATOM   1509  CA  ASP A 212     -14.448  22.269  23.898  1.00 37.70           C
ATOM   1510  CB  ASP A 212     -14.871  22.121  22.417  1.00 37.36           C
ATOM   1511  CG  ASP A 212     -14.723  20.683  21.894  1.00 41.06           C
ATOM   1512  OD1 ASP A 212     -14.967  19.711  22.640  1.00 42.10           O
ATOM   1513  OD2 ASP A 212     -14.400  20.422  20.725  1.00 47.53           O
ATOM   1514  C   ASP A 212     -12.933  22.120  23.941  1.00 35.09           C
ATOM   1515  O   ASP A 212          34.27 1.00  23.453  23.005  12.224-      O
ATOM   1516  N   VAL A 213     -12.462  20.995  24.469  1.00 33.06           N
ATOM   1517  CA  VAL A 213     -11.023  20.776  24.590  1.00 32.70           C
ATOM   1518  CB  VAL A 213     -10.462  20.941  26.046           32.33 1.00  C
ATOM   1519  CG1 VAL A 213      -8.934  20.868  26.036  1.00 29.18           C
ATOM   1520  CG2 VAL A 213     -10.883  22.316  26.682  1.00 30.93           C
ATOM   1521  C   VAL A 213     -10.692  19.426  24.014  1.00 33.38           C
ATOM   1522  O   VAL A 213     -11.220  18.446  24.434  1.00 35.21           O
ATOM   1523  N   ARG A 214      -9.832  19.364  23.023  1.00 34.57           N
ATOM   1524  CA  ARG A 214      -9.581  18.053  22.449  1.00 36.05           C
ATOM   1525  CB  ARG A 214     -10.708  17.638  21.464  1.00 37.44           C
ATOM   1526  CG  ARG A 214     -10.618  18.255  20.056  1.00 41.30           C
ATOM   1527  CD  ARG A 214     -11.954  18.063  19.253  1.00 48.50           C
ATOM   1528  NE  ARG A 214           47.81 1.00  19.142  19.333  12.666-     N
ATOM   1529  CZ  ARG A 214     -12.620  20.175  18.089  1.00 47.92           C
ATOM   1530  NH1 ARG A 214     -11.944  19.902  16.975  1.00 44.27           N
ATOM   1531  NH2 ARG A 214     -13.297  21.313          50.14 1.00  18.166   N
```

Fig. 26 (Cont.)

| ATOM | 1532 | C | ARG A 214 | -8.178 | 17.952 | 21.839 | 1.00 | 35.49 | | | C |
|---|---|---|---|---|---|---|---|---|---|---|---|
| ATOM | 1533 | O | ARG A 214 | -7.568 | 18.975 | 21.442 | 1.00 | 35.13 | | | O |
| ATOM | 1534 | N | VAL A 215 | -7.671 | 16.719 | 21.792 | 1.00 | 35.46 | | | N |
| ATOM | 1535 | CA | VAL A 215 | -6.390 | 16.438 | 21.159 | 1.00 | 36.10 | | | C |
| ATOM | 1536 | CB | VAL A 215 | -5.892 | 15.001 | 21.504 | 1.00 | 37.17 | | | C |
| ATOM | 1537 | CG1 | VAL A 215 | -4.480 | 14.680 | 20.726 | 1.00 | 36.30 | | | C |
| ATOM | 1538 | CG2 | VAL A 215 | -5.765 | 14.871 | 22.990 | 1.00 | 35.21 | | | C |
| ATOM | 1539 | C | VAL A 215 | -6.549 | 16.565 | 19.633 | 1.00 | 36.21 | | | C |
| ATOM | 1540 | O | VAL A 215 | -7.468 | 16.011 | 19.071 | 1.00 | 35.76 | | | O |
| ATOM | 1541 | N | VAL A 216 | | 36.46 | 1.00 | 18.969 | 17.287 | 5.653- | | N |
| ATOM | 1542 | CA | VAL A 216 | -5.797 | 17.486 | 17.524 | 1.00 | 35.77 | | | C |
| ATOM | 1543 | CB | VAL A 216 | -5.926 | 19.002 | 17.131 | 1.00 | 34.87 | | | C |
| ATOM | 1544 | CG1 | VAL A 216 | -7.317 | 19 | | 36.99 | 1.00 | 17.442 | 527. | C |
| ATOM | 1545 | CG2 | VAL A 216 | -4.877 | 19.802 | 17.768 | 1.00 | 31.92 | | | C |
| ATOM | 1546 | C | VAL A 216 | -4.668 | 16.870 | 16.713 | 1.00 | 35.54 | | | C |
| ATOM | 1547 | O | VAL A 216 | -4.770 | 16.832 | 15.524 | 1.00 | 35.08 | | | O |
| ATOM | 1548 | N | ALA A 217 | -3.604 | 16.415 | 17.361 | 1.00 | 35.18 | | | N |
| ATOM | 1549 | CA | ALA A 217 | -2.524 | 15.685 | 16.701 | 1.00 | 35.16 | | | C |
| ATOM | 1550 | CB | ALA A 217 | -1.642 | 16.630 | 15.876 | 1.00 | 34.45 | | | C |
| ATOM | 1551 | C | ALA A 217 | -1.674 | 15.035 | 17.795 | 1.00 | 36.43 | | | C |
| ATOM | 1552 | O | ALA A 217 | -1.573 | 15.563 | 18.970 | 1.00 | 35.76 | | | O |
| ATOM | 1553 | N | GLU A 218 | -1.058 | 13.903 | 17.438 | 1.00 | 36.01 | | | N |
| ATOM | 1554 | CA | GLU A 218 | -0.283 | 13.170 | 18.428 | 1.00 | 36.92 | | | C |
| ATOM | 1555 | CB | GLU A 218 | -1.217 | 12.189 | 19.140 | 1.00 | 36.85 | | | C |
| ATOM | 1556 | CG | GLU A 218 | -2.007 | 11.319 | 18.211 | 1.00 | 41.31 | | | C |
| ATOM | 1557 | CD | GLU A 218 | -3.192 | | 48.35 | 1.00 | 18.937 | 10.712 | | C |
| ATOM | 1558 | OE1 | GLU A 218 | -3.812 | 9.825 | 18.372 | 1.00 | 49.59 | | | O |
| ATOM | 1559 | OE2 | GLU A 218 | -3.484 | 11.103 | 20.086 | 1.00 | 51.24 | | | O |
| ATOM | 1560 | C | GLU A 218 | 0.961 | 12.459 | 17.882 | 1.00 | | 35.60 | | C |
| ATOM | 1561 | O | GLU A 218 | 1.309 | 12.638 | 16.721 | 1.00 | 36.76 | | | O |
| ATOM | 1562 | N | GLY A 219 | 1.615 | 11.650 | 18.715 | 1.00 | 33.76 | | | N |
| ATOM | 1563 | CA | GLY A 219 | 2.759 | 10.852 | 18.269 | 1.00 | 32.34 | | | C |
| ATOM | 1564 | C | GLY A 219 | 4.047 | 11.661 | 18.089 | 1.00 | 33.60 | | | C |
| ATOM | 1565 | O | GLY A 219 | 4.916 | 11.228 | 17.385 | 1.00 | 33.73 | | | O |
| ATOM | 1566 | N | PHE A 220 | 4.167 | 12.836 | 18.715 | 1.00 | 33.06 | | | N |
| ATOM | 1567 | CA | PHE A 220 | 5.340 | 13.697 | 18.561 | 1.00 | 34.63 | | | C |
| ATOM | 1568 | CB | PHE A 220 | 4.972 | 15.145 | 18.840 | 1.00 | 34.25 | | | C |
| ATOM | 1569 | CG | PHE A 220 | 4.084 | 15.733 | 17.817 | 1.00 | 37.73 | | | C |
| ATOM | 1570 | CD1 | PHE A 220 | 4.610 | | 41.73 | 1.00 | 16.709 | 16.380 | | C |
| ATOM | 1571 | CE1 | PHE A 220 | 3.756 | 16.934 | 15.723 | 1.00 | 43.00 | | | C |
| ATOM | 1572 | CZ | PHE A 220 | 2.384 | 16.846 | 15.858 | 1.00 | 39.52 | | | C |
| ATOM | 1573 | CE2 | PHE A 220 | 1.859 | 16.257 | 17.013 | | | 45.41 | 1.00 | C |
| ATOM | 1574 | CD2 | PHE A 220 | 2.710 | 15.694 | 17.978 | 1.00 | 42.24 | | | C |
| ATOM | 1575 | C | PHE A 220 | 6.508 | 13.366 | 19.480 | 1.00 | 34.67 | | | C |
| ATOM | 1576 | O | PHE A 220 | 6.325 | 13.095 | 20.695 | 1.00 | 35.59 | | | O |
| ATOM | 1577 | N | ASP A 221 | 7.706 | 13.435 | 18.904 | 1.00 | 33.89 | | | N |
| ATOM | 1578 | CA | ASP A 221 | 8.948 | 13.416 | 19.663 | 1.00 | 33.44 | | | C |
| ATOM | 1579 | CB | ASP A 221 | 10.020 | 12.854 | 18.721 | 1.00 | 33.92 | | | C |
| ATOM | 1580 | CG | ASP A 221 | 11.304 | 12.473 | 19.436 | 1.00 | 35.43 | | | C |
| ATOM | 1581 | OD1 | ASP A 221 | 11.437 | 12.839 | 20.617 | 1.00 | 35.11 | | | O |
| ATOM | 1582 | OD2 | ASP A 221 | 12.234 | 11.801 | 18.899 | 1.00 | 41.97 | | | O |
| ATOM | 1583 | C | ASP A 221 | 9 | | 34.54 | 1.00 | 20.086 | 14.891 | 282. | C |
| ATOM | 1584 | O | ASP A 221 | 10.005 | 15.619 | 19.361 | 1.00 | 33.14 | | | O |
| ATOM | 1585 | N | PHE A 222 | 8.747 | 15.330 | 21.231 | 1.00 | 33.94 | | | N |
| ATOM | 1586 | CA | PHE A 222 | 9.047 | 16.674 | 21.761 | | | 33.30 | 1.00 | C |
| ATOM | 1587 | CB | PHE A 222 | 10.566 | 16.854 | 22.053 | 1.00 | 32.65 | | | C |
| ATOM | 1588 | CG | PHE A 222 | 10.891 | 17.773 | 23.255 | 1.00 | 33.66 | | | C |
| ATOM | 1589 | CD1 | PHE A 222 | 11.593 | 17.277 | 24.372 | 1.00 | 36.34 | | | C |
| ATOM | 1590 | CE1 | PHE A 222 | 11.880 | 18.160 | 25.505 | 1.00 | 38.03 | | | C |
| ATOM | 1591 | CZ | PHE A 222 | 11.494 | 19.546 | 25.450 | 1.00 | 36.47 | | | C |
| ATOM | 1592 | CE2 | PHE A 222 | 10.813 | 20.032 | 24.345 | 1.00 | 34.11 | | | C |

Fig. 26 (Cont.)

| ATOM | 1593 | CD2 | PHE | A | 222 | 10.496 | 19.131 | 23.269 | 1.00 | 35.96 | | C |
|------|------|-----|-----|---|-----|--------|--------|--------|------|-------|------|---|
| ATOM | 1594 | C | PHE | A | 222 | 8.420 | 17.855 | 20.958 | 1.00 | 34.04 | | C |
| ATOM | 1595 | O | PHE | A | 222 | 9.126 | 18.730 | 20.423 | 1.00 | 32.37 | | O |
| ATOM | 1596 | N | ALA | A | 223 | 34.22 | 1.00 | 20.913 | 17.908 | 7.074 | | N |
| ATOM | 1597 | CA | ALA | A | 223 | 6.406 | 19.013 | 20.213 | 1.00 | 34.27 | | C |
| ATOM | 1598 | CB | ALA | A | 223 | 4.863 | 18.822 | 20.190 | 1.00 | 34.06 | | C |
| ATOM | 1599 | C | ALA | A | 223 | 6.760 | 20.296 | 20 | | 35.31 | 1.00 960. | C |
| ATOM | 1600 | O | ALA | A | 223 | 6.821 | 20.301 | 22.191 | 1.00 | 37.19 | | O |
| ATOM | 1601 | N | ASN | A | 224 | 6.980 | 21.390 | 20.253 | 1.00 | 34.59 | | N |
| ATOM | 1602 | CA | ASN | A | 224 | 7.650 | 22.488 | 20.880 | 1.00 | 35.73 | | C |
| ATOM | 1603 | CB | ASN | A | 224 | 9.202 | 22.365 | 20.626 | 1.00 | 36.23 | | C |
| ATOM | 1604 | CG | ASN | A | 224 | 10.002 | 23.318 | 21.552 | 1.00 | 40.60 | | C |
| ATOM | 1605 | OD1 | ASN | A | 224 | 9.567 | 24.480 | 21.767 | 1.00 | 42.19 | | O |
| ATOM | 1606 | ND2 | ASN | A | 224 | 11.090 | 22.851 | 22.138 | 1.00 | 36.47 | | N |
| ATOM | 1607 | C | ASN | A | 224 | 7.000 | 23.782 | 20.315 | 1.00 | 36.15 | | C |
| ATOM | 1608 | O | ASN | A | 224 | 5.852 | 24.113 | 20.682 | 1.00 | 36.50 | | O |
| ATOM | 1609 | N | GLY | A | 225 | 35.82 | 1.00 | 19.364 | 24.471 | 7.628 | | N |
| ATOM | 1610 | CA | GLY | A | 225 | 6.993 | 25.684 | 18.820 | 1.00 | 34.57 | | C |
| ATOM | 1611 | C | GLY | A | 225 | 5.700 | 25.371 | 18.073 | 1.00 | 35.14 | | C |
| ATOM | 1612 | O | GLY | A | 225 | 5.492 | 24.256 | | | 35.30 | 1.00 17.572 | O |
| ATOM | 1613 | N | ILE | A | 226 | 4.834 | 26.372 | 17.997 | 1.00 | 34.19 | | N |
| ATOM | 1614 | CA | ILE | A | 226 | 3.637 | 26.320 | 17.256 | 1.00 | 34.22 | | C |
| ATOM | 1615 | CB | ILE | A | 226 | 2.522 | 25.670 | 18.071 | 1.00 | 35.34 | | C |
| ATOM | 1616 | CG1 | ILE | A | 226 | 1.258 | 25.449 | 17.205 | 1.00 | 32.85 | | C |
| ATOM | 1617 | CD1 | ILE | A | 226 | 0.353 | 24.265 | 17.910 | 1.00 | 33.04 | | C |
| ATOM | 1618 | CG2 | ILE | A | 226 | 2.238 | 26.412 | 19.407 | 1.00 | 32.98 | | C |
| ATOM | 1619 | C | ILE | A | 226 | 3.229 | 27.743 | 16.836 | 1.00 | 35.59 | | C |
| ATOM | 1620 | O | ILE | A | 226 | 3.402 | 28.751 | 17.578 | 1.00 | 35.03 | | O |
| ATOM | 1621 | N | ASN | A | 227 | 2.680 | 27.825 | 15.641 | 1.00 | 33.34 | | N |
| ATOM | 1622 | CA | ASN | A | 227 | 35.08 | 1.00 | 15.208 | 29.118 | 2.221 | | C |
| ATOM | 1623 | CB | ASN | A | 227 | 3.443 | 30.028 | 14.830 | 1.00 | 33.87 | | C |
| ATOM | 1624 | CG | ASN | A | 227 | 3.156 | 31.492 | 15.149 | 1.00 | 39.07 | | C |
| ATOM | 1625 | OD1 | ASN | A | 227 | 2.038 | 32.013 | | | 38.03 | 1.00 14.811 | O |
| ATOM | 1626 | ND2 | ASN | A | 227 | 4.091 | 32.142 | 15.857 | 1.00 | 33.37 | | N |
| ATOM | 1627 | C | ASN | A | 227 | 1.219 | 28.898 | 14.047 | 1.00 | 33.72 | | C |
| ATOM | 1628 | O | ASN | A | 227 | 0.829 | 27.759 | 13.755 | 1.00 | 32 | 82. | O |
| ATOM | 1629 | N | ILE | A | 228 | 0.810 | 29.989 | 13.426 | 1.00 | 33.95 | | N |
| ATOM | 1630 | CA | ILE | A | 228 | -0.287 | 29.998 | 12.491 | 1.00 | 34.03 | | C |
| ATOM | 1631 | CB | ILE | A | 228 | -1.607 | 30.305 | 13.267 | 1.00 | 34.51 | | C |
| ATOM | 1632 | CG1 | ILE | A | 228 | -2.817 | 29.997 | 12.400 | 1.00 | 34.96 | | C |
| ATOM | 1633 | CD1 | ILE | A | 228 | -4.091 | 29.933 | 13.306 | 1.00 | 35.98 | | C |
| ATOM | 1634 | CG2 | ILE | A | 228 | -1.676 | 31.847 | 13.851 | 1.00 | 34.14 | | C |
| ATOM | 1635 | C | ILE | A | | 35.04 | 1.00 | 11.358 | 31.026 | 0.012- | 228 | C |
| ATOM | 1636 | O | ILE | A | 228 | 0.711 | 31.993 | 11.575 | 1.00 | 35.49 | | O |
| ATOM | 1637 | N | SER | A | 229 | -0.545 | 30.805 | 10.160 | 1.00 | 35.67 | | N |
| ATOM | 1638 | CA | SER | A | 229 | -0.343 | 31.728 | | | 35.66 | 1.00 9.058 | C |
| ATOM | 1639 | CB | SER | A | 229 | -0.757 | 31.066 | 7.765 | 1.00 | 34.71 | | C |
| ATOM | 1640 | OG | SER | A | 229 | -2.137 | 30.758 | 7.799 | 1.00 | 38.04 | | O |
| ATOM | 1641 | C | SER | A | 229 | -1.237 | 32.962 | 9.309 | 1.00 | | 36.98 | C |
| ATOM | 1642 | O | SER | A | 229 | -2.203 | 32.858 | 10.016 | 1.00 | 36.31 | | O |
| ATOM | 1643 | N | PRO | A | 230 | -0.901 | 34.131 | 8.747 | 1.00 | 38.20 | | N |
| ATOM | 1644 | CA | PRO | A | 230 | -1.669 | 35.371 | 8.996 | 1.00 | 37.65 | | C |
| ATOM | 1645 | CB | PRO | A | 230 | -1.003 | 36.404 | 8.092 | 1.00 | 36.93 | | C |
| ATOM | 1646 | CG | PRO | A | 230 | 0.448 | 35.846 | 7.906 | 1.00 | 39.20 | | C |
| ATOM | 1647 | CD | PRO | A | 230 | 0.250 | 34.343 | 7.851 | 1.00 | 37.52 | | C |
| ATOM | 1648 | C | PRO | A | 230 | -3.131 | 35.243 | 8.566 | 1.00 | 38.23 | | C |
| ATOM | 1649 | O | PRO | A | 230 | -3.966 | 35.905 | 9.150 | 1.00 | 37.26 | | O |
| ATOM | 1650 | N | ASP | A | 231 | -3.450 | 34.417 | 7.579 | 1.00 | 38.05 | | N |
| ATOM | 1651 | CA | ASP | A | 231 | -4.865 | | 38.03 | 1.00 | 7.213 | 34.269 | C |
| ATOM | 1652 | CB | ASP | A | 231 | -5.010 | 33.982 | 5.712 | 1.00 | 38.26 | | C |
| ATOM | 1653 | CG | ASP | A | 231 | -4.456 | 32.603 | 5.293 | 1.00 | 39.32 | | C |

Fig. 26 (Cont.)

```
ATOM   1654  OD1 ASP A 231      -4.033  31.814   6.154  1              38.99 00.0
ATOM   1655  OD2 ASP A 231      -4.404  32.212   4.081  1.00 44.52           O
ATOM   1656  C   ASP A 231      -5.574  33.180   8.043  1.00 37.92           C
ATOM   1657  O   ASP A 231      -6.713  32.863   7.769  1.00 37.83           O
ATOM   1658  N   GLY A 232      -4.869  32.544   8.974  1.00 36.65           N
ATOM   1659  CA  GLY A 232      -5.503  31.580   9.847  1.00 37.03           C
ATOM   1660  C   GLY A 232      -5.762  30.189   9.274  1.00 37.14           C
ATOM   1661  O   GLY A 232      -6.376  29.336   9.953  1.00 36.74           O
ATOM   1662  N   LYS A 233      -5.318  29.949   8.043  1.00 37.01           N
ATOM   1663  CA  LYS A 233      -5.631  28.710   7.327  1.00 36.22           C
ATOM   1664  CB  LYS A 233      -5              36.25 1.00  5.838  28.948 577.C
ATOM   1665  CG  LYS A 233      -6.931  29.462   5.201  1.00 41.63           C
ATOM   1666  CD  LYS A 233      -6.707  29.815   3.703  1.00 46.11           C
ATOM   1667  CE  LYS A 233      -7.778  30.744   3.113              51.09 1.00  C
ATOM   1668  NZ  LYS A 233      -8.057  30.295   1.697  1.00 50.52           N
ATOM   1669  C   LYS A 233      -4.669  27.561   7.658  1.00 35.76           C
ATOM   1670  O   LYS A 233      -5.015  26.408   7.464  1.00 35.59           O
ATOM   1671  N   TYR A 234      -3.462  27.869   8.145  1.00 35.12           N
ATOM   1672  CA  TYR A 234      -2.410  26.871   8.263  1.00 34.22           C
ATOM   1673  CB  TYR A 234      -1.330  27.053   7.145  1.00 34.06           C
ATOM   1674  CG  TYR A 234      -1.896  26.919   5.732  1.00 32.79           C
ATOM   1675  CD1 TYR A 234      -2.148  25.670   5.174  1.00 32.97           C
ATOM   1676  CE1 TYR A 234      -2.745  25.543   3.856  1.00 33.54           C
ATOM   1677  CZ  TYR A 234               33.71 1.00   3.140  26.720  3.064-   C
ATOM   1678  OH  TYR A 234      -3.580  26.644   1.890  1.00 36.22           O
ATOM   1679  CE2 TYR A 234      -2.815  27.975   3.694  1.00 33.01           C
ATOM   1680  CD2 TYR A 234      -2.221  28.061   4              33.12 1.00  974.C
ATOM   1681  C   TYR A 234      -1.819  26.963   9.637  1.00 34.94           C
ATOM   1682  O   TYR A 234      -1.568  28.074  10.114  1.00 34.72           O
ATOM   1683  N   VAL A 235      -1.623  25.809  10.293  1.00 35.14           N
ATOM   1684  CA  VAL A 235      -0.927  25.757  11.582  1.00 33.30           C
ATOM   1685  CB  VAL A 235      -1.784  25.013  12.660  1.00 34.41           C
ATOM   1686  CG1 VAL A 235      -0.989  24.687  13.999  1.00 32.89           C
ATOM   1687  CG2 VAL A 235      -3.024  25.863  13.023  1.00 30.91           C
ATOM   1688  C   VAL A 235       0.404  25.042  11.360  1.00 34.91           C
ATOM   1689  O   VAL A 235       0.468  24.051  10.587  1.00 35.77           O
ATOM   1690  N   TYR A 236               35.36 1.00  12.040  25.521  1.455    N
ATOM   1691  CA  TYR A 236       2.834  24.989  11.942  1.00 34.33           C
ATOM   1692  CB  TYR A 236       3.740  26.156  11.579  1.00 33.89           C
ATOM   1693  CG  TYR A 236       3.267  26.934              33.74 1.00  10.372 C
ATOM   1694  CD1 TYR A 236       3.099  26.288   9.127  1.00 34.90           C
ATOM   1695  CE1 TYR A 236       2.669  27.002   8.003  1.00 34.10           C
ATOM   1696  CZ  TYR A 236       2.457  28.374   8.130  1.00 32.56           C
ATOM   1697  OH  TYR A 236       2.046  29.045   7.039  1.00 30.56           O
ATOM   1698  CE2 TYR A 236       2.570  29.034   9.349  1.00 31.47           C
ATOM   1699  CD2 TYR A 236       3.009  28.334  10.450  1.00 31.61           C
ATOM   1700  C   TYR A 236       3.310  24.506  13.324  1.00 34.81           C
ATOM   1701  O   TYR A 236       3.156  25.201  14.358  1.00 33.79           O
ATOM   1702  N   ILE A 237       3.895  23.321  13.373  1.00 34.17           N
ATOM   1703  CA  ILE A 237               33.45 1.00  14.684  22.734  4.228    C
ATOM   1704  CB  ILE A 237       3.213  21.589  15.038  1.00 33.13           C
ATOM   1705  CG1 ILE A 237       1.748  22.142  15.043  1.00 32.08           C
ATOM   1706  CD1 ILE A 237       0.668  21.123              33.48 1.00  15.510 C
ATOM   1707  CG2 ILE A 237       3.519  21.003  16.437  1.00 31.16           C
ATOM   1708  C   ILE A 237       5.650  22.201  14.644  1.00 34.69           C
ATOM   1709  O   ILE A 237       5.961  21.381  13.808  1.00 34              41.O
ATOM   1710  N   ALA A 238       6.505  22.641  15.561  1.00 34.85           N
ATOM   1711  CA  ALA A 238       7.872  22.144  15.541  1.00 36.25           C
ATOM   1712  CB  ALA A 238       8.873  23.180  16.073  1.00 34.69           C
ATOM   1713  C   ALA A 238       7.958  20.846  16.328  1.00 36.17           C
ATOM   1714  O   ALA A 238       7.392  20.736  17.403  1.00 37.20           O
```

Fig. 26 (Cont.)

| ATOM | 1715 | N   | GLU A 239 | 8.703  | 19.888 | 15.799 | 1.00 | 34.77 |        | N |
|------|------|-----|-----------|--------|--------|--------|------|-------|--------|---|
| ATOM | 1716 | CA  | GLU A     | 35.09  | 1.00   | 16.527 | 18.654 | 8.956 | 239 | C |
| ATOM | 1717 | CB  | GLU A 239 | 8.442  | 17.456 | 15.732 | 1.00 | 31.86 |        | C |
| ATOM | 1718 | CG  | GLU A 239 | 8.367  | 16.212 | 16.541 | 1.00 | 31.78 |        | C |
| ATOM | 1719 | CD  | GLU A 239 | 8.051  | 14     |        | 34.25 | 1.00 | 15.664  954 | C |
| ATOM | 1720 | OE1 | GLU A 239 | 7.968  | 15.046 | 14.428 | 1.00 | 32.40 |        | O |
| ATOM | 1721 | OE2 | GLU A 239 | 7.888  | 13.868 | 16.217 | 1.00 | 31.65 |        | O |
| ATOM | 1722 | C   | GLU A 239 | 10.503 | 18.571 | 16.849 | 1.00 |       | 35.45  | C |
| ATOM | 1723 | O   | GLU A 239 | 11.326 | 18.085 | 16.017 | 1.00 | 34.63 |        | O |
| ATOM | 1724 | N   | LEU A 240 | 10.865 | 18.992 | 18.072 | 1.00 | 35.01 |        | N |
| ATOM | 1725 | CA  | LEU A 240 | 12.246 | 19.327 | 18.366 | 1.00 | 35.44 |        | C |
| ATOM | 1726 | CB  | LEU A 240 | 12.392 | 19.738 | 19.828 | 1.00 | 35.07 |        | C |
| ATOM | 1727 | CG  | LEU A 240 | 13.820 | 20.118 | 20.250 | 1.00 | 36.87 |        | C |
| ATOM | 1728 | CD1 | LEU A 240 | 14.025 | 21.662 | 20.091 | 1.00 | 34.53 |        | C |
| ATOM | 1729 | CD2 | LEU A 240 | 13.853 | 19.729 | 21.724 | 1.00 | 35.75 |        | C |
| ATOM | 1730 | C   | LEU A 240 | 13.204 | 18.198 | 18.043 | 1.00 | 34.48 |        | C |
| ATOM | 1731 | O   | LEU A 240 | 14.136 | 18.385 | 17.290 | 1.00 | 35.08 |        | O |
| ATOM | 1732 | N   | LEU A 241 | 12.961 |        | 33.89  | 1.00 | 18.643 | 17.026 | N |
| ATOM | 1733 | CA  | LEU A 241 | 13.903 | 15.948 | 18.584 | 1.00 | 33.80 |        | C |
| ATOM | 1734 | CB  | LEU A 241 | 13.876 | 15.078 | 19.843 | 1.00 | 33.54 |        | C |
| ATOM | 1735 | CG  | LEU A 241 | 14.353 | 15.748 | 21.142 | 1    |       | 34.64 00. | C |
| ATOM | 1736 | CD1 | LEU A 241 | 14.050 | 14.802 | 22.404 | 1.00 | 34.17 |        | C |
| ATOM | 1737 | CD2 | LEU A 241 | 15.889 | 16.154 | 21.148 | 1.00 | 34.36 |        | C |
| ATOM | 1738 | C   | LEU A 241 | 13.734 | 15.125 | 17.312 | 1.00 | 33.66 |        | C |
| ATOM | 1739 | O   | LEU A 241 | 14.592 | 14.349 | 16.982 | 1.00 | 35.43 |        | O |
| ATOM | 1740 | N   | ALA A 242 | 12.680 | 15.330 | 16.562 | 1.00 | 32.37 |        | N |
| ATOM | 1741 | CA  | ALA A 242 | 12.623 | 14.706 | 15.244 | 1.00 | 32.65 |        | C |
| ATOM | 1742 | CB  | ALA A 242 | 11.163 | 14.415 | 14.859 | 1.00 | 31.55 |        | C |
| ATOM | 1743 | C   | ALA A 242 | 13.256 | 15.662 | 14.238 | 1.00 | 32.61 |        | C |
| ATOM | 1744 | O   | ALA A 242 | 13.515 | 15.246 | 13.123 | 1.00 | 30.32 |        | O |
| ATOM | 1745 | N   | HIS A 243 | 13.469 |        | 32.82  | 1.00 | 14.620 | 16.945 | N |
| ATOM | 1746 | CA  | HIS A 243 | 14.081 | 17.947 | 13.709 | 1.00 | 34.94 |        | C |
| ATOM | 1747 | CB  | HIS A 243 | 15.457 | 17.478 | 13.059 | 1.00 | 34.98 |        | C |
| ATOM | 1748 | CG  | HIS A 243 | 16.451 | 16.816 | 13.983 |      |       | 35.62 1.00 | C |
| ATOM | 1749 | ND1 | HIS A 243 | 16.402 | 16.898 | 15.368 | 1.00 | 37.40 |        | N |
| ATOM | 1750 | CE1 | HIS A 243 | 17.429 | 16.237 | 15.879 | 1.00 | 35.13 |        | C |
| ATOM | 1751 | NE2 | HIS A 243 | 18.158 | 15.755 | 14.878 | 1.00 | 34.26 |        | N |
| ATOM | 1752 | CD2 | HIS A 243 | 17.579 | 16.120 | 13.691 | 1.00 | 33.81 |        | C |
| ATOM | 1753 | C   | HIS A 243 | 13.153 | 18.231 | 12.500 | 1.00 | 35.27 |        | C |
| ATOM | 1754 | O   | HIS A 243 | 13.632 | 18.266 | 11.377 | 1.00 | 35.17 |        | O |
| ATOM | 1755 | N   | LYS A 244 | 11.857 | 18.450 | 12.752 | 1.00 | 36.19 |        | N |
| ATOM | 1756 | CA  | LYS A 244 | 10.822 | 18.552 | 11.707 | 1.00 | 37.11 |        | C |
| ATOM | 1757 | CB  | LYS A 244 | 10.004 | 17.272 | 11.640 | 1.00 | 35.54 |        | C |
| ATOM | 1758 | CG  | LYS A 244 | 10.703 |        | 38.78  | 1.00 | 11.009 | 16.044 | C |
| ATOM | 1759 | CD  | LYS A 244 | 9.741  | 14.818 | 11.142 | 1.00 | 38.63 |        | C |
| ATOM | 1760 | CE  | LYS A 244 | 10.174 | 13.473 | 10.451 | 1.00 | 44.51 |        | C |
| ATOM | 1761 | NZ  | LYS A 244 | 11.534 | 13.637 | 9.940  |      |       | 45.51 1.00 | N |
| ATOM | 1762 | C   | LYS A 244 | 9.828  | 19.697 | 11.984 | 1.00 | 36.10 |        | C |
| ATOM | 1763 | O   | LYS A 244 | 9.600  | 20.046 | 13.126 | 1.00 | 37.18 |        | O |
| ATOM | 1764 | N   | ILE A 245 | 9.255  | 20.275 | 10.942 | 1.00 | 34.68 |        | N |
| ATOM | 1765 | CA  | ILE A 245 | 8.171  | 21.181 | 11.125 | 1.00 | 34.01 |        | C |
| ATOM | 1766 | CB  | ILE A 245 | 8.518  | 22.635 | 10.739 | 1.00 | 35.09 |        | C |
| ATOM | 1767 | CG1 | ILE A 245 | 9.496  | 23.233 | 11.786 | 1.00 | 36.46 |        | C |
| ATOM | 1768 | CD1 | ILE A 245 | 9.980  | 24.701 | 11.527 | 1.00 | 35.88 |        | C |
| ATOM | 1769 | CG2 | ILE A 245 | 7.225  | 23.456 | 10.774 | 1.00 | 34.11 |        | C |
| ATOM | 1770 | C   | ILE A 245 | 7.023  | 20.630 | 10.342 | 1.00 | 34.14 |        | C |
| ATOM | 1771 | O   | ILE A 245 |        | 32.50  | 1.00   | 9.176 | 20.321 | 7.169 | O |
| ATOM | 1772 | N   | HIS A 246 | 5.908  | 20.419 | 11.028 | 1.00 | 33.94 |        | N |
| ATOM | 1773 | CA  | HIS A 246 | 4.698  | 19.875 | 10.435 | 1.00 | 36.13 |        | C |
| ATOM | 1774 | CB  | HIS A 246 | 3.983  | 18.964 | 11.459 |      |       | 37.40 1.00 | C |
| ATOM | 1775 | CG  | HIS A 246 | 4.800  | 17.786 | 11.876 | 1.00 | 40.85 |        | C |

Fig. 26 (Cont.)

| ATOM | 1776 | ND1 | HIS A 246 | 4.511 | 16.493 | 11.475 | 1.00 | 40.37 | | N |
|------|------|-----|-----------|-------|--------|--------|------|-------|---|---|
| ATOM | 1777 | CE1 | HIS A 246 | 5.426 | 15.671 | 11.960 | 1.00 | 41.19 | | C |
| ATOM | 1778 | NE2 | HIS A 246 | 6.288 | 16.384 | 12.673 | 1.00 | 42.78 | | N |
| ATOM | 1779 | CD2 | HIS A 246 | 5.934 | 17.713 | 12.612 | 1.00 | 41.46 | | C |
| ATOM | 1780 | C   | HIS A 246 | 3.755 | 21.028 | 10.057 | 1.00 | 35.27 | | C |
| ATOM | 1781 | O   | HIS A 246 | 3.528 | 21.946 | 10.834 | 1.00 | 34.92 | | O |
| ATOM | 1782 | N   | VAL A 247 | 3.196 | 20.949 | 8.867  | 1.00 | 34.55 | | N |
| ATOM | 1783 | CA  | VAL A 247 | 2.257 | 21.965 | 8.411  | 1.00 | 33.69 | | C |
| ATOM | 1784 | CB  | VAL A 247 | 33.00 | 1.00 | 7.016 | 22.477 | 2.633 | | C |
| ATOM | 1785 | CG1 | VAL A 247 | 1.596 | 23.524 | 6.525  | 1.00 | 32.18 | | C |
| ATOM | 1786 | CG2 | VAL A 247 | 4.117 | 22.931 | 6.967  | 1.00 | 30.96 | | C |
| ATOM | 1787 | C   | VAL A 247 | 0.859 | 21.329 | | 33.03 | 1.00 | 8.325 | C |
| ATOM | 1788 | O   | VAL A 247 | 0.706 | 20.276 | 7.730  | 1.00 | 33.28 | | O |
| ATOM | 1789 | N   | TYR A 248 | -0.163 | 21.996 | 8.844 | 1.00 | 33.01 | | N |
| ATOM | 1790 | CA  | TYR A 248 | -1.514 | 21.417 | 8.818 | 1.00 | 33.18 | | C |
| ATOM | 1791 | CB  | TYR A 248 | -1.993 | 21.150 | 10.255 | 1.00 | 32.34 | | C |
| ATOM | 1792 | CG  | TYR A 248 | -1.165 | 20.148 | 11.021 | 1.00 | 33.30 | | C |
| ATOM | 1793 | CD1 | TYR A 248 | -1.553 | 18.769 | 11.097 | 1.00 | 36.14 | | C |
| ATOM | 1794 | CE1 | TYR A 248 | -0.794 | 17.840 | 11.787 | 1.00 | 32.15 | | C |
| ATOM | 1795 | CZ  | TYR A 248 | 0.380 | 18.290 | 12.425 | 1.00 | 37.72 | | C |
| ATOM | 1796 | OH  | TYR A 248 | 1.167 | 17.426 | 13.152 | 1.00 | 37.96 | | O |
| ATOM | 1797 | CE2 | TYR A 248 | | 36.39 | 1.00 | 12.404 | 19.630 | 0.759 | C |
| ATOM | 1798 | CD2 | TYR A 248 | 0.006 | 20.546 | 11.677 | 1.00 | 35.95 | | C |
| ATOM | 1799 | C   | TYR A 248 | -2.456 | 22.426 | 8.211 | 1.00 | 34.62 | | C |
| ATOM | 1800 | O   | TYR A 248 | -2.283 | 23 | | 36.34 | 1.00 | 8.426 634.0 | |
| ATOM | 1801 | N   | GLU A 249 | -3.464 | 21.964 | 7.493 | 1.00 | 34.62 | | N |
| ATOM | 1802 | CA  | GLU A 249 | -4.632 | 22.778 | 7.217 | 1.00 | 36.83 | | C |
| ATOM | 1803 | CB  | GLU A 249 | -5.435 | 22.161 | 6.106 | 1.00 | 37.13 | | C |
| ATOM | 1804 | CG  | GLU A 249 | -5.532 | 23.024 | 4.872 | 1.00 | 41.49 | | C |
| ATOM | 1805 | CD  | GLU A 249 | -5.984 | 22.180 | 3.685 | 1.00 | 48.05 | | C |
| ATOM | 1806 | OE1 | GLU A 249 | -5.206 | 22.074 | 2.711 | 1.00 | 52.01 | | O |
| ATOM | 1807 | OE2 | GLU A 249 | -7.081 | 21.574 | 3.757 | 1.00 | 49.57 | | O |
| ATOM | 1808 | C   | GLU A 249 | -5.532 | 22.824 | 8.442 | 1.00 | 37.27 | | C |
| ATOM | 1809 | O   | GLU A 249 | -5.920 | 21.759 | 8.983 | 1.00 | 37.16 | | O |
| ATOM | 1810 | N   | LYS A 250 | -5.860 | 24.041 | 8.877 | 1.00 | 38.48 | | N |
| ATOM | 1811 | CA  | LYS A 250 | -6.791 | 24.273 | 9.983 | 1.00 | 39.55 | | C |
| ATOM | 1812 | CB  | LYS A 250 | -6.439 | 25.558 | 10.658 | 1.00 | 39.73 | | C |
| ATOM | 1813 | CG  | LYS A 250 | -7.575 | | 42.77 | 1.00 | 11.482 | 26.197 | C |
| ATOM | 1814 | CD  | LYS A 250 | -6.838 | 26.983 | 12.568 | 1.00 | 45.98 | | C |
| ATOM | 1815 | CE  | LYS A 250 | -7.589 | 28.251 | 13.103 | 1.00 | 48.52 | | C |
| ATOM | 1816 | NZ  | LYS A 250 | -8.159 | 29.168 | 12.046 | 1.00 | | 44.19 | N |
| ATOM | 1817 | C   | LYS A 250 | -8.203 | 24.489 | 9.442 | 1.00 | 41.62 | | C |
| ATOM | 1818 | O   | LYS A 250 | -8.425 | 25.516 | 8.813 | 1.00 | 41.69 | | O |
| ATOM | 1819 | N   | HIS A 251 | -9.129 | 23.557 | 9.709 | 1.00 | 42.98 | | N |
| ATOM | 1820 | CA  | HIS A 251 | -10.588 | 23.703 | 9.378 | 1.00 | 44.92 | | C |
| ATOM | 1821 | CB  | HIS A 251 | -11.248 | 22.305 | 9.247 | 1.00 | 43.65 | | C |
| ATOM | 1822 | CG  | HIS A 251 | -10.583 | 21.476 | 8.181 | 1.00 | 45.89 | | C |
| ATOM | 1823 | ND1 | HIS A 251 | -9.401 | 20.793 | 8.399 | 1.00 | 47.41 | | N |
| ATOM | 1824 | CE1 | HIS A 251 | -9.011 | 20.218 | 7.269 | 1.00 | 45.50 | | C |
| ATOM | 1825 | NE2 | HIS A 251 | -9.864 | 20.551 | 6.318 | 1.00 | 43.93 | | N |
| ATOM | 1826 | CD2 | HIS A 251 | -10.842 | | 43.66 | 1.00 | 6.853 | 21.354 | C |
| ATOM | 1827 | C   | HIS A 251 | -11.417 | 24.703 | 10.253 | 1.00 | 45.28 | | C |
| ATOM | 1828 | O   | HIS A 251 | -11.040 | 25.031 | 11.368 | 1.00 | 45.73 | | O |
| ATOM | 1829 | N   | ALA A 252 | -12.516 | 25.215 | 9.694 | | 45.70 | 1.00 | N |
| ATOM | 1830 | CA  | ALA A 252 | -13.409 | 26.175 | 10.350 | 1.00 | 44.79 | | C |
| ATOM | 1831 | CB  | ALA A 252 | -14.680 | 26.478 | 9.452 | 1.00 | 45.82 | | C |
| ATOM | 1832 | C   | ALA A 252 | -13.835 | 25.722 | 11.751 | 1.00 | 44.37 | | C |
| ATOM | 1833 | O   | ALA A 252 | -13.919 | 26.594 | 12.654 | 1.00 | 44.24 | | O |
| ATOM | 1834 | N   | ASN A 253 | -14.098 | 24.400 | 11.909 | 1.00 | 42.76 | | N |
| ATOM | 1835 | CA  | ASN A 253 | -14.238 | 23.686 | 13.207 | 1.00 | 40.47 | | C |
| ATOM | 1836 | CB  | ASN A 253 | -15.012 | 22.415 | 12.963 | 1.00 | 41.89 | | C |

Fig. 26 (Cont.)

| ATOM | 1837 | CG | ASN A 253 | -14.189 | 21.349 | 12.301 | 1.00 | 40.91 | | C |
|---|---|---|---|---|---|---|---|---|---|---|
| ATOM | 1838 | OD1 | ASN A 253 | -13.009 | 21.510 | 12.099 | 1.00 | 38.94 | | O |
| ATOM | 1839 | ND2 | ASN A 253 | -14 | | 44.42 | 1.00 | 11.942 | 20.239 832. | N |
| ATOM | 1840 | C | ASN A 253 | -12.976 | 23.299 | 14.060 | 1.00 | 40.89 | | C |
| ATOM | 1841 | O | ASN A 253 | -13.076 | 22.445 | 15.009 | 1.00 | 40.45 | | O |
| ATOM | 1842 | N | TRP A 254 | -11.794 | 23.878 | 13.717 | | 37.62 | 1.00 | N |
| ATOM | 1843 | CA | TRP A 254 | -10.558 | 23.719 | 14.465 | 1.00 | 36.82 | | C |
| ATOM | 1844 | CB | TRP A 254 | -10.704 | 24.179 | 15.932 | 1.00 | 37.12 | | C |
| ATOM | 1845 | CG | TRP A 254 | -11.568 | 25.369 | 16.005 | 1.00 | 37.87 | | C |
| ATOM | 1846 | CD1 | TRP A 254 | -12.935 | 25.413 | 16.252 | 1.00 | 38.34 | | C |
| ATOM | 1847 | NE1 | TRP A 254 | -13.375 | 26.720 | 16.188 | 1.00 | 40.57 | | N |
| ATOM | 1848 | CE2 | TRP A 254 | -12.300 | 27.530 | 15.883 | 1.00 | 41.09 | | C |
| ATOM | 1849 | CD2 | TRP A 254 | -11.155 | 26.703 | 15.769 | 1.00 | 36.76 | | C |
| ATOM | 1850 | CE3 | TRP A 254 | -9.922 | 27.294 | 15.454 | 1.00 | 39.99 | | C |
| ATOM | 1851 | CZ3 | TRP A 254 | -9.861 | 28.691 | 15.277 | 1.00 | 41.21 | | C |
| ATOM | 1852 | CH2 | TRP A 254 | | 41.39 | 1.00 | 15.427 | 29.480 | 11.002- | C |
| ATOM | 1853 | CZ2 | TRP A 254 | -12.236 | 28.928 | 15.717 | 1.00 | 42.68 | | C |
| ATOM | 1854 | C | TRP A 254 | -9.834 | 22.393 | 14.387 | 1.00 | 36.97 | | C |
| ATOM | 1855 | O | TRP A 254 | -8.801 | 22.231 | 14 | | 38.32 | 1.00 977. | O |
| ATOM | 1856 | N | THR A 255 | -10.343 | 21.454 | 13.632 | 1.00 | 36.63 | | N |
| ATOM | 1857 | CA | THR A 255 | -9.619 | 20.255 | 13.242 | 1.00 | 36.57 | | C |
| ATOM | 1858 | CB | THR A 255 | -10.656 | 19.501 | 12.336 | 1.00 | 36.57 | | C |
| ATOM | 1859 | OG1 | THR A 255 | -11.817 | 19.214 | 13.159 | 1.00 | 38.45 | | O |
| ATOM | 1860 | CG2 | THR A 255 | -10.198 | 18.171 | 11.849 | 1.00 | 33.27 | | C |
| ATOM | 1861 | C | THR A 255 | -8.309 | 20.583 | 12.465 | 1.00 | 37.10 | | C |
| ATOM | 1862 | O | THR A 255 | -8.290 | 21.584 | 11.733 | 1.00 | 38.03 | | O |
| ATOM | 1863 | N | LEU A 256 | -7.262 | 19.744 | 12.572 | 1.00 | 36.14 | | N |
| ATOM | 1864 | CA | LEU A 256 | -6.017 | 19.923 | 11.808 | 1.00 | 37.54 | | C |
| ATOM | 1865 | CB | LEU A 256 | | 36.50 | 1.00 | 12.772 | 20.061 | 4.819- | C |
| ATOM | 1866 | CG | LEU A 256 | -4.843 | 21.299 | 13.693 | 1.00 | 34.37 | | C |
| ATOM | 1867 | CD1 | LEU A 256 | -3.547 | 21.451 | 14.513 | 1.00 | 34.14 | | C |
| ATOM | 1868 | CD2 | LEU A 256 | -5.083 | 22.531 | | 30.29 | 1.00 | 12.881 | C |
| ATOM | 1869 | C | LEU A 256 | -5.764 | 18.753 | 10.844 | 1.00 | 38.98 | | C |
| ATOM | 1870 | O | LEU A 256 | -5.777 | 17.611 | 11.286 | 1.00 | 41.04 | | O |
| ATOM | 1871 | N | THR A 257 | -5.549 | 18.979 | 9.548 | 1.00 | 38.73 | | N |
| ATOM | 1872 | CA | THR A 257 | -5.203 | 17.829 | 8.724 | 1.00 | 39.22 | | C |
| ATOM | 1873 | CB | THR A 257 | -6.232 | 17.572 | 7.571 | 1.00 | 40.16 | | C |
| ATOM | 1874 | OG1 | THR A 257 | -6.423 | 18.767 | 6.811 | 1.00 | 42.00 | | O |
| ATOM | 1875 | CG2 | THR A 257 | -7.650 | 17.261 | 8.146 | 1.00 | 38.88 | | C |
| ATOM | 1876 | C | THR A 257 | -3.784 | 17.969 | 8.190 | 1.00 | 39.91 | | C |
| ATOM | 1877 | O | THR A 257 | -3.442 | 19.014 | 7.635 | 1.00 | 40.06 | | O |
| ATOM | 1878 | N | PRO A 258 | | 40.23 | 1.00 | 8.316 | 16.923 | 2.949- | N |
| ATOM | 1879 | CA | PRO A 258 | -1.541 | 17.056 | 7.913 | 1.00 | 39.16 | | C |
| ATOM | 1880 | CB | PRO A 258 | -0.956 | 15.667 | 8.155 | 1.00 | 38.49 | | C |
| ATOM | 1881 | CG | PRO A 258 | -2.156 | 14.732 | | 40.70 | 1.00 | 8.220 | C |
| ATOM | 1882 | CD | PRO A 258 | -3.286 | 15.554 | 8.791 | 1.00 | 40.04 | | C |
| ATOM | 1883 | C | PRO A 258 | -1.478 | 17.438 | 6.433 | 1.00 | 38.89 | | C |
| ATOM | 1884 | O | PRO A 258 | -2.216 | 16.926 | 5.563 | 1.00 | 38 | 18. | O |
| ATOM | 1885 | N | LEU A 259 | -0.614 | 18.385 | 6.136 | 1.00 | 39.12 | | N |
| ATOM | 1886 | CA | LEU A 259 | -0.420 | 18.756 | 4.737 | 1.00 | 39.83 | | C |
| ATOM | 1887 | CB | LEU A 259 | -0.902 | 20.191 | 4.549 | 1.00 | 40.10 | | C |
| ATOM | 1888 | CG | LEU A 259 | -0.963 | 20.721 | 3.137 | 1.00 | 44.26 | | C |
| ATOM | 1889 | CD1 | LEU A 259 | -2.276 | 20.374 | 2.407 | 1.00 | 46.73 | | C |
| ATOM | 1890 | CD2 | LEU A 259 | -0.773 | 22.211 | 3.283 | 1.00 | 47.50 | | C |
| ATOM | 1891 | C | LEU A | 39.16 | 1.00 | 4.217 | 18.484 | 1.015 | 259 | C |
| ATOM | 1892 | O | LEU A 259 | 1.203 | 17.954 | 3.106 | 1.00 | 39.34 | | O |
| ATOM | 1893 | N | ARG A 260 | 2.025 | 18.848 | 4.994 | 1.00 | 38.61 | | N |
| ATOM | 1894 | CA | ARG A 260 | 3.404 | 18.445 | | 38.48 | 1.00 | 4.700 | C |
| ATOM | 1895 | CB | ARG A 260 | 4.201 | 19.383 | 3.776 | 1.00 | 39.66 | | C |
| ATOM | 1896 | CG | ARG A 260 | 3.742 | 20.726 | 3.426 | 1.00 | 40.88 | | C |
| ATOM | 1897 | CD | ARG A 260 | 3.847 | 20.826 | 1.876 | 1.00 | | 51.43 | C |

Fig. 26 (Cont.)

| ATOM | 1898 | NE | ARG A 260 | 2.587 | 20.284 | 1.335 | 1.00 | 53.92 | | | N |
|------|------|-----|-----------|--------|--------|--------|------|-------|-------|-------|---|
| ATOM | 1899 | CZ | ARG A 260 | 2.221 | 20.249 | 0.082 | 1.00 | 52.78 | | | C |
| ATOM | 1900 | NH1 | ARG A 260 | 3.063 | 20.646 | -0.866 | 1.00 | 56.34 | | | N |
| ATOM | 1901 | NH2 | ARG A 260 | 1.023 | 19.730 | -0.216 | 1.00 | 55.10 | | | N |
| ATOM | 1902 | C | ARG A 260 | 4.262 | 18.423 | 5.935 | 1.00 | 37.66 | | | C |
| ATOM | 1903 | O | ARG A 260 | 3.931 | 19.017 | 6.945 | 1.00 | 37.77 | | | O |
| ATOM | 1904 | N | VAL A 261 | 5.458 | 17.888 | 5.764 | 1.00 | 37.57 | | | N |
| ATOM | 1905 | CA | VAL A 261 | 6.448 | 17.816 | 6.819 | 1.00 | 38.02 | | | C |
| ATOM | 1906 | CB | VAL A 261 | 6.521 | 16.357 | 7.401 | 1.00 | 38.76 | | | C |
| ATOM | 1907 | CG1 | VAL A 261 | 7.766 | | 39.41 | 1.00 | 8.295 | | 16.189 | C |
| ATOM | 1908 | CG2 | VAL A 261 | 5.223 | 16.048 | 8.198 | 1.00 | 38.00 | | | C |
| ATOM | 1909 | C | VAL A 261 | 7.795 | 18.277 | 6.269 | 1.00 | 37.12 | | | C |
| ATOM | 1910 | O | VAL A 261 | 8.288 | 17.729 | 5.297 | 1 | | 38.13 | 00. | O |
| ATOM | 1911 | N | LEU A 262 | 8.366 | 19.303 | 6.865 | 1.00 | 37.51 | | | N |
| ATOM | 1912 | CA | LEU A 262 | 9.737 | 19.713 | 6.531 | 1.00 | 38.67 | | | C |
| ATOM | 1913 | CB | LEU A 262 | 9.883 | 21.269 | 6.572 | 1.00 | 38.26 | | | C |
| ATOM | 1914 | CG | LEU A 262 | 9.412 | 21.981 | 5.286 | 1.00 | 41.28 | | | C |
| ATOM | 1915 | CD1 | LEU A 262 | 7.869 | 21.808 | 5.122 | 1.00 | 43.41 | | | C |
| ATOM | 1916 | CD2 | LEU A 262 | 9.776 | 23.472 | 5.339 | 1.00 | 39.71 | | | C |
| ATOM | 1917 | C | LEU A 262 | 10.725 | 19.062 | 7.488 | 1.00 | 37.27 | | | C |
| ATOM | 1918 | O | LEU A 262 | 10.500 | 19.067 | 8.700 | 1.00 | 36.24 | | | O |
| ATOM | 1919 | N | SER A 263 | 11.832 | 18.583 | 6.941 | 1.00 | 36.36 | | | N |
| ATOM | 1920 | CA | SER A 263 | 12 | | 38.04 | 1.00 | 7.731 | 18.047 | 943. | C |
| ATOM | 1921 | CB | SER A 263 | 13.368 | 16.666 | 7.148 | 1.00 | 36.52 | | | C |
| ATOM | 1922 | OG | SER A 263 | 12.346 | 15.772 | 7.523 | 1.00 | 40.72 | | | O |
| ATOM | 1923 | C | SER A 263 | 14.168 | 18.972 | 7.718 | | | 37.83 | 1.00 | C |
| ATOM | 1924 | O | SER A 263 | 14.446 | 19.538 | 6.686 | 1.00 | 38.42 | | | O |
| ATOM | 1925 | N | PHE A 264 | 14.919 | 19.043 | 8.827 | 1.00 | 36.61 | | | N |
| ATOM | 1926 | CA | PHE A 264 | 16.083 | 19.936 | 8.980 | 1.00 | 36.30 | | | C |
| ATOM | 1927 | CB | PHE A 264 | 15.726 | 21.115 | 9.935 | 1.00 | 36.87 | | | C |
| ATOM | 1928 | CG | PHE A 264 | 14.507 | 21.889 | 9.475 | 1.00 | 37.45 | | | C |
| ATOM | 1929 | CD1 | PHE A 264 | 14.649 | 22.910 | 8.511 | 1.00 | 37.79 | | | C |
| ATOM | 1930 | CE1 | PHE A 264 | 13.553 | 23.568 | 8.018 | 1.00 | 39.33 | | | C |
| ATOM | 1931 | CZ | PHE A 264 | 12.287 | 23.215 | 8.456 | 1.00 | 39.36 | | | C |
| ATOM | 1932 | CE2 | PHE A 264 | 12.122 | 22.176 | 9.378 | 1.00 | 38.00 | | | C |
| ATOM | 1933 | CD2 | PHE A 264 | | | 34.60 | 1.00 | 9.870 | 21.504 | 13.241 | C |
| ATOM | 1934 | C | PHE A 264 | 17.206 | 19.136 | 9.592 | 1.00 | 36.50 | | | C |
| ATOM | 1935 | O | PHE A 264 | 16.970 | 18.070 | 10.158 | 1.00 | 36.85 | | | O |
| ATOM | 1936 | N | ASP A 265 | 18.421 | 19.660 | 9 | | 36.87 | 1.00 | 563. | N |
| ATOM | 1937 | CA | ASP A 265 | 19.516 | 18.968 | 10.283 | 1.00 | 37.94 | | | C |
| ATOM | 1938 | CB | ASP A 265 | 20.831 | 18.952 | 9.457 | 1.00 | 38.26 | | | C |
| ATOM | 1939 | CG | ASP A 265 | 21.274 | 20.364 | 9.035 | 1.00 | 43.72 | | | C |
| ATOM | 1940 | OD1 | ASP A 265 | 20.777 | 21.396 | 9.578 | 1.00 | 45.33 | | | O |
| ATOM | 1941 | OD2 | ASP A 265 | 22.149 | 20.550 | 8.151 | 1.00 | 54.99 | | | O |
| ATOM | 1942 | C | ASP A 265 | 19.765 | 19.579 | 11.669 | 1.00 | 37.07 | | | C |
| ATOM | 1943 | O | ASP A 265 | 20.901 | 19.509 | 12.156 | 1.00 | 37.89 | | | O |
| ATOM | 1944 | N | THR A 266 | 18.737 | 20.195 | 12.282 | 1.00 | 35.90 | | | N |
| ATOM | 1945 | CA | THR A 266 | 18.895 | 20.966 | 13.500 | 1.00 | 35.44 | | | C |
| ATOM | 1946 | CB | THR A 266 | | | 36.08 | 1.00 | 13.157 | 22.460 | 19.248 | C |
| ATOM | 1947 | OG1 | THR A 266 | 19.646 | 23.162 | 14.358 | 1.00 | 36.78 | | | O |
| ATOM | 1948 | CG2 | THR A 266 | 18.081 | 23.261 | 12.662 | 1.00 | 34.22 | | | C |
| ATOM | 1949 | C | THR A 266 | 17.632 | 20.812 | | | | 36.81 | 1.00 14.372 | C |
| ATOM | 1950 | O | THR A 266 | 16.584 | 20.461 | 13.841 | 1.00 | 37.12 | | | O |
| ATOM | 1951 | N | LEU A 267 | 17.743 | 21.018 | 15.696 | 1.00 | 37.50 | | | N |
| ATOM | 1952 | CA | LEU A 267 | 16.608 | 20.894 | 16.630 | 1.00 | 37.98 | | | C |
| ATOM | 1953 | CB | LEU A 267 | 17.103 | 20.588 | 18.067 | 1.00 | 35.64 | | | C |
| ATOM | 1954 | CG | LEU A 267 | 17.568 | 19.192 | 18.430 | 1.00 | 35.22 | | | C |
| ATOM | 1955 | CD1 | LEU A 267 | 18.899 | 18.818 | 17.688 | 1.00 | 30.53 | | | C |
| ATOM | 1956 | CD2 | LEU A 267 | 17.760 | 19.016 | 19.885 | 1.00 | 31.11 | | | C |
| ATOM | 1957 | C | LEU A 267 | 15.808 | 22.190 | 16.606 | 1.00 | 39.17 | | | C |
| ATOM | 1958 | O | LEU A 267 | 16.283 | 23.202 | 17.095 | 1.00 | 42.51 | | | O |

Fig. 26 (Cont.)

```
ATOM   1959  N   VAL A 268          39.30  1.00 16.078  22.176  14.599           N
ATOM   1960  CA  VAL A 268  13.806  23.403 15.880  1.00 37.75                    C
ATOM   1961  CB  VAL A 268  12.877  23.234 14.640  1.00 38.35                    C
ATOM   1962  CG1 VAL A 268  13.732  23.136         38.24  1.00 13.328            C
ATOM   1963  CG2 VAL A 268  12.104  21.903 14.690  1.00 35.74                    C
ATOM   1964  C   VAL A 268  12.984  23.638 17.179  1.00 38.43                    C
ATOM   1965  O   VAL A 268  12.308  22.717 17.683  1.00 37             53.0      O
ATOM   1966  N   ASP A 269  13.037  24.853 17.699  1.00 37.17                    N
ATOM   1967  CA  ASP A 269  12.410  25.205 18.945  1.00 37.21                    C
ATOM   1968  CB  ASP A 269  13.412  25.883 19.851  1.00 35.99                    C
ATOM   1969  CG  ASP A 269  13.025  25.735 21.335  1.00 42.48                    C
ATOM   1970  OD1 ASP A 269  13.811  25.162 22.161  1.00 42.40                    O
ATOM   1971  OD2 ASP A 269  11.908  26.084 21.787  1.00 41.03                    O
ATOM   1972  C   ASP A     36.62  1.00 18.672  26.058  11.140          269       C
ATOM   1973  O   ASP A 269  10.140  25.514 18.234  1.00 35.87                    O
ATOM   1974  N   ASN A 270  11.167  27.376 18.880  1.00 35.81                    N
ATOM   1975  CA  ASN A 270   9.976  28            34.09  1.00 18.661   198.      C
ATOM   1976  CB  ASN A 270   9.900  29.328 19.686  1.00 33.24                    C
ATOM   1977  CG  ASN A 270   9.777  28.797 21.125  1.00 37.60                    C
ATOM   1978  OD1 ASN A 270   9.474  27.592 21.334  1.00           37.71          O
ATOM   1979  ND2 ASN A 270  10.002  29.650 22.109  1.00 40.19                    N
ATOM   1980  C   ASN A 270   9.906  28.754 17.220  1.00 35.29                    C
ATOM   1981  O   ASN A 270  10.942  29.118 16.630  1.00 33.80                    O
ATOM   1982  N   ILE A 271   8.669  28.838 16.701  1.00 34.26                    N
ATOM   1983  CA  ILE A 271   8.309  29.431 15.432  1.00 34.37                    C
ATOM   1984  CB  ILE A 271   7.282  28.512 14.723  1.00 34.35                    C
ATOM   1985  CG1 ILE A 271   7.860  27.083 14.520  1.00 34.42                    C
ATOM   1986  CD1 ILE A 271   6.757  25.991 13.994  1.00 31.41                    C
ATOM   1987  CG2 ILE A 271   6.835  29.095 13.364  1.00 33.52                    C
ATOM   1988  C   ILE A 271   7.660         36.19  1.00 15.644  30.812            C
ATOM   1989  O   ILE A 271   6.680  30.907 16.442  1.00 35.72                    O
ATOM   1990  N   SER A 272   8.168  31.845 14.917  1.00 34.15                    N
ATOM   1991  CA  SER A 272   7.482  33.144 14.663  1            35.58 00.        C
ATOM   1992  CB  SER A 272   8.475  34.344 14.746  1.00 34.34                    C
ATOM   1993  OG  SER A 272   8.930  34.237 16.116  1.00 45.11                    O
ATOM   1994  C   SER A 272   7.065  33.167 13.217  1.00 34.65                    C
ATOM   1995  O   SER A 272   7.662  32.503 12.369  1.00 35.86                    O
ATOM   1996  N   VAL A 273   6.072  33.983 12.942  1.00 34.06                    N
ATOM   1997  CA  VAL A 273   5.552  34.186 11.611  1.00 33.23                    C
ATOM   1998  CB  VAL A 273   4.048  33.706 11.516  1.00 32.49                    C
ATOM   1999  CG1 VAL A 273   3.485  34.051 10.187  1.00 30.14                    C
ATOM   2000  CG2 VAL A 273   4.023  32.178 11.700  1.00 34.15                    C
ATOM   2001  C   VAL A 273   5.671         33.51  1.00 11.290  35.692            C
ATOM   2002  O   VAL A 273   5.210  36.545 12.066  1.00 33.38                    O
ATOM   2003  N   ASP A 274   6.297  36.008 10.151  1.00 33.40                    N
ATOM   2004  CA  ASP A 274   6.292  37.355  9.675              33.25  1.00       C
ATOM   2005  CB  ASP A 274   7.408  37.537  8.672  1.00 33.45                    C
ATOM   2006  CG  ASP A 274   7.375  38.935  8.011  1.00 37.92                    C
ATOM   2007  OD1 ASP A 274   6.923  39.900  8.673  1.00 40.51                    O
ATOM   2008  OD2 ASP A 274   7.758  39.199  6.831  1.00 42.64                    O
ATOM   2009  C   ASP A 274   4.888  37.647  9.072  1.00 34.23                    C
ATOM   2010  O   ASP A 274   4.488  37.020  8.088  1.00 33.77                    O
ATOM   2011  N   PRO A 275   4.140  38.586  9.653  1.00 35.07                    N
ATOM   2012  CA  PRO A 275   2.729  38.798  9.218  1.00 36.57                    C
ATOM   2013  CB  PRO A 275   2.165  39.873 10.199  1.00 35.47                    C
ATOM   2014  CG  PRO A 275         38.43  1.00 10.741  40.623  3.583             C
ATOM   2015  CD  PRO A 275   4.541  39.431 10.820  1.00 34.55                    C
ATOM   2016  C   PRO A 275   2.686  39.285  7.791  1.00 37.81                    C
ATOM   2017  O   PRO A 275   1.696  38.995  7.080              38.36  1.00       O
ATOM   2018  N   VAL A 276   3.744  39.984  7.329  1.00 38.59                    N
ATOM   2019  CA  VAL A 276   3.675  40.547  5.973  1.00 36.29                    C
```

Fig. 26 (Cont.)

| | | | | | | | | | |
|---|---|---|---|---|---|---|---|---|---|
| ATOM | 2020 | CB | VAL | A | 276 | 4.694 | 41.683 | 5.742 | 1.00 37.07 | C |
| ATOM | 2021 | CG1 | VAL | A | 276 | 4.540 | 42.240 | 4.371 | 1.00 36.17 | C |
| ATOM | 2022 | CG2 | VAL | A | 276 | 4.506 | 42.816 | 6.733 | 1.00 37.33 | C |
| ATOM | 2023 | C | VAL | A | 276 | 3.879 | 39.460 | 4.934 | 1.00 36.27 | C |
| ATOM | 2024 | O | VAL | A | 276 | 3.203 | 39.417 | 3.957 | 1.00 37.78 | O |
| ATOM | 2025 | N | THR | A | 277 | 4.792 | 38.544 | 5.108 | 1.00 35.62 | N |
| ATOM | 2026 | CA | THR | A | 277 | 5.058 | 37.601 | 3.995 | 1.00 34.69 | C |
| ATOM | 2027 | CB | THR | A | 277 | 35.19 1.00 | 3.845 | 37.326 6.630 | | C |
| ATOM | 2028 | OG1 | THR | A | 277 | 7.177 | 36.964 | 5.135 | 1.00 30.50 | O |
| ATOM | 2029 | CG2 | THR | A | 277 | 7.394 | 38.542 | 3.375 | 1.00 35.59 | C |
| ATOM | 2030 | C | THR | A | 277 | 4.474 | 36.221 | | 34.81 1.00 4.344 | C |
| ATOM | 2031 | O | THR | A | 277 | 4.446 | 35.356 | 3.473 | 1.00 32.82 | O |
| ATOM | 2032 | N | GLY | A | 278 | 4.208 | 35.978 | 5.643 | 1.00 33.60 | N |
| ATOM | 2033 | CA | GLY | A | 278 | 3.989 | 34.616 | 6.100 | 1.00 34.17 | C |
| ATOM | 2034 | C | GLY | A | 278 | 5.206 | 33.698 | 6.375 | 1.00 35.09 | C |
| ATOM | 2035 | O | GLY | A | 278 | 5.017 | 32.527 | 6.812 | 1.00 35.28 | O |
| ATOM | 2036 | N | ASP | A | 279 | 6.433 | 34.167 | 6.115 | 1.00 34.69 | N |
| ATOM | 2037 | CA | ASP | A | 279 | 7.656 | 33.401 | 6.391 | 1.00 34.40 | C |
| ATOM | 2038 | CB | ASP | A | 279 | 8.945 | 34.272 | 6.187 | 1.00 35.43 | C |
| ATOM | 2039 | CG | ASP | A | 279 | 9.145 | 34.732 | 4.776 | 1.00 34.63 | C |
| ATOM | 2040 | OD1 | ASP | A | 279 | 39.15 1.00 | 3.816 | 34.305 8.400 | | O |
| ATOM | 2041 | OD2 | ASP | A | 279 | 10.086 | 35.524 | 4.515 | 1.00 37.56 | O |
| ATOM | 2042 | C | ASP | A | 279 | 7.721 | 32.961 | 7.835 | 1.00 35.01 | C |
| ATOM | 2043 | O | ASP | A | 279 | 7.336 | 33.729 | | 35.36 1.00 8.728 | O |
| ATOM | 2044 | N | LEU | A | 280 | 8.206 | 31.733 | 8.066 | 1.00 33.92 | N |
| ATOM | 2045 | CA | LEU | A | 280 | 8.508 | 31.285 | 9.406 | 1.00 34.98 | C |
| ATOM | 2046 | CB | LEU | A | 280 | 8.380 | 29.757 | 9.477 | 1.00 35.21 | C |
| ATOM | 2047 | CG | LEU | A | 280 | 6.944 | 29.217 | 9.510 | 1.00 34.96 | C |
| ATOM | 2048 | CD1 | LEU | A | 280 | 6.240 | 29.563 | 8.189 | 1.00 37.82 | C |
| ATOM | 2049 | CD2 | LEU | A | 280 | 7.065 | 27.655 | 9.748 | 1.00 33.44 | C |
| ATOM | 2050 | C | LEU | A | 280 | 9.945 | 31.695 | 9.758 | 1.00 35.04 | C |
| ATOM | 2051 | O | LEU | A | 280 | 10.832 | 31.675 | 8.879 | 1.00 34.34 | O |
| ATOM | 2052 | N | TRP | A | 281 | 10.153 | 32.127 | 11.007 | 1.00 33.43 | N |
| ATOM | 2053 | CA | TRP | A | 281 | 34.97 1.00 | 11.500 | 32.436 11.486 | | C |
| ATOM | 2054 | CB | TRP | A | 281 | 11.596 | 33.923 | 11.934 | 1.00 33.74 | C |
| ATOM | 2055 | CG | TRP | A | 281 | 11.665 | 34.802 | 10.738 | 1.00 35.21 | C |
| ATOM | 2056 | CD1 | TRP | A | 281 | 10.611 | 35 | | 33.44 1.00 9.929 196. | C |
| ATOM | 2057 | NE1 | TRP | A | 281 | 11.096 | 35.979 | 8.919 | 1.00 35.39 | N |
| ATOM | 2058 | CE2 | TRP | A | 281 | 12.467 | 36.030 | 9.003 | 1.00 33.61 | C |
| ATOM | 2059 | CD2 | TRP | A | 281 | 12.847 | 35.299 | 10.131 | 1.00 33.93 | C |
| ATOM | 2060 | CE3 | TRP | A | 281 | 14.224 | 35.231 | 10.454 | 1.00 36.39 | C |
| ATOM | 2061 | CZ3 | TRP | A | 281 | 15.150 | 35.865 | 9.626 | 1.00 35.04 | C |
| ATOM | 2062 | CH2 | TRP | A | 281 | 14.720 | 36.608 | 8.529 | 1.00 38.12 | C |
| ATOM | 2063 | CZ2 | TRP | A | 281 | 13.390 | 36.690 | 8.203 | 1.00 36.72 | C |
| ATOM | 2064 | C | TRP | A | 281 | 11.635 | 31.534 | 12.706 | 1.00 35.53 | C |
| ATOM | 2065 | O | TRP | A | 281 | 10.721 | 31.512 | 13.579 | 1.00 35.08 | O |
| ATOM | 2066 | N | VAL | A | 282 | 12.734 | 30.785 | 12.747 | 1.00 35.23 | N |
| ATOM | 2067 | CA | VAL | A | 282 | 12.804 | 29.647 | 13.654 | 1.00 35.76 | C |
| ATOM | 2068 | CB | VAL | A | 282 | 12.674 | 28.314 | 12.870 | 1.00 35.91 | C |
| ATOM | 2069 | CG1 | VAL | A | 282 | 12.641 | | 34.14 1.00 | 13.838 27.059 | C |
| ATOM | 2070 | CG2 | VAL | A | 282 | 11.363 | 28.325 | 12.102 | 1.00 34.49 | C |
| ATOM | 2071 | C | VAL | A | 282 | 14.032 | 29.700 | 14.534 | 1.00 36.31 | C |
| ATOM | 2072 | O | VAL | A | 282 | 15.164 | 29.866 | 14.046 | 1.00 37.64 | O |
| ATOM | 2073 | N | GLY | A | 283 | 13.846 | 29.552 | 15.829 | 1.00 35.84 | N |
| ATOM | 2074 | CA | GLY | A | 283 | 14.993 | 29.482 | 16.734 | 1.00 36.35 | C |
| ATOM | 2075 | C | GLY | A | 283 | 15.415 | 28.014 | 16.892 | 1.00 37.25 | C |
| ATOM | 2076 | O | GLY | A | 283 | 14.544 | 27.172 | 17.155 | 1.00 38.11 | O |
| ATOM | 2077 | N | CYS | A | 284 | 16.701 | 27.706 | 16.751 | 1.00 35.43 | N |
| ATOM | 2078 | CA | CYS | A | 284 | 17.173 | 26.285 | 16.745 | 1.00 36.36 | C |
| ATOM | 2079 | CB | CYS | A | 284 | 17.664 | 25.903 | 15.329 | 1.00 38.08 | C |
| ATOM | 2080 | SG | CYS | A | 284 | 16.369 | 26.160 | 14.079 | 1.00 38.55 | S |

Fig. 26 (Cont.)

| | | | | | | | | | | |
|---|---|---|---|---|---|---|---|---|---|---|
| ATOM | 2081 | C | CYS | A | 284 | 18.402 | 26.044 | 17.626 | 1.00 35.59 | C |
| ATOM | 2082 | O | CYS | A | 284 | 19.202 | | 34.97 | 1.00 17.896 26.959 | O |
| ATOM | 2083 | N | HIS | A | 285 | 18.547 | 24.798 | 18.042 | 1.00 35.57 | N |
| ATOM | 2084 | CA | HIS | A | 285 | 19.703 | 24.277 | 18.733 | 1.00 34.90 | C |
| ATOM | 2085 | CB | HIS | A | 285 | 19.242 | 23.522 | 19.989 | 35.13 1.00 | C |
| ATOM | 2086 | CG | HIS | A | 285 | 18.358 | 24.331 | 20.870 | 1.00 35.99 | C |
| ATOM | 2087 | ND1 | HIS | A | 285 | 18.771 | 25.516 | 21.435 | 1.00 38.14 | N |
| ATOM | 2088 | CE1 | HIS | A | 285 | 17.795 | 25.998 | 22.199 | 1.00 39.90 | C |
| ATOM | 2089 | NE2 | HIS | A | 285 | 16.764 | 25.172 | 22.135 | 1.00 39.47 | N |
| ATOM | 2090 | CD2 | HIS | A | 285 | 17.089 | 24.118 | 21.315 | 1.00 40.71 | C |
| ATOM | 2091 | C | HIS | A | 285 | 20.411 | 23.286 | 17.842 | 1.00 34.03 | C |
| ATOM | 2092 | O | HIS | A | 285 | 19.916 | 22.151 | 17.681 | 1.00 33.69 | O |
| ATOM | 2093 | N | PRO | A | 286 | 21.590 | 23.665 | 17.315 | 1.00 33.15 | N |
| ATOM | 2094 | CA | PRO | A | 286 | 22.401 | 22.766 | 16.465 | 1.00 32.00 | C |
| ATOM | 2095 | CB | PRO | A | 286 | 23 | 31.30 1.00 | 16.236 | 23.571 720.C | |
| ATOM | 2096 | CG | PRO | A | 286 | 23.257 | 25.016 | 16.382 | 1.00 34.51 | C |
| ATOM | 2097 | CD | PRO | A | 286 | 22.238 | 24.965 | 17.555 | 1.00 32.15 | C |
| ATOM | 2098 | C | PRO | A | 286 | 22.734 | 21.430 | 17.151 | 32.05 1.00 | C |
| ATOM | 2099 | O | PRO | A | 286 | 22.743 | 20.386 | 16.486 | 1.00 32.50 | O |
| ATOM | 2100 | N | ASN | A | 287 | 23.012 | 21.459 | 18.458 | 1.00 32.77 | N |
| ATOM | 2101 | CA | ASN | A | 287 | 23.553 | 20.284 | 19.184 | 1.00 34.73 | C |
| ATOM | 2102 | CB | ASN | A | 287 | 25.055 | 20.480 | 19.528 | 1.00 33.92 | C |
| ATOM | 2103 | CG | ASN | A | 287 | 25.691 | 19.232 | 20.173 | 1.00 35.28 | C |
| ATOM | 2104 | OD1 | ASN | A | 287 | 25.215 | 18.754 | 21.189 | 1.00 36.25 | O |
| ATOM | 2105 | ND2 | ASN | A | 287 | 26.798 | 18.736 | 19.605 | 1.00 32.23 | N |
| ATOM | 2106 | C | ASN | A | 287 | 22.694 | 20.037 | 20.409 | 1.00 35.00 | C |
| ATOM | 2107 | O | ASN | A | 287 | 22.555 | 20.898 | 21.275 | 1.00 34.09 | O |
| ATOM | 2108 | N | GLY | A | 288 | | 37.42 1.00 | 20.454 | 18.854 22.082 | N |
| ATOM | 2109 | CA | GLY | A | 288 | 21.085 | 18.518 | 21.479 | 1.00 37.60 | C |
| ATOM | 2110 | C | GLY | A | 288 | 21.784 | 18.243 | 22.802 | 1.00 37.64 | C |
| ATOM | 2111 | O | GLY | A | 288 | 21.250 | 18.536 | 23 | 38.35 1.00 875.O | |
| ATOM | 2112 | N | MET | A | 289 | 23.016 | 17.768 | 22.732 | 1.00 37.85 | N |
| ATOM | 2113 | CA | MET | A | 289 | 23.762 | 17.457 | 23.971 | 1.00 38.03 | C |
| ATOM | 2114 | CB | MET | A | 289 | 25.070 | 16.761 | 23.666 | 1.00 37.67 | C |
| ATOM | 2115 | CG | MET | A | 289 | 24.888 | 15.399 | 23.042 | 1.00 41.85 | C |
| ATOM | 2116 | SD | MET | A | 289 | 23.939 | 14.291 | 24.171 | 1.00 50.34 | S |
| ATOM | 2117 | CE | MET | A | 289 | 25.464 | 13.782 | 25.263 | 1.00 37.58 | C |
| ATOM | 2118 | C | MET | A | 289 | 24.028 | 18.717 | 24.787 | 1.00 37.36 | C |
| ATOM | 2119 | O | MET | A | 289 | 23.968 | 18.679 | 26.029 | 1.00 37.56 | O |
| ATOM | 2120 | N | ARG | A | 290 | 24.314 | 19.819 | 24.091 | 1.00 35.15 | N |
| ATOM | 2121 | CA | ARG | A | 290 | | 35.57 1.00 | 24.740 | 20.993 24.878 | C |
| ATOM | 2122 | CB | ARG | A | 290 | 25.619 | 21.921 | 23.767 | 1.00 34.46 | C |
| ATOM | 2123 | CG | ARG | A | 290 | 27.026 | 21.515 | 23.429 | 1.00 37.28 | C |
| ATOM | 2124 | CD | ARG | A | 290 | 27.582 | 22.348 | | 40.66 1.00 22.248 | C |
| ATOM | 2125 | NE | ARG | A | 290 | 28.784 | 21.717 | 21.803 | 1.00 41.34 | N |
| ATOM | 2126 | CZ | ARG | A | 290 | 29.132 | 21.502 | 20.545 | 1.00 39.79 | C |
| ATOM | 2127 | NH1 | ARG | A | 290 | 28.382 | 21.917 | 19.510 | 1.00 33.83 | N |
| ATOM | 2128 | NH2 | ARG | A | 290 | 30.265 | 20.850 | 20.355 | 1.00 33.16 | N |
| ATOM | 2129 | C | ARG | A | 290 | 23.748 | 21.750 | 25.353 | 1.00 36.26 | C |
| ATOM | 2130 | O | ARG | A | 290 | 23.952 | 22.453 | 26.346 | 1.00 35.82 | O |
| ATOM | 2131 | N | ILE | A | 291 | 22.564 | 21.629 | 24.743 | 1.00 36.88 | N |
| ATOM | 2132 | CA | ILE | A | 291 | 21.380 | 22.223 | 25.317 | 1.00 38.88 | C |
| ATOM | 2133 | CB | ILE | A | 291 | 20.380 | 22.730 | 24.223 | 1.00 38.73 | C |
| ATOM | 2134 | CG1 | ILE | A | 291 | | 42.08 1.00 | 24.819 | 23.809 19.468 | C |
| ATOM | 2135 | CD1 | ILE | A | 291 | 20.177 | 25.146 | 24.995 | 1.00 40.92 | C |
| ATOM | 2136 | CG2 | ILE | A | 291 | 19.560 | 21.612 | 23.706 | 1.00 38.94 | C |
| ATOM | 2137 | C | ILE | A | 291 | 20.700 | 21.410 | | 40.12 1.00 26.422 | C |
| ATOM | 2138 | O | ILE | A | 291 | 20.185 | 22.026 | 27.368 | 1.00 41.63 | O |
| ATOM | 2139 | N | PHE | A | 292 | 20.675 | 20.071 | 26.329 | 1.00 40.96 | N |
| ATOM | 2140 | CA | PHE | A | 292 | 20.029 | 19.214 | 27.354 | 1.00 41 48.C | |
| ATOM | 2141 | CB | PHE | A | 292 | 19.474 | 17.893 | 26.746 | 1.00 40.75 | C |

Fig. 26 (Cont.)

```
ATOM  2142  CG   PHE A 292    18.157  18.077  26.009  1.00 43.64           C
ATOM  2143  CD1  PHE A 292    16.929  18.027  26.712  1.00 44.72           C
ATOM  2144  CE1  PHE A 292    15.714  18.265  26.061  1.00 44.23           C
ATOM  2145  CZ   PHE A 292    15.715  18.515  24.701  1.00 44.35           C
ATOM  2146  CE2  PHE A 292    16.916  18.543  23.989  1.00 41.07           C
ATOM  2147  CD2  PHE A         37.68 1.00  24.636  18.331  18.134      292 C
ATOM  2148  C    PHE A 292    20.935  18.898  28.558  1.00 42.81           C
ATOM  2149  O    PHE A 292    20.468  18.866  29.693  1.00 44.34           O
ATOM  2150  N    PHE A 293    22.213  18.645          42.69 1.00   28.311  N
ATOM  2151  CA   PHE A 293    23.173  18.293  29.349  1.00 43.21           C
ATOM  2152  CB   PHE A 293    23.788  16.910  29.038  1.00 43.75           C
ATOM  2153  CG   PHE A 293    22.740  15.901  28.717  1.00        48.75    C
ATOM  2154  CD1  PHE A 293    22.126  15.175  29.736  1.00 55.30           C
ATOM  2155  CE1  PHE A 293    21.065  14.302  29.434  1.00 58.20           C
ATOM  2156  CZ   PHE A 293    20.598  14.191  28.096  1.00 57.23           C
ATOM  2157  CE2  PHE A 293    21.203  14.915  27.100  1.00 54.30           C
ATOM  2158  CD2  PHE A 293    22.247  15.780  27.414  1.00 52.21           C
ATOM  2159  C    PHE A 293    24.180  19.417  29.507  1.00 42.79           C
ATOM  2160  O    PHE A 293    25.315  19.326  29.100  1.00 41.80           O
ATOM  2161  N    TYR A 294    23.702  20.479  30.135  1.00 43.57           N
ATOM  2162  CA   TYR A 294    24.401  21.746  30.284  1.00 45.02           C
ATOM  2163  CB   TYR A 294    23.526          46.01 1.00   31.037  22.799  C
ATOM  2164  CG   TYR A 294    24.152  24.205  30.977  1.00 47.51           C
ATOM  2165  CD1  TYR A 294    24.006  24.985  29.812  1.00 44.90           C
ATOM  2166  CE1  TYR A 294    24.593  26.224  29.694  1          44.75 00. C
ATOM  2167  CZ   TYR A 294    25.352  26.741  30.744  1.00 47.58           C
ATOM  2168  OH   TYR A 294    25.905  28.003  30.542  1.00 46.57           O
ATOM  2169  CE2  TYR A 294    25.551  25.993  31.946  1.00 48.38           C
ATOM  2170  CD2  TYR A 294    24.959  24.713  32.045  1.00 47.99           C
ATOM  2171  C    TYR A 294    25.714  21.656  30.995  1.00 45.14           C
ATOM  2172  O    TYR A 294    25.856  20.952  31.994  1.00 44.98           O
ATOM  2173  N    ASP A 295    26.696  22.369  30.458  1.00 45.72           N
ATOM  2174  CA   ASP A 295    27.841  22.770  31.289  1.00 44.85           C
ATOM  2175  CB   ASP A 295    28.846  21.656  31.525  1.00 45.38           C
ATOM  2176  CG   ASP A 295    29              45.74 1.00   30.410  21.533  826.C
ATOM  2177  OD1  ASP A 295    29.314  21.714  29.268  1.00 51.35           O
ATOM  2178  OD2  ASP A 295    31.049  21.298  30.557  1.00 29.57           O
ATOM  2179  C    ASP A 295    28.482  24.038  30.778          44.90 1.00   C
ATOM  2180  O    ASP A 295    28.721  24.215  29.559  1.00 43.68           O
ATOM  2181  N    ALA A 296    28.691  24.946  31.730  1.00 45.37           N
ATOM  2182  CA   ALA A 296    29.368  26.229  31.514  1.00 45.73           C
ATOM  2183  CB   ALA A 296    29.614  26.940  32.916  1.00 45.62           C
ATOM  2184  C    ALA A 296    30.688  26.163  30.637  1.00 45.45           C
ATOM  2185  O    ALA A 296    30.946  27.107  29.875  1.00 46.29           O
ATOM  2186  N    GLU A 297    31.471  25.070  30.697  1.00 43.77           N
ATOM  2187  CA   GLU A 297    32.705  24.932  29.849  1.00 44.04           C
ATOM  2188  CB   GLU A 297    33.700  23.883  30.400  1.00 43.14           C
ATOM  2189  CG   GLU A 297           49.50 1.00   30.341  24.294  35.192   C
ATOM  2190  CD   GLU A 297    35.787  24.492  28.910  1.00 53.17           C
ATOM  2191  OE1  GLU A 297    35.807  25.653  28.377  1.00 52.55           O
ATOM  2192  OE2  GLU A 297    36.267  23.486  28              53.99 1.00  314.O
ATOM  2193  C    GLU A 297    32.483  24.644  28.344  1.00 42.21           C
ATOM  2194  O    GLU A 297    33.424  24.716  27.554  1.00 42.70           O
ATOM  2195  N    ASN A 298    31.267  24.289  27.961  1.00 40.33           N
ATOM  2196  CA   ASN A 298    30.946  23.865  26.612  1.00 39.13           C
ATOM  2197  CB   ASN A 298    31.202  22.346  26.506  1.00 40.35           C
ATOM  2198  CG   ASN A 298    30.966  21.794  25.094  1.00 41.67           C
ATOM  2199  OD1  ASN A 298    31.206  22.476  24.090  1.00 41.46           O
ATOM  2200  ND2  ASN A 298    30.453  20.561  25.020  1.00 43.79           N
ATOM  2201  C    ASN A 298    29.488  24.274  26.247  1.00 38.55           C
ATOM  2202  O    ASN A 298           37.77 1.00   25.985  23.441  28.605   O
```

Fig. 26 (Cont.)

| ATOM | 2203 | N | PRO A 299 | 29.221 | 25.579 | 26.255 | 1.00 | 36.84 | | | N |
|---|---|---|---|---|---|---|---|---|---|---|---|
| ATOM | 2204 | CA | PRO A 299 | 27.834 | 26.019 | 26.174 | 1.00 | 35.68 | | | C |
| ATOM | 2205 | CB | PRO A 299 | 27.901 | 27.514 | | | 35.75 | 1.00 | 26.553 | C |
| ATOM | 2206 | CG | PRO A 299 | 29.323 | 27.943 | 26.181 | 1.00 | 36.52 | | | C |
| ATOM | 2207 | CD | PRO A 299 | 30.191 | 26.702 | 26.355 | 1.00 | 37.08 | | | C |
| ATOM | 2208 | C | PRO A 299 | 27.255 | 25.788 | 24.769 | 1.00 | 34.77 | | | C |
| ATOM | 2209 | O | PRO A 299 | 28.038 | 25.687 | 23.782 | 1.00 | 33.59 | | | O |
| ATOM | 2210 | N | PRO A 300 | 25.923 | 25.696 | 24.690 | 1.00 | 32.17 | | | N |
| ATOM | 2211 | CA | PRO A 300 | 25.229 | 25.526 | 23.391 | 1.00 | 32.30 | | | C |
| ATOM | 2212 | CB | PRO A 300 | 23.735 | 25.351 | 23.792 | 1.00 | 31.15 | | | C |
| ATOM | 2213 | CG | PRO A 300 | 23.648 | 26.069 | 25.204 | 1.00 | 30.01 | | | C |
| ATOM | 2214 | CD | PRO A 300 | 24.993 | 25.853 | 25.836 | 1.00 | 32.39 | | | C |
| ATOM | 2215 | C | PRO A 300 | | 32.34 | 1.00 | 22.554 | 26.797 | 25.362 | | C |
| ATOM | 2216 | O | PRO A 300 | 25.383 | 27.905 | 23.147 | 1.00 | 33.39 | | | O |
| ATOM | 2217 | N | GLY A 301 | 25.413 | 26.655 | 21.229 | 1.00 | 31.94 | | | N |
| ATOM | 2218 | CA | GLY A 301 | 25.392 | 27.792 | | | 32.75 | 1.00 | 20.343 | C |
| ATOM | 2219 | C | GLY A 301 | 23.982 | 28.245 | 19.999 | 1.00 | 34.70 | | | C |
| ATOM | 2220 | O | GLY A 301 | 22.986 | 27.985 | 20.726 | 1.00 | 35.06 | | | O |
| ATOM | 2221 | N | SER A 302 | 23.870 | 28.924 | 18.868 | 1.00 | 34 | | 81. | N |
| ATOM | 2222 | CA | SER A 302 | 22.566 | 29.439 | 18.418 | 1.00 | 34.70 | | | C |
| ATOM | 2223 | CB | SER A 302 | 22.423 | 30.929 | 18.756 | 1.00 | 34.64 | | | C |
| ATOM | 2224 | OG | SER A 302 | 22.385 | 31.153 | 20.152 | 1.00 | 37.96 | | | O |
| ATOM | 2225 | C | SER A 302 | 22.462 | 29.348 | 16.892 | 1.00 | 34.82 | | | C |
| ATOM | 2226 | O | SER A 302 | 23.496 | 29.357 | 16.180 | 1.00 | 33.53 | | | O |
| ATOM | 2227 | N | GLU A 303 | 21.216 | 29.255 | 16.405 | 1.00 | 33.94 | | | N |
| ATOM | 2228 | CA | GLU A | | 34.57 | 1.00 | 14.992 | 29.180 | 20.959 | 303 | C |
| ATOM | 2229 | CB | GLU A 303 | 21.179 | 27.770 | 14.478 | 1.00 | 33.10 | | | C |
| ATOM | 2230 | CG | GLU A 303 | 20.760 | 27.578 | 13.023 | 1.00 | 37.29 | | | C |
| ATOM | 2231 | CD | GLU A 303 | 20.942 | 26 | | 44.41 | 1.00 | 12.506 | 143. | C |
| ATOM | 2232 | OE1 | GLU A 303 | 20.864 | 25.112 | 13.265 | 1.00 | 47.93 | | | O |
| ATOM | 2233 | OE2 | GLU A 303 | 21.185 | 26.019 | 11.295 | 1.00 | 49.48 | | | O |
| ATOM | 2234 | C | GLU A 303 | 19.511 | 29.660 | 14.705 | 1.00 | | | 35.72 | C |
| ATOM | 2235 | O | GLU A 303 | 18.551 | 29.309 | 15.456 | 1.00 | 36.17 | | | O |
| ATOM | 2236 | N | VAL A 304 | 19.383 | 30.463 | 13.638 | 1.00 | 35.06 | | | N |
| ATOM | 2237 | CA | VAL A 304 | 18.100 | 31.054 | 13.256 | 1.00 | 34.47 | | | C |
| ATOM | 2238 | CB | VAL A 304 | 18.056 | 32.637 | 13.431 | 1.00 | 34.01 | | | C |
| ATOM | 2239 | CG1 | VAL A 304 | 16.692 | 33.197 | 12.839 | 1.00 | 32.39 | | | C |
| ATOM | 2240 | CG2 | VAL A 304 | 18.317 | 33.093 | 14.934 | 1.00 | 32.02 | | | C |
| ATOM | 2241 | C | VAL A 304 | 17.872 | 30.700 | 11.762 | 1.00 | 34.27 | | | C |
| ATOM | 2242 | O | VAL A 304 | 18.733 | 30.964 | 10.925 | 1.00 | 32.33 | | | O |
| ATOM | 2243 | N | LEU A 305 | 16.702 | 30.143 | 11.475 | 1.00 | 32.99 | | | N |
| ATOM | 2244 | CA | LEU A 305 | 16.351 | | 35.13 | 1.00 | 10.127 | 29.737 | | C |
| ATOM | 2245 | CB | LEU A 305 | 15.795 | 28.295 | 10.107 | 1.00 | 32.88 | | | C |
| ATOM | 2246 | CG | LEU A 305 | 16.737 | 27.149 | 10.494 | 1.00 | 37.33 | | | C |
| ATOM | 2247 | CD1 | LEU A 305 | 15.985 | 25.811 | 10.257 | 1 | | 37.45 | 00. | C |
| ATOM | 2248 | CD2 | LEU A 305 | 17.966 | 27.235 | 9.615 | 1.00 | 34.93 | | | C |
| ATOM | 2249 | C | LEU A 305 | 15.190 | 30.609 | 9.616 | 1.00 | 35.01 | | | C |
| ATOM | 2250 | O | LEU A 305 | 14.251 | 30.923 | 10.372 | 1.00 | 34.81 | | | O |
| ATOM | 2251 | N | ARG A 306 | 15.236 | 30.939 | 8.333 | 1.00 | 32.90 | | | N |
| ATOM | 2252 | CA | ARG A 306 | 14.104 | 31.591 | 7.759 | 1.00 | 32.92 | | | C |
| ATOM | 2253 | CB | ARG A 306 | 14.555 | 32.865 | 7.026 | 1.00 | 30.94 | | | C |
| ATOM | 2254 | CG | ARG A 306 | 13.433 | 33.508 | 6.277 | 1.00 | 32.03 | | | C |
| ATOM | 2255 | CD | ARG A 306 | 13.965 | 34.592 | 5.244 | 1.00 | 30.57 | | | C |
| ATOM | 2256 | NE | ARG A 306 | 12.838 | 35.385 | 4.716 | 1.00 | 30.42 | | | N |
| ATOM | 2257 | CZ | ARG A 306 | 13.043 | | 32.05 | 1.00 | 3.868 | | 36.420 | C |
| ATOM | 2258 | NH1 | ARG A 306 | 14.261 | 36.672 | 3.472 | 1.00 | 24.57 | | | N |
| ATOM | 2259 | NH2 | ARG A 306 | 12.044 | 37.104 | 3.316 | 1.00 | 28.69 | | | N |
| ATOM | 2260 | C | ARG A 306 | 13.532 | 30.531 | 6.780 | | | 32.38 | 1.00 | C |
| ATOM | 2261 | O | ARG A 306 | 14.344 | 29.904 | 6.071 | 1.00 | 31.43 | | | O |
| ATOM | 2262 | N | ILE A 307 | 12.187 | 30.379 | 6.748 | 1.00 | 31.20 | | | N |
| ATOM | 2263 | CA | ILE A 307 | 11.503 | 29.503 | 5.798 | 1.00 | 32.30 | | | C |

Fig. 26 (Cont.)

| ATOM | 2264 | CB | ILE A 307 | 10.849 | 28.279 | 6.485 | 1.00 | 33.51 | | | C |
|---|---|---|---|---|---|---|---|---|---|---|---|
| ATOM | 2265 | CG1 | ILE A 307 | 11.927 | 27.577 | 7.338 | 1.00 | 34.04 | | | C |
| ATOM | 2266 | CD1 | ILE A 307 | 11.284 | 26.848 | 8.510 | 1.00 | 36.39 | | | C |
| ATOM | 2267 | CG2 | ILE A 307 | 10.210 | 27.308 | 5.411 | 1.00 | 29.05 | | | C |
| ATOM | 2268 | C | ILE A 307 | 10.465 | 30.218 | 5.018 | 1.00 | 32.29 | | | C |
| ATOM | 2269 | O | ILE A 307 | 9.518 | 30.733 | 5.572 | 1.00 | 32.83 | | | O |
| ATOM | 2270 | N | GLN A 308 | 10.671 | | 31.49 | 1.00 | 3.723 | 30.243 | | N |
| ATOM | 2271 | CA | GLN A 308 | 9.808 | 30.948 | 2.760 | 1.00 | 33.45 | | | C |
| ATOM | 2272 | CB | GLN A 308 | 10.662 | 31.827 | 1.780 | 1.00 | 32.08 | | | C |
| ATOM | 2273 | CG | GLN A 308 | 11.357 | 32.995 | 2.545 | | | 31.42 | 1.00 | C |
| ATOM | 2274 | CD | GLN A 308 | 12.353 | 33.681 | 1.630 | 1.00 | 35.03 | | | C |
| ATOM | 2275 | OE1 | GLN A 308 | 13.580 | 33.383 | 1.654 | 1.00 | 35.64 | | | O |
| ATOM | 2276 | NE2 | GLN A 308 | 11.844 | 34.551 | 0.780 | 1.00 | 26.57 | | | N |
| ATOM | 2277 | C | GLN A 308 | 9.046 | 29.937 | 1.909 | 1.00 | 33.56 | | | C |
| ATOM | 2278 | O | GLN A 308 | 9.621 | 28.911 | 1.481 | 1.00 | 33.92 | | | O |
| ATOM | 2279 | N | ASP A 309 | 7.790 | 30.269 | 1.591 | 1.00 | 35.41 | | | N |
| ATOM | 2280 | CA | ASP A 309 | 6.969 | 29.462 | 0.653 | 1.00 | 36.64 | | | C |
| ATOM | 2281 | CB | ASP A 309 | 7.667 | 29.401 | -0.729 | 1.00 | 36.59 | | | C |
| ATOM | 2282 | CG | ASP A 309 | 7.896 | 30.761 | -1.278 | 1.00 | 42.67 | | | C |
| ATOM | 2283 | OD1 | ASP A 309 | | 48.64 | 1.00 | 1.251- | 31.517 | 6.908 | | O |
| ATOM | 2284 | OD2 | ASP A 309 | 9.017 | 31.206 | -1.723 | 1.00 | 52.49 | | | O |
| ATOM | 2285 | C | ASP A 309 | 6.830 | 28.039 | 1.152 | 1.00 | 35.97 | | | C |
| ATOM | 2286 | O | ASP A 309 | 7.160 | 27.104 | | | 35.17 | 1.00 | 0.427 | O |
| ATOM | 2287 | N | ILE A 310 | 6.373 | 27.885 | 2.388 | 1.00 | 37.23 | | | N |
| ATOM | 2288 | CA | ILE A 310 | 6.356 | 26.582 | 3.013 | 1.00 | 38.56 | | | C |
| ATOM | 2289 | CB | ILE A 310 | 6.101 | 26.753 | 4.536 | 1.00 | 39.56 | | | C |
| ATOM | 2290 | CG1 | ILE A 310 | 6.617 | 25.510 | 5.299 | 1.00 | 38.66 | | | C |
| ATOM | 2291 | CD1 | ILE A 310 | 6.648 | 25.707 | 6.865 | 1.00 | 40.54 | | | C |
| ATOM | 2292 | CG2 | ILE A 310 | 4.625 | 27.186 | 4.794 | 1.00 | 36.29 | | | C |
| ATOM | 2293 | C | ILE A 310 | 5.419 | 25.545 | 2.328 | 1.00 | 40.77 | | | C |
| ATOM | 2294 | O | ILE A 310 | 5.595 | 24.336 | 2.522 | 1.00 | 41.99 | | | O |
| ATOM | 2295 | N | LEU A 311 | 4.502 | 25.998 | 1.461 | 1.00 | 42.27 | | | N |
| ATOM | 2296 | CA | LEU A 311 | | 44.50 | 1.00 | 0.771 | 25.115 | 3.574 | | C |
| ATOM | 2297 | CB | LEU A 311 | 2.209 | 25.797 | 0.532 | 1.00 | 44.55 | | | C |
| ATOM | 2298 | CG | LEU A 311 | 1.544 | 26.192 | 1.822 | 1.00 | 45.84 | | | C |
| ATOM | 2299 | CD1 | LEU A 311 | 0.079 | 26.701 | | | 47.10 | 1.00 | 1.592 | C |
| ATOM | 2300 | CD2 | LEU A 311 | 1.580 | 24.905 | 2.675 | 1.00 | 49.09 | | | C |
| ATOM | 2301 | C | LEU A 311 | 4.073 | 24.653 | -0.572 | 1.00 | 45.43 | | | C |
| ATOM | 2302 | O | LEU A 311 | 3.456 | 23.746 | -1.159 | 1.00 | 45.84 | | | O |
| ATOM | 2303 | N | SER A 312 | 5.121 | 25.305 | -1.098 | 1.00 | 45.20 | | | N |
| ATOM | 2304 | CA | SER A 312 | 5.545 | 25.028 | -2.459 | 1.00 | 45.64 | | | C |
| ATOM | 2305 | CB | SER A 312 | 6.444 | 26.145 | -3.016 | 1.00 | 44.81 | | | C |
| ATOM | 2306 | OG | SER A 312 | 7.633 | 26.269 | -2.237 | 1.00 | 46.77 | | | O |
| ATOM | 2307 | C | SER A 312 | 6.252 | 23.675 | -2.438 | 1.00 | 45.99 | | | C |
| ATOM | 2308 | O | SER A 312 | 6.459 | 23.085 | -1.335 | 1.00 | 45.29 | | | O |
| ATOM | 2309 | N | GLU A 313 | | 45.62 | 1.00 | 3.632- | 23.191 | 6.606 | | N |
| ATOM | 2310 | CA | GLU A 313 | 7.414 | 21.973 | -3.787 | 1.00 | 47.22 | | | C |
| ATOM | 2311 | CB | GLU A 313 | 7.584 | 21.619 | -5.267 | 1.00 | 47.95 | | | C |
| ATOM | 2312 | CG | GLU A 313 | 6.853 | 22 | | | 51.59 | 1.00 | 6.202- 586. | C |
| ATOM | 2313 | CD | GLU A 313 | 6.113 | 21.871 | -7.346 | 1.00 | 56.25 | | | C |
| ATOM | 2314 | OE1 | GLU A 313 | 6.712 | 21.737 | -8.458 | 1.00 | 53.22 | | | O |
| ATOM | 2315 | OE2 | GLU A 313 | 4.932 | 21.461 | -7.131 | 1.00 | 57.42 | | | O |
| ATOM | 2316 | C | GLU A 313 | 8.800 | 22.047 | -3.093 | 1.00 | 46.93 | | | C |
| ATOM | 2317 | O | GLU A 313 | 9.113 | 21.145 | -2.300 | 1.00 | 46.13 | | | O |
| ATOM | 2318 | N | GLU A 314 | 9.639 | 23.060 | -3.414 | 1.00 | 46.96 | | | N |
| ATOM | 2319 | CA | GLU A 314 | 10.798 | 23.407 | -2.511 | 1.00 | 46.16 | | | C |
| ATOM | 2320 | CB | GLU A 314 | 12.208 | 23.167 | -3.070 | 1.00 | 45.38 | | | C |
| ATOM | 2321 | CG | GLU A 314 | 12.366 | 23.309 | -4.543 | 1.00 | 51.80 | | | C |
| ATOM | 2322 | CD | GLU A 314 | 12.522 | 21.947 | -5.205 | 1.00 | 55.04 | | | C |
| ATOM | 2323 | OE1 | GLU A 314 | 13.021 | 21.902 | -6.346 | 1.00 | 52.19 | | | O |
| ATOM | 2324 | OE2 | GLU A 314 | 12.138 | 20.926 | -4.560 | 1.00 | 58.46 | | | O |

Fig. 26 (Cont.)

```
ATOM  2325  C    GLU A 314   10.765            43.66  1.00   1.745-  24.735  C
ATOM  2326  O    GLU A 314   11.088  25.825   -2.240  1.00  42.48                 O
ATOM  2327  N    PRO A 315   10.412  24.599   -0.496  1.00  42.48                 N
ATOM  2328  CA   PRO A 315   10.575  25.689    0.454  1.00          41.36         C
ATOM  2329  CB   PRO A 315   10.272  25.024    1.774  1.00  40.46                 C
ATOM  2330  CG   PRO A 315    9.264  24.029    1.374  1.00  42.34                 C
ATOM  2331  CD   PRO A 315    9.857  23.382    0.132  1.00  42.09                 C
ATOM  2332  C    PRO A 315   12.014  26.136    0.443  1.00  41.18                 C
ATOM  2333  O    PRO A 315   12.987  25.366    0.379  1.00  40.20                 O
ATOM  2334  N    LYS A 316   12.144  27.443    0.517  1.00  40.96                 N
ATOM  2335  CA   LYS A 316   13.442  28.055    0.542  1.00  40.82                 C
ATOM  2336  CB   LYS A 316   13.327  29.368   -0.226  1.00  40.10                 C
ATOM  2337  CG   LYS A 316   14.535  30.205   -0.153  1.00  46.23                 C
ATOM  2338  CD   LYS A 316   14.628            53.48  1.00   1.344-  31.196  C
ATOM  2339  CE   LYS A 316   15.848  32.141   -1.107  1.00  55.35                 C
ATOM  2340  NZ   LYS A 316   17.066  31.298   -1.135  1.00  53.94                 N
ATOM  2341  C    LYS A 316   13.818  28.210    2.052         39.44  1.00          C
ATOM  2342  O    LYS A 316   13.137  28.891    2.763  1.00  39.57                 O
ATOM  2343  N    VAL A 317   14.873  27.529    2.507  1.00  38.15                 N
ATOM  2344  CA   VAL A 317   15.280  27.513    3.910  1.00  36.46                 C
ATOM  2345  CB   VAL A 317   15.331  26.047    4.446  1.00  37.28                 C
ATOM  2346  CG1  VAL A 317   15.665  26.005    5.958  1.00  37.33                 C
ATOM  2347  CG2  VAL A 317   13.990  25.272    4.141  1.00  34.34                 C
ATOM  2348  C    VAL A 317   16.673  28.172    3.973  1.00  36.41                 C
ATOM  2349  O    VAL A 317   17.567  27.818    3.193  1.00  34.02                 O
ATOM  2350  N    THR A 318   16.849  29.142    4.876  1.00  35.15                 N
ATOM  2351  CA   THR A 318   18      36.18    1.00    4.924       29.938  071. C
ATOM  2352  CB   THR A 318   17.856  31.403    4.403  1.00  36.44                 C
ATOM  2353  OG1  THR A 318   17.248  31.353    3.114  1.00  38.74                 O
ATOM  2354  CG2  THR A 318   19.266  32.099    4.094         38.78  1.00          C
ATOM  2355  C    THR A 318   18.530  30.041    6.373  1.00  36.12                 C
ATOM  2356  O    THR A 318   17.742  30.358    7.230  1.00  34.95                 O
ATOM  2357  N    VAL A 319   19.826  29.782    6.621  1.00  36.69                 N
ATOM  2358  CA   VAL A 319   20.351  30.045    7.929  1.00  35.01                 C
ATOM  2359  CB   VAL A 319   21.699  29.259    8.175  1.00  36.15                 C
ATOM  2360  CG1  VAL A 319   22.132  29.588    9.594  1.00  34.57                 C
ATOM  2361  CG2  VAL A 319   21.488  27.700    8.025  1.00  31.36                 C
ATOM  2362  C    VAL A 319   20.627  31.560    7.999  1.00  34.45                 C
ATOM  2363  O    VAL A 319   21.507  32.024    7.330  1.00  31.52                 O
ATOM  2364  N    VAL A 320           32.67    1.00    8.823       32.328  19.932  N
ATOM  2365  CA   VAL A 320   20.196  33.784    8.790  1.00  33.50                 C
ATOM  2366  CB   VAL A 320   18.854  34.537    9.030  1.00  35.95                 C
ATOM  2367  CG1  VAL A 320   19.040  36.042    9             34.52  1.00  078. C
ATOM  2368  CG2  VAL A 320   17.834  34.128    7.883  1.00  33.77                 C
ATOM  2369  C    VAL A 320   21.267  34.211    9.806  1.00  33.50                 C
ATOM  2370  O    VAL A 320   21.968  35.220    9.631  1.00  33.28                 O
ATOM  2371  N    TYR A 321   21.422  33.389   10.847  1.00  33.06                 N
ATOM  2372  CA   TYR A 321   22.326  33.668   11.963  1.00  32.96                 C
ATOM  2373  CB   TYR A 321   21.704  34.599   13.021  1.00  31.81                 C
ATOM  2374  CG   TYR A 321   22.689  34.969   14.119  1.00  33.38                 C
ATOM  2375  CD1  TYR A 321   23.706  35.909   13.900  1.00  32.58                 C
ATOM  2376  CE1  TYR A 321   24.679  36.214   14.905  1.00  30.44                 C
ATOM  2377  CZ   TYR A 321           35.55    1.00   16.151      35.566  24.523   C
ATOM  2378  OH   TYR A 321   25.321  35.809   17.184  1.00  36.87                 O
ATOM  2379  CE2  TYR A 321   23.544  34.647   16.382  1.00  31.93                 C
ATOM  2380  CD2  TYR A 321   22.624  34.335                 34.48  1.00  15.364   C
ATOM  2381  C    TYR A 321   22.681  32.322   12.590  1.00  32.12                 C
ATOM  2382  O    TYR A 321   21.785  31.502   12.803  1.00  33.37                 O
ATOM  2383  N    ALA A 322   23.982  32.115   12.887  1.00  31.45                 N
ATOM  2384  CA   ALA A 322   24.462  30.916   13.583  1.00  30.50                 C
ATOM  2385  CB   ALA A 322   24.621  29.797   12.619  1.00  29.06                 C
```

Fig. 26 (Cont.)

```
ATOM  2386  C    ALA A 322     25.816  31.246  14.266  1.00 31.39           C
ATOM  2387  O    ALA A 322     26.622  31.953  13.686  1.00 30.97           O
ATOM  2388  N    GLU A 323     26.073  30.747  15.469  1.00 30.36           N
ATOM  2389  CA   GLU A 323     27.353  31.050  16.114  1.00 32.61           C
ATOM  2390  CB   GLU A 323             32.00 1.00  16.762  32.461  27.340   C
ATOM  2391  CG   GLU A 323     26.298  32.463  17.875  1.00 35.44           C
ATOM  2392  CD   GLU A 323     26.727  33.300  19.056  1.00 39.61           C
ATOM  2393  OE1  GLU A 323     25.967  34.276          38.78 1.00  19.309   O
ATOM  2394  OE2  GLU A 323     27.798  33.022  19.695  1.00 37.11           O
ATOM  2395  C    GLU A 323     27.539  29.953  17.192  1.00 32.54           C
ATOM  2396  O    GLU A 323     26.565  29.263  17.554  1.00 30       85.0   O
ATOM  2397  N    ASN A 324     28.786  29.768  17.621  1.00 31.60           N
ATOM  2398  CA   ASN A 324     29.095  28.722  18.577  1.00 32.76           C
ATOM  2399  CB   ASN A 324     30.544  28.251  18.448  1.00 31.19           C
ATOM  2400  CG   ASN A 324     31.523  29.293  18.880  1.00 32.35           C
ATOM  2401  OD1  ASN A 324     31.145  30.300  19.459  1.00 28.40           O
ATOM  2402  ND2  ASN A 324     32.811  29.050  18.631  1.00 35.19           N
ATOM  2403  C    ASN A         33.96 1.00  20.055  29.006  28.704     324   C
ATOM  2404  O    ASN A 324     28.958  28.180  20.926  1.00 34.06           O
ATOM  2405  N    GLY A 325     28.009  30.107  20.325  1.00 34.86           N
ATOM  2406  CA   GLY A 325     27.626  30.381          36.73 1.00  21.688   C
ATOM  2407  C    GLY A 325     28.651  31.196  22.453  1.00 38.13           C
ATOM  2408  O    GLY A 325     28.507  31.347  23.650  1.00 40.83           O
ATOM  2409  N    THR A 326     29.703  31.716  21.838  1.00          37.15  N
ATOM  2410  CA   THR A 326     30.534  32.580  22.637  1.00 36.52           C
ATOM  2411  CB   THR A 326     32.042  32.569  22.228  1.00 37.65           C
ATOM  2412  OG1  THR A 326     32.306  33.560  21.232  1.00 40.25           O
ATOM  2413  CG2  THR A 326     32.425  31.271  21.578  1.00 36.84           C
ATOM  2414  C    THR A 326     29.927  33.984  22.798  1.00 36.02           C
ATOM  2415  O    THR A 326     30.375  34.737  23.642  1.00 35.49           O
ATOM  2416  N    VAL A 327     28.904  34.334  22.006  1.00 34.74           N
ATOM  2417  CA   VAL A 327     28.210  35.573  22.213  1.00 33.79           C
ATOM  2418  CB   VAL A 327     28.111  36.444  20.917  1.00 34.65           C
ATOM  2419  CG1  VAL A 327     27.041          34.73 1.00  21.090  37.598   C
ATOM  2420  CG2  VAL A 327     29.480  37.047  20.526  1.00 33.11           C
ATOM  2421  C    VAL A 327     26.817  35.192  22.751  1.00 34.33           C
ATOM  2422  O    VAL A 327     26.471  35.577  23.846  1            35.26 00.O
ATOM  2423  N    LEU A 328     26.037  34.406  22.015  1.00 32.87           N
ATOM  2424  CA   LEU A 328     24.671  34.063  22.409  1.00 32.60           C
ATOM  2425  CB   LEU A 328     23.636  34.653  21.410  1.00 30.22           C
ATOM  2426  CG   LEU A 328     22.163  34.591  21.883  1.00 33.68           C
ATOM  2427  CD1  LEU A 328     21.843  35.670  22.998  1.00 31.39           C
ATOM  2428  CD2  LEU A 328     21.165  34.666  20.712  1.00 32.41           C
ATOM  2429  C    LEU A 328     24.496  32.537  22.573  1.00 33.15           C
ATOM  2430  O    LEU A 328     24.635  31.784  21.620  1.00 34.69           O
ATOM  2431  N    GLN A 329     24.152  32.092  23.779  1.00 33.03           N
ATOM  2432  CA   GLN A 329     24              32.71 1.00  24.103  30.673  009.C
ATOM  2433  CB   GLN A 329     24.520  30.421  25.505  1.00 32.14           C
ATOM  2434  CG   GLN A 329     25.987  30.568  25.658  1.00 35.91           C
ATOM  2435  CD   GLN A 329     26.415  30.467  27.176          39.08 1.00   C
ATOM  2436  OE1  GLN A 329     25.625  30.109  28.058  1.00 41.20           O
ATOM  2437  NE2  GLN A 329     27.614  30.807  27.429  1.00 37.75           N
ATOM  2438  C    GLN A 329     22.552  30.286  24.113  1.00 32.52           C
ATOM  2439  O    GLN A 329     21.766  30.951  24.784  1.00 33.15           O
ATOM  2440  N    GLY A 330     22.200  29.232  23.364  1.00 32.96           N
ATOM  2441  CA   GLY A 330     20.928  28.523  23.460  1.00 33.47           C
ATOM  2442  C    GLY A 330     19.722  29.201  22.837  1.00 36.19           C
ATOM  2443  O    GLY A 330     18.685  29.210  23.467  1.00 37.52           O
ATOM  2444  N    SER A 331     19.833  29.771  21.623  1.00 36.46           N
ATOM  2445  CA   SER A 331             36.80 1.00  20.977  30.408  18.689   C
ATOM  2446  CB   SER A 331     19.016  30.858  19.517  1.00 36.23           C
```

Fig. 26 (Cont.)

| ATOM | 2447 | OG | SER | A | 331 | 19.530 | 29.750 | 18.760 | 1.00 | 34.76 | | | O |
|---|---|---|---|---|---|---|---|---|---|---|---|---|---|
| ATOM | 2448 | C | SER | A | 331 | 17.507 | 29.500 | 20 | | 36.85 | 1.00 | 902. | C |
| ATOM | 2449 | O | SER | A | 331 | 17.651 | 28.311 | 20.518 | 1.00 | 37.28 | | | O |
| ATOM | 2450 | N | THR | A | 332 | 16.332 | 30.068 | 21.202 | 1.00 | 35.77 | | | N |
| ATOM | 2451 | CA | THR | A | 332 | 15.070 | 29.368 | 21.029 | 1.00 | 34.22 | | | C |
| ATOM | 2452 | CB | THR | A | 332 | 14.361 | 29.198 | 22.374 | 1.00 | 36.00 | | | C |
| ATOM | 2453 | OG1 | THR | A | 332 | 14.299 | 30.461 | 23.097 | 1.00 | 32.94 | | | O |
| ATOM | 2454 | CG2 | THR | A | 332 | 15.130 | 28.232 | 23.293 | 1.00 | 32.12 | | | C |
| ATOM | 2455 | C | THR | A | 332 | 14.089 | 30.071 | 20.106 | 1.00 | 35.91 | | | C |
| ATOM | 2456 | O | THR | A | 332 | 13.113 | 29.446 | 19.702 | 1.00 | 37.18 | | | O |
| ATOM | 2457 | N | VAL | A | 333 | 14.248 | 31.378 | 19.838 | 1.00 | 34.78 | | | N |
| ATOM | 2458 | CA | VAL | A | 333 | | 32.96 | 1.00 | 19.157 | 32.060 | 13.190 | | C |
| ATOM | 2459 | CB | VAL | A | 333 | 12.151 | 32.527 | 20.197 | 1.00 | 32.77 | | | C |
| ATOM | 2460 | CG1 | VAL | A | 333 | 12.785 | 33.526 | 21.167 | 1.00 | 32.29 | | | C |
| ATOM | 2461 | CG2 | VAL | A | 333 | 10.948 | 33.191 | | | 30.74 | 1.00 | 19.472 | C |
| ATOM | 2462 | C | VAL | A | 333 | 13.808 | 33.246 | 18.428 | 1.00 | 33.51 | | | C |
| ATOM | 2463 | O | VAL | A | 333 | 14.841 | 33.783 | 18.852 | 1.00 | 35.47 | | | O |
| ATOM | 2464 | N | ALA | A | 334 | 13.217 | 33.645 | 17.333 | 1.00 | 33.44 | | | N |
| ATOM | 2465 | CA | ALA | A | 334 | 13.703 | 34.831 | 16.584 | 1.00 | 35.26 | | | C |
| ATOM | 2466 | CB | ALA | A | 334 | 14.847 | 34.444 | 15.577 | 1.00 | 34.38 | | | C |
| ATOM | 2467 | C | ALA | A | 334 | 12.553 | 35.397 | 15.810 | 1.00 | 34.75 | | | C |
| ATOM | 2468 | O | ALA | A | 334 | 11.709 | 34.626 | 15.354 | 1.00 | 35.65 | | | O |
| ATOM | 2469 | N | ALA | A | 335 | 12.517 | 36.724 | 15.678 | 1.00 | 33.81 | | | N |
| ATOM | 2470 | CA | ALA | A | 335 | 11.469 | 37.408 | 14.944 | 1.00 | 33.51 | | | C |
| ATOM | 2471 | CB | ALA | A | 335 | | 34.69 | 1.00 | 15.895 | 37.745 | 10.282 | | C |
| ATOM | 2472 | C | ALA | A | 335 | 12.040 | 38.697 | 14.421 | 1.00 | 33.33 | | | C |
| ATOM | 2473 | O | ALA | A | 335 | 13.008 | 39.228 | 14.977 | 1.00 | 32.05 | | | O |
| ATOM | 2474 | N | VAL | A | 336 | 11.396 | 39.222 | | | 33.22 | 1.00 | 13.371 | N |
| ATOM | 2475 | CA | VAL | A | 336 | 11.948 | 40.294 | 12.586 | 1.00 | 33.00 | | | C |
| ATOM | 2476 | CB | VAL | A | 336 | 12.294 | 39.889 | 11.095 | 1.00 | 34.01 | | | C |
| ATOM | 2477 | CG1 | VAL | A | 336 | 13.532 | 38.912 | 11.054 | 1.00 | 35 | | 22. | C |
| ATOM | 2478 | CG2 | VAL | A | 336 | 11.082 | 39.248 | 10.332 | 1.00 | 30.46 | | | C |
| ATOM | 2479 | C | VAL | A | 336 | 10.991 | 41.451 | 12.638 | 1.00 | 34.58 | | | C |
| ATOM | 2480 | O | VAL | A | 336 | 9.760 | 41.264 | 12.574 | 1.00 | 34.26 | | | O |
| ATOM | 2481 | N | TYR | A | 337 | 11.563 | 42.654 | 12.677 | 1.00 | 33.45 | | | N |
| ATOM | 2482 | CA | TYR | A | 337 | 10.760 | 43.825 | 12.636 | 1.00 | 32.42 | | | C |
| ATOM | 2483 | CB | TYR | A | 337 | 10.314 | 44.238 | 14.059 | 1.00 | 33.08 | | | C |
| ATOM | 2484 | CG | TYR | A | | 31.65 | 1.00 | 14.029 | 45.436 | 9.389 | | 337 | C |
| ATOM | 2485 | CD1 | TYR | A | 337 | 8.042 | 45.297 | 13.612 | 1.00 | 30.15 | | | C |
| ATOM | 2486 | CE1 | TYR | A | 337 | 7.186 | 46.349 | 13.597 | 1.00 | 29.45 | | | C |
| ATOM | 2487 | CZ | TYR | A | 337 | 7.670 | 47 | | 33.39 | 1.00 | 13.948 | 619. | C |
| ATOM | 2488 | OH | TYR | A | 337 | 6.822 | 48.691 | 13.925 | 1.00 | 35.91 | | | O |
| ATOM | 2489 | CE2 | TYR | A | 337 | 9.002 | 47.815 | 14.326 | 1.00 | 32.75 | | | C |
| ATOM | 2490 | CD2 | TYR | A | 337 | 9.852 | 46.693 | 14.364 | 1.00 | | | 31.83 | C |
| ATOM | 2491 | C | TYR | A | 337 | 11.558 | 44.912 | 12.005 | 1.00 | 32.19 | | | C |
| ATOM | 2492 | O | TYR | A | 337 | 12.650 | 45.295 | 12.498 | 1.00 | 33.04 | | | O |
| ATOM | 2493 | N | LYS | A | 338 | 11.044 | 45.388 | 10.877 | 1.00 | 31.70 | | | N |
| ATOM | 2494 | CA | LYS | A | 338 | 11.638 | 46.529 | 10.184 | 1.00 | 31.53 | | | C |
| ATOM | 2495 | CB | LYS | A | 338 | 11.189 | 47.858 | 10.793 | 1.00 | 30.25 | | | C |
| ATOM | 2496 | CG | LYS | A | 338 | 9.678 | 48.002 | 10.597 | 1.00 | 34.31 | | | C |
| ATOM | 2497 | CD | LYS | A | 338 | 9.159 | 49.413 | 10.881 | 1.00 | 37.55 | | | C |
| ATOM | 2498 | CE | LYS | A | 338 | 7.585 | 49.436 | 10.862 | 1.00 | 39.59 | | | C |
| ATOM | 2499 | NZ | LYS | A | 338 | 7.082 | 49.079 | 9.501 | 1.00 | 40.16 | | | N |
| ATOM | 2500 | C | LYS | A | 338 | 13.150 | | | 31.22 | 1.00 | 10.024 | 46.474 | C |
| ATOM | 2501 | O | LYS | A | 338 | 13.845 | 47.456 | 10.343 | 1.00 | 29.04 | | | O |
| ATOM | 2502 | N | GLY | A | 339 | 13.631 | 45.349 | 9.466 | 1.00 | 31.17 | | | N |
| ATOM | 2503 | CA | GLY | A | 339 | 15.053 | 45.226 | 9.078 | 1 | | | 31.84 00. | C |
| ATOM | 2504 | C | GLY | A | 339 | 15.948 | 44.749 | 10.227 | 1.00 | 32.40 | | | C |
| ATOM | 2505 | O | GLY | A | 339 | 17.178 | 44.771 | 10.121 | 1.00 | 33.32 | | | O |
| ATOM | 2506 | N | LYS | A | 340 | 15.316 | 44.375 | 11.339 | 1.00 | 32.48 | | | N |
| ATOM | 2507 | CA | LYS | A | 340 | 16.000 | 43.943 | 12.540 | 1.00 | 33.84 | | | C |

Fig. 26 (Cont.)

```
ATOM  2508  CB  LYS A 340      15.680  44.909  13.666  1.00 35.56           C
ATOM  2509  CG  LYS A 340      16.856  45.690  13.979  1.00 38.06           C
ATOM  2510  CD  LYS A 340      16.791  47.031  13.596  1.00 40.83           C
ATOM  2511  CE  LYS A 340      18.041  47.619  14.256  1.00 48.53           C
ATOM  2512  NZ  LYS A 340      18.012  49.139  14.319  1.00 51.84           N
ATOM  2513  C   LYS A 340      15.541          33.15  1.00  13.008  42.595  C
ATOM  2514  O   LYS A 340      14.378  42.198  12.799  1.00 32.21           O
ATOM  2515  N   LEU A 341      16.462  41.904  13.657  1.00 32.75           N
ATOM  2516  CA  LEU A 341      16.249  40.537  14.086          32.13 1.00   C
ATOM  2517  CB  LEU A 341      17.286  39.627  13.421  1.00 31.36           C
ATOM  2518  CG  LEU A 341      17.184  38.115  13.775  1.00 31.96           C
ATOM  2519  CD1 LEU A 341      15.775  37.521  13.403  1.00 33.12           C
ATOM  2520  CD2 LEU A 341      18.201  37.258  13.124  1.00 32.42           C
ATOM  2521  C   LEU A 341      16.409  40.472  15.599  1.00 32.38           C
ATOM  2522  O   LEU A 341      17.451  40.847  16.151  1.00 33.16           O
ATOM  2523  N   LEU A 342      15.393  39.992  16.289  1.00 32.83           N
ATOM  2524  CA  LEU A 342      15.495  39.842  17.721  1.00 33.35           C
ATOM  2525  CB  LEU A 342      14.313  40.520  18.439  1.00 31.97           C
ATOM  2526  CG  LEU A 342      14.297          34.68  1.00  19.977  40.437  C
ATOM  2527  CD1 LEU A 342      15.513  41.130  20.653  1.00 29.46           C
ATOM  2528  CD2 LEU A 342      12.955  41.030  20.513  1.00 31.54           C
ATOM  2529  C   LEU A 342      15.539  38.371  18.069          33.83 1.00   C
ATOM  2530  O   LEU A 342      14.604  37.649  17.722  1.00 34.86           O
ATOM  2531  N   ILE A 343      16.582  37.941  18.787  1.00 33.16           N
ATOM  2532  CA  ILE A 343      16.776  36.529  19.083  1.00 32.18           C
ATOM  2533  CB  ILE A 343      18.169  35.989  18.502  1.00 32.76           C
ATOM  2534  CG1 ILE A 343      18.451  36.450  17.020  1.00 31.94           C
ATOM  2535  CD1 ILE A 343      19.960  36.080  16.509  1.00 31.84           C
ATOM  2536  CG2 ILE A 343      18.240  34.460  18.589  1.00 28.32           C
ATOM  2537  C   ILE A 343      16.789  36.305  20.591  1.00 34.11           C
ATOM  2538  O   ILE A 343      17.551  36.977  21.304  1.00 34.14           O
ATOM  2539  N   GLY A 344              33.18 1.00   21.079  35.322  16.037  N
ATOM  2540  CA  GLY A 344      16.062  35.053  22.493  1.00 34.05           C
ATOM  2541  C   GLY A 344      16.535  33.633  22.780  1.00 35.49           C
ATOM  2542  O   GLY A 344      16.694  32.844  21.823          36.09 1.00   O
ATOM  2543  N   THR A 345      16.771  33.295  24.063  1.00 34.56           N
ATOM  2544  CA  THR A 345      17.365  31.999  24.451  1.00 34.01           C
ATOM  2545  CB  THR A 345      18.893  32.177  24.799  1.00 34.75           C
ATOM  2546  OG1 THR A 345      19.034  32.920  26.021  1.00 31.95           O
ATOM  2547  CG2 THR A 345      19.610  33.085  23.747  1.00 33.41           C
ATOM  2548  C   THR A 345      16.659  31.410  25.676  1.00 35.17           C
ATOM  2549  O   THR A 345      15.935  32.109  26.394  1.00 34.61           O
ATOM  2550  N   VAL A 346      16.925  30.145  25.987  1.00 36.14           N
ATOM  2551  CA  VAL A 346      16.134  29.487  27.026  1.00 35.62           C
ATOM  2552  CB  VAL A 346              35.92 1.00   26.973  27.932  16.250  C
ATOM  2553  CG1 VAL A 346      17.712  27.485  27.145  1.00 38.59           C
ATOM  2554  CG2 VAL A 346      15.396  27.286  28.079  1.00 36.02           C
ATOM  2555  C   VAL A 346      16.510  30.126          36.16 1.00  28.373   C
ATOM  2556  O   VAL A 346      15.602  30.492  29.140  1.00 35.64           O
ATOM  2557  N   PHE A 347      17.802  30.389  28.605  1.00 35.43           N
ATOM  2558  CA  PHE A 347      18.265  30.715  29.961  1.00 38.68           C
ATOM  2559  CB  PHE A 347      19.042  29.511  30.600  1.00 39.33           C
ATOM  2560  CG  PHE A 347      18.135  28.340  30.969  1.00 45.18           C
ATOM  2561  CD1 PHE A 347      16.801  28.582  31.464  1.00 48.30           C
ATOM  2562  CE1 PHE A 347      15.893  27.476  31.831  1.00 50.09           C
ATOM  2563  CZ  PHE A 347      16.369  26.104  31.681  1.00 51.06           C
ATOM  2564  CE2 PHE A 347      17.737  25.855  31.175  1.00 48.00           C
ATOM  2565  CD2 PHE A 347              48.28 1.00   30.821  26.987  18.592  C
ATOM  2566  C   PHE A 347      19.166  31.908  30.074  1.00 39.98           C
ATOM  2567  O   PHE A 347      19.564  32.283  31.186  1.00 40.10           O
ATOM  2568  N   HIS A 348      19.563  32              40.83  1.00  28.950  499.N
```

Fig. 26 (Cont.)

```
ATOM   2569  CA   HIS A 348      20.558  33.528  29.101  1.00 41.72           C
ATOM   2570  CB   HIS A 348      21.948  32.970  28.832  1.00 43.21           C
ATOM   2571  CG   HIS A 348      22.409  32.036  29.935  1.00 49.93           C
ATOM   2572  ND1  HIS A 348      22.721  32.486  31.219  1.00 52.33           N
ATOM   2573  CE1  HIS A 348      23.070  31.455  31.974  1.00 51.53           C
ATOM   2574  NE2  HIS A 348      22.978  30.352  31.243  1.00 54.82           N
ATOM   2575  CD2  HIS A 348      22.545  30.679  29.967  1.00 50.39           C
ATOM   2576  C    HIS A 348      20.259  34.903  28.529  1.00 40.57           C
ATOM   2577  O    HIS A 348      19.492  35.643  29.132  1.00 40.88           O
ATOM   2578  N    LYS A 349      20.860  35.267  27.399  1.00 38.67           N
ATOM   2579  CA   LYS A 349      20.765  36.630  26.942  1.00 35.44           C
ATOM   2580  CB   LYS A 349      22.170  37.123  26.571  1.00 34.83           C
ATOM   2581  CG   LYS A 349      23.067          31.45   1.00 27.804   37.129 C
ATOM   2582  CD   LYS A 349      24.444  37.769  27.573  1.00 30.24           C
ATOM   2583  CE   LYS A 349      25.461  37.279  28.605  1.00 29.62           C
ATOM   2584  NZ   LYS A 349      26.808  37.959  28.269  1.00                 32.99 N
ATOM   2585  C    LYS A 349      19.779  36.743  25.803  1.00 34.65           C
ATOM   2586  O    LYS A 349      19.028  35.812  25.511  1.00 34.18           O
ATOM   2587  N    ALA A 350      19.796  37.896  25.162  1.00 33.77           N
ATOM   2588  CA   ALA A 350      19.099  38.088  23.887  1.00 33.49           C
ATOM   2589  CB   ALA A 350      17.681  38.681  24.111  1.00 32.05           C
ATOM   2590  C    ALA A 350      19.933  39.036  23.012  1.00 32.27           C
ATOM   2591  O    ALA A 350      20.647  39.882  23.524  1.00 31.81           O
ATOM   2592  N    LEU A 351      19.734  38.941  21.704  1.00 32.03           N
ATOM   2593  CA   LEU A 351      20.548  39.614  20.730  1.00 32.98           C
ATOM   2594  CB   LEU A 351      21.404          32.08   1.00 20.013   38.577 C
ATOM   2595  CG   LEU A 351      22.578  39.087  19.200  1.00 34.41           C
ATOM   2596  CD1  LEU A 351      23.686  39.792  20.060  1.00 36.80           C
ATOM   2597  CD2  LEU A 351      23.175  37.919  18.364          33.03 1.00   C
ATOM   2598  C    LEU A 351      19.666  40.378  19.746  1.00 33.10           C
ATOM   2599  O    LEU A 351      18.644  39.883  19.309  1.00 34.98           O
ATOM   2600  N    TYR A 352      20.028  41.622  19.485  1.00 34.23           N
ATOM   2601  CA   TYR A 352      19.295  42.497  18.583  1.00 35.12           C
ATOM   2602  CB   TYR A 352      18.793  43.715  19.321  1.00 34.78           C
ATOM   2603  CG   TYR A 352      17.662  44.464  18.621  1.00 34.31           C
ATOM   2604  CD1  TYR A 352      16.644  43.781  18.011  1.00 30.74           C
ATOM   2605  CE1  TYR A 352      15.594  44.464  17.377  1.00 33.11           C
ATOM   2606  CZ   TYR A 352      15.581  45.852  17.328  1.00 34.26           C
ATOM   2607  OH   TYR A 352      14              37.46   1.00 16.697   46.465 546.O
ATOM   2608  CE2  TYR A 352      16.601  46.599  17.892  1.00 34.76           C
ATOM   2609  CD2  TYR A 352      17.668  45.888  18.536  1.00 34.22           C
ATOM   2610  C    TYR A 352      20.225  42.913  17.479          34.64 1.00   C
ATOM   2611  O    TYR A 352      21.229  43.545  17.773  1.00 36.10           O
ATOM   2612  N    CYS A 353      19.941  42.480  16.239  1.00 35.79           N
ATOM   2613  CA   CYS A 353      20.886  42.635  15.055  1.00 37.35           C
ATOM   2614  CB   CYS A 353      21.311  41.272  14.463  1.00 37.59           C
ATOM   2615  SG   CYS A 353      21.597  39.936  15.687  1.00 44.94           S
ATOM   2616  C    CYS A 353      20.238  43.322  13.858  1.00 37.04           C
ATOM   2617  O    CYS A 353      19.023  43.197  13.679  1.00 36.03           O
ATOM   2618  N    ASP A 354      21.040  43.962  13.006  1.00 36.33           N
ATOM   2619  CA   ASP A 354      20.573  44.285  11.660  1.00 37.32           C
ATOM   2620  CB   ASP A 354              37.30   1.00    10.994  45.320 21.475 C
ATOM   2621  CG   ASP A 354      21.496  46.683  11.742  1.00 39.53           C
ATOM   2622  OD1  ASP A 354      20.610  47.011  12.520  1.00 35.09           O
ATOM   2623  OD2  ASP A 354      22.406  47.509  11              47.05 1.00   625.O
ATOM   2624  C    ASP A 354      20.516  43.000  10.783  1.00 39.24           C
ATOM   2625  O    ASP A 354      21.443  42.201  10.844  1.00 39.21           O
ATOM   2626  N    LEU A 355      19.460  42.828   9.958  1.00 39.69           N
ATOM   2627  CA   LEU A 355      19.429  41.815   8.875  1.00 40.83           C
ATOM   2628  CB   LEU A 355      18.058  41.723   8.209  1.00 39.93           C
ATOM   2629  CG   LEU A 355      16.980  41.104   9.077  1.00 39.47           C
```

Fig. 26 (Cont.)

| | | | | | | | | | | | |
|---|---|---|---|---|---|---|---|---|---|---|---|
| ATOM | 2630 | CD1 | LEU | A | 355 | 15.610 | 41.160 | 8.360 | 1.00 | 38.70 | C |
| ATOM | 2631 | CD2 | LEU | A | 355 | 17.363 | 39.650 | 9.400 | 1.00 | 36.95 | C |
| ATOM | 2632 | C | LEU | A | 355 | 20.492 | 42.064 | 7.798 | 1.00 | 42.04 | C |
| ATOM | 2633 | O | LEU | A | 355 | | 42.68 | 1.00 | 7.649 | 43.214 20.963 | O |
| ATOM | 2634 | OT | LEU | A | 355 | 20.869 | 41.067 | 7.149 | 1.00 | 42.29 | O |
| ATOM | 2635 | CA | CA | B | 400 | 4.902 | 31.422 | 21.076 | 1.00 | 37.87 | CA |
| ATOM | 2636 | CA | CA | B | 401 | 9.862 | 26.279 | | 37.77 | 1.00 23.131 | CA |
| ATOM | 2637 | P | PO4 | B | 402 | 12.263 | 24.882 | 25.290 | 1.00 | 47.29 | P |
| ATOM | 2638 | O1 | PO4 | B | 402 | 10.821 | 25.112 | 24.781 | 1.00 | 41.35 | O |
| ATOM | 2639 | O2 | PO4 | B | 402 | 12.995 | 23.970 | 24.323 | 1.00 | 44.02 | O |
| ATOM | 2640 | O3 | PO4 | B | 402 | 12.237 | 24.170 | 26.585 | 1.00 | 43.60 | O |
| ATOM | 2641 | O4 | PO4 | B | 402 | 13.018 | 26.210 | 25.500 | 1.00 | 49.26 | O |
| ATOM | 2642 | O | HOH | C | 1 | 25.416 | 24.056 | 19.747 | 1.00 | 18.97 | O |
| ATOM | 2643 | O | HOH | C | 2 | 14.777 | 31.585 | 3.318 | 1.00 | 31.43 | O |
| ATOM | 2644 | O | HOH | C | 3 | -2.838 | 22.102 | 32.773 | 1.00 | 34.21 | O |
| ATOM | 2645 | O | HOH | C | 4 | 2.443 | 31.629 | 7.007 | 1.00 | 30.71 | O |
| ATOM | 2646 | O | HOH | C | | 38.23 | 1.00 | 20.249 | 33.617 | 4.934 5 | O |
| ATOM | 2647 | O | HOH | C | 6 | 13.472 | 32.347 | 29.984 | 1.00 | 35.48 | O |
| ATOM | 2648 | O | HOH | C | 7 | 4.732 | 35.100 | 15.815 | 1.00 | 36.10 | O |
| ATOM | 2649 | O | HOH | C | 8 | 6.795 | 31.628 | | 36.29 | 1.00 19.665 | O |
| ATOM | 2650 | O | HOH | C | 9 | 21.431 | 25.874 | 21.319 | 1.00 | 36.22 | O |
| ATOM | 2651 | O | HOH | C | 10 | 10.779 | 32.224 | 29.452 | 1.00 | 36.57 | O |
| ATOM | 2652 | O | HOH | C | 11 | 6.449 | 29.013 | 18.581 | 1.00 | 34 88.0 | O |
| ATOM | 2653 | O | HOH | C | 12 | 22.786 | 23.625 | 20.765 | 1.00 | 28.77 | O |
| ATOM | 2654 | O | HOH | C | 13 | -1.362 | 24.630 | 38.658 | 1.00 | 42.56 | O |
| ATOM | 2655 | O | HOH | C | 14 | 8.208 | 27.701 | 24.353 | 1.00 | 37.72 | O |
| ATOM | 2656 | O | HOH | C | 15 | 6.452 | 37.826 | 16.477 | 1.00 | 41.78 | O |
| ATOM | 2657 | O | HOH | C | 16 | -8.766 | 31.917 | 36.839 | 1.00 | 38.98 | O |
| ATOM | 2658 | O | HOH | C | 17 | 3.247 | 30.704 | 19.507 | 1.00 | 36.33 | O |
| ATOM | 2659 | O | HOH | C | | 46.90 | 1.00 | 1.141 | 21.870 | 6.424 18 | O |
| ATOM | 2660 | O | HOH | C | 19 | 30.634 | 31.425 | 16.498 | 1.00 | 27.70 | O |
| ATOM | 2661 | O | HOH | C | 20 | 1.750 | 33.065 | 18.713 | 1.00 | 38.81 | O |
| ATOM | 2662 | O | HOH | C | 21 | 2.111 | 31.472 | | 40.55 | 1.00 39.170 | O |
| ATOM | 2663 | O | HOH | C | 22 | 20.248 | 29.991 | 27.165 | 1.00 | 37.04 | O |
| ATOM | 2664 | O | HOH | C | 23 | 25.057 | 34.217 | 26.293 | 1.00 | 46.33 | O |
| ATOM | 2665 | O | HOH | C | 24 | 9.035 | 37.144 | 12.537 | 1.00 | 35.56 | O |
| ATOM | 2666 | O | HOH | C | 25 | 8.566 | 41.109 | 5.556 | 1.00 | 34.21 | O |
| ATOM | 2667 | O | HOH | C | 26 | 6.861 | 22.115 | 29.280 | 1.00 | 38.56 | O |
| ATOM | 2668 | O | HOH | C | 27 | 22.244 | 36.251 | 7.273 | 1.00 | 38.34 | O |
| ATOM | 2669 | O | HOH | C | 28 | 0.557 | 11.252 | 21.591 | 1.00 | 43.77 | O |
| ATOM | 2670 | O | HOH | C | 29 | -2.123 | 31.614 | 40.953 | 1.00 | 34.78 | O |
| ATOM | 2671 | O | HOH | C | 30 | 21.112 | 40.250 | 26.898 | 1.00 | 35.06 | O |
| ATOM | 2672 | O | HOH | C | 31 | -9.076 | 25.997 | 33.766 | 1.00 | 36.50 | O |
| ATOM | 2673 | O | HOH | C | 32 | -3.513 | 49.009 | 26.259 | 1.00 | 37.66 | O |
| ATOM | 2674 | O | HOH | C | 33 | 8.125 | 14.064 | 23.832 | 1.00 | 33.99 | O |
| ATOM | 2675 | O | HOH | C | 34 | 2.622 | | 30.17 | 1.00 | 35.173 11.524 | O |
| ATOM | 2676 | O | HOH | C | 35 | 6.216 | 21.134 | 31.899 | 1.00 | 38.41 | O |
| ATOM | 2677 | O | HOH | C | 36 | 9.787 | 10.559 | 23.826 | 1.00 | 36.64 | O |
| ATOM | 2678 | O | HOH | C | 37 | -8.082 | 25.521 | 41.012 | 1 | 47.14 00.0 | O |
| ATOM | 2679 | O | HOH | C | 38 | 16.237 | 25.619 | 0.821 | 1.00 | 39.12 | O |
| ATOM | 2680 | O | HOH | C | 39 | -11.257 | 28.900 | 18.934 | 1.00 | 51.23 | O |
| ATOM | 2681 | O | HOH | C | 40 | -9.574 | 18.677 | 32.756 | 1.00 | 37.09 | O |
| ATOM | 2682 | O | HOH | C | 41 | 17.141 | 35.834 | 4.392 | 1.00 | 39.65 | O |
| ATOM | 2683 | O | HOH | C | 42 | 34.118 | 26.392 | 32.175 | 1.00 | 35.06 | O |
| ATOM | 2684 | O | HOH | C | 43 | 7.193 | 11.711 | 24.368 | 1.00 | 26.04 | O |
| ATOM | 2685 | O | HOH | C | 44 | 0.406 | 12.036 | 33.279 | 1.00 | 51.34 | O |
| ATOM | 2686 | O | HOH | C | 45 | 0.263 | 34.604 | 12.212 | 1.00 | 40.95 | O |
| ATOM | 2687 | O | HOH | C | 46 | 6.843 | 34.374 | 18.048 | 1.00 | 47.69 | O |
| ATOM | 2688 | O | HOH | C | 47 | 21 | | 46.41 | 1.00 | 5.289 34.395 888.0 | O |
| ATOM | 2689 | O | HOH | C | 48 | -5.426 | 46.033 | 25.055 | 1.00 | 40.26 | O |
| ATOM | 2690 | O | HOH | C | 49 | 6.523 | 32.834 | 2.939 | 1.00 | 37.13 | O |

Fig. 26 (Cont.)

| | | | | | | | | | | |
|---|---|---|---|---|---|---|---|---|---|---|
| ATOM | 2691 | O | HOH C | 50 | 18.508 | 24.117 | 6.259 | | 52.30 1.00 | O |
| ATOM | 2692 | O | HOH C | 51 | 18.335 | 22.263 | 7.981 | 1.00 45.60 | | O |
| ATOM | 2693 | O | HOH C | 52 | -2.154 | 35.559 | 13.235 | 1.00 48.07 | | O |
| ATOM | 2694 | O | HOH C | 54 | 2.611 | 13.006 | 14.424 | 1.00 41.91 | | O |
| ATOM | 2695 | O | HOH C | 55 | 26.270 | 22.668 | 27.332 | 1.00 30.96 | | O |
| ATOM | 2696 | O | HOH C | 56 | -0.309 | 40.005 | 16.952 | 1.00 57.62 | | O |
| ATOM | 2697 | O | HOH C | 57 | 10.206 | 37.442 | 6.580 | 1.00 37.46 | | O |
| ATOM | 2698 | O | HOH C | 58 | -1.683 | 33.893 | 5.328 | 1.00 42.44 | | O |
| ATOM | 2699 | O | HOH C | 59 | 3.798 | 28.537 | 0.632 | 1.00 45.82 | | O |
| ATOM | 2700 | O | HOH C | 60 | 3.980 | 20.668 | 33.282 | 1.00 36.07 | | O |
| ATOM | 2701 | O | HOH C | 61 | | 47.51 1.00 | 13.548 | 31.638 | 7.651- | O |
| ATOM | 2702 | O | HOH C | 62 | -1.415 | 29.958 | 38.148 | 1.00 40.19 | | O |
| ATOM | 2703 | O | HOH C | 63 | -4.150 | 31.418 | 39.301 | 1.00 35.73 | | O |
| ATOM | 2704 | O | HOH C | 64 | 2.632 | 38.223 | 16 | | 54.94 1.00 | 361.O |
| ATOM | 2705 | O | HOH C | 65 | 1.160 | 32.335 | 4.746 | 1.00 39.33 | | O |
| ATOM | 2706 | O | HOH C | 66 | -0.191 | 46.319 | 17.177 | 1.00 43.43 | | O |
| ATOM | 2707 | O | HOH C | 67 | -4.515 | 38.523 | 16.699 | 1.00 44.18 | | O |
| ATOM | 2708 | O | HOH C | 68 | 0.004 | 5.610 | 21.831 | 1.00 42.81 | | O |
| ATOM | 2709 | O | HOH C | 69 | 6.755 | 38.052 | 13.941 | 1.00 45.39 | | O |
| ATOM | 2710 | O | HOH C | 70 | 1.484 | 36.838 | 11.727 | 1.00 48.01 | | O |
| ATOM | 2711 | O | HOH C | 71 | 11.347 | 38.766 | 1.463 | 1.00 40.35 | | O |
| ATOM | 2712 | O | HOH C | 72 | 10.803 | 2.521 | 21.920 | 1.00 39.86 | | O |
| ATOM | 2713 | O | HOH C | 73 | 6.257 | 46.235 | 9.482 | 1.00 32.20 | | O |
| ATOM | 2714 | O | HOH C | 74 | | 36.72 1.00 | 4.068 | 18.604 | 12.273 | O |
| ATOM | 2715 | O | HOH C | 75 | 26.852 | 43.345 | 22.771 | 1.00 36.45 | | O |
| ATOM | 2716 | O | HOH C | 76 | 4.545 | 42.095 | 38.551 | 1.00 37.17 | | O |
| ATOM | 2717 | O | HOH C | 77 | 6.173 | 40.625 | | 29.69 1.00 | 34.445 | O |
| ATOM | 2718 | O | HOH C | 78 | 17.757 | 39.446 | 33.552 | 1.00 33.40 | | O |
| ATOM | 2719 | O | HOH C | 79 | -1.810 | 47.142 | 19.553 | 1.00 43.25 | | O |
| ATOM | 2720 | O | HOH C | 80 | -0.261 | 5.530 | 24.453 | 1.00 41.11 | | O |
| ATOM | 2721 | O | HOH C | 81 | 27.755 | 41.917 | 14.870 | 1.00 40.21 | | O |
| ATOM | 2722 | O | HOH C | 82 | -2.810 | 43.733 | 41.772 | 1.00 30.48 | | O |
| ATOM | 2723 | O | HOH C | 83 | 23.268 | 46.982 | 8.565 | 1.00 47.12 | | O |
| ATOM | 2724 | O | HOH C | 84 | 9.064 | 35.101 | 1.155 | 1.00 36.99 | | O |
| ATOM | 2725 | O | HOH C | 85 | -9.299 | 14.474 | 22.813 | 1.00 40.07 | | O |
| ATOM | 2726 | O | HOH C | 86 | -7.301 | 17.445 | 14.157 | 1.00 37.86 | | O |
| ATOM | 2727 | O | HOH C | 87 | | 33.93 1.00 | 18.618 | 6.795 | 13.806 | O |
| ATOM | 2728 | O | HOH C | 88 | 13.004 | 8.186 | 42.001 | 1.00 38.57 | | O |
| ATOM | 2729 | O | HOH C | 89 | -14.146 | 19.502 | 26.726 | 1.00 51.48 | | O |
| ATOM | 2730 | O | HOH C | 90 | 24.308 | 8.974 | | 49.15 1.00 | 26.646 | O |
| ATOM | 2731 | O | HOH C | 91 | 34.768 | 31.860 | 18.488 | 1.00 35.21 | | O |
| ATOM | 2732 | O | HOH C | 92 | 21.505 | 28.792 | 4.395 | 1.00 43.28 | | O |
| ATOM | 2733 | O | HOH C | 93 | 0.147 | 20.019 | 34.435 | 1.00 37 | | 26.O |
| ATOM | 2734 | O | HOH C | 94 | -4.020 | 47.145 | 19.051 | 1.00 42.42 | | O |
| ATOM | 2735 | O | HOH C | 95 | 24.891 | 27.086 | 9.597 | 1.00 44.39 | | O |
| ATOM | 2736 | O | HOH C | 97 | 18.602 | 46.192 | 8.814 | 1.00 40.24 | | O |
| ATOM | 2737 | O | HOH C | 98 | 2.232 | 15.638 | 10.158 | 1.00 42.49 | | O |
| ATOM | 2738 | O | HOH C | 99 | 7.589 | 33.943 | -0.709 | 1.00 43.47 | | O |
| ATOM | 2739 | O | HOH C | 100 | 5.528 | 15.536 | 3.834 | 1.00 44.16 | | O |
| ATOM | 2740 | O | HOH C | | 39.62 1.00 | 12.801 | 14.851 | 0.629 | 101 | O |
| ATOM | 2741 | O | HOH C | 102 | 6.812 | 4.456 | 20.770 | 1.00 48.37 | | O |
| ATOM | 2742 | O | HOH C | 103 | -1.949 | 14.371 | 12.595 | 1.00 39.66 | | O |
| ATOM | 2743 | O | HOH C | 104 | 0.844 | 34 | | 53.95 1.00 | 16.486 | 429.O |
| ATOM | 2744 | O | HOH C | 105 | 7.768 | 1.761 | 21.718 | 1.00 38.28 | | O |
| ATOM | 2745 | O | HOH C | 106 | -13.022 | 19.911 | 29.013 | 1.00 37.60 | | O |
| ATOM | 2746 | O | HOH C | 107 | 12.029 | 0.880 | 23.767 | 1.00 | | 33.66 O |
| ATOM | 2747 | O | HOH C | 108 | 20.457 | 38.723 | 6.443 | 1.00 38.04 | | O |
| ATOM | 2748 | O | HOH C | 110 | -10.534 | 30.508 | 36.167 | 1.00 43.56 | | O |
| ATOM | 2749 | O | HOH C | 111 | -2.490 | 19.454 | 33.945 | 1.00 45.84 | | O |
| ATOM | 2750 | O | HOH C | 112 | -2.624 | 11.620 | 23.689 | 1.00 54.05 | | O |
| ATOM | 2751 | O | HOH C | 113 | -8.535 | 28.736 | 37.398 | 1.00 47.83 | | O |

Fig. 26 (Cont.)

| | | | | | | | | | | |
|---|---|---|---|---|---|---|---|---|---|---|
| ATOM | 2752 | O | HOH C 114 | 4.993 | 12.357 | 14.030 | 1.00 | 48.45 | | O |
| ATOM | 2753 | O | HOH C 115 | 21.043 | 6.659 | 26.003 | 1.00 | 43.96 | | O |
| ATOM | 2754 | O | HOH C 116 | 11.046 | 31.860 | 16.286 | 1.00 | 31.59 | | O |
| ATOM | 2755 | O | HOH C 117 | 4.213 | 51.982 | 15.574 | 1.00 | 45.89 | | O |
| ATOM | 2756 | O | HOH C 118 | 13.73 | | 45.89 | 1.00 | 29.31 | 24.01 | O |

Fig. 26 (Cont.)

SEQUENCE LISTING

```
<160> NUMBER OF SEQ ID NOS: 89

<210> SEQ ID NO 1
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 1
cgacgaaacc atggcgaagc tgattgcg                                           28

<210> SEQ ID NO 2
<211> LENGTH: 23
```

```
<212> TYPE: DNA
<213> ORGANISM: Artificial sequence
<220> FEATURE:
<223> OTHER INFORMATION: Single strand DNA oligonucleotide

<400> SEQUENCE: 2
ccgggagctg catgtgtcag agg                                              23

<210> SEQ ID NO 3
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 3
tcaatccgac tagtggttct ggtatggcga agctgattgc g                          41

<210> SEQ ID NO 4
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 4
ctgtcaagga attcatggcg aagctgattg cg                                    32

<210> SEQ ID NO 5
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 5
gtcccgggct gcagttatta gagctcacag taaaga                                36

<210> SEQ ID NO 6
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 6
cgacaaggcc atggcgaagc tgctagcact cacc                                  34

<210> SEQ ID NO 7
<211> LENGTH: 64
<212> TYPE: DNA
<213> ORGANISM: Artificial sequence
<220> FEATURE:
<223> OTHER INFORMATION: Single strand DNA oligonucleotide

<400> SEQUENCE: 7
cgacaaggcc atggcgaagc tgctagcact caccctcgtg ggactggtgt tggcactttc      60
caag                                                                   64

<210> SEQ ID NO 8
<211> LENGTH: 44
<212> TYPE: DNA
<213> ORGANISM: Artificial sequence
<220> FEATURE:
<223> OTHER INFORMATION: Single strand DNA oligonucleotide
```

```
<400> SEQUENCE: 8
gctcgagtgc ggccgcttac agatcacagt aaagagcttt gtgg          44

<210> SEQ ID NO 9
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 9
gctcgagtgc ggccgcttac aggtaacaac aaagagctct gtgg          44

<210> SEQ ID NO 10
<211> LENGTH: 6
<212> TYPE: DNA
<213> ORGANISM: Artificial sequence
<220> FEATURE:
<223> OTHER INFORMATION: Random hexamers
<220> FEATURE:
<221> NAME/KEY: misc_feature
<222> LOCATION: (1)..(6)
<223> OTHER INFORMATION: n is a, c, g, or t

<400> SEQUENCE: 10 nnnnnn                                                    6

<210> SEQ ID NO 11
<211> LENGTH: 22
<212> TYPE: DNA
<213> ORGANISM: Artificial sequence
<220> FEATURE:
<223> OTHER INFORMATION: Oligo dT
<220> FEATURE:
<221> NAME/KEY: misc_feature
<222> LOCATION: (22)..(22)
<223> OTHER INFORMATION: n is a, c, g, or t

<400> SEQUENCE: 11
tttttttttt tttttttttt vn                                  22

<210> SEQ ID NO 12
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 12
cgacaaggcc atggctaaac tgacagcgct c                        31

<210> SEQ ID NO 13
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 13
gctcgagtgc ggccgcttaa ttggcctgtg agagctcaca g             41

<210> SEQ ID NO 14
<211> LENGTH: 26
<212> TYPE: DNA
<213> ORGANISM: Artificial sequence
<220> FEATURE:
<223> OTHER INFORMATION: Single strand DNA oligonucleotide
```

<400> SEQUENCE: 14
cgcggttctg gtatgaaaga aaccgc                                    26

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15
cccgtttaga ggccccaagg gg                                        22

<210> SEQ ID NO 16
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 16
ggcagccaac tcagcttcc                                            19

<210> SEQ ID NO 17
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 17
cgaacgccag cacatgg                                              17

<210> SEQ ID NO 18
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 18
ccgggagctg catgtgtcag agg                                       23

<210> SEQ ID NO 19
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 19
cgacaaggcc atggggaagc tcgtggc                                   27

<210> SEQ ID NO 20
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 20
gctcgagtgc ggccgcttac agatcacagt aaagagcttt gtgg                44

<210> SEQ ID NO 21

```
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 21
cgacaaggcc atggggcacc tcgtggc                                        27

<210> SEQ ID NO 22
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 22
gctcgagtgc ggccgcttat tagagttcac agtacaaggc tttctgg                  47

<210> SEQ ID NO 23
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 23
cgacaaggcc atggcgaagc tcctgctgc                                      29

<210> SEQ ID NO 24
<211> LENGTH: 1065
<212> TYPE: DNA
<213> ORGANISM: Homo sapiens

<400> SEQUENCE: 24
atggcgaagc tgattgcgct caccctcttg gggatgggac tggcactctt caggaaccac    60
cagtcttctt accaaacacg acttaatgct ctccgagagg tacaacccgt agaacttcct   120
aactgtaatt tagttaaagg aatcgaaact ggctctgaag acttggagat actgcctaat   180
ggactggctt tcattagctc tggattaaag tatcctggaa taaagagctt caaccccaac   240
agtcctggaa aaatacttct gatggacctg aatgaagaag atccaacagt gttggaattg   300
gggatcactg gaagtaaatt tgatgtatct tcatttaacc ctcatgggat tagcacattc   360
acagatgaag ataatgccat gtacctcctg gtggtgaacc atccagatgc caagtccaca   420
gtggagttgt ttaaatttca agaagaagaa aaatcgcttt tgcatctaaa aaccatcaga   480
cataaacttc tgcctaattt gaatgatatt gttgctgtgg gacctgagca ctttttatggc   540
acaaatgatc actattttct tgacccctac ttacaatcct gggagatgta tttgggttta   600
gcgtggtcgt atgttgtcta ctatagtcca agtgaagttc gagtggtggc agaaggattt   660
gattttgcta tggaatcaa catttcaccc gatggcaagt atgtctatat agctgagttg   720
ctggctcata agattcatgt gtatgaaaag catgctaatt ggactttaac tccattgaag   780
tcccttgact ttaatacccct cgtggataac atatctgtgg atcctgagac aggagacctt   840
tgggttggat gccatcccaa tggcatgaaa atcttcttct atgactcaga gaatcctcct   900
gcatcagagg tgcttcgaat ccagaacatt ctaacgaaag aacctaaagt gacacaggtt   960
tatgcagaaa atggcacagt gttgcaaggc agtacagttg cctctgtgta caagggaaa   1020
ctgctgattg gcacagtgtt tcacaaagct ctttactgtg agctc                  1065
```

<210> SEQ ID NO 25
<211> LENGTH: 1065
<212> TYPE: DNA
<213> ORGANISM: Artificial sequence
<220> FEATURE:
<223> OTHER INFORMATION: In vitro evolved PON variant G1A5

<400> SEQUENCE: 25

```
atggctaaac tgacagcgct cacgctcttg gggctgggat tggcactctt cgatggacag    60
aagtcttctt tccaaacacg atttaatgtt caccgtgaag taactccagt ggaacttcct   120
aactgtaatt tagttaaagg gattgacaat ggttctgaag acttggaaat actgcccaat   180
ggactggctt tcatcagctc cggattaaaa tatcctggaa taatgagctt tgaccctgat   240
aagtctggaa agatacttct aatggacctg aatgaggaag acccagtagt gttggaactg   300
ggcattactg gaaatacatt ggatatatct tcatttaacc ctcatgggat tagcacattc   360
atagatgaag ataacactgt gtacctactg gtggtaaaac atccagactc ctcgtccact   420
gtggaggtat ttaaatttca agaaaaagaa aaatcacttt tgcatctgaa aaccatcaga   480
cacaagcttc tgcctagtgt gaatgacatt gtcgctgtgg acctgaaca cttttatgct   540
accaatgatc actatttat tgacccttac ttaaaatcct gggaaatgca tttgggatta   600
gcgtggtcat tgttactta ttatagtccc aatgatgttc gagtagtggc agaaggattt   660
gattttgcta acggaatcaa catctcacca gacggcaagt atgtctatat agctgaactg   720
ctggctcata gatccatgt gtatgaaaag cacgctaatt ggactttaac tccattgaag   780
tccctcgact ttaacactct tgtggacaac atatccgtgg atcctgtgac aggggacctt   840
tgggttggtt gtcatcccaa tggcatgcga atcttctact atgacccaga gaatcctccc   900
ggctcagagg tgcttcgaat ccagaacatt ttatccaaag agccaaagt gacagtggtt   960
tatgcagaga atggtaccgt cctgcaaggc accacggtcg cctctgtgta caaagggaaa  1020
ctgctgattg gcactgtgtt ccacaaagct ctttactgtg agctc                  1065
```

<210> SEQ ID NO 26
<211> LENGTH: 1065
<212> TYPE: DNA
<213> ORGANISM: Artificial sequence
<220> FEATURE:
<223> OTHER INFORMATION: In vitro evolved PON variant G1C4

<400> SEQUENCE: 26

```
atggcgaagc tgctagcact caccctcgtg ggactgggat tggcactctt cgatggacag    60
aagtcttctt tccaaacacg atttaatgtt caccgtgaag taacgccagt agaacttcct   120
aactgtaatt tagttaaagg aatcgagacg ggtgctgaag acttagagat tctgcctaat   180
ggactggctt tcatcagctc cggattaaaa tatcctggaa taatgagctt tgaccctgat   240
aagtctggaa agatacttct aatggacctg aatgaggaag acccagtagt gttggaactg   300
ggcattactg gaagtacatt tgatttatct tcatttaacc ctcatgggat tagtacattc   360
acagatgaag ataacactgt gtacctactg gtggtaaaac atccagactc ctcgtccact   420
gtggaggtat ttaaatttca agaaaaagaa aaatcacttt tgcatctgaa aaccatcaga   480
cacaagcttc tgcctagtgt gaatgacatt gtcgctgtgg acctgaaca cttttatgct   540
accaatgatc actatttat tgacccttac ttaaaatcct gggaaatgca tttgggatta   600
gcgtggtcat tgttactta ttatagtccc aatgatgttc gagtagtggc agaaggattt   660
gattttgcta acggaatcaa catctcacca gacggcaagt atgtctatat agctgaattg   720
```

```
ctggctcaca agattcacgt gtatgaaaag cacgctaatt ggactttaac tccattgaag      780
tccctcgact ttaacactct tgtggacaac atatccgtgg atcctgtgac aggggacctt      840
tgggttggtt gtcatcccaa tggcatgcga atcttctact atgacccaaa gaatcctcct      900
gcatcagagg tgcttcgaat ccaggacatt ttatccgaag accccaaaat aactgtagtt      960
tatgcagaga atggtaccgt cctgcaaggc accacggtcg cctctgtgta caagggaaa      1020 ctgctgattg gcacagtgtt tcacaaagct ctttactgtg atctg                     1065
```

<210> SEQ ID NO 27
<211> LENGTH: 1065
<212> TYPE: DNA
<213> ORGANISM: Artificial sequence
<220> FEATURE:
<223> OTHER INFORMATION: In vitro evolved PON variant G2D6

<400> SEQUENCE: 27

```
atggctaaac tgacagcgct cacgctcttg gggctgggat ggcactcttt cgatagacag       60
aagtcttctt tccaaacacg atttaatgtt caccgtgaag taactccagt ggaacttcct      120
aactgtaatt tagttaaagg gattgacaat ggttctgaag acttggaaat actgcccaat      180
ggactggctt tcatcagctc cggattaaaa tatcctggaa taatgagctt tgaccctgat      240
aagtctggaa agatacttct aatggacctg aatgaggaag acccagtagt gttggaactg      300
ggcattactg gaagtacatt tgatttatct tcatttaacc ctcatgggat tagcacattc      360
acagatgaag ataacactgt gtacctactg gtagtaaaac atccagactc ctcgtccact      420
gtggaggtat ttaaatttca agaaaaggag agatcacttt tgcatctgaa accatcaga      480 cacaagcttc tgcctagtgt gaatgacatt gtcgctgtgg acctgagag cttctatgcc      540 acaaatgatc actattttgc tgacccttac ttaaaatcct gggaaatgca tttgggatta      600
gcgtggtcat ttgttactta ttatagtccc aatgatgttc gagtagtggc agaaggattt      660
gattttgcta acggaatcaa catctcaccc gatggcaagt atgtctatat agctgaactg      720
ctggctcata agatccatgt gtatgaaaag cacgctaatt ggactttaac tccattgaag      780
tccctcgact ttaacactct tgtggataac atctctgtgg atcctgtgac aggggacctc      840
tgggtgggat gccatcccaa tggcatgcga atcttctact atgacccaga gaatcctccc      900
ggctcagagg tacttcgaat ccaggacatt ttatccaaag agcccaaagt gacagtggtt      960
tatgcagaaa atggcactgt gttacagggc agcacggtgg ccgctgtgta caagggaaa      1020 ctgctgattg gcactgtgtt ccacaaagct ctttactgtg atctg                     1065
```

<210> SEQ ID NO 28
<211> LENGTH: 1065
<212> TYPE: DNA
<213> ORGANISM: Artificial sequence
<220> FEATURE:
<223> OTHER INFORMATION: In vitro evolved PON variant G2E6

<400> SEQUENCE: 28

```
atggctaagc tgacagcgct caccctcttg gggatgggac tggcactctt cgataggcag       60
aagtcttctt tccaaacacg atttaatgtt caccgtgaag taacgccagt agaacttcct      120
aactgtaatt tagttaaagg gattgacaat ggttctgaag acttggaaat actgcccaat      180
ggactggctt tcatcagctc cggattaaaa tatcctggaa taatgagctt tgaccctgat      240
aagtctggaa agatacttct aatggacctg aatgagaagg agccagcagt gtcagagtta      300
gaaattatag gaaatacatt ggatatatct tcatttaacc ctcatgggat tagcacattc      360
```

```
atagatgatg ataacactgt gtacctactg gtggtaaacc atccaggctc ctcgtccact      420
gtggaggtat ttaaatttca agaagaagaa aaatcgcttt tgcatctgaa aaccatcaga      480
cacaagcttc tgcctagtgt gaatgacatt gtcgctgtgg gacctgaaca cttttatgct      540
accaatgatc actattttat tgacccttac ttaaaatcct gggaaatgca tttgggatta      600
gcgtggtcat tgttacctta ttatagtccc aatgatgttc gagtagtggc agaaggattt      660
gattttgcta acggaatcaa catctcacca gacggcaagt atgtctatat agctgaactg      720
ctggctcata agatccatgt gtatgaaaag cacgctaatt ggactttaac gccattgagg      780
gtcctcagct ttgacaccct tgtggataac atatccgtgg atcctgtgac aggggacctt      840
tgggttggtt gtcatcccaa cggaatgagg atcttttttct atgacgcaga gaatcctccc      900
ggctcagagg tgcttcgaat ccaggacatt ttatccgaag agcccaagt gacagtggtt       960 tatgcagaaa atggcactgt gttacagggc agcacggtgg ccgctgtgta caaagggaaa     1020
ctgctgattg gcacagtgtt tcacaaagct ctttactgtg atctg                     1065
```

<210> SEQ ID NO 29
<211> LENGTH: 1065
<212> TYPE: DNA
<213> ORGANISM: Artificial sequence
<220> FEATURE:
<223> OTHER INFORMATION: In vitro evolved PON variant G3H8

<400> SEQUENCE: 29

```
atggctaaac tgacagcgcc cacgctcttg gggctgggat tggcactctt cgatagacag       60
aagtcttctt tccaaacacg atttaatgtt caccgtgaag taactccagt ggaacttcct      120
aactgtaatt tagttaaagg gattgacaat ggttctgaag acttggaaat actgcccaat      180
ggactggctt tcatcagctc cggattaaaa tatcctggaa taatgagctt tgaccctgat      240
aagtctggaa agatacttct aatggacctg aatgaggaag acccagtagt gttgaactg       300 ggcattactg gaagtacatt tgatttatct tcatttaacc ctcatgggat tagcacattc      360
acagatgaag ataacactgt gtacctactg gtagtaaacc atccagactc ctcgtccact      420
gtggaggtat ttaaatttca agaaaaggag agatcacttt tgcatctgaa aaccatcaga      480
cacaagcttc tgcctagtgt gaatgacatt gtcgctgtgg gacctgagag cttttatgcc      540
acaaatgatc actattttgc tgacccttac ttaaaatcct gggaaatgca tttgggatta      600
gcgtggtcat tgttacctta ttatagtccc aatgatgttc gagtagtggc agaaggattt      660
gattttgcta acggaatcaa catctcaccc gatggcaagt atgtctatat agctgaactg      720
ctggctcata agatccatgt gtatgaaaag cacgccaatt ggactttaac tccattgaag      780
tccctcgact ttaacactct tgtggataac atctctgtgg atcctgtgac aggggacctc      840
tgggtgggat gccatcccaa tggcatgcga atcttctact atgacccaga gaatcctccc      900
ggctcagagg tacttcgaat ccaggacatt ttatccaaag agcccaaagt gacagtggtt      960
tatgcagaaa atggcactgt gttacagggc agcacggtgg ccgctgtgta caaagggaaa     1020
ctgctgattg gcactgtgtt ccacaaagct ctttactgtg atctg                     1065
```

<210> SEQ ID NO 30
<211> LENGTH: 1062
<212> TYPE: DNA
<213> ORGANISM: Oryctolagus cuniculus

<400> SEQUENCE: 30

```
atggcgaagc tcctgctgct gaccctgctg ggggccagcc tcgccttcgt cggggagagg      60
ttgctggcgt ttagaaacag ctttggtgca gttcaagaac tggagccagt agaaccccag     120
aactgtgtcc ttattgaggg actcgaaaat ggctcggaag atattgatat acttcctagt     180
gggctggctt ttatctccag tggattaaaa tatccaggca tgccaaactt tgcaccagat     240
gagccaggaa aaatcttctt gatagatatg aatgagaaga acccaagagc acaagagctg     300
gaaatcagca atggatttga aaagaatca ttcaatccac atgggatcag cactttcatt      360
gataaagacc atactgtgta tctttatgtt gtgaatcatc cccacatgaa gtctactgtg     420
gagatattta aatttgagga acaacaacgc tctcttgtac acctgaaaac tataaaacat     480
gaacttctca agagtgtgaa taacattgtg gttcttggac cggaacagtt ctacgccacc     540
agagaccact attttaccaa ctatgtctta gcacttcttg agatgttttt ggatcttcac     600
tggacttccg ttcttttcta cagccccaaa gaggtcaaag tggtggccaa aggattcagt     660
tctgccaatg ggatcacagt ctcactagat aagaagtatg tctatgttgc tgatgccaca     720
gctaagaatg tgcatgtaat ggaaaaacat gacaactggg atttaactga actgaaggta     780
atacacttgg acaccttagt ggataatttg tctgttgatc ctgccacggg agatatcttg     840
gcaggatgcc atcctaatgg catgaagctt ctgaactata accctgagga tcctccagga     900
tcagaagtac ttcgtatcca gaatgttttg tctgagaagc ccagggtgag caccgtgtac     960
accaatgacg ctctgtgct tcagggctcc accgtggctt ctgtgtacca agggaagatt    1020
ctcataggca ctatatttca caaaactctg tattgtgtgc tc                      1062

<210> SEQ ID NO 31
<211> LENGTH: 1062
<212> TYPE: DNA
<213> ORGANISM: Homo sapiens

<400> SEQUENCE: 31
atggggaagc tcgtggcgct ggtcctgctg ggggtcggcc tgtccttagt cggggagatg      60
ttcctggcgt ttagagaaag ggtgaatgcc tctcgagaag tggagccagt agaacctgaa     120
aactgccacc ttattgagga acttgaaagt ggctctgaag atattgatat acttcctagt     180
gggctggctt ttatctccag tggattaaaa tatccaggca tgccaaactt tgcgccagat     240
gaaccaggaa aaatcttctt gatggatctg aatgaacaaa acccaagggc acaagcacta     300
gaaatcagtg gtggatttga caagaattaa tttaatccac atgggatcag tattttcatc     360
gacaaagaca tactgtgta tctttatgtt gtgaatcatc cccacatgaa gtccactgtg      420
gagatattta aatttgagga acaacaacgt tctctggtat acctgaaaac tataaaacat     480
gaacttctca aaagtgtgaa tgacattgtg gttcttggac cagaacagtt ctatgccacc     540
agagaccact attttaccaa ctccctcctg tcatttttg agatgatctt ggatcttcgc     600
tggacttatg ttctttttcta cagcccaagg gaggttaaag tggtggccaa aggattttgt    660
agtgccaatg ggatcacagt ctcagcagac agaagtatg tctatgtagc tgatgtagca     720
gctaagaaca ttcacataat ggaaaaacat gataactggg atttaactca actgaaggtg     780
atacagttgg gcaccttagt ggataacctg actgtcgatc ctgccacagg agacattttg     840
gcaggatgcc atcctaatcc tatgaagcta ctgaactata accctgagga ccctccagga     900
tcagaagtac ttcgcatcca gaatgttttg tctgagaagc ccagggtgag caccgtgtat     960
gccaacaatg ctctgtgct tcagggcacc tctgtggctt ctgtgtacca tgggaaaatt    1020
ctcataggca ccgtatttca caaaactctg tactgtgagc tc                      1062
```

<210> SEQ ID NO 32
<211> LENGTH: 1062
<212> TYPE: DNA
<213> ORGANISM: Mus musculus
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 32

| | | | | | |
|---|---|---|---|---|---|
| atggggcacc | tcgtggcgct | gcccttgctg | ggagcctgtc | tggccttaat | angggnaagg | 60 |
| ctgctgaatt | ttagagaacg | agttagtaca | actcgagaaa | taaaggccac | agaaccacaa | 120 |
| aactgccacc | tgattgaggg | cctcgagaat | ggctctgaag | atattgatat | acttcctagc | 180 |
| gggctggctt | ttatctccac | tggattaaaa | tatccgggca | tgccagcgtt | tgcaccggac | 240 |
| aaaccaggaa | gaatctttct | gatggatctg | aatgagcaaa | acccagaggc | gcaagcactg | 300 |
| gaaatcagtg | gtgggcttga | ccaggagtca | ctaaatcctc | acgggatcag | cactttcatc | 360 |
| gacaaagaca | acactgctta | tctttatgtc | gtgaatcacc | ccaacatgga | ctccactgtg | 420 |
| gagatattta | agtttgaaga | caacaacgc | tctctcatcc | acctgaaaac | tctaaaacat | 480 |
| gaacttctca | agagtgtgaa | tgacattgtg | gttcttgggc | cagagcagtt | ctatgccaca | 540 |
| agagaccatt | actttaccag | ttatttcttg | gtacttctgg | agatgatctt | ggaccctcac | 600 |
| tggacttccg | tcgttttcta | cagcccaaaa | gaggtcaaag | ttgtggccca | aggattcagt | 660 |
| tctgccaacg | gaatcacagt | ctcactagac | cagaagtttg | tctatgtagc | tgatgtaaca | 720 |
| gctaagaaca | ttcacataat | ggaaaaacat | gataattggg | atttaactcc | agtgaaggtc | 780 |
| attcagctgg | ggaccttagt | ggataacctg | accgttgctc | cagccacggg | agatattttg | 840 |
| gcaggctgcc | accctaaccc | catgaagctg | ttgatctata | atcctgaggg | ccctccagga | 900 |
| tcagaagtac | tacgcatcca | ggactctttg | tcagataagc | ccagggtgag | cacactgtat | 960 |
| gcgaacaacg | gctctgtgct | tcagggcagc | accgtggctt | ctgtgtatca | taagagaatg | 1020 |
| ctcataggta | ctatatttca | caaagctctg | tactgtgacc | tc | | 1062 |

<210> SEQ ID NO 33
<211> LENGTH: 1065
<212> TYPE: DNA
<213> ORGANISM: Oryctolagus cuniculus

<400> SEQUENCE: 33

| | | | | | |
|---|---|---|---|---|---|
| atggctaaac | tgacagcgct | cacgctcttg | gggctgggat | tggcactctt | cgatggacag | 60 |
| aagtcttctt | tccaaacacg | atttaatgtt | caccgtgaag | taactccagt | ggaacttcct | 120 |
| aactgtaatt | tagttaaagg | gattgacaat | ggttctgaag | acttggaaat | actgccaat | 180 |
| ggactggctt | tcatcagctc | cggattaaaa | tatcctggaa | taatgagctt | tgaccctgat | 240 |
| aagtctggaa | agatacttct | aatggacctg | aatgaggaag | acccagtagt | gttggaactg | 300 |
| ggcattactg | gaagtacatt | tgatttatct | tcatttaacc | ctcatgggat | tagcacattc | 360 |
| acagatgaag | ataatatcgt | ctacctgatg | gtggtgaacc | atccagattc | aaagtccaca | 420 |
| gtggagttgt | ttaaattcca | agaaaaagaa | aaatcacttt | tgcatctgaa | accatcaga | 480 |
| cacaagcttc | tgcctagtgt | gaatgacatt | gtcgctgtgg | gacctgaaca | cttttatgct | 540 |

```
accaatgatc actattttat tgacccttac ttaaaatcct gggaaatgca tttgggatta      600
gcgtggtcat ttgttactta ttatagtccc aatgatgttc gagtagtggc agaaggattt      660
gattttgcta acggaatcaa catctcacca gacggcaagt atgtctatat agctgaactg      720
ctggctcata agatccatgt gtatgaaaag cacgctaatt ggactttaac tccattgaag      780
tccctcgact ttaacactct tgtggacaac atatccgtgg atcctgtgac aggggacctt      840
tgggttggtt gtcatcccaa tggcatgcga atcttctact atgacccaaa gaatcctcct      900
gcatcagagg tgcttcgaat ccaggacatt ttatccaaag agcccaaagt gacagtggct      960
tatgcagaaa atggcactgt gttacagggc agcacggtgg ccgctgtgta caaagggaaa     1020
atgctggttg gcaccgtgtt ccacaaagct ctctactgtg agctc                     1065

<210> SEQ ID NO 34
<211> LENGTH: 1065
<212> TYPE: DNA
<213> ORGANISM: Mus musculus

<400> SEQUENCE: 34
atggcgaagc tgctagcact caccctcgtg ggactggtgt tggcacttta caagaaccat       60
cggtcttcct atcaaacaag attaaatgct ttccgtgaag taacgccagt agaacttcct      120
aactgtaatt tagttaaagg aatcgagacg ggtgctgaag acttagagat tctgcctaat      180
ggactaactt tctttagcac tgggctaaag tatcctggaa taaaaagttt cgatcccagt      240
aagcctggaa aaatacttct gatggacttg aacaagaagg agccagcagt gtcagagtta      300
gaaattatag gaaatacatt ggatatatct tcatttaacc ctcatgggat tagtacattc      360
acagatgaag ataacactgt gtacctactg gtggtaaacc atccagactc ctcgtccact      420
gtggaggtat ttaaatttca agaagaggaa agatcactct tgcatctgaa aaccatcaca      480
catgaacttc tgcctagcat caacgatata gctgctattg acctgagag cttttatgcc       540 acaaatgatc actatttggc tgacccatac ttacggtcct gggaaatgta cttgggtctg      600
tcgtggtcca atgttgttta ctacagtcca gataaagtcc aggtggtagc agaagggttt      660
gatttcgcga atggcattgg catttccctt gatggcaagt atgtctatat agctgaattg      720
ctggctcaca agattcatgt gtatgaaaag catgctaatt ggactttaac accattgaag      780
gtcctcaact ttgacacccct tgtggataac atctctgtgg atcctgtgac aggggacctc      840
tgggtgggat gccatcccaa cggaatgagg atcttttttct atgacgcaga gaatcctccc      900
ggctcagagg tgcttcgaat ccagaacatt ttatccgaag accccaaaat aactgtagtt      960
tatgcagaga atggtaccgt cctgcaaggc accacggtcg cctctgtgta caaagggaaa     1020
ctgctgattg gcactgtgtt ccacaaagct ctttactgtg atctg                     1065

<210> SEQ ID NO 35
<211> LENGTH: 1068
<212> TYPE: DNA
<213> ORGANISM: Rattus norvegicus

<400> SEQUENCE: 35
atggcgaaac tgctagggct caccctcgtg ggactggtgt tggcacttta caagaaccat       60
cggtcttcct atcaaacaag attaaatgct ttccgtgaag taacaccggt agatcttcct      120
aactgtactt tagttaaagg aatcgaagcg ggtgctgaag acttagagat tctgcctaat      180
ggactaactt tctttagcac agggttaaag tatcctggaa taaaaagttt cgatcccagt      240
aagcctggaa aaatacttct gatggacttg aatgagaagg agccagcagt gtcagaatta      300
```

```
gcaattatgg gaaatacgtt ggatatgtct tcatttaacc ctcatgggat tagcacattc    360
atagatgaag ataacactgt gtacctactg gtggtaagcc acccagactc ctcgtccacc    420
gtggaggtgt ttaaatttca agaagaggaa agatcacttt tgcatctgaa accatcacc     480 catgaacttc tgcctagcat caacgatata gctgctgttg gacctgagag cttctatgcc    540
acaaatgatc actattttgc tgacccatac ttacggtcct gggaaatgta cttgggcctg    600
tcatggtcca atgttgtata ctacagtcca gataaagtcc gagtggtagc agatggattt    660
gatttcgcta atggcattgg catttcccct tgatggcaagt atgtctatat cgctgaattg    720
ctggctcaca agattcacgt gtatgaaaag catgctaatt ggactttaac gccattgaag    780
gtcctcagct ttgacaccct tgtggataac atctctgtgg atcctgtgac aggggacctc    840
tgggttggat gccatcccaa tgggatgagg attttttttct atgactcgga gaatcctcct    900
ggctcagagg tgcttcggat ccagagcatt ttatccgaag accccaaagt aactgtagtt    960
tatgcagaga atggcacggt gttgcaaggt acgacagtcg ctgctgtgta caaaggaaaa   1020
ctgctgattg gaacggtgtt ccacagagct ctttgttgtg acctgtga                1068
```

<210> SEQ ID NO 36
<211> LENGTH: 355
<212> TYPE: PRT
<213> ORGANISM: Homo sapiens

<400> SEQUENCE: 36

```
Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Leu Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Tyr Phe Leu Asp Pro Tyr Leu Gln
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240
```

```
Leu Ala His Lys Ile His Val Tyr Glu Lys His Ala Asn Trp Thr Leu
            245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
            275                 280                 285

Met Lys Ile Phe Phe Tyr Asp Ser Glu Asn Pro Ala Ser Glu Val
            290                 295                 300

Leu Arg Ile Gln Asn Ile Leu Thr Glu Pro Lys Val Thr Gln Val
305                 310                 315                 320

Tyr Ala Glu Asn Gly Thr Val Leu Gln Gly Ser Thr Val Ala Ser Val
            325                 330                 335

Tyr Lys Gly Lys Leu Leu Ile Gly Thr Val Phe His Lys Ala Leu Tyr
            340                 345                 350

Cys Glu Leu
        355

<210> SEQ ID NO 37
<211> LENGTH: 355
<212> TYPE: PRT
<213> ORGANISM: Oryctolagus cuniculus

<400> SEQUENCE: 37

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Ile
            35                  40                  45

Asp Asn Gly Ser Glu Asp Leu Glu Ile Leu Pro Asn Gly Leu Ala Phe
        50                  55                  60

Ile Ser Ser Gly Leu Lys Tyr Pro Gly Ile Met Ser Phe Asp Pro Asp
65              70                  75                  80

Lys Ser Gly Lys Ile Leu Leu Met Asp Leu Asn Glu Glu Asp Pro Val
            85                  90                  95

Val Leu Glu Leu Gly Ile Thr Gly Ser Thr Phe Asp Leu Ser Ser Phe
            100                 105                 110

Asn Pro His Gly Ile Ser Thr Phe Thr Asp Glu Asp Asn Ile Val Tyr
            115                 120                 125

Leu Met Val Val Asn His Pro Asp Ser Lys Ser Thr Val Glu Leu Phe
        130                 135                 140

Lys Phe Gln Glu Lys Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ile Asp Pro Tyr Leu Lys
            180                 185                 190

Ser Trp Glu Met His Leu Gly Leu Ala Trp Ser Phe Val Thr Tyr Tyr
            195                 200                 205

Ser Pro Asn Asp Val Arg Val Val Ala Glu Gly Phe Asp Phe Ala Asn
        210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
```

```
                         245                 250                 255
Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
            275                 280                 285

Met Arg Ile Phe Tyr Tyr Asp Pro Lys Asn Pro Ala Ser Glu Val
            290                 295                 300

Leu Arg Ile Gln Asp Ile Leu Ser Lys Glu Pro Lys Val Thr Val Ala
305                 310                 315                 320

Tyr Ala Glu Asn Gly Thr Val Leu Gln Gly Ser Thr Val Ala Ala Val
                325                 330                 335

Tyr Lys Gly Lys Met Leu Val Gly Thr Val Phe His Lys Ala Leu Tyr
            340                 345                 350

Cys Glu Leu
        355

<210> SEQ ID NO 38
<211> LENGTH: 355
<212> TYPE: PRT
<213> ORGANISM: Mus musculus

<400> SEQUENCE: 38

Met Ala Lys Leu Leu Ala Leu Thr Leu Val Gly Leu Val Leu Ala Leu
1               5                   10                  15

Tyr Lys Asn His Arg Ser Ser Tyr Gln Thr Arg Leu Asn Ala Phe Arg
            20                  25                  30

Glu Val Thr Pro Val Glu Leu Pro Asn Cys Asn Leu Val Lys Gly Ile
        35                  40                  45

Glu Thr Gly Ala Glu Asp Leu Glu Ile Leu Pro Asn Gly Leu Thr Phe
    50                  55                  60

Phe Ser Thr Gly Leu Lys Tyr Pro Gly Ile Lys Ser Phe Asp Pro Ser
65                  70                  75                  80

Lys Pro Gly Lys Ile Leu Leu Met Asp Leu Asn Lys Lys Glu Pro Ala
                85                  90                  95

Val Ser Glu Leu Glu Ile Ile Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Arg Ser Leu Leu His Leu Lys Thr Ile Thr
145                 150                 155                 160

His Glu Leu Leu Pro Ser Ile Asn Asp Ile Ala Ala Ile Gly Pro Glu
                165                 170                 175

Ser Phe Tyr Ala Thr Asn Asp His Tyr Leu Ala Asp Pro Tyr Leu Arg
            180                 185                 190

Ser Trp Glu Met Tyr Leu Gly Leu Ser Trp Ser Asn Val Val Tyr Tyr
        195                 200                 205

Ser Pro Asp Lys Val Gln Val Val Ala Glu Gly Phe Asp Phe Ala Asn
    210                 215                 220

Gly Ile Gly Ile Ser Leu Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255
```

```
Thr Pro Leu Lys Val Leu Asn Phe Asp Thr Leu Val Asp Asn Ile Ser
        260                 265                 270

Val Asp Pro Val Thr Gly Asp Leu Trp Val Gly Cys His Pro Asn Gly
        275                 280                 285

Met Arg Ile Phe Phe Tyr Asp Ala Glu Asn Pro Pro Gly Ser Glu Val
        290                 295                 300

Leu Arg Ile Gln Asn Ile Leu Ser Glu Asp Pro Lys Ile Thr Val Val
305                 310                 315                 320

Tyr Ala Glu Asn Gly Thr Val Leu Gln Gly Thr Thr Val Ala Ser Val
                325                 330                 335

Tyr Lys Gly Lys Leu Leu Ile Gly Thr Val Phe His Lys Ala Leu Tyr
                340                 345                 350

Cys Asp Leu
        355

<210> SEQ ID NO 39
<211> LENGTH: 355
<212> TYPE: PRT
<213> ORGANISM: Rattus norvegicus

<400> SEQUENCE: 39

Met Ala Lys Leu Leu Gly Leu Thr Leu Val Gly Leu Val Leu Ala Leu
1               5                   10                  15

Tyr Lys Asn His Arg Ser Ser Tyr Gln Thr Arg Leu Asn Ala Phe Arg
                20                  25                  30

Glu Val Thr Pro Val Asp Leu Pro Asn Cys Thr Leu Val Lys Gly Ile
            35                  40                  45

Glu Ala Gly Ala Glu Asp Leu Glu Ile Leu Pro Asn Gly Leu Thr Phe
        50                  55                  60

Phe Ser Thr Gly Leu Lys Tyr Pro Gly Ile Lys Ser Phe Asp Pro Ser
65                  70                  75                  80

Lys Pro Gly Lys Ile Leu Leu Met Asp Leu Asn Glu Lys Glu Pro Ala
                85                  90                  95

Val Ser Glu Leu Ala Ile Met Gly Asn Thr Leu Asp Met Ser Ser Phe
            100                 105                 110

Asn Pro His Gly Ile Ser Thr Phe Ile Asp Glu Asp Asn Thr Val Tyr
        115                 120                 125

Leu Leu Val Val Ser His Pro Asp Ser Ser Ser Thr Val Glu Val Phe
130                 135                 140

Lys Phe Gln Glu Glu Glu Arg Ser Leu Leu His Leu Lys Thr Ile Thr
145                 150                 155                 160

His Glu Leu Leu Pro Ser Ile Asn Asp Ile Ala Ala Val Gly Pro Glu
                165                 170                 175

Ser Phe Tyr Ala Thr Asn Asp His Tyr Phe Ala Asp Pro Tyr Leu Arg
            180                 185                 190

Ser Trp Glu Met Tyr Leu Gly Leu Ser Trp Ser Asn Val Val Tyr Tyr
        195                 200                 205

Ser Pro Asp Lys Val Arg Val Val Ala Asp Gly Phe Asp Phe Ala Asn
    210                 215                 220

Gly Ile Gly Ile Ser Leu Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Val Leu Ser Phe Asp Thr Leu Val Asp Asn Ile Ser
            260                 265                 270
```

-continued

Val Asp Pro Val Thr Gly Asp Leu Trp Val Gly Cys His Pro Asn Gly
            275                 280                 285

Met Arg Ile Phe Phe Tyr Asp Ser Glu Asn Pro Pro Gly Ser Glu Val
        290                 295                 300

Leu Arg Ile Gln Ser Ile Leu Ser Glu Asp Pro Lys Val Thr Val Val
305                 310                 315                 320

Tyr Ala Glu Asn Gly Thr Val Leu Gln Gly Thr Thr Val Ala Ala Val
                325                 330                 335

Tyr Lys Gly Lys Leu Leu Ile Gly Thr Val Phe His Arg Ala Leu Cys
            340                 345                 350

Cys Asp Leu
        355

<210> SEQ ID NO 40
<211> LENGTH: 354
<212> TYPE: PRT
<213> ORGANISM: Homo sapiens

<400> SEQUENCE: 40

Met Gly Lys Leu Val Ala Leu Val Leu Leu Gly Val Gly Leu Ser Leu
1               5                   10                  15

Val Gly Glu Met Phe Leu Ala Phe Arg Glu Arg Val Asn Ala Ser Arg
            20                  25                  30

Glu Val Glu Pro Val Glu Pro Glu Asn Cys His Leu Ile Glu Glu Leu
        35                  40                  45

Glu Ser Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Met Asp Leu Asn Glu Gln Asn Pro Arg
                85                  90                  95

Ala Gln Ala Leu Glu Ile Ser Gly Gly Phe Asp Lys Glu Leu Phe Asn
            100                 105                 110

Pro His Gly Ile Ser Ile Phe Ile Asp Lys Asp Asn Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val Tyr Leu Lys Thr Ile Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp His Tyr Phe Thr Asn Ser Leu Leu Ser Phe
            180                 185                 190

Phe Glu Met Ile Leu Asp Leu Arg Trp Thr Tyr Val Leu Phe Tyr Ser
        195                 200                 205

Pro Arg Glu Val Lys Val Val Ala Lys Gly Phe Cys Ser Ala Asn Gly
    210                 215                 220

Ile Thr Val Ser Ala Asp Gln Lys Tyr Val Tyr Val Ala Asp Val Ala
225                 230                 235                 240

Ala Lys Asn Ile His Ile Met Glu Lys His Asp Asn Trp Asp Leu Thr
                245                 250                 255

Gln Leu Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met

-continued

```
                275                 280                 285
Lys Leu Leu Asn Tyr Asn Pro Glu Asp Pro Pro Gly Ser Glu Val Leu
    290                 295                 300
Arg Ile Gln Asn Val Leu Ser Glu Lys Pro Arg Val Ser Thr Val Tyr
305                 310                 315                 320
Ala Asn Asn Gly Ser Val Leu Gln Gly Thr Ser Val Ala Ser Val Tyr
                325                 330                 335
His Gly Lys Ile Leu Ile Gly Thr Val Phe His Lys Thr Leu Tyr Cys
                340                 345                 350
Glu Leu

<210> SEQ ID NO 41
<211> LENGTH: 354
<212> TYPE: PRT
<213> ORGANISM: Oryctolagus cuniculus

<400> SEQUENCE: 41

Met Ala Lys Leu Leu Leu Thr Leu Leu Gly Ala Ser Leu Ala Phe
1               5                   10                  15
Val Gly Glu Arg Leu Leu Ala Phe Arg Asn Ser Phe Gly Ala Val Gln
                20                  25                  30
Glu Leu Glu Pro Val Glu Pro Gln Asn Cys Val Leu Ile Glu Gly Leu
            35                  40                  45
Glu Asn Gly Ser Glu Asp Ile Asp Ile Leu Pro Ser Gly Leu Ala Phe
        50                  55                  60
Ile Ser Ser Gly Leu Lys Tyr Pro Gly Met Pro Asn Phe Ala Pro Asp
65                  70                  75                  80
Glu Pro Gly Lys Ile Phe Leu Ile Asp Met Asn Glu Lys Asn Pro Arg
                85                  90                  95
Ala Gln Glu Leu Glu Ile Ser Asn Gly Phe Glu Lys Glu Ser Phe Asn
            100                 105                 110
Pro His Gly Ile Ser Thr Phe Ile Asp Lys Asp His Thr Val Tyr Leu
        115                 120                 125
Tyr Val Val Asn His Pro His Met Lys Ser Thr Val Glu Ile Phe Lys
    130                 135                 140
Phe Glu Glu Gln Gln Arg Ser Leu Val His Leu Lys Thr Ile Lys His
145                 150                 155                 160
Glu Leu Leu Lys Ser Val Asn Asn Ile Val Val Leu Gly Pro Glu Gln
                165                 170                 175
Phe Tyr Ala Thr Arg Asp His Tyr Phe Thr Asn Tyr Val Leu Ala Leu
            180                 185                 190
Leu Glu Met Phe Leu Asp Leu His Trp Thr Ser Val Leu Phe Tyr Ser
        195                 200                 205
Pro Lys Glu Val Lys Val Ala Lys Gly Phe Ser Ser Ala Asn Gly
    210                 215                 220
Ile Thr Val Ser Leu Asp Lys Lys Tyr Val Tyr Val Ala Asp Ala Thr
225                 230                 235                 240
Ala Lys Asn Val His Val Met Glu Lys His Asp Asn Trp Asp Leu Thr
                245                 250                 255
Glu Leu Lys Val Ile His Leu Asp Thr Leu Val Asp Asn Leu Ser Val
            260                 265                 270
Asp Pro Ala Thr Gly Asp Ile Leu Ala Gly Cys His Pro Asn Gly Met
        275                 280                 285
Lys Leu Leu Asn Tyr Asn Pro Glu Asp Pro Pro Gly Ser Glu Val Leu
```

```
                290                 295                 300
Arg Ile Gln Asn Val Leu Ser Glu Lys Pro Arg Val Ser Thr Val Tyr
305                 310                 315                 320

Thr Asn Asp Gly Ser Val Leu Gln Gly Ser Thr Val Ala Ser Val Tyr
                325                 330                 335

Gln Gly Lys Ile Leu Ile Gly Thr Ile Phe His Lys Thr Leu Tyr Cys
                340                 345                 350

Val Leu

<210> SEQ ID NO 42
<211> LENGTH: 354
<212> TYPE: PRT
<213> ORGANISM: Mus musculus
<220> FEATURE:
<221> NAME/KEY: misc_feature
<222> LOCATION: (18)..(19)
<223> OTHER INFORMATION: Xaa can be any naturally occurring amino acid

<400> SEQUENCE: 42

Met Gly His Leu Val Ala Leu Pro Leu Leu Gly Ala Cys Leu Ala Leu
1               5                   10                  15

Ile Xaa Xaa Arg Leu Leu Asn Phe Arg Glu Arg Val Ser Thr Thr Arg
                20                  25                  30

Glu Ile Lys Ala Thr Glu Pro Gln Asn Cys His Leu Ile Glu Gly Leu
            35                  40                  45

Glu Asn Gly Ser Glu Asp Ile Asp Ile Leu Pro Ser Gly Leu Ala Phe
        50                  55                  60

Ile Ser Thr Gly Leu Lys Tyr Pro Gly Met Pro Ala Phe Ala Pro Asp
65                  70                  75                  80

Lys Pro Gly Arg Ile Phe Leu Met Asp Leu Asn Glu Gln Asn Pro Glu
                85                  90                  95

Ala Gln Ala Leu Glu Ile Ser Gly Gly Leu Asp Gln Glu Ser Leu Asn
            100                 105                 110

Pro His Gly Ile Ser Thr Phe Ile Asp Lys Asp Asn Thr Ala Tyr Leu
        115                 120                 125

Tyr Val Val Asn His Pro Asn Met Asp Ser Thr Val Glu Ile Phe Lys
130                 135                 140

Phe Glu Glu Gln Gln Arg Ser Leu Ile His Leu Lys Thr Leu Lys His
145                 150                 155                 160

Glu Leu Leu Lys Ser Val Asn Asp Ile Val Leu Gly Pro Glu Gln
                165                 170                 175

Phe Tyr Ala Thr Arg Asp His Tyr Phe Thr Ser Tyr Phe Leu Val Leu
            180                 185                 190

Leu Glu Met Ile Leu Asp Pro His Trp Thr Ser Val Val Phe Tyr Ser
        195                 200                 205

Pro Lys Glu Val Lys Val Ala Gln Gly Phe Ser Ser Ala Asn Gly
            210                 215                 220

Ile Thr Val Ser Leu Asp Gln Lys Phe Val Tyr Val Ala Asp Val Thr
225                 230                 235                 240

Ala Lys Asn Ile His Ile Met Glu Lys His Asp Asn Trp Asp Leu Thr
                245                 250                 255

Pro Val Lys Val Ile Gln Leu Gly Thr Leu Val Asp Asn Leu Thr Val
            260                 265                 270

Ala Pro Ala Thr Gly Asp Ile Leu Ala Gly Cys His Pro Asn Pro Met
        275                 280                 285
```

-continued

```
Lys Leu Leu Ile Tyr Asn Pro Glu Gly Pro Pro Gly Ser Glu Val Leu
        290                 295                 300

Arg Ile Gln Asp Ser Leu Ser Asp Lys Pro Arg Val Ser Thr Leu Tyr
305                 310                 315                 320

Ala Asn Asn Gly Ser Val Leu Gln Gly Ser Thr Val Ala Ser Val Tyr
                325                 330                 335

His Lys Arg Met Leu Ile Gly Thr Ile Phe His Lys Ala Leu Tyr Cys
            340                 345                 350

Asp Leu
```

<210> SEQ ID NO 43
<211> LENGTH: 1062
<212> TYPE: DNA
<213> ORGANISM: Artificial sequence
<220> FEATURE:
<223> OTHER INFORMATION: In vitro evolved PON variant G1A7

<400> SEQUENCE: 43

| | | |
|---|---|---|
| atggcgaagc tcctgctgct gaccctgctg ggggtcggcc tgtccttagt cggggagagg | 60 |
| ttgctggcgt ttagaaacag ctttggtgca gttcaagaac tggagccagt agaaccgcaa | 120 |
| aactgccacc tgattgaggg cctcgagaat ggctcggaag atattgatat acttcctagc | 180 |
| gggctggctt ttatctccag tggattaaaa tatccaggca tgccagcgtt tgcaccggac | 240 |
| aaaccaggaa gaatctttct gatggatctg aatgagcaaa acccagaggc gcaagcactg | 300 |
| gaaatcagtg gtgggcttga ccaggagtca ctaaatcctc acgggatcag cactttcatc | 360 |
| gacaaagaca gcactgctta tctttatgtc gtgaatcacc ccaacatgga ctccactgtg | 420 |
| gagatattta aatttgagga caacaacgt tctctggtac acatgaaaac tataaaacat | 480 |
| gaacttctca agagtgtgaa taacattgtg gttcttggac cggaacagtt ctacgccacc | 540 |
| agagaccact attttaccaa ctcccctcctg tcatttttg agatgatctt ggaccctcac | 600 |
| tggacttccg tcgttttcta cagcccaagg gaggttaaag tggtggccaa aggattcagt | 660 |
| tctgccaacg gaatcacagt ctcactagat aagaagtatg tctatgttgc tgatgccaca | 720 |
| gctaagaatg tgcatgtaat ggaaaaacat gataactggg atttaactga actgaaggta | 780 |
| atacacttgg acaccttagt ggataacttg accgttgatc cagccacggg agatattttg | 840 |
| gcaggctgcc accctaaccc catgaagctg ttgatctata cccctgagga tcctccaggg | 900 |
| tcagaagtac tacgcatcca ggactctttg tcagataagc ccagggtgag cacactgtat | 960 |
| gcgaacaacg gctccgtgct tcagggcacc tctgtggctt ctgtgtacca cggaaaaatt | 1020 |
| ctcataggca ctatatttca caaaactctg tactgtgacc tc | 1062 |

<210> SEQ ID NO 44
<211> LENGTH: 1062
<212> TYPE: DNA
<213> ORGANISM: Artificial sequence
<220> FEATURE:
<223> OTHER INFORMATION: In vitro evolved PON variant G1B11

<400> SEQUENCE: 44

| | | |
|---|---|---|
| atggcgaagc tcctgctgct gaccctgctg ggagcctgtc tggccttaat aggggaaagg | 60 |
| ctgctgaatt ttagagaacg agttagtaca actcgagaaa taaggccac agaaccacaa | 120 |
| aactgccacc tgattgaggg cctcgagaat ggctctgaag atattgatat acttcctagc | 180 |
| gggctggctt ttatctccag tggattaaaa tatccaggca tgccaaactt tgcaccagat | 240 |
| gaaccaggaa aaatcttctt gatagatatg aatgaacaaa acccaaggggc acaagcacta | 300 |

```
gaaatcagtg gtggatttga caaagaatta tttaatccac atgggatcag cactttcatt    360
gataaagacc atactgtgta tctttatgtt gtgaatcacc ccaacatgga ctccactgtg    420
gagatattta agtttgaaga acaacaacac tctctcatcc acctgaaaac tctaaaacat    480
gaacttctca agagtgtgaa tgacattgtg gttcttggac cggaacagtt ctacgccacc    540
agagaccact attttaccaa ctatgtctta gcacttctga gatgttttt ggatcttcgc     600 tggacttccg ttcttttcta cagccccaaa gaggtcaaag tggtggccaa aggattcagt    660
tctgccaatg ggatcacagt ctcactagat aagaagtatg tctatgttgc tgatgccaca    720
gctaagaatg tgcatgtaat ggaaaaacat gacaactggg atttaactga actgaaggtg    780
atacagttgg gcaccttagt ggataacctg actgtcgatc ctgccacagg agacattttg    840
gcaggatgcc atcctaatcc tatgaagctg ttgatctata accctgagga ccctccagga    900
tcagaagtac ttcgcatcca ggatgttttt tctgagaagc ccagggtgag caccgtgtat    960
gcgaacaacg gctctgtgct tcagggctcc accgtggctt ctgtgtacca agggaagatt    1020
ctcataggca ctatatttca caaaactctg tattgtgtac tc                      1062

<210> SEQ ID NO 45
<211> LENGTH: 1062
<212> TYPE: DNA
<213> ORGANISM: Artificial sequence
<220> FEATURE:
<223> OTHER INFORMATION: In vitro evolved PON variant G2C2

<400> SEQUENCE: 45
atggcgaagc tcctgctgct gaccctgctg ggggtcggcc tgtccttagt cggggagagg    60
ttgctggcgt ttagaaacag ctttggtgct gttcaagaac tggagccagt agaaccccag    120
aactgtgtcc ttattgaggg actcgaaaat ggctcggaag atattgatat acttcctagc    180
gggctggctt ttatctccac tggattaaaa tatccaggca tgccaaactt tgcaccagat    240
gagccaggaa aaatcttctt gatggatctg aatgaacaaa acccaagggc acaggcacta    300
gaaatcagtg gtggatttga caaagaatta tttaatccac atgggatcag cactttcatt    360
gataaagaca atactgtgta tctttatgtt gtgaatcatc cccacatgga gtccactgtg    420
gagatattta aatttgagga acaacaacac tctctcatcc acctgaaaac tataaaacat    480
gaacttctca aaagtgtgaa tgacattgtg gttcttggac cggaacagtt ctacgccacc    540
agagaccact attttaccaa ctatgtctta gcacgtcttg atgatgatctt ggatcttcgc    600 tggacttatg ttcttttcta cagcccaagg gaggttaaag tggtggccaa aggattcagt    660
tctgccaatg ggatcacagt ctcactagat aagaagtatg tctatgttgc tgatgccaca    720
gctaagaatg tgcatgtaat ggaaaaacat gacaactggg atttaactca actgaaggtg    780
atacagttgg gcaccttagt ggataatttg tctgttgatc ctgccacggg agatatcttg    840
gcaggatgcc atcctaatcc tatgaagcta ctgaactata accctgagga ccctccagga    900
tcagaagtac ttcgcatcca gaatgttttt tctgagaagc ccagggtgag caccgtgtac    960
accaatgacg gctctgtgct tcagggcacc tctgtggctt ctgtgtatca agggaagatt    1020
ctcataggca ctatatttca caaagctctg cactgtgacc tc                      1062

<210> SEQ ID NO 46
<211> LENGTH: 1062
<212> TYPE: DNA
<213> ORGANISM: Artificial sequence
<220> FEATURE:
```

-continued

<223> OTHER INFORMATION: In vitro evolved PON variant G3A5

<400> SEQUENCE: 46

| | | | | | |
|---|---|---|---|---|---|
| atgggcgaac | tcctgctgct | gaccctgctg | ggggccagcc | tcgccttcgt | cggggagatg | 60 |
| ttcctggcgt | ttagagaaag | ggtgaatgcc | tctcgagaag | tggagccagt | agaacccag | 120 |
| aactgtgtcc | ttattgaggg | actcgaaaat | ggctcggaag | atattgatat | acttcctaat | 180 |
| gggctggctt | ttatctccag | tggattaaaa | tatccaggca | tgccaaactt | tgcaccagat | 240 |
| gaaccaggaa | aaatcttctt | gatggatctg | aatgaacaaa | acccaagagc | acaagagctg | 300 |
| gaaatcagca | atggatttga | aaagaatca | ttcaatccac | atgggatcag | cactttcatc | 360 |
| gacaaagacc | atactgtgta | tctttatgtt | gtgaatcacc | ccaacatgga | ctccactgtg | 420 |
| gagatattta | aatttgagga | acgacaacgt | tctcttgtgc | acctgaaaac | tataaaacat | 480 |
| gaacttctca | aaagtgtgaa | tgacattgtg | gttcttggac | cggaacagtt | ctatgccacc | 540 |
| agagaccgct | attttaccaa | ctatgtctta | gcacttcttg | agatgatttt | ggatcctcac | 600 |
| tggacttccg | tcgttttcta | cagcccaaaa | gaggtcaaag | ttgtggccca | aggattcagt | 660 |
| tctgccaacg | gaatcacagt | ctcactagat | aagaagtatg | tctatgttgc | tgatgccaca | 720 |
| gctaaaaatg | tgcatgtaat | ggaaaaacat | gacaactggg | atttaactcc | agtgaaggtc | 780 |
| attcagctgg | gaaccttagt | ggataatttg | tctgttgatc | ctgccacggg | agatatcttg | 840 |
| gcaggatgcc | atcctaatcc | tatgaagcta | ctgaactata | accctgagga | ccctccagga | 900 |
| tcagaagtac | ttcgcatccg | gaatgttttg | tctgagaagc | caggggtgag | caccgtgtac | 960 |
| accaatgacg | gctctgtgct | tcagggcacc | tctgtggctt | ctgtgtatca | agggaagatt | 1020 |
| ctcataggca | ctatatttca | caaaactctg | tattgtgacc | tc | | 1062 |

<210> SEQ ID NO 47
<211> LENGTH: 1062
<212> TYPE: DNA
<213> ORGANISM: Artificial sequence
<220> FEATURE:
<223> OTHER INFORMATION: In vitro evolved PON variant G3G3

<400> SEQUENCE: 47

| | | | | | |
|---|---|---|---|---|---|
| atggcgaagc | tcctgctgct | gaccctgctg | ggggccagcc | tcgccttcgt | cggggagagg | 60 |
| ttgctggcgt | ttagagacag | ctttggtgca | gttcaagaac | tggagccagt | agaacccag | 120 |
| aactgtgtcc | ttattgaggg | actcgaaaat | ggctcggaag | atattgatat | acttcctagt | 180 |
| gggctggctt | ttatctccag | tggattaaaa | tatccaggca | tgccaaactt | tgcaccagat | 240 |
| gaaccaggaa | aaatcttctt | gatagatatg | aatgagaaga | acccaagagc | acaggcacta | 300 |
| gaaatcagtg | gtggatttga | caagaatca | ttcaatccac | atgggatcag | cactttcatt | 360 |
| gataaagacc | atactgtgta | tctttatgtt | gtgaatcacc | ccaacatgga | ctccactgtg | 420 |
| gaggtattta | aatttgagga | acaacaacac | tctctcatcc | acctgaaaac | tataaaacat | 480 |
| gaacttctca | aaagtgtgaa | tgacattgtg | gttcttggac | cggaacagtt | ctacgccacc | 540 |
| agagaccact | attttaccaa | ctccctcctg | tcattttttg | agatgatctt | ggatcttcgc | 600 |
| tggacttccg | ttcttttcta | cagcccaagg | gaggttaaag | tggtggccaa | aggattcagt | 660 |
| tctgccaatg | ggatcacagt | ctcactagat | aaaaagtatg | tctatgtagc | tgatgtagca | 720 |
| gctaagaaca | ttcacataat | ggaaaaacat | gacaactggg | atttaactga | actgaaggta | 780 |
| atacacttgg | acaccttagt | ggataacctg | accgttgatc | cagccacggg | agatattttg | 840 |
| gcaggatgcc | atcctaatcc | tatgaagcta | ctgaactata | accctgagga | ccctccagga | 900 |

| | | | |
|---|---|---|---|
| tcagaagtac tccgtatcca | gaatgttttg tctgagaagc | ccagggtgag caccgtgtac | 960 |
| gccaacaatg gctctgtgct | tcagggcacc tccgtggctt | ctgtgtacca cggaagatt | 1020 |
| ctcataggca ctatatttca | caaaactctg tactgtgacc | tc | 1062 |

<210> SEQ ID NO 48
<211> LENGTH: 1062
<212> TYPE: DNA
<213> ORGANISM: Artificial sequence
<220> FEATURE:
<223> OTHER INFORMATION: In vitro evolved PON variant G3H9

<400> SEQUENCE: 48

| | | | |
|---|---|---|---|
| atggcgaagc tcctgctgct | gaccctgctg ggggtcggcc | tgtccttagt cggggagagg | 60 |
| ttgctggcgt ttagaaacag | cttcggtgca gttcaagaac | tggagtcagt agaaccccag | 120 |
| aactgtgtcc ttattgaggg | actcgaaaat ggttcggaag | atattgatat acttcctagc | 180 |
| gggctggctt ttatctccag | tggattaaaa tatccaggca | tgccaaactt tgcaccagat | 240 |
| gaaccaggaa aaatcttctt | gatagatatg aatgagaaga | cccaagagc acaagagctg | 300 |
| aaaatcagca atggatttga | aaagaatca ttcaatccac | atgggatcag cactttcatt | 360 |
| gataaagacc atactgtgta | tctttatgtt gtgaatcacc | ccaacatgga ttccactgtg | 420 |
| gagatattta aatttgagga | acaacaacgc tctcttgtac | acctgaaaac tataaaacat | 480 |
| gaacttctca aaagtgtgaa | tgacattgtg gttcttggac | cggaacagtt ctatgccacc | 540 |
| agagaccact attttaccaa | ctccctcctg tcatttttg | agatgatctt ggatcttcgc | 600 |
| tggacttccg tcgttttcta | cagcccaaaa gaggtcaaag | tggtggccaa aggattcagt | 660 |
| tctgccaacg gaatcacagt | ctcactagat aagaagtatg | tctatgttgc tgatgccacg | 720 |
| gctaagaatg tgcatgtaat | ggaaaaacat gacaactggg | atttaactcc agtgaaggtc | 780 |
| attcagctgg gaaccttagt | ggataacttg actgttgatc | ctgccacggg agatattttg | 840 |
| gcaggctgcc accctaaccc | catgaagcta ctgaactata | accctgagga ccctccagga | 900 |
| tcagaagtac ttcgcatcca | gaatgttttg tctgagaagc | ccagggtgag caccgtgtac | 960 |
| accaatgacg gctctgtgct | tcagggcacc tctgtggctt | ctgtgtacca agggaagatt | 1020 |
| ctcataggca ctatatttca | caaagctctg tactgtgacc | tc | 1062 |

<210> SEQ ID NO 49
<211> LENGTH: 354
<212> TYPE: PRT
<213> ORGANISM: Artificial sequence
<220> FEATURE:
<223> OTHER INFORMATION: In vitro evolved PON variant G1A7

<400> SEQUENCE: 49

Met Ala Lys Leu Leu Leu Leu Thr Leu Leu Gly Val Gly Leu Ser Leu
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys His Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Ala Phe Ala Pro Asp
65                  70                  75                  80

Lys Pro Gly Arg Ile Phe Leu Met Asp Leu Asn Glu Gln Asn Pro Glu

```
                    85                  90                  95
Ala Gln Ala Leu Glu Ile Ser Gly Gly Leu Asp Gln Glu Ser Leu Asn
            100                 105                 110

Pro His Gly Ile Ser Thr Phe Ile Asp Lys Asp Ser Thr Ala Tyr Leu
        115                 120                 125

Tyr Val Val Asn His Pro Asn Met Asp Ser Thr Val Glu Ile Phe Lys
    130                 135                 140

Phe Glu Glu Gln Gln Arg Ser Leu Val His Met Lys Thr Ile Lys His
145                 150                 155                 160

Glu Leu Leu Lys Ser Val Asn Asn Ile Val Val Leu Gly Pro Glu Gln
                165                 170                 175

Phe Tyr Ala Thr Arg Asp His Tyr Phe Thr Asn Ser Leu Leu Ser Phe
            180                 185                 190

Phe Glu Met Ile Leu Asp Pro His Trp Thr Ser Val Val Phe Tyr Ser
        195                 200                 205

Pro Arg Glu Val Lys Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile His Leu Asp Thr Leu Val Asp Asn Leu Thr Val
            260                 265                 270

Asp Pro Ala Thr Gly Asp Ile Leu Ala Gly Cys His Pro Asn Pro Met
        275                 280                 285

Lys Leu Leu Ile Tyr Asn Pro Glu Asp Pro Pro Gly Ser Glu Val Leu
    290                 295                 300

Arg Ile Gln Asp Ser Leu Ser Asp Lys Pro Arg Val Ser Thr Leu Tyr
305                 310                 315                 320

Ala Asn Asn Gly Ser Val Leu Gln Gly Thr Ser Val Ala Ser Val Tyr
                325                 330                 335

His Gly Lys Ile Leu Ile Gly Thr Ile Phe His Lys Thr Leu Tyr Cys
            340                 345                 350

Asp Leu

<210> SEQ ID NO 50
<211> LENGTH: 354
<212> TYPE: PRT
<213> ORGANISM: Artificial sequence
<220> FEATURE:
<223> OTHER INFORMATION: In vitro evolved PON variant G1B11

<400> SEQUENCE: 50

Met Ala Lys Leu Leu Leu Thr Leu Leu Gly Ala Cys Leu Ala Leu
1               5                   10                  15

Ile Gly Glu Arg Leu Leu Asn Phe Arg Glu Arg Val Ser Thr Thr Arg
            20                  25                  30

Glu Ile Lys Ala Thr Glu Pro Gln Asn Cys His Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Gln Asn Pro Arg
                85                  90                  95
```

```
Ala Gln Ala Leu Glu Ile Ser Gly Gly Phe Asp Lys Glu Leu Phe Asn
            100                 105                 110

Pro His Gly Ile Ser Thr Phe Ile Asp Lys Asp His Thr Val Tyr Leu
            115                 120                 125

Tyr Val Val Asn His Pro Asn Met Asp Ser Thr Val Glu Ile Phe Lys
        130                 135                 140

Phe Glu Glu Gln Gln His Ser Leu Ile His Leu Lys Thr Leu Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp His Tyr Phe Thr Asn Tyr Val Leu Ala Leu
            180                 185                 190

Leu Lys Met Phe Leu Asp Leu Arg Trp Thr Ser Val Leu Phe Tyr Ser
            195                 200                 205

Pro Lys Glu Val Lys Val Ala Lys Gly Phe Ser Ser Ala Asn Gly
        210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met
            275                 280                 285

Lys Leu Leu Ile Tyr Asn Pro Glu Asp Pro Pro Gly Ser Glu Val Leu
        290                 295                 300

Arg Ile Gln Asp Val Leu Ser Glu Lys Pro Arg Val Ser Thr Val Tyr
305                 310                 315                 320

Ala Asn Asn Gly Ser Val Leu Gln Gly Ser Thr Val Ala Ser Val Tyr
                325                 330                 335

Gln Gly Lys Ile Leu Ile Gly Thr Ile Phe His Lys Thr Leu Tyr Cys
            340                 345                 350

Val Leu

<210> SEQ ID NO 51
<211> LENGTH: 354
<212> TYPE: PRT
<213> ORGANISM: Artificial sequence
<220> FEATURE:
<223> OTHER INFORMATION: In vitro evolved PON variant G2C2

<400> SEQUENCE: 51

Met Ala Lys Leu Leu Leu Thr Leu Leu Gly Val Gly Leu Ser Leu
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Thr Gly Leu Lys Tyr Pro Gly Met Pro Asn Phe Ala Pro Asp
65                  70                  75                  80

Glu Pro Gly Lys Ile Phe Leu Met Asp Leu Asn Glu Gln Asn Pro Arg
            85                  90                  95
```

```
Ala Gln Ala Leu Glu Ile Ser Gly Gly Phe Asp Lys Glu Leu Phe Asn
            100                 105                 110

Pro His Gly Ile Ser Thr Phe Ile Asp Lys Asp Asn Thr Val Tyr Leu
            115                 120                 125

Tyr Val Val Asn His Pro His Met Glu Ser Thr Val Glu Ile Phe Lys
        130                 135                 140

Phe Glu Glu Gln Gln His Ser Leu Ile His Leu Lys Thr Ile Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp His Tyr Phe Thr Asn Tyr Val Leu Ala Arg
            180                 185                 190

Leu Glu Met Ile Leu Asp Leu Arg Trp Thr Tyr Val Leu Phe Tyr Ser
            195                 200                 205

Pro Arg Glu Val Lys Val Val Ala Lys Gly Phe Ser Ser Ala Asn Gly
        210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Gln Leu Lys Val Ile Gln Leu Gly Thr Leu Val Asp Asn Leu Ser Val
            260                 265                 270

Asp Pro Ala Thr Gly Asp Ile Leu Ala Gly Cys His Pro Asn Pro Met
            275                 280                 285

Lys Leu Leu Asn Tyr Asn Pro Glu Asp Pro Gly Ser Glu Val Leu
        290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Gly Thr Ser Val Ala Ser Val Tyr
                325                 330                 335

Gln Gly Lys Ile Leu Ile Gly Thr Ile Phe His Lys Ala Leu His Cys
            340                 345                 350

Asp Leu

<210> SEQ ID NO 52
<211> LENGTH: 354
<212> TYPE: PRT
<213> ORGANISM: Artificial sequence
<220> FEATURE:
<223> OTHER INFORMATION: In vitro evolved PON variant G3A5

<400> SEQUENCE: 52

Met Gly Glu Leu Leu Leu Thr Leu Leu Gly Ala Ser Leu Ala Phe
1               5                   10                  15

Val Gly Glu Met Phe Leu Ala Phe Arg Glu Arg Val Asn Ala Ser Arg
            20                  25                  30

Glu Val Glu Pro Val Glu Pro Gln Asn Cys Val Leu Ile Glu Gly Leu
        35                  40                  45

Glu Asn Gly Ser Glu Asp Ile Asp Ile Leu Pro Asn Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Met Asp Leu Asn Glu Gln Asn Pro Arg
                85                  90                  95

Ala Gln Glu Leu Glu Ile Ser Asn Gly Phe Glu Lys Glu Ser Phe Asn
```

```
                100                 105                 110
Pro His Gly Ile Ser Thr Phe Ile Asp Lys Asp His Thr Val Tyr Leu
        115                 120                 125

Tyr Val Val Asn His Pro Asn Met Asp Ser Thr Val Glu Ile Phe Lys
130                 135                 140

Phe Glu Glu Arg Gln Arg Ser Leu Val His Leu Lys Thr Ile Lys His
145                 150                 155                 160

Glu Leu Leu Lys Ser Val Asn Asp Ile Val Val Leu Gly Pro Glu Gln
                165                 170                 175

Phe Tyr Ala Thr Arg Asp Arg Tyr Phe Thr Asn Tyr Val Leu Ala Leu
            180                 185                 190

Leu Glu Met Ile Leu Asp Pro His Trp Thr Ser Val Val Phe Tyr Ser
                195                 200                 205

Pro Lys Glu Val Lys Val Val Ala Gln Gly Phe Ser Ser Ala Asn Gly
            210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Pro Val Lys Val Ile Gln Leu Gly Thr Leu Val Asp Asn Leu Ser Val
            260                 265                 270

Asp Pro Ala Thr Gly Asp Ile Leu Ala Gly Cys His Pro Asn Pro Met
        275                 280                 285

Lys Leu Leu Asn Tyr Asn Pro Glu Asp Pro Pro Gly Ser Glu Val Leu
        290                 295                 300

Arg Ile Arg Asn Val Leu Ser Glu Lys Pro Arg Val Ser Thr Val Tyr
305                 310                 315                 320

Thr Asn Asp Gly Ser Val Leu Gln Gly Thr Ser Val Ala Ser Val Tyr
                325                 330                 335

Gln Gly Lys Ile Leu Ile Gly Thr Ile Phe His Lys Thr Leu Tyr Cys
            340                 345                 350

Asp Leu

<210> SEQ ID NO 53
<211> LENGTH: 354
<212> TYPE: PRT
<213> ORGANISM: Artificial sequence
<220> FEATURE:
<223> OTHER INFORMATION: In vitro evolved PON variant G3G3

<400> SEQUENCE: 53

Met Ala Lys Leu Leu Leu Thr Leu Leu Gly Ala Ser Leu Ala Phe
1               5                   10                  15

Val Gly Glu Arg Leu Leu Ala Phe Arg Asp Ser Phe Gly Ala Val Gln
                20                  25                  30

Glu Leu Glu Pro Val Glu Pro Gln Asn Cys Val Leu Ile Glu Gly Leu
            35                  40                  45

Glu Asn Gly Ser Glu Asp Ile Asp Ile Leu Pro Ser Gly Leu Ala Phe
        50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Ala Leu Glu Ile Ser Gly Gly Phe Asp Lys Glu Ser Phe Asn
            100                 105                 110
```

-continued

```
Pro His Gly Ile Ser Thr Phe Ile Asp Lys Asp His Thr Val Tyr Leu
        115                 120                 125

Tyr Val Val Asn His Pro Asn Met Asp Ser Thr Val Glu Val Phe Lys
130                 135                 140

Phe Glu Glu Gln Gln His Ser Leu Ile His Leu Lys Thr Ile Lys His
145                 150                 155                 160

Glu Leu Leu Lys Ser Val Asn Asp Ile Val Leu Gly Pro Glu Gln
                165                 170                 175

Phe Tyr Ala Thr Arg Asp His Tyr Phe Thr Asn Ser Leu Leu Ser Phe
            180                 185                 190

Phe Glu Met Ile Leu Asp Leu Arg Trp Thr Ser Val Leu Phe Tyr Ser
        195                 200                 205

Pro Arg Glu Val Lys Val Val Ala Lys Gly Phe Ser Ser Ala Asn Gly
    210                 215                 220

Ile Thr Val Ser Leu Asp Lys Lys Tyr Val Tyr Val Ala Asp Val Ala
225                 230                 235                 240

Ala Lys Asn Ile His Ile Met Glu Lys His Asp Asn Trp Asp Leu Thr
                245                 250                 255

Glu Leu Lys Val Ile His Leu Asp Thr Leu Val Asp Asn Leu Thr Val
            260                 265                 270

Asp Pro Ala Thr Gly Asp Ile Leu Ala Gly Cys His Pro Asn Pro Met
        275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Ala Asn Asn Gly Ser Val Leu Gln Gly Thr Ser Val Ala Ser Val Tyr
                325                 330                 335

His Gly Lys Ile Leu Ile Gly Thr Ile Phe His Lys Thr Leu Tyr Cys
            340                 345                 350

Asp Leu

<210> SEQ ID NO 54
<211> LENGTH: 354
<212> TYPE: PRT
<213> ORGANISM: Artificial sequence
<220> FEATURE:
<223> OTHER INFORMATION: In vitro evolved PON variant G3H9

<400> SEQUENCE: 54

Met Ala Lys Leu Leu Leu Thr Leu Leu Gly Val Gly Leu Ser Leu
1               5                   10                  15

Val Gly Glu Arg Leu Leu Ala Phe Arg Asn Ser Phe Gly Ala Val Gln
            20                  25                  30

Glu Leu Glu Ser Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Lys Ile Ser Asn Gly Phe Glu Lys Glu Ser Phe Asn
            100                 105                 110
```

```
Pro His Gly Ile Ser Thr Phe Ile Asp Lys Asp His Thr Val Tyr Leu
        115                 120                 125

Tyr Val Val Asn His Pro Asn Met Asp Ser Thr Val Glu Ile Phe Lys
    130                 135                 140

Phe Glu Glu Gln Gln Arg Ser Leu Val His Leu Lys Thr Ile Lys His
145                 150                 155                 160

Glu Leu Leu Lys Ser Val Asn Asp Ile Val Leu Gly Pro Glu Gln
                165                 170                 175

Phe Tyr Ala Thr Arg Asp His Tyr Phe Thr Asn Ser Leu Leu Ser Phe
            180                 185                 190

Phe Glu Met Ile Leu Asp Leu Arg Trp Thr Ser Val Phe Tyr Ser
        195                 200                 205

Pro Lys Glu Val Lys Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Pro Val Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met
        275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Gly Thr Ser Val Ala Ser Val Tyr
                325                 330                 335

Gln Gly Lys Ile Leu Ile Gly Thr Ile Phe His Lys Ala Leu Tyr Cys
            340                 345                 350

Asp Leu
```

<210> SEQ ID NO 55
<211> LENGTH: 1065
<212> TYPE: DNA
<213> ORGANISM: Artificial sequence
<220> FEATURE:
<223> OTHER INFORMATION: In vitro evolved PON variant G3C9

<400> SEQUENCE: 55

```
atggctaaac tgacagcgct cacactcttg gggctgggat tggcactctt cgatggacag    60
aagtcttctt tccaaacacg atttaatgtt caccgtgaag taactccagt ggaacttcct   120
aactgtaatt tagttaaagg ggttgacaat ggttctgaag acttggaaat actgcccaat   180
ggactggctt tcatcagctc cggattaaag tatcctggaa taatgagctt tgaccctgat   240
aagtctggaa agatacttct aatggacctg aatgaggaag acccagtagt gttggaactg   300
ggcattactg gaaatacatt ggatatatct tcatttaacc ctcatgggat tagcacattc   360
acagatgaag ataacactgt gtacctactg gtggtaaacc atccagactc ctcgtccacc   420
gtggaggtgt ttaaatttca agaagaagaa aaatcacttt tgcatctgaa accatcaga    480
cacaagcttc tgcctagtgt gaatgacatt gtcgctgtgg acctgaaca ttttatgcc    540
acaaatgatc actattttgc tgaccccttac ttaaaatcct gggaaatgca tttgggatta   600
gcgtggtcat ttgttactta ttatagtccc aatgatgttc gagtagtggc agaaggattt   660
```

```
gattttgcta acggaatcaa catctcacca gacggcaagt atgtctatat agctgagttg    720
ctggctcata agatccatgt gtatgaaaag cacgctaatt ggactttaac tccattgaag    780
tccctcgact ttgacaccct tgtggataac atctctgtgg atcctgtgac aggggacctc    840
tgggtgggat gccatcccaa cggaatgcga atcttctact atgacccaaa gaatcctccc    900
ggctcagagg tgcttcgaat ccaggacatt ttatccgaag agcccaaagt gacagtggtt    960
tatgcagaaa atggcactgt gttacagggc agcacggtgg ccgctgtgta caaagggaaa   1020
ctgctgattg gcacagtgtt tcacaaagct ctttactgtg agctg                  1065
```

<210> SEQ ID NO 56
<211> LENGTH: 355
<212> TYPE: PRT
<213> ORGANISM: Artificial sequence
<220> FEATURE:
<223> OTHER INFORMATION: In vitro evolved PON variant G3C9

<400> SEQUENCE: 56

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
```

```
            290                 295                 300
Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
                340                 345                 350

Cys Glu Leu
        355

<210> SEQ ID NO 57
<211> LENGTH: 355
<212> TYPE: PRT
<213> ORGANISM: Artificial sequence
<220> FEATURE:
<223> OTHER INFORMATION: In vitro evolved PON variant G1A5

<400> SEQUENCE: 57

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
                20                  25                  30

Glu Val Thr Pro Val Glu Leu Pro Asn Cys Asn Leu Val Lys Gly Ile
                35                  40                  45

Asp Asn Gly Ser Glu Asp Leu Glu Ile Leu Pro Asn Gly Leu Ala Phe
            50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
                100                 105                 110

Asn Pro His Gly Ile Ser Thr Phe Ile Asp Glu Asp Asn Thr Val Tyr
            115                 120                 125

Leu Leu Val Val Asn His Pro Asp Ser Ser Thr Val Glu Val Phe
                130                 135                 140

Lys Phe Gln Glu Lys Glu Lys Ser Leu Leu His Leu Lys Thr Ile Arg
145                 150                 155                 160

His Lys Leu Leu Pro Ser Val Asn Asp Ile Ala Val Gly Pro Glu
                165                 170                 175

His Phe Tyr Ala Thr Asn Asp His Tyr Phe Ile Asp Pro Tyr Leu Lys
                180                 185                 190

Ser Trp Glu Met His Leu Gly Leu Ala Trp Ser Phe Val Thr Tyr Tyr
                195                 200                 205

Ser Pro Asn Asp Val Arg Val Val Ala Glu Gly Phe Asp Phe Ala Asn
            210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
                275                 280                 285

Met Arg Ile Phe Tyr Tyr Asp Pro Glu Asn Pro Pro Gly Ser Glu Val
```

```
                290                 295                 300
Leu Arg Ile Gln Asn Ile Leu Ser Lys Glu Pro Lys Val Thr Val Val
305                 310                 315                 320

Tyr Ala Glu Asn Gly Thr Val Leu Gln Gly Thr Thr Val Ala Ser Val
                325                 330                 335

Tyr Lys Gly Lys Leu Leu Ile Gly Thr Val Phe His Lys Ala Leu Tyr
                340                 345                 350

Cys Glu Leu
        355

<210> SEQ ID NO 58
<211> LENGTH: 355
<212> TYPE: PRT
<213> ORGANISM: Artificial sequence
<220> FEATURE:
<223> OTHER INFORMATION: In vitro evolved PON variant G1C4

<400> SEQUENCE: 58

Met Ala Lys Leu Leu Ala Leu Thr Leu Val Gly Leu Gly Leu Ala Leu
1               5                   10                  15

Phe Asp Gly Gln Lys Ser Ser Phe Gln Thr Arg Phe Asn Val His Arg
                20                  25                  30

Glu Val Thr Pro Val Glu Leu Pro Asn Cys Asn Leu Val Lys Gly Ile
            35                  40                  45

Glu Thr Gly Ala Glu Asp Leu Glu Ile Leu Pro Asn Gly Leu Ala Phe
        50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Ser Thr Phe Asp Leu Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
130                 135                 140

Lys Phe Gln Glu Lys Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ile Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Ala Ser Glu Val
```

```
            290                 295                 300
Leu Arg Ile Gln Asp Ile Leu Ser Glu Asp Pro Lys Ile Thr Val Val
305                 310                 315                 320

Tyr Ala Glu Asn Gly Thr Val Leu Gln Gly Thr Thr Val Ala Ser Val
                325                 330                 335

Tyr Lys Gly Lys Leu Leu Ile Gly Thr Val Phe His Lys Ala Leu Tyr
                340                 345                 350

Cys Asp Leu
        355

<210> SEQ ID NO 59
<211> LENGTH: 355
<212> TYPE: PRT
<213> ORGANISM: Artificial sequence
<220> FEATURE:
<223> OTHER INFORMATION: In vitro evolved PON variant G2D6

<400> SEQUENCE: 59

Met Ala Lys Leu Thr Ala Leu Thr Leu Leu Gly Leu Gly Leu Ala Leu
1               5                   10                  15

Phe Asp Arg Gln Lys Ser Ser Phe Gln Thr Arg Phe Asn Val His Arg
                20                  25                  30

Glu Val Thr Pro Val Glu Leu Pro Asn Cys Asn Leu Val Lys Gly Ile
            35                  40                  45

Asp Asn Gly Ser Glu Asp Leu Glu Ile Leu Pro Asn Gly Leu Ala Phe
        50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Ser Thr Phe Asp Leu Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
        130                 135                 140

Lys Phe Gln Glu Lys Glu Arg Ser Leu Leu His Leu Lys Thr Ile Arg
145                 150                 155                 160

His Lys Leu Leu Pro Ser Val Asn Asp Ile Ala Val Gly Pro Glu
                165                 170                 175

Ser Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Glu Asn Pro Pro Gly Ser Glu Val
```

```
                290                 295                 300
Leu Arg Ile Gln Asp Ile Leu Ser Lys Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
                340                 345                 350

Cys Asp Leu
        355

<210> SEQ ID NO 60
<211> LENGTH: 355
<212> TYPE: PRT
<213> ORGANISM: Artificial sequence
<220> FEATURE:
<223> OTHER INFORMATION: In vitro evolved PON variant G2E6

<400> SEQUENCE: 60

Met Ala Lys Leu Thr Ala Leu Thr Leu Leu Gly Met Gly Leu Ala Leu
1               5                   10                  15

Phe Asp Arg Gln Lys Ser Ser Phe Gln Thr Arg Phe Asn Val His Arg
                20                  25                  30

Glu Val Thr Pro Val Glu Leu Pro Asn Cys Asn Leu Val Lys Gly Ile
            35                  40                  45

Asp Asn Gly Ser Glu Asp Leu Glu Ile Leu Pro Asn Gly Leu Ala Phe
        50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Lys Glu Pro Ala
                85                  90                  95

Val Ser Glu Leu Glu Ile Ile Gly Asn Thr Leu Asp Ile Ser Ser Phe
            100                 105                 110

Asn Pro His Gly Ile Ser Thr Phe Ile Asp Asp Asn Thr Val Tyr
        115                 120                 125

Leu Leu Val Val Asn His Pro Gly Ser Ser Ser Thr Val Glu Val Phe
130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ile Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Arg Val Leu Ser Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Phe Tyr Asp Ala Glu Asn Pro Pro Gly Ser Glu Val
```

```
                290                 295                 300
Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
                340                 345                 350

Cys Asp Leu
        355

<210> SEQ ID NO 61
<211> LENGTH: 355
<212> TYPE: PRT
<213> ORGANISM: Artificial sequence
<220> FEATURE:
<223> OTHER INFORMATION: In vitro evolved PON variant G3H8

<400> SEQUENCE: 61

Met Ala Lys Leu Thr Ala Pro Thr Leu Leu Gly Leu Gly Leu Ala Leu
1               5                   10                  15

Phe Asp Arg Gln Lys Ser Ser Phe Gln Thr Arg Phe Asn Val His Arg
                20                  25                  30

Glu Val Thr Pro Val Glu Leu Pro Asn Cys Asn Leu Val Lys Gly Ile
                35                  40                  45

Asp Asn Gly Ser Glu Asp Leu Glu Ile Leu Pro Asn Gly Leu Ala Phe
            50                  55                  60

Ile Ser Ser Gly Leu Lys Tyr Pro Gly Ile Met Ser Phe Asp Pro Asp
65              70                  75                  80

Lys Ser Gly Lys Ile Leu Leu Met Asp Leu Asn Glu Glu Asp Pro Val
                85                  90                  95

Val Leu Glu Leu Gly Ile Thr Gly Ser Thr Phe Asp Leu Ser Ser Phe
                100                 105                 110

Asn Pro His Gly Ile Ser Thr Phe Thr Asp Glu Asp Asn Thr Val Tyr
            115                 120                 125

Leu Leu Val Val Asn His Pro Asp Ser Ser Thr Val Glu Val Phe
            130                 135                 140

Lys Phe Gln Glu Lys Glu Arg Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

Ser Phe Tyr Ala Thr Asn Asp His Tyr Phe Ala Asp Pro Tyr Leu Lys
                180                 185                 190

Ser Trp Glu Met His Leu Gly Leu Ala Trp Ser Phe Val Thr Tyr Tyr
                195                 200                 205

Ser Pro Asn Asp Val Arg Val Val Ala Glu Gly Phe Asp Phe Ala Asn
            210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
            275                 280                 285

Met Arg Ile Phe Tyr Tyr Asp Pro Glu Asn Pro Pro Gly Ser Glu Val
```

```
                290                 295                 300
Leu Arg Ile Gln Asp Ile Leu Ser Lys Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
                340                 345                 350

Cys Asp Leu
        355

<210> SEQ ID NO 62
<211> LENGTH: 1065
<212> TYPE: DNA
<213> ORGANISM: Artificial sequence
<220> FEATURE:
<223> OTHER INFORMATION: In vitro evolved PON variant G3C9.10

<400> SEQUENCE: 62
atggctaaac tgacagcgct cacactcttg gggctgggat tggcactctt cgatggacag     60
aagtcttctt tccaaacacg atttaatgtt caccgtgaag taactccagt ggaacttcct    120
aactgtaatt tagttaaagg ggttgacaat ggttctgaag acttggaaat actgcccaat    180
ggactggctt tcatcagctc cggagtaaag tatcctggaa taatgagctt tgaccctgat    240
aagtctggaa agatacttct aatggacctg aatgaggaag acccagtagt gttggaactg    300
ggcattactg gaaatacatt ggatatatct tcatttaacc ctcatgggat tagcacattc    360
acggatgaag ataacactgt gtacctactg gtggtaaacc atccagactc ctcgtccacc    420
gtggaggtgt ttaaatttca agaagaagaa aaatcacttt tgcatctgaa accatcaga    480
cacaagcttc tgcctagtgt gaatgacatt gtcgctgtgg acctgaaca cttttatgcc    540
acaaatgatc actattttgc tgaccettac ttaaaatcct gggaaatgca tttgggatta    600
gcgtggtcat ttgttactta ttatagcccc aatgatgttc gagtagtggc agacggattt    660
gattttgcta acggaatcaa catctcacca gacggcaagt atgtctatat agctgagttg    720
ctggctcata agatccatgt gtatgaaaag cacgctaatt ggactttaac tccattgaag    780
tccctcgact tgacaccct tgtggataac atctctgtgg atcctgtgac aggggacctc    840
tgggtgggat gccatcccaa cggaatgcga atcttctact atgacccaaa gaatcctccc    900
ggctcagagg tgcttcgaat ccaggacatt ttatccgaag agcccaaagt gacagtggtt    960
tatgcagaaa atggcactgt gttacagggc agcacggtgg ccgctgtgta caagggaaaa   1020
ctgctgattg gcacagtgtt tcacaaagct ctttactgtg agctg                   1065

<210> SEQ ID NO 63
<211> LENGTH: 355
<212> TYPE: PRT
<213> ORGANISM: Artificial sequence
<220> FEATURE:
<223> OTHER INFORMATION: In vitro evolved PON variant G3C9.10

<400> SEQUENCE: 63

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
                20                  25                  30

Glu Val Thr Pro Val Glu Leu Pro Asn Cys Asn Leu Val Lys Gly Val
        35                  40                  45
```

```
Asp Asn Gly Ser Glu Asp Leu Glu Ile Leu Pro Asn Gly Leu Ala Phe
 50                  55                  60
Ile Ser Ser Gly Val Lys Tyr Pro Gly Ile Met Ser Phe Asp Pro Asp
 65                  70                  75                  80
Lys Ser Gly Lys Ile Leu Leu Met Asp Leu Asn Glu Glu Asp Pro Val
                 85                  90                  95
Val Leu Glu Leu Gly Ile Thr Gly Asn Thr Leu Asp Ile Ser Ser Phe
             100                 105                 110
Asn Pro His Gly Ile Ser Thr Phe Thr Asp Glu Asp Asn Thr Val Tyr
         115                 120                 125
Leu Leu Val Val Asn His Pro Asp Ser Ser Ser Thr Val Glu Val Phe
     130                 135                 140
Lys Phe Gln Glu Glu Lys Ser Leu His Leu Lys Thr Ile Arg
145                 150                 155                 160
His Lys Leu Leu Pro Ser Val Asn Asp Ile Ala Val Gly Pro Glu
                165                 170                 175
His Phe Tyr Ala Thr Asn Asp His Tyr Phe Ala Asp Pro Tyr Leu Lys
            180                 185                 190
Ser Trp Glu Met His Leu Gly Leu Ala Trp Ser Phe Val Thr Tyr Tyr
        195                 200                 205
Ser Pro Asn Asp Val Arg Val Val Ala Asp Gly Phe Asp Phe Ala Asn
210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asp Thr Leu Val Asp Asn Ile Ser
            260                 265                 270
Val Asp Pro Val Thr Gly Asp Leu Trp Val Gly Cys His Pro Asn Gly
        275                 280                 285
Met Arg Ile Phe Tyr Tyr Asp Pro Lys Asn Pro Pro Gly Ser Glu Val
290                 295                 300
Leu Arg Ile Gln Asp Ile Leu Ser Glu Glu Pro Lys Val Thr Val Val
305                 310                 315                 320
Tyr Ala Glu Asn Gly Thr Val Leu Gln Gly Ser Thr Val Ala Ala Val
                325                 330                 335
Tyr Lys Gly Lys Leu Leu Ile Gly Thr Val Phe His Lys Ala Leu Tyr
            340                 345                 350
Cys Glu Leu
        355

<210> SEQ ID NO 64
<211> LENGTH: 1065
<212> TYPE: DNA
<213> ORGANISM: Artificial sequence
<220> FEATURE:
<223> OTHER INFORMATION: In vitro evolved PON variant G3C9.49

<400> SEQUENCE: 64
atggctaaac tgacagcgct cacactcttg gggctgggat tggcactctt cgatagacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggattaaag tatcctggaa taatgagctt tgaccctgat     240
aagtctggaa agatacttct aatggacctg aatgaggaag acccagtagt gttggaactg     300
```

```
ggcattactg gaaatacatt ggatatatct tcatttaacc ctcatgggat tagcacattc    360
acagacgaag ataacactgt gtatctactg gtggtaaacc atccagactc ctcgtccacc    420
gtggaggtgt ttaaatttca agaagaagaa aaatcacttt tgcatctgaa aaccatcaga    480
cacaagcttc tgcctagtgt gaatgacatt gtcgctgtgg gacctgaaca cttttatgcc    540
acaaatgatc actattttgc tgacccttac ttaaaacccct gggaaatgca tttgggatta    600
gcgtggtcat ttgttactta ctatagtccc aatgatgttc gagtagtggc agaaggattt    660
gattttgcta acggaatcaa catctcacca gacggcaagt atgtctatat agctgagttg    720
ctggctcata agatccatgt gtatgaaaag cacgctaatt ggactttaac tccattgaag    780
tccctcgact ttgacaccct tgtggataac atctctgtgg atcctgtgac aggggacctc    840
tgggtgggat gccatcccga cggaatgcga atcttctact atgacccaaa gaatcctccc    900
ggctcagagg tgcttcgaat ccaggacatt ttatccgaag agcccaaagt gacagtggtg    960
tatgcagaaa atggcactgt gttacagggc agcacggtgg ccgctgtgta caagggaaaa   1020
ctgctgattg gcacagcgtt tcacaaagct ctttactgtg agctg                   1065
```

<210> SEQ ID NO 65
<211> LENGTH: 355
<212> TYPE: PRT
<213> ORGANISM: Artificial sequence
<220> FEATURE:
<223> OTHER INFORMATION: In vitro evolved PON variant G3C9.49

<400> SEQUENCE: 65

```
Met Ala Lys Leu Thr Ala Leu Thr Leu Leu Gly Leu Gly Leu Ala Leu
1               5                   10                  15

Phe Asp Arg Gln Lys Ser Ser Phe Gln Thr Arg Phe Asn Val His Arg
                20                  25                  30

Glu Val Thr Pro Val Glu Leu Pro Asn Cys Asn Leu Val Lys Gly Val
            35                  40                  45

Asp Asn Gly Ser Glu Asp Leu Glu Ile Leu Pro Asn Gly Leu Ala Phe
        50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Pro Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220
```

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
            245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asp Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu
        355

<210> SEQ ID NO 66
<211> LENGTH: 1065
<212> TYPE: DNA
<213> ORGANISM: Artificial sequence
<220> FEATURE:
<223> OTHER INFORMATION: In vitro evolved PON variant 7PC

<400> SEQUENCE: 66
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggtcgacaat ggttctgaag acttggaaat actgcccaat     180
ggactggctt tcatcagctc cggattaaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa accatcaga     480
cacaagcttc tgcctagtgt gaatgacatt gtcgctgtgg acctgaaca ctttttatgcc     540
acaaatgatc actattttgc tgacccttac ttaaaatcct gggaaatgca tttgggatta     600
gcgtggtcat tgttacttta ttatagtccc aatgatgttc gagtagtggc agaaggattt     660
gattttgcta acggaatcaa catctcacca gacggcaagt atgtctatat agctgagttg     720
ctggctcata gatccatgt gtatgaaaag cacgctaatt ggactttaac tccattgaag     780
tccctcgact tgacacccct tgtggataac atctctgtgg atcctgtgac aggggacctc     840
tgggtgggat gccatcccaa cggaatgcga atcttctact atgacccaaa gaatcctccc     900
ggctcagagg tgcttcgaat ccaggacatt ttatccgaag agcccaaagt gacagtggtt     960
tatgcagaaa atggcactgt gttacagggc agcacggtgg ccgctgtgta caagggaaaa    1020
ctgctgattg gcacagtgtt tcacaaagct ctttactgtg agctg                    1065

<210> SEQ ID NO 67
<211> LENGTH: 355
<212> TYPE: PRT
<213> ORGANISM: Artificial sequence
<220> FEATURE:

<223> OTHER INFORMATION: In vitro evolved PON variant 7PC

<400> SEQUENCE: 67

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
                20                  25                  30

Glu Val Thr Pro Val Glu Leu Pro Asn Cys Asn Leu Val Lys Gly Val
            35                  40                  45

Asp Asn Gly Ser Glu Asp Leu Glu Ile Leu Pro Asn Gly Leu Ala Phe
        50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu
        355
```

<210> SEQ ID NO 68
<211> LENGTH: 1065
<212> TYPE: DNA
<213> ORGANISM: Artificial sequence
<220> FEATURE:

<223> OTHER INFORMATION: In vitro evolved PON variant 4PC

<400> SEQUENCE: 68

```
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggagtaaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa aaccatcaga     480
cacaagcttc tgcctagtgt gaatgacatt gtcgctgtgg acctgaaca cttttatgcc     540
acaaatgatc actattttgc tgacccttac ttaaaaccct gggaaatgca tttgggatta     600
gcgtggtcat ttgttactta ttatagtccc aatgatgttc gagtagtggc agaaggattt     660
gattttgcta acggaatcaa catctcacca gacggcaagt atgtctatat agctgagttg     720
ctggctcata agatccatgt gtatgaaaag cacgctaatt ggactttaac tccattgaag     780
tccctcgact tgacaccct tgtggataac atttctgtgg atcctgtgac aggggacctc     840
tgggtgggat gccatcccaa cggaatgcga atcttctact atgacccaaa gaatcctccc     900
ggctcagagg tgcttcgaat ccaggacatt ttatccgaag agcccaaagt gacagtggtt     960
tatgcagaaa atggcactgt gttacagggc agcacggtgg ccgctgtgta caagggaaaa    1020
ctgctgattg gcacagcgtt tcacaaagct ctttactgtg agctg                    1065
```

<210> SEQ ID NO 69
<211> LENGTH: 355
<212> TYPE: PRT
<213> ORGANISM: Artificial sequence
<220> FEATURE:
<223> OTHER INFORMATION: In vitro evolved PON variant 4PC

<400> SEQUENCE: 69

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
    130                 135                 140

Lys Phe Gln Glu Glu Glu Lys Ser Leu Leu His Leu Lys Thr Ile Arg
145                 150                 155                 160
```

```
His Lys Leu Leu Pro Ser Val Asn Asp Ile Val Ala Val Gly Pro Glu
                165                 170                 175
His Phe Tyr Ala Thr Asn Asp His Tyr Phe Ala Asp Pro Tyr Leu Lys
            180                 185                 190
Pro Trp Glu Met His Leu Gly Leu Ala Trp Ser Phe Val Thr Tyr Tyr
        195                 200                 205
Ser Pro Asn Asp Val Arg Val Ala Glu Gly Phe Asp Phe Ala Asn
    210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asp Thr Leu Val Asp Asn Ile Ser
            260                 265                 270
Val Asp Pro Val Thr Gly Asp Leu Trp Val Gly Cys His Pro Asn Gly
        275                 280                 285
Met Arg Ile Phe Tyr Tyr Asp Pro Lys Asn Pro Pro Gly Ser Glu Val
    290                 295                 300
Leu Arg Ile Gln Asp Ile Leu Ser Glu Glu Pro Lys Val Thr Val Val
305                 310                 315                 320
Tyr Ala Glu Asn Gly Thr Val Leu Gln Gly Ser Thr Val Ala Ala Val
                325                 330                 335
Tyr Lys Gly Lys Leu Leu Ile Gly Thr Ala Phe His Lys Ala Leu Tyr
            340                 345                 350
Cys Glu Leu
        355

<210> SEQ ID NO 70
<211> LENGTH: 1065
<212> TYPE: DNA
<213> ORGANISM: Artificial sequence
<220> FEATURE:
<223> OTHER INFORMATION: In vitro evolved PON variant 1HT

<400> SEQUENCE: 70
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggattaaag tatcctggaa taatgagctt tgaccctgat     240
aagtctggaa agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa accatcaga      480 cacaagcttc tgcctagtgt gaatgacatt gtcgctgtgg gacctgaaca cttttatgcc     540
acaaatgatc actattttgc tgacccttac ttaaaatcct gggaaatgca tttgggatta     600
gcgtggtcat ttgttactta ttatagtccc aatgatgttc gagtagtggc agaaggattt     660
gattttgcta acggaatcaa catctcacca gacggcaagt atgtctatat agctgagttg     720
ctggctcata agatccatgt gtatgaaaag cacgctaatt ggactttaac tccattgaag     780
tccctcgact tgacaccct tgtggataac atctctgtgg atcctgtgac agggacctc      840 tgggtgggat gccatcccaa cggaatgcga ctcttctact atgacccaaa gaatcctccc     900
```

```
ggctcagagg tgcttcgaat ccaggacatt ttatccgaag agcccaaagt gacagtggtt      960
tatgcagaaa atggcactgt gttacagggc agcgcggtgg ccgctgtgta caaagagaaa     1020
ctgctgattg gcacagtgtt tcacaaagct ctttactgtg agctg                     1065
```

<210> SEQ ID NO 71
<211> LENGTH: 355
<212> TYPE: PRT
<213> ORGANISM: Artificial sequence
<220> FEATURE:
<223> OTHER INFORMATION: In vitro evolved PON variant 1HT

<400> SEQUENCE: 71

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Gly Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Leu Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ala Val Ala Ala Val
                325                 330                 335
```

Tyr Lys Glu Lys Leu Leu Ile Gly Thr Val Phe His Lys Ala Leu Tyr
         340                 345                 350

Cys Glu Leu
        355

<210> SEQ ID NO 72
<211> LENGTH: 1065
<212> TYPE: DNA
<213> ORGANISM: Artificial sequence
<220> FEATURE:
<223> OTHER INFORMATION: In vitro evolved PON variant 2AC

<400> SEQUENCE: 72

| | | | | | |
|---|---|---|---|---|---|
| atggctaaac | tgacagcgct | cacactcttg | gggctgggat | tggcactctt | cgatggacag | 60 |
| aagtcttctt | tccaaacacg | atttaatgct | caccgtgaag | taactccagt | ggaacttcct | 120 |
| aactgtaatt | tagttaaagg | ggttgacaat | ggttctgaag | acttggaaat | actgcccaat | 180 |
| ggactggctt | tcatcagctc | cggattaaag | tatcctggaa | taatgagctt | tgaccctgat | 240 |
| aagtctggaa | agatacttct | aatggacctg | aatgaggaag | acccagtagt | gttggaactg | 300 |
| ggcattactg | gaaatacatt | ggatatatct | tcatttaacc | ctcatgggat | tagcacattc | 360 |
| acagatgaag | ataacactgt | gtacctactg | gtggtaaacc | atccagactc | ctcgtccacc | 420 |
| gtggaggtgt | ttaaatttca | agaagaagaa | aaatcacttt | tgcatctgaa | aaccatcaga | 480 |
| cacaagcttc | tgcctagtgt | gaatgacatt | gtcgctgtgg | gacctgaaca | ctttttatgcc | 540 |
| acaaatgatc | actattttgc | tgacccttac | ttaaaatcct | gggaaatgca | tttgggatta | 600 |
| gcgtggtcat | ttgttactta | ttatagtccc | aatgatgttc | gagtagtggc | agaaggattt | 660 |
| gatttttgcta | acggaatcaa | catctcacca | gacggcaagt | atgtctatat | agctgagttg | 720 |
| ctggctcata | gatccatgt | gtataaaaag | cacgctaatt | ggactttaac | tccattgaag | 780 |
| tccctcgact | tgacaccct | tgtggataac | atctctgtgg | atcctgtgac | aggggacctc | 840 |
| tgggtgggat | gccatcccaa | cggaatgcga | atctcctact | atgacccaaa | gaatcctccc | 900 |
| ggctcagagg | tgcttcgaat | ccaggacatt | ttatccgaag | agcccaaagt | gacagtggtt | 960 |
| tatgcagaaa | atggcactgt | gttacagggc | agcacggtgg | ccgctgtgta | caagggaaa | 1020 |
| ctgctgattg | gcacaatgtt | tcacaaagct | ctttactgtg | agctg | | 1065 |

<210> SEQ ID NO 73
<211> LENGTH: 355
<212> TYPE: PRT
<213> ORGANISM: Artificial sequence
<220> FEATURE:
<223> OTHER INFORMATION: In vitro evolved PON variant 2AC

<400> SEQUENCE: 73

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Ala His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val

|     | 85              |     |     |     | 90  |     |     |     | 95  |     |     |
| --- | --------------- | --- | --- | --- | --- | --- | --- | --- | --- | --- | --- |
| Val | Leu Glu Leu Gly | Ile | Thr | Gly | Asn | Thr | Leu | Asp | Ile | Ser | Ser Phe |

Val Leu Glu Leu Gly Ile Thr Gly Asn Thr Leu Asp Ile Ser Ser Phe
                85                  90                  95

Asn Pro His Gly Ile Ser Thr Phe Thr Asp Glu Asp Asn Thr Val Tyr
            100                 105                 110

Leu Leu Val Val Asn His Pro Asp Ser Ser Thr Val Glu Val Phe
        115                 120                 125

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Lys Lys His Ala Asn Trp Thr Leu
            245                 250                 255

Thr Pro Leu Lys Ser Leu Asp Phe Asp Thr Leu Val Asp Asn Ile Ser
        260                 265                 270

Val Asp Pro Val Thr Gly Asp Leu Trp Val Gly Cys His Pro Asn Gly
    275                 280                 285

Met Arg Ile Ser Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Ala Phe His Lys Ala Leu Tyr
            340                 345                 350

Cys Glu Leu
        355

<210> SEQ ID NO 74
<211> LENGTH: 1065
<212> TYPE: DNA
<213> ORGANISM: Artificial sequence
<220> FEATURE:
<223> OTHER INFORMATION: In vitro evolved PON variant 7HY

<400> SEQUENCE: 74

```
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggattaaag tatcctggaa taatgagctt tgaccctgat     240
aagtctggaa agatacttct aatggacctg aatgaggaag acccagtagt gttggaactg     300
ggcattactg gaaatacatt ggatatgtct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa aaccatcaga     480
```

```
cacaagcttc tgcctagtgt gaatgacatt gtcgctgtgg gacctgaaca cttttatgcc    540
acaaatgatc actattttgc tgacccttac ttaaaatcct gggaaatgca tttgggatta    600
gcgtggtcat tgttactta ttatagtccc aatgatgttc gagtagtggc agaaggattt    660
gattttgcta acggaatcaa catctcacca gacggcaagt atgtctatat agctgagttg    720
ctggctcata agatccatgt gtatgaaaag cacgctaatt ggactttaac tccattgaag    780
tccctcgact ttgacaccct tgtggataac atctctgtgg atcctgtgac aggggacctc    840
tgggtgggat gccatcccaa cggaatgcga atcgtcgact atgacccaaa gaatcctccc    900
ggctcagagg tgcttcgaat ccaggacatt ttatccgaag agcccaaagt gacagtggtt    960
tatgcagaaa atggcactgt gttacagggc agcacggtgg ccgctgtgta caaagggaaa   1020
ctgctgattg gcacagtgtt tcacaaagct ctttactgtg agctg                   1065
```

<210> SEQ ID NO 75
<211> LENGTH: 355
<212> TYPE: PRT
<213> ORGANISM: Artificial sequence
<220> FEATURE:
<223> OTHER INFORMATION: In vitro evolved PON variant 7HY

<400> SEQUENCE: 75

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Met Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
```

-continued

```
                260                 265                 270
Val Asp Pro Val Thr Gly Asp Leu Trp Val Gly Cys His Pro Asn Gly
        275                 280                 285

Met Arg Ile Val Asp Tyr Asp Pro Lys Asn Pro Pro Gly Ser Glu Val
    290                 295                 300

Leu Arg Ile Gln Asp Ile Leu Ser Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu
        355

<210> SEQ ID NO 76
<211> LENGTH: 1065
<212> TYPE: DNA
<213> ORGANISM: Artificial sequence
<220> FEATURE:
<223> OTHER INFORMATION: In vitro evolved PON variant 4HY

<400> SEQUENCE: 76
atggctaaac tgacagcgct cacactcttg gggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat     180
ggactggctt tcatcagctc cggattaaag tatcctggac taatgagctt tgaccctgat     240
aagtctggac agatacttct aatggacctg aatgaggaag acccagtagt gttggaactg     300
ggcattactg gaaatacatt ggatatatct tcatttaacc ctcatgggat tagcacattc     360
acagatgaag ataacactgt gtacctactg gtggtaaacc atccagactc ctcgtccacc     420
gtggaggtgt ttaaatttca agaagaagaa aaatcacttt tgcatctgaa aaccatcaga     480
cacaagcttc tgcctagtgt gaatgacatt gtcgctgtgg acctgaaca cttttatgcc     540 acaaatgatc actattttgc tgacccttac ttaaaatcct gggaaatgca tttgggatta     600
gcgtggtcat tgttactta ttatagtccc aatgatgttc gagtagtggc agaaggattt     660
gattttgcta acggaatcaa catctcacca gacggcaagt atgtctatat agctgagttg     720
ctggctcata gatccatgt gtatgaaaag cacgctaatt ggactttaac tccattgaag     780
tccctcgact ttgacaccct tgtggataac atctctgtgg atcctgtgac aggggacctc     840
tgggtgggat gccatcccaa cggaatgcga atcctctact atgacccaaa gaatcctccc     900
ggctcagagg tgcttcgaat ccaggacatt ttatccgaag agcccaaagt gacagtggtt     960
tatgcagaaa atggcactgt gttacagggc agcacggtgg ccgctgtgta caaagggaaa    1020
ctgctgatgg gcacagtgtt tcacaaagct ctttactgtg agctg                    1065

<210> SEQ ID NO 77
<211> LENGTH: 355
<212> TYPE: PRT
<213> ORGANISM: Artificial sequence
<220> FEATURE:
<223> OTHER INFORMATION: In vitro evolved PON variant 4HY

<400> SEQUENCE: 77

Met Ala Lys Leu Thr Ala Leu Thr Leu Leu Gly Leu Gly Leu Ala Leu
1               5                   10                  15
```

```
Phe Asp Gly Gln Lys Ser Ser Phe Gln Thr Arg Phe Asn Val His Arg
             20                  25                  30

Glu Val Thr Pro Val Glu Leu Pro Asn Cys Asn Leu Val Lys Gly Val
         35                  40                  45

Asp Asn Gly Ser Glu Asp Leu Glu Ile Leu Pro Asn Gly Leu Ala Phe
 50                  55                  60

Ile Ser Ser Gly Leu Lys Tyr Pro Gly Leu Met Ser Phe Asp Pro Asp
 65                  70                  75                  80

Lys Ser Gly Gln Ile Leu Leu Met Asp Leu Asn Glu Glu Asp Pro Val
                 85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Leu Tyr Tyr Asp Pro Lys Asn Pro Pro Gly Ser Glu Val
290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Met Gly Thr Val Phe His Lys Ala Leu Tyr
            340                 345                 350

Cys Glu Leu
        355

<210> SEQ ID NO 78
<211> LENGTH: 1065
<212> TYPE: DNA
<213> ORGANISM: Artificial sequence
<220> FEATURE:
<223> OTHER INFORMATION: In vitro evolved PON variant G1A9

<400> SEQUENCE: 78
atggctaaac tgacagcgct cacgctcttg gggctgggat tggcactctt cgatggacag      60
aagtcttctt tccaaacacg atttaatgtt caccgtgaag taactccagt ggaacttcct     120
```

| | |
|---|---:|
| aactgtaatt tagttaaagg gattgacaat ggttctgaag acttggaaat actgcctaat | 180 |
| ggactggctt tcattagctc tggattaaaa tatcctggaa taatgagctt tgaccctgat | 240 |
| aagtctggaa agatacttct aatggacctg aatgaggaag acccagtagt gttggaactg | 300 |
| ggcattactg gaagtacatt tgatttatct tcatttaacc ctcatgggat tagcacattc | 360 |
| acagatgaag ataatatcgt ctacctgatg gtggtgaacc atccagattc aaagtccaca | 420 |
| gtggaggtat ttaaatttca agaagaagaa aaatcgcttt tgcatctaaa aactatcaga | 480 |
| cataaacttc tgcctaattt gaatgatatt gttgctgtgg gacctgaaca ctttttatgct | 540 |
| accaatgatc actattttct tgaccoctac ttacgatcct gggaaatgta cttgggtctg | 600 |
| tcgtggtcca atgttgttta ctacagtcca gataaagtcc aggtggtagc agaagggttt | 660 |
| gatttcgcta atggaatcaa catttcaccc gatggcaagt atgtctatat agctgagttg | 720 |
| ctggctcata agattcatgt gtatgaaaag catgctaatt ggactttaac gccattgaag | 780 |
| gtcctcagct ttgacaccct tgtggataac atctctgtgg atcctgtgac aggggacctc | 840 |
| tgggtgggat gccatcccaa cggaatgagg atctttttct atgacgcaga gaatcctccc | 900 |
| ggctcagagg tgcttcgaat ccaggacatt ttatccaaag agcccaaagt gacagtggtt | 960 |
| tatgcagaaa atggcactgt gttgcaaggc agtacagttg cctctgtgta caagggaaa | 1020 |
| ctgctgattg gcaccgtgtt ccacaaagct ctttactgtg agctc | 1065 |

<210> SEQ ID NO 79
<211> LENGTH: 1065
<212> TYPE: DNA
<213> ORGANISM: Artificial sequence
<220> FEATURE:
<223> OTHER INFORMATION: In vitro evolved PON variant G2D4

<400> SEQUENCE: 79

| | |
|---|---:|
| atggctaaac tgacagcgct cacgctcttg gggctgggat tggcactctt cgatagacag | 60 |
| aagtcttctt tccaaacacg atttaatgtt caccgtgaag taactccagt ggaacttcct | 120 |
| aactgtaatt tagttaaagg gattgacaat ggttctgaag acttggaaat actgcccaat | 180 |
| ggactggctt tcatcagctc cggattaaaa tatcctggaa taatgagctt tgaccctgat | 240 |
| aagtctggaa agatacttct aatggacctg aatgaggaag acccagtagt gttggaactg | 300 |
| ggcattcctg gaagtacatt tgatttatct tcatttaacc ctcatgggat tagcacattc | 360 |
| acagatgaag ataatatcgt ctacctgatg gtggtgaacc atccagattc aaagtccaca | 420 |
| gtggagttgt ttaaattcca agaagaggaa agatcacttt tgcatctgaa accatcacc | 480 |
| catgagcttc tgcctagtgt gaatgacatt gtcgctgtgg gacctgagag cttctatgct | 540 |
| accaatgatc actattttat tgacccttac ttaaaatcct gggaaatgta cttgggtctg | 600 |
| tcgtggtcca atgttgttta ctacagtcca gataaagtcc aggtggtggc agaaggatt | 660 |
| gattttgcta acggaatcaa catttcaccc gatggcaagt atgtctatat agctgaactg | 720 |
| ctggctcata agatccatgt gtatgaaaag cacgctaatt ggactttaac gccattgaag | 780 |
| gtcctcaact ttgacaccct tgtggataac atctctgtgg atcctgtgac aggggacctc | 840 |
| tgggtgggat gccatcccaa cggaatgagg atctttttct atgacgcaga gaatcctccc | 900 |
| ggctcagagg tgcttcgaat ccaggacatt ttatccaaag agcccaaagt gacagtggtt | 960 |
| tatgcagaaa atggcactgt gttgcaaggc agcacggtcg cctctgtgta caagggaaa | 1020 |
| ctgctgattg gcactgtgtt ccacaaagct ctttactgtg atctg | 1065 |

<210> SEQ ID NO 80
<211> LENGTH: 1065
<212> TYPE: DNA
<213> ORGANISM: Artificial sequence
<220> FEATURE:
<223> OTHER INFORMATION: In vitro evolved PON variant G3H10

<400> SEQUENCE: 80

```
atggctaaac tgacagcgcc cacgctcttg gggctgggat tggcactctt cgatagacag        60
aagtcttctt ccaaacacg atttaatgtt caccgtgaag taactccagt ggaacttcct       120
aactgtaatt tagttaaagg gattgacaat ggttctgaag acttggaaat actgcccaat       180
ggactggctt tcatcagctc cggattaaaa tatcctggaa taatgagctt tgaccctgat       240
aagtctggaa agatacttct aatggacctg aatgaggaag acccagtagt gttggaactg       300
ggcattactg gaagtacatt tgatttatct tcatttaacc ctcatgggat tagcacattc       360
acagatgaag ataacactgt gtacctactg gtagtaaacc atccagactc ctcgtccact       420
gtggaggtat ttaaatttca agaaaaggag agatcacttt tgcatctgaa aaccatcaga       480
cacaagcttc tgcctagtgt gaatgacatt gtcgctgtgg acctgagag cttttatgcc       540 acaaatgatc actattttgc tgacccttac ttaaaatcct gggaaatgca tttgggatta       600
gcgtggtcat tgttactta ttatagtccc aatgatgttc gagtagtggc agaaggatt       660 gattttgcta acggaatcaa catctcaccc gatggcaagt atgtctatat agctgaactg       720
ctggctcata agatccatgt gtatgaaaag cacgctaatt ggactttaac tccattgaag       780
tccctcgact ttaacactct tgtggataac atctctgtgg atcctgtgac agggacctc       840 tgggtgggat gccatcccaa tggcatgcga atcttctact atgacccaga gaatcctccc       900
ggctcagagg tacttcgaat ccaggacatt ttatccaaag agccccaagt gacagtggtt       960
tatgcagaaa atggcactgt gttacagggc agcacggtgg ccgctgtgta caaagggaaa      1020
ctgctgattg gcactgtgtt ccacaaagct ctttactgtg atctg                       1065
```

<210> SEQ ID NO 81
<211> LENGTH: 1062
<212> TYPE: DNA
<213> ORGANISM: Artificial sequence
<220> FEATURE:
<223> OTHER INFORMATION: In vitro evolved PON variant G1E10
<220> FEATURE:
<221> NAME/KEY: misc_feature
<222> LOCATION: (427)..(427)
<223> OTHER INFORMATION: n is a, c, g, or t

<400> SEQUENCE: 81

```
atggcgaagc tcctgctgct gaccctgctg ggggtcggcc tgtccttagt cggggagatg        60
ttcctggcgt ttagagaaag ggtgaatgcc tctcgagaac tggagccagt agaaccccag       120
aactgtgtcc ttattgaggg actcgaaaat ggctcggaag atattgatat acttcctagc       180
gggctggctt ttatctccac tggattaaaa tatccaggca tgccaaactt tgcaccagat       240
gagccaggaa aaatcttctt gatggatctg aatgagcaaa acccagaggc gcaagcactg       300
gaaatcagtg gtgggcttga ccaggagtca ctaaatcctc acgggatcag cactttcatc       360
gacaaagaca atactgtgta tctttatgtt gtgaatcacc ccaacatgga ctccactgtg       420
gagatantta aatttgagga acaacaacgc tctcttgtac acctgaaaac tataaaacat       480
gaacttctca agagtgtgaa tgacattgtg gttcttgggc cagagcagtt ctatgccacc       540
agagaccact attttaccaa ctccctcctg tcatttttg agatgatctt ggaccctcac       600
```

```
tggacttccg tcgttttcta cagcccaaaa gaggtcaaag ttgtggccca aggattcagt    660
tctgccaacg gaatcacagt ctcagcagac cagaagtatg tctatgtagc tgatgtagca    720
gctaagaaca ttcacataat ggaaaaacat gacaactggg atttaactca actgaaggtg    780
atacagttgg acaccttagt ggataatttg tctgttgatc ctgccacggg agatattttg    840
gcaggatgcc atcctaatcc tatgaagcta ctggactata accctgagga tcctccagga    900
tcagaagtac ttcgtatcca gaatgttttg tctgagaagc ccagggtgag caccgtgtat    960
gccaatgacg gctctgtgct tcagggctcc accgtggctt ctgtgtacca agggaagatt   1020
ctcataggca ctatatttca caaaactctg tattgtgtac tc                      1062
```

<210> SEQ ID NO 82
<211> LENGTH: 1062
<212> TYPE: DNA
<213> ORGANISM: Artificial sequence
<220> FEATURE:
<223> OTHER INFORMATION: In vitro evolved PON variant G1G7
<220> FEATURE:
<221> NAME/KEY: misc_feature
<222> LOCATION: (571)..(571)
<223> OTHER INFORMATION: n is a, c, g, or t

<400> SEQUENCE: 82

```
atggggaagc tcgtggcgct ggtcctgctg ggggtcggcc tgtccttagt cggggagatg     60
ttcctggcgt ttggagaaag ggtgaatgcc tctcgagaag tggagccagt agaacctgaa    120
aactgccacc ttattgaggg cctcgagaat ggctctgaag atattgatat acttcctagc    180
gggctggctt ttatctccac tggattaaaa tatccaggca tgccaaactt tgcgccagat    240
gaaccaggaa aaatcttctt gatagatatg aatgagaaga acccaagagc acaagagctg    300
gaaatcagca atggatttga aaaagaatca ttcaatccac atgggatcag cactttcatc    360
gacaaagaca atactgctta tctttatgtc gtgaatcacc ccaacatgga ctccactgtg    420
gagatattta gtttgaaga acaacaacac tctctcatcc acctgaaaac tctaaaacat    480
gaacttctca agagtgtgaa tgacattgtg gttcttggac cggaacagtt ctatgccacc    540
agagaccact attttaccaa ctatgtctta ncacttcttg agatgttttt ggaccctcac    600
tggacttccg tcgttttcta cagcccaaaa gaggtcaaag ttgtggccca aggattcagt    660
tctgccaatg ggatcacagt ctcactagat aagaagtatg tctatgttgc tgatgccaca    720
gctaagaatg tgcatgtaat ggaaaaacat gataactggg atttaactcc agtgaaggtc    780
attcagctgg gaaccttagt ggataacttg accgttgatc cagccacggg agatattttg    840
gcaggctgcc accctaaccc catgaagcta ctgaactata accctgagga ccctccagga    900
tcagaagtac ttcgcatcca ggactctttg tcagataagc ccagggtgag caccgtgtat    960
gccaacaatg gctctgtgct tcagggctcc accgtggctt ctgtgtacca agggaagatt   1020
ctcataggca ctatatttca caaagctctg tactgtgacc tc                      1062
```

<210> SEQ ID NO 83
<211> LENGTH: 1062
<212> TYPE: DNA
<213> ORGANISM: Artificial sequence
<220> FEATURE:
<223> OTHER INFORMATION: In vitro evolved PON variant G2E11
<220> FEATURE:
<221> NAME/KEY: misc_feature
<222> LOCATION: (775)..(775)
<223> OTHER INFORMATION: n is a, c, g, or t

```
<400> SEQUENCE: 83
atggcgaagc tcctgctgct gaccctgctg ggggccagcc tcgccttcgt cggggagagg        60
ttgctggcgt ttagaaaaag ggtgaatgcc tctcgagaag tggagccagt agaaccaaaa       120
aactgccacc ttattgaggg actcgaaaat ggctcggaag atattgatat acttcctagt       180
gggctggctt ttatctccac tggattaaaa tatccaggca tgccaaactt tgcaccagat       240
gagccaggaa aaatcttctt gatagacatg aatgagaaga cccaagagc acaagagctg        300 gaaatcagca atggatttga aaagaatca ttcaatccac atgggatcag cactttcatc        360
gacaaagacc atactgtgta tctttatgtt gtgaatcacc caacatgga ttccactgtg        420 gagatattta aatttgagga acaacaacgt tctctggtat acctgaaaac tctaaaacat       480
gaacttctca agagtgtgaa tgacattgtg gttcttggac cggaacagtt ctatgccacc       540
agagaccact attttaccaa ctccctcctg tcattttttg agatgttctt ggatcttcgc       600
tggacttatg ttcttttcta cagcccaaaa gaagtcaaag tggtggccaa aggattcagt       660
tctgccaatg ggatcacagt ctcactagat aagaagtatg tctatgtagc tgatgtagca       720
gctaagaaca ttcacataat ggaaaaacat gacaactggg attaactga actgnaggta       780 atacacttgg acaccttagt ggataatttg tctgttgatc ctgccacggg agatatcttg       840
gcaggatgcc atcctaatgg catgaagctt ctgaactata accctgagga ccctccagga       900
tcagaagtac ttcgcatcca gaatgttttg tctgagaagc ccagggtgag caccgtgtac       960
accaatgacg gctctgtgct tcagggcacc tctgtggctt ctgtgtacca agggaagatt      1020
ctcataggca ctatatttca caaaactctg tactgtgacc tc                         1062

<210> SEQ ID NO 84
<211> LENGTH: 1062
<212> TYPE: DNA
<213> ORGANISM: Artificial sequence
<220> FEATURE:
<223> OTHER INFORMATION: In vitro evolved PON variant G2A7

<400> SEQUENCE: 84
atggcgaagc tcgtggcgct ggtcctgctg ggggtcgggc tgtccttagt cggggagatg        60
ttcctggcgt ttagagaaag ggtggatgcc tctcgagaag tggagccagt agaaccccag       120
aactgtgtcc ttattgaggg actcgaaaat ggctcggaag atattgatat acttcctagt       180
gggctggctt ttatctccag tggattaaaa tatccaggca tgccaaactt tgcaccagat       240
gagccaggaa aaatcttctt gatggatctg aatgagaaga cccaagagc acaagagctg        300 gaaatcagca atggatttga aaagaatca ttcaatccac atgggatcag cactttcatc        360
gacaaagaca cactgctta tctttatgtc gtgaatcacc caacatgga ctccactgtg        420 gagatattta aatttgagga acaacaacac tctctcatcc acctgaaaac tataaaacat       480
gaacttctca aaagtgtgaa tgacattgtg gttcttggac cggaacagtt ctacgccacc       540
agagaccact attttaccaa ctccctcctg tcattttttg agatgatctt ggatcttcgc       600
tggacttatg ttcttttcta cagccccaaa gaggccaaag tggtggccaa aggattcagt       660
tctgccaatg ggatcacagt ctcactagat aagaagtatg tctatgttgc tgatgccaca       720
gctaagaatg tgcacataat ggaaaaacat gacaactggg attaactga actgaaggta       780 gtacacttgg acaccttagt ggataacttg accgttgatc cagccacggg agatatttg       840 gcaggctgcc accctaaccc catgaagctg ttgaactata accctgagga ccctccagga       900
tcagaagtac ttcgcatcca gaatgttttg tctgagaagc ccagggtgag caccgtgtac       960
```

```
accaatgacg gctctgtgct tcagggcacc tctgtggctt ctgtgtacca agggaagatt    1020
ctcataggca ctatatttca caaaactctg tattgtgtac tt                      1062
```

<210> SEQ ID NO 85
<211> LENGTH: 1062
<212> TYPE: DNA
<213> ORGANISM: Artificial sequence
<220> FEATURE:
<223> OTHER INFORMATION: In vitro evolved PON variant G2F8

<400> SEQUENCE: 85

```
atggcgaagc tcctgctgct gaccctgctg ggggccagcc tcgccttcgt cggggagagg    60
ttgctggcgt ttagagacag cttttggtgca gttcaagaac tggagccagt ggaaccccag   120
aactgtgtcc ttattgaggg actcgaaaat ggctcggaag atattgatat acttcctaat   180
gggctggctt ttatctccag tggattaaaa tatccaggca tgccaaactt tgcaccagat   240
gagccaggaa aaatcttctt gatagatatg aatgagaaga acccaagagc acaagagctg   300
gaaatcagca atggatttga aaagaatca ttcaatccac atgggatcag cactttcatc    360
gataaagacc atactgtgta tctttatgtt gtgaatcatc cccacatgaa gtccactgtg    420
gagatattta gtttgaaga caacaacgt tctctggtat acctgaaaac tctaaaacat     480
gaacttctca agagtgtgaa tgacattgtg gttcttggac cggaacagtt ctatgccacc    540
agagaccact attttaccaa ctccctcctg tcatttttg agatgatctt ggatcttcgc     600
tggacttccg ttctttttcta cagcccaagg gaggttaaag tggtggccaa aggattcagt    660
tctgccaatg ggatcacagt ctcactagat aagaagtatg tctatgtagc tgatgtagca    720
gctaagaatg tgcatgtaat ggaaaaacat gataactggg atttaactga actgaaggta    780
atacacttgg acaccttagt ggataacttg accgttgatc cagccacagg agacattttg    840
gcaggatgcc atcctaaccc catgaagcta ctgaactata accctgagga ccctccagga    900
tcagaagtac ttcgcatcca gaatgttttg tctgagaagc ccagggtgag caccgtgtat    960
gccaacaatg gctctgtgct tcagggcacc tctgtggctt ctgtgtacca cgggaaaatt    1020
ctcataggca ctatatttca caaagctctg tactgtgacc tc                       1062
```

<210> SEQ ID NO 86
<211> LENGTH: 1062
<212> TYPE: DNA
<213> ORGANISM: Artificial sequence
<220> FEATURE:
<223> OTHER INFORMATION: In vitro evolved PON variant G3C6

<400> SEQUENCE: 86

```
atggggaagc tcctgctgct gaccctgctg ggggccagcc tcaccttcgt cggggagagg    60
ttgctggcgt ttagaaacag cttttggtgca gttcaagaac tggagccagt agaacccggg   120
aactgtgtcc ttattgaggg actcgaaaat ggctcggaag atattgatat acttcctagt   180
gggctggctt ttatctccag tggattaaaa tatccaggca tgccaaactt tgcaccagat   240
gagccaggaa aaatcttctt gatagacatg aatgagaaga acccaagagc acaagagctg    300
gaaatcagca atggatttga aaagaatca ttcaatccac atgggatcag cactttcatc    360
gataaagacc atactgtgta tctttatgtc gtgaatcacc ccaacatgga ctccactgtg    420
gagatattta gtttaagga caacaacgc tctcttgtac acctgaaaac tataaaacat      480
gaacttctca aaagtgtgaa tgacattgtg gttcttggac cagaacagtt ctatgccacc    540
```

```
agagaccact attttaccaa ctccctcctg tcattttttg agatgatctt ggatcttcgc    600
tggacctatg ttcttttcta cagccccaaa gaggtcaaag ttgtggccaa aggattcagt    660
tctgccaacg gaatcacagt ctcactagat aagaagtatg tctatgttgc tgatgccaca    720
gctaagaatg tgcatgtaat ggaaaaacat gataactggg atttaactga actgaaggtc    780
attcagctgg gaaccttagt ggataacttg actgtcgatc ccgccacagg agacattttg    840
gcaggctgcc acccaacccc catgaagcta ctgaactata ccctgagga ccctccagga     900 tcagaagtac ttcgcatcca ggatgttttg tctgagaagc ccagggtgag caccgtgtat    960
gccaatgacg gctctgtgct tcagggcacc tctgtggctt ctgtatacca cgggaaaatt   1020
ctcataggca ctatatttca caaaactctg tactgtgtac tc                      1062
```

<210> SEQ ID NO 87
<211> LENGTH: 1062
<212> TYPE: DNA
<213> ORGANISM: Artificial sequence
<220> FEATURE:
<223> OTHER INFORMATION: In vitro evolved PON variant G3G5

<400> SEQUENCE: 87

```
atggcgaagc tcctgctgct gacccggctg ggggccagcc tcgccttcgt cggggagagg     60
ttgctggcgt ttagaaaaag ggtgaatgcc tctcgagaag tggagccagt agaaccccag    120
aactgtgtcc ttattgaggg actcgaaaat ggctcggaag atattgatat acttcctagt    180
gggctggctt ttatctccac tggattaaaa tatccaggca tgccaaactt tgcaccagat    240
gaaccaggaa aaatcttctt gatggatctg aatgaacaaa cccaagagc acaagcacta    300 gaaatcagtg gtggatttga caagaatta tttaatccac atgggatcag cactttcatt    360
gataaagaca atactgtgta tctttatgtt gtgaatcatc cccacatgaa gtctactgtg    420
gagatattta aatttgagga caacaacgt tctctggtat acctgaaaac tataaaacat    480
gaacttctca aaagtgtgaa tgacattgtg gttcttgggc cggaacagtt ctatgccacc    540
agagaccact attttaccaa ctccctcctg tcattttttg agatgttttt ggatcttcgc    600
tggacttacg ttcttttcta cagcccaagg gaggttaaag tggtggccaa aggattcagt    660
tctgccaatg ggatcacagt ctcactagat aagaagtatg tctatgttgc tgatgccacg    720
gctaagaatg tgcatgtaat ggaaaaacat gataactggg atttaactcc actgaaggta    780
atacacttgg acaccttagt ggataatttg tctgttgatc ctgccacggg agatattttg    840
gcaggatgcc atcctaatcc catgaagctg ttgaactata ccctgagga ccctccagga    900 tcagaagtac ttcgcatcca gaatgttttg tctgggaagc ccagggtgag caccgtgtat    960
gccaacaatg gctctgtgct tcagggcacc tctgtggctt ctgtgtacca agggaagatt   1020
ctcataggca ctatatttca caaaactctg tactgtgagc tc                      1062
```

<210> SEQ ID NO 88
<211> LENGTH: 354
<212> TYPE: PRT
<213> ORGANISM: Homo sapiens

<400> SEQUENCE: 88

```
Met Gly Lys Leu Val Ala Leu Val Leu Leu Gly Val Gly Leu Ser Leu
1               5                   10                  15

Val Gly Glu Met Phe Leu Ala Phe Arg Glu Arg Val Asn Ala Ser Arg
            20                  25                  30

Glu Val Glu Pro Val Glu Pro Glu Asn Cys His Leu Ile Glu Glu Leu
```

-continued

```
                35                  40                  45
Glu Ser Gly Ser Glu Asp Ile Asp Ile Leu Pro Ser Gly Leu Ala Phe
 50                  55                  60
Ile Ser Ser Gly Leu Lys Tyr Pro Gly Met Pro Asn Phe Ala Pro Asp
 65                  70                  75                  80
Glu Pro Gly Lys Ile Phe Leu Met Asp Leu Asn Glu Gln Asn Pro Arg
                 85                  90                  95
Ala Gln Ala Leu Glu Ile Ser Gly Gly Phe Asp Lys Glu Leu Phe Asn
                100                 105                 110
Pro His Gly Ile Ser Ile Phe Ile Asp Lys Asp Asn Thr Val Tyr Leu
            115                 120                 125
Tyr Val Val Asn His Pro His Met Lys Ser Thr Val Glu Ile Phe Lys
130                 135                 140
Phe Glu Glu Gln Gln Arg Ser Leu Val Tyr Leu Lys Thr Ile Lys His
145                 150                 155                 160
Glu Leu Leu Lys Ser Val Asn Asp Ile Val Val Leu Gly Pro Glu Gln
                165                 170                 175
Phe Tyr Ala Thr Arg Asp His Tyr Phe Thr Asn Ser Leu Leu Ser Phe
                180                 185                 190
Phe Glu Met Ile Leu Asp Leu Arg Trp Thr Tyr Val Leu Phe Tyr Ser
            195                 200                 205
Pro Arg Glu Val Lys Val Val Ala Lys Gly Phe Cys Ser Ala Asn Gly
            210                 215                 220
Ile Thr Val Ser Ala Asp Gln Lys Tyr Val Tyr Val Ala Asp Val Ala
225                 230                 235                 240
Ala Lys Asn Ile His Ile Met Glu Lys His Asp Asn Trp Asp Leu Thr
                245                 250                 255
Gln Leu Lys Val Ile Gln Leu Gly Thr Leu Val Asp Asn Leu Thr Val
            260                 265                 270
Asp Pro Ala Thr Gly Asp Ile Leu Ala Gly Cys His Pro Asn Pro Met
            275                 280                 285
Lys Leu Leu Asn Tyr Asn Pro Glu Asp Pro Pro Gly Ser Glu Val Leu
290                 295                 300
Arg Ile Gln Asn Val Leu Ser Glu Lys Pro Arg Val Ser Thr Val Tyr
305                 310                 315                 320
Ala Asn Asn Gly Ser Val Leu Gln Gly Thr Ser Val Ala Ser Val Tyr
                325                 330                 335
His Gly Lys Ile Leu Ile Gly Thr Val Phe His Lys Thr Leu Tyr Cys
            340                 345                 350
Glu Leu

<210> SEQ ID NO 89
<211> LENGTH: 367
<212> TYPE: PRT
<213> ORGANISM: Caenorhabditis elegans

<400> SEQUENCE: 89

Met Leu Val Lys Val Val Leu Phe Gly Leu Leu Gly Val Ser Ile His
 1               5                  10                  15
Phe Ile Phe Asn Thr Leu Leu Thr Leu Asp Ile Asn Lys Arg Val Tyr
                20                  25                  30
Asn His Arg Pro Gly Glu Cys Arg Lys Ile Glu Gly Pro Val His Gly
            35                  40                  45
Ser Glu Asp Ile Glu Val Ile Asp Lys Leu Gln Ile Ala Phe Ile Ser
```

```
                50                  55                   60
Ser Gly Leu Val Tyr Leu Pro Asn Ser Ala Ser Asp Val Lys Trp Lys
65                  70                  75                  80

Gly Gln Ile Phe Leu Tyr Asp Leu Thr Lys Arg Ser Tyr Lys Ala Glu
                85                  90                  95

Pro Ile Pro Val Leu Asn Leu Glu Asp Val Asp Gly Phe His Pro His
                100                 105                 110

Gly Leu Ser His Trp Ile Leu Asn Asn Arg Thr Val Arg Leu Phe Val
                115                 120                 125

Val Val His Ser Lys Thr Phe Lys His Ser Ile Val Ile Leu Asp Tyr
                130                 135                 140

Asn Ser Ala Lys Arg Glu Leu Asn His Val Lys Thr Ile Arg Gly Glu
145                 150                 155                 160

Lys Phe Val Arg Pro Asn Asp Ile Val Ala Thr Gly Glu Asn Ser Phe
                165                 170                 175

Leu Val Ser Asn Asp Gly Gly Ala Gln Thr Ala Leu Gly Asn Val Trp
                180                 185                 190

Glu Ile Leu Ser Gly Phe Tyr Lys Gly Gly Leu Val Tyr Tyr Asn Gly
                195                 200                 205

Lys Lys Ser Gln Phe Leu Met Glu Asn Asn Ile Ala Asn Gly Ile Ile
                210                 215                 220

Leu Ser Arg Asp Gln Lys Thr Leu Phe Val Ser His Ile Asn Gln Glu
225                 230                 235                 240

Thr Ile Gly Val Tyr Thr Trp Asn Gln Lys Asp Gly Glu Ile Gln Lys
                245                 250                 255

Ile Ser Glu Ile Glu Thr Leu Thr Gly Cys Asp Asn Phe Tyr Val Asp
                260                 265                 270

Thr Gln Asp His Leu Trp Ala Gly Cys His Pro Val Val Lys Asp Ala
                275                 280                 285

Ala Gly His Leu Gly Asn Val Ser Asp Ser Thr Leu Tyr Gly Pro Ser
                290                 295                 300

Gln Val Leu Arg Val Ser Phe Ser Lys Asp Leu Lys Thr Ala Glu Ile
305                 310                 315                 320

Val Glu Val Leu Ala Asp Asp Gly Arg Phe Val Ser Ala Ser Thr Ile
                325                 330                 335

Ala Ile Pro Phe Asp Asp Gly Lys Gln Met Ile Val Gly Thr Val Ala
                340                 345                 350

Arg Pro Ala Ile His Cys Asp Ile Asn Val Ser Leu Asn Leu Tyr
                355                 360                 365
```

PON POLYPEPTIDES POLYNUCLEOTIDES ENCODING SAME AND COMPOSITIONS AND METHODS UTILIZING SAME

RELATED PATENT APPLICATION

This application is a National Phase Application of PCT/IL2004/000216 having International Filing Date of 4 Mar. 2004, which claims the benefit of U.S. Provisional Patent Application No. 60/451,267 filed 4 Mar. 2003 and the benefit of U.S. Provisional Patent Application No. 60/512,925 filed 22 Oct. 2003. The contents of the above Application are all incorporated herein by reference.

STATEMENT REGARDING FEDERALLY SPONSORED RESEARCH OR DEVELOPMENT

This invention was made in part by government support under Contract No. DAMD17-02-1-0675 warded by the Army/MRMC. The United States government has certain rights in the invention.

FIELD AND BACKGROUND OF THE INVENTION

The present invention relates to novel PON polypeptides and polynucleotides encoding same and to compositions and methods utilizing same. More particularly, the present invention relates to compositions including mutated PON polynucleotides or polypeptides and to methods of utilizing same for detoxification and decontamination, and for treating PON-associated diseases such as atherosclerosis.

Serum paraoxonases (PON1s) are calcium dependent phosphotriesterases which are essential to the detoxification process of organophosphates (OPs) such as the insecticide paraoxon and the nerve agents sarin and soman (Davies et al., 1996). Approximately 16% of the population is deficient in this enzyme and at high risk for damage from exposure to these and other OP agents, which are effected by the enzyme. PON1s also catalyze the hydrolysis of a broad range of carboxy-esters including lactones and thiolactones (Billecke et al., 2000; Jakubowski, 2000). PON1 resides within the cholesterol-carrying particles HDL ("good cholesterol") and exhibits a multitude of activities related to the metabolism of drugs, lipids and other molecules associated with atherosclerotic vascular and cardiac diseases (Ahmed et al., 2001; Billecke et al., 2000; Rodrigo et al., 2001). The levels of PON1 in the blood and its catalytic proficiency appear to have a major impact on susceptibility to athreosclerosis, cardiac and vascular diseases, cholesterol reducing drugs and various toxins and pollutants including insecticides (Smolen et al., 1991). It was also shown that mice lacking the PON1 gene are susceptible to atherosclerosis and organophosphate toxicity much more than PON1-carrying mice (Shih et al., 1998).

Despite its physiological and therapeutic importance, the structure and mechanism of action of PON1 have yet to be elucidated. PON1 appears to exhibit a curiously broad range of hydrolytic activities—catalyzing both phosphotriesters and carboxy-esters, as well as thiolactones (Billeclke et al., 2000). In addition, PON1 has been implicated in the reduction of lipid peroxides suggesting that it may also function as a peroxireductase (Aviram et al., 1998). Whether the latter is related to PON1's hydrolytic activities or not, is yet to be determined.

Almost all the research on PON1 has been performed on protein samples purified from sera. However, the yields of sera-purified PON1 are low, and the intimate association of PON1 with HDL can result in contamination by other HDL-associated enzymes including PON3 (Ahmed et al., 2001). The newly-reported activities of PON1 are orders of magnitude lower than with its well-characterized substrates—For example, hydrolysis of homocysteine thiolactone by such purified enzymes is 2,800-25000 times lower than with phenylacetate depending on the enzyme preparation (Billeclke et al., 2000; Jakubowski, 2000). Such low activities may result from miniscule amounts of a contaminating enzyme, such as PON3 [i.e., a variant of PON1 which is also found in HDL; (Ahmed et al., 2001)], or other serum enzymes. The difficulties in characterizing PON1 are highlighted by the recent discussion regarding its hydrolytic activity with PAF [i.e., platelet activating factor; (Rodrigo et al., 2001)]. Whilst one set of experiments suggests that PAF hydrolysis is mediated by PON1 and is not due to contamination of the purified PON1 with PAFAH (PAF acetyl hydrolase), a more recent publication argues that this activity is due to very low PAFAH contaminations (Marathe et al., 2002).

Amongst the issues yet to be clarified is the role of PON1 glycosylation in the enzyme's activity. Josse et al mutated two putative N-linked glycosylation sites (N252 and N323) of hPON1 expressed in human embryonic kidney cell line with no effect on its esterolytic activity (Josse et al., 1999). In contrast, enzymatic deglycosilation of hPON1 expressed in baculovirus abolished the enzyme's arylesterase activity, suggesting that glycosylation is essential to the enzyme's activity, and that sites other than N252 and N323 may be involved (Brushia et al., 2001). It was also shown that PON1 could not be functionally expressed in E. coli, presumably due to the absence of glycosylation in prokaryotes and the aggregation of the over-expressed protein into inclusion bodies (Brushia et al., 2001; Josse et al., 2002). PON1s also posses a disulphide bond, the formation of which may be hindered by the reducing environment present in E. coli's cytoplasm. Indeed, attempts to express hPON1 in E. coli under a broad range of conditions failed to yield soluble and active protein.

The availability of bacterially over-expressed PON1 that is soluble and catalytically active is of prime clinical value. Furthermore, the expression and purification of PON1 from E. coli can shed light on the different activities attributed to the enzyme, making it possible to explore its less pronounced activities while unambiguously ruling out contamination by other mammalian enzymes. The mechanism of PON1 activity could be investigated using biophysical methods which require high amounts of purified protein. Finally, functional expression in E. coli is the key for future attempts to engineer or directly evolve PON1 to have improved catalytic efficiencies towards therapeutic targets such as highly toxic nerve agents, or cardiac and vascular diseases related substrates such as lipid peroxides and homocysteine thiolactone.

Low solubility of proteins expressed in host systems is a major obstacle in the structural and functional characterization of numerous proteins (Waldo, 2003). Several methods have been developed to screen for mutant proteins with increased solubility. One approach using GFP fusion protein as a folding reporter is based on the correlation between folding of the target protein and the fluorescence of the E. coli cells expressing the GFP fusion (Waldo et al., 1999; Yang et al., 2003). Another approach is based on fusion of chloramphenicol acyltransferase (CAT) to the target protein allowing soluble mutants to be selected by growths at high levels on chloramphenicol (Maxwell et al., 1999). The main drawback of these approaches is, that selection pressure for solubility can only generate soluble mutant proteins with significant structural alterations and no function. In contrast, a direct screening for function ensures that soluble protein variants retain function [for the evolution of a soluble galactose oxidase in *E. coli* by a functional screen see Sun et al. (2001)].

While reducing the present invention to practice, the present inventors employed a directed evolution approach in order to engineer highly expressed recombinant variants of PON exhibiting activity spectra comparable to that of respective wild-type PONs purified from sera. Using the same approach, the present inventors also generated PON variants with specialized catalytic activities.

As is further described in the Examples section which follows, the availability of recombinant PON variants exhibiting kinetic parameters similar to those reported for PONs purified from sera enabled elucidation of the three dimensional (3D) structure of PON1, shedding light on its unique active site and catalytic mechanism. These findings allow, for the first time, to generate and use PON enzymes with improved catalytic efficiencies towards therapeutic targets such as highly toxic nerve agents, or cardiac and vascular diseases related substrates such as lipid peroxides and homocysteine thiolactone.

SUMMARY OF THE INVENTION

According to one aspect of the present invention there is provided an isolated polynucleotide comprising a nucleic acid sequence encoding a mutated PON1 enzyme, the mutated PON1 enzyme being characterized by: (i) a substrate specificity which is substantially identical to that of a respective wild-type PON; and (ii) no substantial formation of aggregates when expressed in bacteria.

According to another aspect of the present invention there is provided an isolated polypeptide comprising an amino acid sequence of a mutated PON1 enzyme, the mutated PON1 enzyme being characterized by: (i) a substrate specificity which is substantially identical to that of a respective wild-type PON; and (ii) no substantial formation of aggregates when expressed in bacteria.

According to yet another aspect of the present invention there is provided an isolated polynucleotide comprising a nucleic acid sequence encoding a mutated PON1 enzyme, wherein an amino acid sequence of a hydrophobic region of the mutated PON1 enzyme includes at least one amino acid substitution with respect to an amino acid sequence of a respective hydrophobic region of a human PON1, the mutated PON1 enzyme being characterized by: (i) a substrate specificity which is substantially identical to that of a respective wild-type PON; and (ii) no substantial formation of aggregates when expressed in bacteria.

According to still another aspect of the present invention there is provided an isolated polypeptide comprising an amino acid sequence of a mutated PON1 enzyme, wherein an amino acid sequence of a hydrophobic region of the mutated PON1 enzyme includes at least one amino acid substitution with respect to an amino acid sequence of a respective hydrophobic region of a human PON1, the mutated PON1 enzyme being characterized by: (i) a substrate specificity which is substantially identical to that of a respective wild-type PON; and (ii) no substantial formation of aggregates when expressed in bacteria.

According to still further features in the described preferred embodiments the bacteria is *E. coli*.

According to still further features in the described preferred embodiments the *E. coli* is selected from the group of strains consisting of BL21, BL21 (DE3), Origami B (DE3) and RIL (DE3).

According to still further features in the described preferred embodiments the isolated polypeptide further comprising a tag, the tag being fused in-frame to the mutated PON1 enzyme.

According to still further features in the described preferred embodiments the tag is selected from the group consisting of thioredoxin, NUS, GST and MBP.

According to still further features in the described preferred embodiments the isolated polypeptide is as set forth in SEQ ID NO: 57, 58, 59, 60, 61 or 56.

According to still further features in the described preferred embodiments the amino acid sequence of the mutated PON1 enzyme is of an origin selected from the group consisting of a mouse, a human, a rat, a rabbit and a combination thereof.

According to still further features in the described preferred embodiments the mutated PON1 enzyme further includes a lysine at a position equivalent to amino acid coordinate 192 of rabbit PON1.

According to still further features in the described preferred embodiments the hydrophobic region of the human PON1 is set forth by amino acid coordinates 126-142 of SEQ ID NO: 36 and/or amino acid coordinates 301-343 of SEQ ID NO: 36.

According to still further features in the described preferred embodiments the at least one amino acid substitution is of amino acid I126, M130, K137, L142, A301, A320 M341 or V343 of the human PON1.

According to still further features in the described preferred embodiments the mutated PON1 enzyme is as set forth in SEQ ID NO: 57, 58, 59, 60, 61 or 56.

According to an additional aspect of the present invention there is provided an isolated polypeptide as set forth in SEQ ID NO: 49, 50, 51, 52, 53, 54, 56, 57, 58, 59, 60, 61, 63, 65, 67, 69, 71, 73, 75 or 77.

According to yet an additional aspect of the present invention there is provided an isolated polynucleotide as set forth in SEQ ID NO: 25, 26, 27 28 29, 43, 44, 45, 46, 47, 48, 55, 62, 64, 66, 68, 70, 72, 74 or 76.

According to still an additional aspect of the present invention there is provided an isolated polypeptide comprising an amino acid sequence as set forth in SEQ ID NO: 49, 50, 51, 52, 53, 54, 56, 57, 58, 59, 60, 61, 63, 65, 67, 69, 71, 73, 75 or 77.

According to a further aspect of the present invention there is provided an isolated polynucleotide comprising a nucleic acid sequence as set forth in SEQ ID NO: 25, 26, 27, 28, 29, 43, 44, 45, 46, 47, 48, 55, 62, 64, 66, 68, 70, 72, 74 or 76.

According to yet a further aspect of the present invention there is provided an isolated polynucleotide comprising a nucleic acid sequence encoding a mutated PON enzyme exhibiting an increased substrate specificity to at least one known PON substrate as compared to a respective wild-type PON.

According to still further features in the described preferred embodiments the at least one known PON substrate is selected from the group consisting of an ester, a phosphotriesters, such as paraoxon, sarin and soman; a lactone, such as, dihydrocuomarin and γ-butyrolactone; thiolactones, such as, γ-butyrothiolactone and homocysteine thiolactone.

According to still further features in the described preferred embodiments the ester is selected from the group consisting of naphtyl, benzyl acetate and lipids.

According to still further features in the described preferred embodiments the phosphotriester is selected from the group consisting of paraoxon, sarin and soman, According to still further features in the described preferred embodiments the lactone is selected from the group consisting of dihydrocuomarin and γ-butyrolactone.

According to still further features in the described preferred embodiments the thiolactone is selected from the group consisting of γ-butyrothiolactone and homocysteine thiolactone.

According to still a further aspect of the present invention there is provided an isolated polypeptide comprising an amino acid sequence of a mutated PON enzyme exhibiting an increased substrate specificity to at least one known PON substrate as compared to a respective wild-type PON.

According to still further features in the described preferred embodiments the at least one known PON substrate is selected from the group consisting of esters, phosphotriesters, lactones and thiolactones.

According to still further features in the described preferred embodiments the mutated PON enzyme includes at least one amino acid substitution which is equivalent to an amino acid coordinate located in an active site of human PON1.

According to still further features in the described preferred embodiments the active site of human PON1 is distant by no more than 15 Å from a Calcium ion of the active site.

According to still further features in the described preferred embodiments the Calcium ion is Ca401.

According to still further features in the described preferred embodiments the increased substrate specificity is at least 3 fold higher $K_{cat}/K_M$ ratio for phosphotriester hysrolysis.

According to still further features in the described preferred embodiments the increased substrate specificity is at least 3 fold higher $K_{cat}/K_M$ ratio for ester hydrolysis.

According to still further features in the described preferred embodiments the increased substrate specificity is at least 3 fold higher $K_{cat}/K_M$ ratio for lactone hysrolysis.

According to still further features in the described preferred embodiments the increased substrate specificity is at least 3 fold higher $K_{cat}/K_M$ ratio for thiolactone hydrolysis.

According to still further features in the described preferred embodiments the increased substrate specificity is at least 3 fold higher $K_{cat}/K_M$ ratio for lipid hydrolysis.

According to still further features in the described preferred embodiments the increased substrate specificity is at least 3 fold higher $K_{cat}/K_M$ ratio for lipid peroxide hydrolysis.

According to still a further aspect of the present invention there is provided an isolated polynucleotide comprising a nucleic acid sequence encoding a mutated PON enzyme exhibiting a modified substrate range as compared to a corresponding wild-type PON.

According to still further features in the described preferred embodiments the PON enzyme is selected from the group consisting of PON1, PON2 and PON3.

According to still further features in the described preferred embodiments the narrower susbstrate range is manifested in an increased phosphotriesterase activity and a decreased esterase activity.

According to still further features in the described preferred embodiments the narrower susbstrate range is manifested in an increased thiolactonase activity and a decreased phosphotriesterase activity.

According to still further features in the described preferred embodiments the PON1 enzyme includes amino acid substitutions equivalent to amino acid coordinates selected from the group consisting of 69, 74, 75, 76, 78, 190, 192, 193, 196, 222, 240, 291, 292, 293, 332, and 346 of human PON1.

According to still further features in the described preferred embodiments the PON1 enzyme includes amino acid substitutions equivalent to amino acid coordinates S193, N287, G19 and V346 of human PON1.

According to still further features in the described preferred embodiments the PON1 enzyme includes amino acid substitutions equivalent to amino acid coordinates L69 and E218 of human PON1.

According to still a further aspect of the present invention there is provided a nucleic acid construct comprising an isolated polynucleotide of the present invention.

According to still further features in the described preferred embodiments a host cell comprising the nucleic acid construct of the present invention.

According to still a further aspect of the present invention there is provided a method of identifying proteins amenable to an in-vitro evolution process, the method comprising identifying proteins which exhibit at least two distinct catalytic activities and/or structural plasticity, the proteins being amenable to the in-vitro evolution process.

According to still further features in the described preferred embodiments the method further comprising subjecting the proteins to the in-vitro evolution process, to thereby test amenability of the proteins to the in-vitro evolution process.

According to still a further aspect of the present invention there is provided a method of generating proteins with desired traits, the method comprising: (a) identifying proteins exhibiting at least two distinct catalytic activities and/or structural plasticity, the proteins being amenable to the in-vitro evolution process; and (b) subjecting the proteins to the in-vitro evolution process thereby generating proteins with desired traits.

According to still further features in the described preferred embodiments the proteins are selected from the group consisting of *E. coli* thioesterase/protease I and human carboxylesterase 1.

According to still further features in the described preferred embodiments identifying the proteins having the at least two distinct catalytic activities is effected by: (a) database annotations; (b) screening for the catalytic activities; and (c) screening for substrate binding.

According to still further features in the described preferred embodiments the identifying the proteins having the structural plasticity is effected by: (a) a biophysical method; and (b) database annotations.

According to still further features in the described preferred embodiments the biophysical method is selected from the group consisting of NMR, X-ray crystallography and circular-dischroism.

According to still a further aspect of the present invention there is provided a composition-of-matter comprising a crystalline form of PON1 at a resolution higher than or equal to 2.2 Å.

According to still a further aspect of the present invention there is provided a method of identifying a putative small molecule inhibitor of PON1, the method comprising: (a) constructing a model using a set of atomic structural coordinates defining a three-dimensional atomic structure of a crystallized PON1; and (b) computationally screening a plurality of compounds for a compound capable of specifically binding an active site of the model, thereby identifying the small molecule inhibitor of PON1.

According to still a further aspect of the present invention there is provided a computing platform for generating a three-dimensional model of PON1, the computing platform comprising: (a) a data-storage device storing the set of atomic structural coordinates listed in FIG. 26; and (b) a processing unit being for generating the three-dimensional model from the data stored in the data-storage device.

According to still a further aspect of the present invention there is provided a method of treating or preventing a PON1-related disease or condition in a subject, the method is effected by administering to the subject a therapeutically effective amount of a mutated PON1 enzyme which: (i) has substrate specificity which is substantially identical to that of human PON1; and (ii) does not substantially form aggregates when expressed in bacteria.

According to still further features in the described preferred embodiments the PON1-related disease or condition is selected from the group consisting of hyperlipidemia, atherosclerosis, neurological disease, cancer and organophosphate poisoning.

According to still further features in the described preferred embodiments the neurological disease is selected from the group consisting of Alzheimer's disease, neurofibromatosis, Huntington's disease, depression, amyotrophic lateral sclerosis, multiple sclerosis, stroke, Parkinson's disease, or multi-infarct dementia.

According to still a further aspect of the present invention there is provided a method of treating or preventing a PON-related disease or condition in a subject, the method is effected by administering to the subject a therapeutically effective amount of a mutated PON enzyme exhibiting an increased substrate specificity to at least one known PON substrate as compared to a respective wild-type PON.

According to still a further aspect of the present invention there is provided a method of treating or preventing a PON-related disease or condition in a subject, the method is effected by administering to the subject a therapeutically effective amount of a mutated PON enzyme exhibiting a modified substrate range as compared to a corresponding wild-type PON.

According to still a further aspect of the present invention there is provided a pharmaceutical composition comprising a therapeutically effective amount of the isolated polypeptide of the present invention.

According to still a further aspect of the present invention there is provided a pharmaceutical composition comprising a therapeutically effective amount of the isolated polynucleotide of the present invention.

According to still a further aspect of the present invention there is provided the compound 7-O-Diethylphosphoryl-(3-cyano-7-hydroxycuomarin).

The present invention successfully addresses the shortcomings of the presently known configurations by providing novel PON polypeptides and polynucleotides encoding same and compositions and methods utilizing same.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings:

FIG. 11a shows selected clones from directed evolution of PON1 pairwise aligned to the HuPON1, RabPON1, MoPON1 and Rat PON1 genes [First generation clones 1-3 are G1C4, G1A5 and G1A9 (SEQ ID NOs: 26, 25 and 78 respectively) respectively; second-generation clones 3-5 are G2D6, G2E6 and G2D4 (SEQ ID NOs: 27, 28 and 79 respectively); third-generation clones 7-9 are G3C9, G3H8 and G3H10 (SEQ ID NOs: 55, 61 and 80 respectively). FIG. 11b shows selected clones from directed evolution of PON3 pairwise aligned to the HuPON3, RabPON3 and MoPON1 genes [First generation clones 1-4 are G1A7, G1B11, G1E10 and G1G7 (SEQ ID NOs: 43, 44, 81 and 82 respectively); second-generation clones 5-8 are G2E11, G2A7, G2C2 and G2F8 (SEQ ID NOs: 83, 84, 45 and 85 respectively third-generation clones 9-12 are G3C6, G3G5, G3H9 and G3A5, (SEQ ID NOs: 86, 87, 48 and 46 respectively).

FIGS. 12a-b are Michealis-Menten plots depicting hydrolysis of DEPCyC (FIG. 12a) and phenylacetate (FIG. 12b) by rPON1 variant G3C9 and its variant G3C9.49 that displays greatly enhanced OP-hydrolyzing activity. Enzyme concentratios are $7.5 \cdot 10^{-8}$ M and $5.6 \cdot 10^{-9}$ M in FIG. 12a and $3.4 \cdot 10^{-7}$ M in FIG. 12b for G3C9 and G3C9.49, respectively. The kinetic parameters derived from the fits are listed in Table 9, below.

FIG. 15a is a view of the 6-bladed β-propeller from the top. The top of the propeller is, by convention, the face carrying the loops connecting the outer β-strand of each blade (strand D) with the inner strand (A) of the next blade [E. I. Scharff, J. Koepke, G. Fritzsch, C. Lucke, H. Ruterjans, Structure 9, 493 (2001)]. Shown are the N- and C-termini, and the two calcium atoms in the central tunnel of the propeller. FIG. 15b is a side view of the propeller. Shown are the three helices at the top of the propeller (H1-H3) and the calcium atoms (Ca-1, in green, Ca-2 in red). Figures were generated using PyMol (http://pymol.sourceforge.net/).

FIGS. 18a-b are schematic illustrations showing PON1's active site viewed from the top of the propeller. FIG. 18a shows the central tunnel of the propeller with the two calcium atoms, and the side-chains of the residues found to be mutated in the newly-evolved PON1 variants for esterase and lactonase (in orange) or for phosphotriesterase activity (in yellow), including position 192 of the Q/R human polymorphism. FIG. 18b is a surface view of the active site. Lys70, Tyr71 and Phe347 are shown as sticks to permit a better view of the active site. At the deepest point of the cavity lies the upper calcium atom (Ca-1, in green) to which a phosphate ion (PO4) is bound.

FIG. 20a is a schematic illustration of PON1's catalytic site: the upper calcium atom (Ca-1), the phosphate ion found at the bottom of the active site, and the postulated His-dyad. FIG. 20b is a schematic representation of the proposed mechanism of action of PON1 on ester substrates such as phenyl and 2-naphthylacetate. The first step involves deprotonation of a water molecule by the His-dyad to generate an hydroxide anion which attacks the ester carbonyl, producing an oxyanionic, tetrahedral intermediate. This intermediate breaks down (second step) to an acetate ion and either phenol or 2-naphthol.

Figures 23A, 23B:
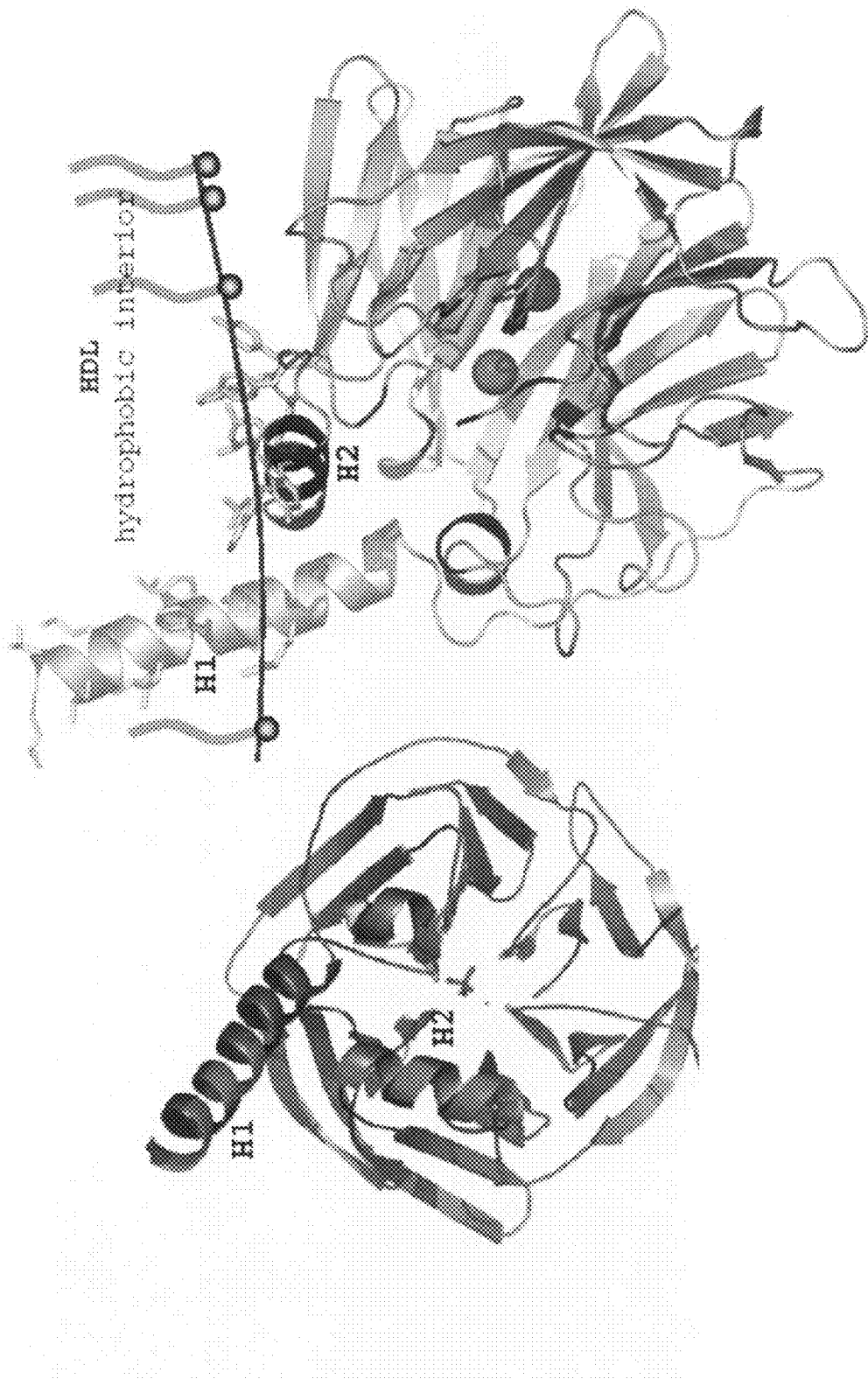

FIGS. 23a-b show a model of anchoring of PON1 to the surface of HDL. FIG. 23a is a tertiary structure cartoon of rPON1 showing its exposed hydrophobic surfaces. N-terminal residues 7-18 missing in the crystal structure and predicted to be helical were modeled as part of H1. Indicated in green are all the hydrophobic residues (L,F,P,I,Y,W,V) appearing with accessible surface area greater than 20 $Å^2$ as calculated by the program AREAIMOL in the CCP4 package [B. Lee, F. M. Richards, J Mol Biol 55, 379 (1971)]. FIG. 23b shows the hydrophobic residues proposed to be involved in HDL-anchoring with their side-chains in yellow. The line— defined by the side chains of Tyr185, Phe 186, Tyr190, Trp194, Trp202 (helix H2 and the adjacent loops) and Lys21 (helix H1)—models the putative interface between HDL's hydrophobic interior and the exterior aqueous phase. The hydrophobic side chains of Leu and Phe residues of H1 are found primarily within the apolar region [J. A. Killian, G. von Heijne, Trends Biochem Sci 25, 429 (2000)]. The active site and the selectivity-determining residues (Table 13, below) are marked in blue, and the proposed glycosylation sites (Asn253 and Asn324) in red.

Figure 24:
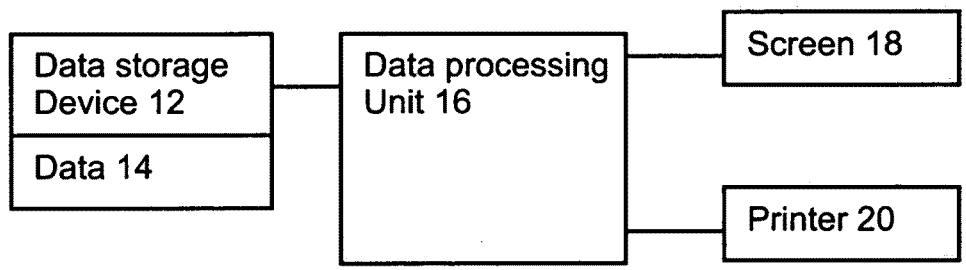

FIG. 24 is a box diagram showing a computing platform 10 which can be used for practicing the present invention and which comprises computer readable medium, e.g., a data storage device 12, storing therein data 14 which is retrievable and processable by data processing unit 16 and the data or processed data can be displayed via a display such as a display screen 18 and/or a printer 20.

Figure 25:
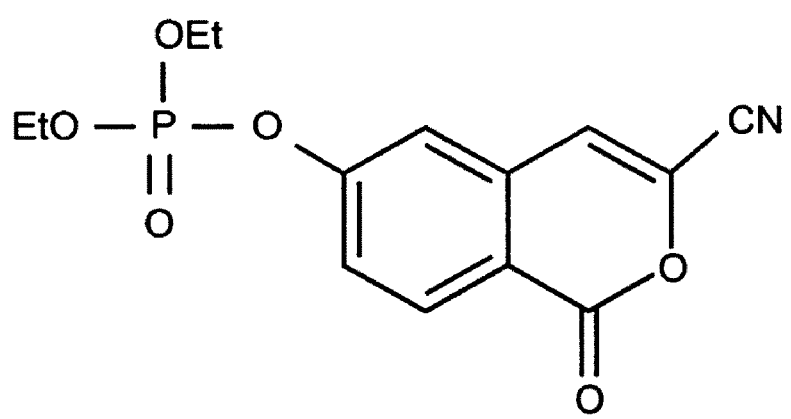

FIG. 25 is a schematic illustration depicting the structure of DEPCyC.

FIG. 26 present the coordinates of the three-dimensional model of PON1 variant G2E6 (SEQ ID NO: 60).

DESCRIPTION OF THE PREFERRED EMBODIMENTS

The present invention is of PON polypeptides, polynucleotides encoding same and compositions and methods utilizing same. Specifically, the present invention can be used for decontamination and detoxification of toxic agents and for treatment of PON-associated diseases and conditions, such as atherosclerosis.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Directed evolution is a powerful tool that enables generation of new protein variants.

Rather than rely upon natural variation, directed evolution generates new variation in one of two ways. The first is by inducing mutations in the gene of interest, either by using mutator strains, or by error-prone PCR (in which the fidelity of Taq polymerase is decreased rather than optimised). The second involves shuffling different regions of members of the same gene family to produce genes in which the inherent variation of the family is recombined to give novel gene products.

Once a population has been produced, screening and selection can isolate those members which most closely match the desired attributes. The whole process can then be repeated using these members as the starting point for the generation of new variation. [Tao (2002) Curr. Opin. Chem. Biol. 6(6):858-64].

Unlike natural evolution, directed evolution has a specific goal, to produce variants which exhibit enhanced functions, lack of unwanted functions or new functions altogether.

One severe drawback of directed evolution is the inability at present to select targets which are more "responsive" to directed evolution.

To date, there is no approach which enables to predict the evolutionary response of a starting point protein and thus in many cases, it is difficult if not impossible to predict the outcome of a directed evolution study.

While reducing the present invention to practice the present inventors designed an approach for the identification of genes that are highly amenable to directed evolution processes. As is further illustrated hereinbelow, the present inventors showed that structural promiscuity and structural plasticity can be used as probes for the evolvability of proteins. Using this approach, the present inventors uncovered one such starting point, the enzyme family of serum paraoxonases, which meets these criteria and serves as starting point for the directed evolution of a variety of hydrolases with pre-determined specificities.

Thus, according to one aspect of the present invention there is provided a method of identifying proteins amenable to an in-vitro evolution process.

As used herein the phrase "in vitro evolution process" (also referred to as "a directed evolution process") refers to the manipulation of genes and selection or screening of a desired activity. A number of methods, which can be utilized to effect in vitro evolution, are known in the art. One approach of executing the in-vitro evolution process is provided in Example 2 of the Examples section.

A protein which is amenable to an in vitro evolution process is a protein, which would exhibit the desired trait selected for (e.g., catalytic activity, thermostability), at early generations of the directed evolution process; preferably, following one cycle of evolution (one generation).

The method, according to this aspect of the present invention is effected by identifying proteins which exhibit at least two distinct catalytic activities and/or structural plasticity. As is described in detail hereinbelow, the present inventors have uncovered that proteins exhibiting such traits are highly amenable to the in-vitro evolution process.

As used herein the phrase "at least two distinct catalytic activities" refers to the ability of a protein to catalyze the turn over of at least two substrates, which differ in the chemical group reacting with the active site of the enzyme, or in groups adjacent thereto (e.g., steric effect). For example, the ability of an enzyme to hydrolyze carboxy esters and phosphotriesters, or, the ability of an enzyme to hydrolyze esters of different carboxylic acids, or esters having different alkoxy or phenoxy leaving groups.

A number of biochemical methods are known in the art which can be efficiently used to screen for enzyme catalysis. These methods employ fluoregenic and chromogenic substrates for detecting hydrolytic activity such as, for example, esterase, lipase, amidase, epoxi hydrolase and phosphatase activities. More recently product sensitive sensors have been used for screening catalysis. Examples of such sensors include monoclonal anti product antibodies and metal chelators [see Lorenz (2002) Curr. Opin. Biotechnol. 13:572-7; Wahler (2001) Curr. Opin. Biotechnol. 12:535-44].

Alternatively, high throughput screening methods can be used to identify substrate binding and thus be used to identify enzymes which exhibit at least two distinct catalytic activities.

Information regarding the catalytic activity of a protein (i.e., annotative information) can also be retrieved from publicly available or proprietary databases. Examples of such databases include, but are not limited to, the Gene Ontology Consortium (geneontology.org/GO.annotation.html), the GeneCards database of the Weizmann institute of Science (rzpd.de/cards/index.html), GenBank (ncbi.nlm.nih.gov/GenBank/), Swiss-Prot (expasy.ch/sprot/sprot-top.html), GDB (gdb.org/), PIR (www.mips.biochem.mpg.de/proj/prostseqdb/), YDB (mips.biochem.mpg.de/proj/yeast/), MIPS (mips.biochem.mpg.de/proj/human), HGI (tigr.org/tdb/hgi/), Celera Assembled Human Genome (celera.com/products/human_ann.cfm and LifeSeq Gold (lifeseqgold.incyte.com) and specialized annotated databases of metabolic pathways (genome.ad.jp/kegg/metabolism.html).

As used herein the phrase "structural plasticity" refers to proteins which have at least two distinct structural isomers (e.g., independent of ligand binding). Examples of proteins which exhibit structural plasticity include, but are not limited to, the prion protein PrPc which interconverts between an all α-helix or all β-sheet conformation [Derreumaux (2001) Biophys J. 81:1657-65].

A number of biophysical methods for determining the structural plasticity of proteins are well known in the art [Bhattacharjya, Xu (2001) Protein Science 10(5): 934-942; Eliezer, Kutluay (2001) Journal of Molecular Biology 307 (4): 1061-1073; Hitchens, Mannervik (2001) Biochemistry 40(39): 11660-11669; and Spoerner, Hermann (2001) Proc Natl Acad Sci USA 98(9): 4944-9]. Examples of such methods include, but are not limited to, NMR, X-ray crystallography and circular-dischroism. For example, NMR analysis has shown that a considerable number of distinct conformers can prevail in a single protein ($\leqq$60) and the structures of some of these conformers can vary dramatically [Choy and Forman-Kay (2001) Journal of Molecular Biology 308(5): 1011-1032]. Single molecule techniques offer unique opportunities to monitor the activity and conformation of protein molecules. Such measurements have already shown that protein molecules exist in various states or conformations that exhibit different levels of activity [Xue and Yeung (1995) Nature 373(6516): 681-3; Dyck and Craig (2002) Luminescence 17: 15-18].

Other tools which provide dynamic structural information include spectroscopic techniques such as fluorescence studies [e.g., FRET, ChaKraborty, Ittah (2001) Biochemistry 40:7228-7238] and scattering techniques such as quasi-elastic and dynamic light scattering, and X-ray and neutron small-angle scattering (for further information see Protein crystallography, DOE Genomes to Life, US doegenomestolife.org/technology/crystallography.html).

Structural data can also be retrieved from protein structure databases. Examples of such databases include, but are not limited to, the Protein Data Bank (PDB at the Brookhaven National Laboratory) and the Database of Molecular Movement, (molmovdb.mbb.yale.edu/molmovdb/). It will be appreciated that in such a case (i.e., retrieval from PDB), further computer modeling should be employed to uncover the distinct conformations of the protein (see further hereinbelow).

Alternatively, protein structural information can be bioinformatically obtained, by using, for example, structural homology algorithms. The combinatorial extension method (CE) finds structural alignments by selecting from sequences from the PDB. The software calculates structural alignments for two chains either from the PDB or uploaded by the user. Structural neighbors are then identified (cl.sdsc.edu/ce.html).

In any case, once such catalytic data and/or structural data are obtained for a given protein, the applicability of this protein to directed evolution can be qualified.

The following describes in detail parameters, which can be used by the present invention to qualify proteins for directed evolution.

Position of structural variance within the protein—Proteins having flexible active sites are considered evolvable, since such proteins would in all likelihood facilitate binding and/or catalysis of multiple ligands or substrates [Huang, Y. T., Liaw, Y. C., Gorbatyuk, V. Y. & Huang, T. H. Backbone dynamics of *Escherichia coli* thioesterase/protease I: Evidence of a flexible active-site environment for a serine protease. Journal of Molecular Biology 307, 1075-1090 (2001); and Bencharit, S., Morton, C. L., Xue, Y., Potter, P. M. & Redinbo, M. R. Structural basis of heroin and cocaine metabolism by a promiscuous human drug-processing enzyme. Nature Structural Biology 10, 349-356 (2003)].

Functional diversity and structural plasticity—Proteins which exhibit both functional diversity (i.e., more than two distinct binding or catalytic activities) and structural plasticity are considered the most amenable to directed evolution, since these properties may be interlinked [James L C, Roversi P, Tawfik D S (2003) Antibody multispecificity mediated by conformational diversity. Science 299: 1362-1367].

Functional promiscuity or diversity—Proteins which exhibit functional promiscuity, or diversity or a broad substrate range, which terms are by enlarge synonymous [James L C, Tawfik D S (2003) Conformational diversity and protein evolution—a 60-year-old hypothesis revisited. Trends Biochem Sci 28: 361-368]. Namely, proteins that exhibit more than two distinct binding or catalytic activities, are considered the most amenable to directed evolution.

Selection of evolvable proteins can be effected on the basis of a single parameter or several parameters considered individually or in combination.

Proteins, which are considered amenable to an in-vitro evolution process are tested in the laboratory (see Example 2 of the Examples section).

Using the above-described methodology the present inventors were able to identify proteins, which are amenable to an in-vitro evolution. Examples include, but are not limited to the *Escherichia coli* thioesterase/protease I [Tyukhtenko, S. I. et al. Sequential structural changes of *Escherichia coli* thioesterase/protease I in the serial formation of Michaelis and tetrahedral complexes with diethyl p-nitrophenyl phosphate. Biochemistry 42, 8289-8297 (2003); Huang, Y. T., Liaw, Y. C., Gorbatyuk, V. Y. & Huang, T. H. Backbone dynamics of *Escherichia coli* thioesterase/protease I: Evidence of a flexible active-site environment for a serine protease. Journal of Molecular Biology 307, 1075-1090 (2001)], and the human carboxylesterase 1 [hCE1, Bencharit, S., Morton, C. L., Xue, Y., Potter, P. M. & Redinbo, M. R. Structural basis of heroin and cocaine metabolism by a promiscuous human drug-processing enzyme. Nature Structural Biology 10, 349-356 (2003)].

Additionally, using the above-described methodology and existing literature, the present inventors identified the PON family (PONs) of enzymes as being highly evolvable. The PONs are catalytically diverse, as they catalyze the hydrolysis of a very broad range of substrates including, but not limited to, carboxy esters, lactones, phosphotriesters [or organophosphates (OPs)], platelet activating factor (PAF), homocysteine thiolactone (L-Hyc; a known factor for atherosclerotic vascular diseases), as well as the reduction and hydrolysis of lipid peroxides (for further details see the preceding Background section). In addition, structural analysis of PON1 identified structural plasticity in the PON family (see Example 6 of the Examples section). Thus, PONs were deemed highly suitable for directed evolution and were used herein as starting points for the evolution of bacteria expressible hydrolases.

As is illustrated in Examples 2-5 of the Examples section which follows, directed evolution studies employing PONs as a starting point yielded PONs with modified substrate range (see Tables 7-9 and 11, below), thus conclusively proving that this family of enzymes is highly amenbale to directed evolution.

Thus, according to another aspect of the present invention there is provided an isolated polynucleotide including a nucleic acid sequence, which encodes a mutated PON1 enzyme.

As used herein the phrase "an isolated polynucleotide" refers to a single or a double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The "mutated PON1 enzyme" of this aspect of the present invention refers to a protein which differs from a respective wild-type PON (i.e., the starting point PON) by at least one mutation (e.g., insertion, deletion, substitution).

The mutated PON1 enzyme of this aspect of the present invention is characterized by:

(i) a substrate specificity which is substantially identical to that of a respective wild-type PON (see preceding Background section, Examples 2-4 of the examples section which follows and U.S. Pat. No. 6,573,370); and (ii) no substantial formation of aggregates (i.e., non-recoverable aggregates) when expressed in bacteria such as E. coli [e.g., BL21, BL21 (DE3), Origami B (DE3), available from Novagen (www.calbiochem.com) and RIL (DE3) available from Stratagene, (www.stratagene.com). Essentially, at least 2%, at least 5%, at least 10%, at least 20%, at least 30%, at least 40%, at least 50%, at least 60%, at least 70%, at least 80%, at least 90%, at least 95% or more, say 100%, of bacterially expressed protein remains soluble (i.e., does not precipitate into inclusion bodies).

According to a preferred embodiment of this aspect of the present invention the nucleic acid sequence which encodes the mutated PON1 enzyme is of a mammalian origin, such as a mouse origin, a human origin, a rat origin, a rabbit origin or a combination thereof (e.g., a result of gene shuffling).

The mutated PON1 enzyme of this aspect of the present invention is characterized by at least one amino acid substitution with respect to an amino acid sequence of a respective hydrophobic region of the wild type PON1. For example, in the case of human PON1, such a substitution would be in a region encompassed by amino acid coordinates 126-142 and/or 301-343 of SEQ ID NO: 36). These amino acid substitutions may be of amino acids I126, M130, K137, L142, A301, A320 M341 or V343 of human PON1.

Additionally or alternatively, the mutated PON1 enzyme of this aspect of the present invention preferably includes a lysine at a position equivalent to amino acid coordinate 192 of rabbit PON1 (GenBank Accession No. AF220943, SEQ ID NO: 37).

As used herein, an equivalent amino acid refers to an amino acid which is homologous (i.e., corresponding in position in either primary or tertiary structure) and/or analogous to a specific residue or portion thereof in a given PON sequence.

In addition to the mutations described above, the isolated polynucleotide encoding the mutated PON1 of this aspect of the present invention may also include an additional nucleic acid sequence, which encodes a tag fused in-frame to the nucleic acid sequence which encodes the mutated PON1 enzyme of this aspect of the present invention. Such a tag may promote receptor solubility (as exemplified in Examples one of the Examples section) and/or may simplify the purification process of the recombinant proteins, as is further described hereinbelow.

According to preferred embodiments of this aspect of the present invention the isolated polynucleotide encoding the mutated PON1 of this aspect of the present invention is as set forth in SEQ ID NO: 25, 26, 27, 28, 29 or 55.

According to other preferred embodiments of this aspect of the present invention the amino acid sequence of the mutated PON1 enzyme is set forth in SEQ ID NO: 57, 58, 59, 60, 61 or 56.

As is illustrated in Example 2 of the Examples section, the above-described soluble PON1 polynucleotide was used as a starting point for the evolution of substrate specialized PON hydrolases.

Thus, according to yet another aspect of the present invention, there is provided an isolated polynucleotide including a nucleic acid sequence encoding a mutated PON enzyme which exhibits a modified substrate range as compared to a respective wild-type PON.

As used herein the phrase "PON enzyme" refers to a nucleic acid or amino acid sequence of a known PON family member (e.g., PON1, PON2 or PON3) and variants thereof. Examples of PON family members include, but are not limited to, Human PON1 (GenBank Accession Nos. NM_00046, S64696, S64615, M63012, U55877, I42585), Rabbit PON1 (GenBank Accession Nos. AF220943, S64616), Mouse PON1 (GenBank Accession Nos. NM_011134, U32684, L40488), Rat PON1 (GenBank Accession Nos. XM_342639, U94856), C. elegans PON1 (GenBank Accession No. AF003141), Dog PON2 (GenBank Accession No. L48515), Human PON2 (GenBank Accession Nos. L48513, AF001602, AR022313, NM_00035), Mouse PON2 (GenBank Accession Nos. L48514, NM_008896), Chicken PON2 (GenBank Accession Nos. L47573), Turkey PON2 (GenBank Accession No. L47572) rabbit PON3 (GenBank Accession No. AF220944), Human PON3 (GenBank Accession No. NM_000940, AC005021), Mouse PON3 (GenBank Accession No. L76193), As used herein the phrase "modified substrate range" refers to an increase or a decrease in the catalytic activity of the respective wild-type PON to at least one known natural or synthetic substrate thereof. In certain cases, a decrease in activity towards one substrate, can be accompanied by an increase in activity towards another substrate.

For example, the modified substrate range of the mutated PON enzyme can be manifested by an increased phosphotriesterase activity and a decreased esterate activity. Such a mutated PON enzyme is expected to find valuable utility in the decontamination of chemical warfare and industrial OP-based insecticides. Other examples include increased thiolactonase activity (e.g., towards Homocysteince thiolactone) or lipase-like activity (e.g., towards oxidized lipids and lipid peroxides).

Table 13 below lists a set of 16 residues which define the perimeter of the active site of the PON family of genes, and thus govern substrates selectivity. Each of these residues can be modified to obtain susbtrate specialized PON hydrolazes as described in this Table.

For example, the mutated PON enzyme of thus aspect of the present invention may include amino acid substitutions which are equivalent to amino acid coordinates S193, N287, G19 and V346 of human PON1, which results in highly expressible, highly active phosphotriesterase.

Alternatively, the mutated PON enzyme of thus aspect of the present invention may include amino acid substitutions which are equivalent to amino acid coordinates I291 and T332 of human PON1, which result in highly expressible, highly active lactonase which may be used for the hydrolysis of Homocysteine thiolactone (HcyT).

Yet alternatively, the mutated PON enzyme of this aspect of the present invention may include amino acid substitutions which are equivalent to amino acid coordinates I74, I291, F292, F293 of human PON1, which result in highly expressible, highly active esterase including hydrolysis of hydrophobic esters (see Table 11, below).

Using this structural data, the present inventors also generated a mutated PON enzyme which exhibits increased susbstrate specificity to at least one known PON susbtrate as compared to a respective (i.e., of the same origin) wild-type PON (e.g., see Example 5 of the Examples section which follows).

As used herein the phrase "increased substrate specificity" refers to an increase in the $K_{cat}/K_M$ ratio of the mutated PON enzyme for a specific substrate as compared to the respective wild-type PON. PON mutants with increased or diminished $K_{cat}/K_M$ ratios are described in the Examples section which follows.

Examples of known synthetic and naturally occurring PON substrates include but are not limited to, esters, such as phenyl, naphtyl and benzyl acetate and lipids; phosphotriesters, such as DEPCyc, paraoxon, sarin and soman; lactones, such as α-angelicolactone, dihydrocuomarin and γ-butyrolactone; thiolactones, such as, γ-butyrothiolactone and homocysteine thiolactone [Draganov, D. I. & La Du, B. N. Pharmacogenetics of paraoxonases: a brief review. Nau Schm Arch Pharmacol (2003); and references therein].

Mutated PON enzymes of this aspect of the present invention preferably include at least one amino acid substituion in an amino acid equivalent to amino acid coordinate that is located in the active site of human PON1, which is preferably defined by a distant not exceeding 15 Å from a Calcium ion, preferably Ca401). Examples of such susbstitutions are illustrated in Table 13 hereinbelow.

According to one preferred embodiment of this aspect of the present invention the mutated PON enzyme exhibits at least 3 folds higher $K_{cat}/K_M$ ratio for phosphotriester hydrolysis, ester hydrolysis, carboxy-ester, lactone hydrolysis, thiolactone hydrolysis, lipid hydrolysis and/or lipid peroxide hydrolysis as compared to the respective wild-type PON.

According to other preferred embodiments of this aspect of the present invention, the isolated polynucleotide encoding the mutated PON enzyme is as set forth in SEQ ID NO: 62, 64, 66, 68, 70, 72, 74 or 76.

According to yet other preferred embodiments of this aspect of the present invention the amino acid sequence of this mutated PON enzyme is as set forth in SEQ ID NO: 63, 65, 67, 69, 71, 73, 75 or 77.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequences of the present invention encode previously unidentified polypeptides, the present invention also encompasses novel PON polypeptides or portions thereof, which are encoded by the isolated polynucleotide and respective nucleic acid fragments thereof described hereinabove.

Thus, the present invention also encompasses polypeptides encoded by the novel PON nucleotide sequences of the present invention. The amino acid sequences of these novel polypeptides are set forth in SEQ ID NO: 49, 50, 51, 52, 53, 54, 56, 57, 58, 59, 60, 61, 63, 65, 67, 69, 71, 73, 75 or 77. The present invention also encompasses functional homologues of these polypeptides, such homologues can be at least 50%, at least 55%, at least 60%, at least 65%, at least 70%, at least 75%, at least 80%, at least 85%, at least 95% or more say 100% homologous to SEQ ID NO: 49, 50, 51, 52, 53, 54, 56, 57, 58, 59, 60, 61, 63, 65, 67, 69, 71, 73, 75 or 77. Finally, the present invention also encompasses fragments of the above described polypeptides and polypeptides having mutations, such as deletions, insertions or substitutions of one or more amino acids, either naturally occurring or man induced, either randomly or in a targeted fashion.

Recombinant techniques are preferably used to generate the polypeptides of the present invention. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce a polypeptide of the present invention using recombinant technology, a polynucleotide encoding a polypeptide of the present invention (e.g., SEQ ID NO: 62, 64, 66, 68, 70, 72, 74 or 76) is ligated into a nucleic acid expression construct, which includes the polynucleotide sequence under the transcriptional control of a promoter sequence suitable for directing constitutive or inducible transcription in the host cells, as further described hereinbelow.

Other than containing the necessary elements for the transcription and translation of the inserted coding sequence, the expression construct of the present invention can also include sequences (i.e., tags) engineered to enhance stability, production, purification, yield or toxicity of the expressed polypeptide. Such a fusion protein can be designed so that the fusion protein can be readily isolated by affinity chromatography; e.g., by immobilization on a column specific for the heterologous protein. Where a cleavage site is engineered between the peptide moiety and the heterologous protein, the peptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

A variety of prokaryotic or eukaryotic cells can be used as host-expression systems to express the peptide coding sequence. These include, but are not limited to, microorganisms, such as bacteria transformed with a recombinant bacteriophage DNA, plasmid DNA or cosmid DNA expression vector containing the peptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence. Mammalian expression systems can also be used to express the peptides of the present invention. Bacterial systems are preferably used to produce recombinant polypeptides, according to the present invention, thereby enabling a high production volume at low cost.

Other expression systems such as insects and mammalian host cell systems, which are well known in the art can also be used by the present invention.

In any case, transformed cells are cultured under effective conditions, which allow for the expression of high amounts of recombinant polypeptides. Effective culture conditions include, but are not limited to, effective media, bioreactor, temperature, pH and oxygen conditions that permit protein production. An effective medium refers to any medium in which a cell is cultured to produce the recombinant peptides of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art (see Example 1 of the Examples section).

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

Following a certain time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The availability of large amounts of recombinant PON1 allowed the present inventors to elucidate the three dimensional (3D) structure of the protein, using x-ray crystallography. As is exemplified in Example 6 of the Examples section which follows, the 3D structure of PON1 provides key insights as to how the substrate and reaction selectivity of different PONs is determined. As mentioned hereinabove, a set of 16 residues which constitute the walls and perimeter of the PON active site and governs substrate selectivity was defined (see Table 13 below).

Using this structural information it is possible to computationally identify inhibitor molecules (e.g., small molecules) of PONs, such as PON1. These inhibitors may be complete inhibitors, or partial inhibitors which can modify substrate specificity, as described above. For example, such small molecule inhibitors may shift the substrate specificity of PON1 towards the thiolactonase active configuration of the protein, thereby serving as valuable therapeutics in the treatment of atherosclerosis.

Thus, the present invention also provides a method of identifying a putative inhibitor of PON1.

As used herein the phrase "an inhibitor of PON1" refers to an inhibitor or a partial inhibitor of PON1 (e.g., modifies the substrate range of PON1), preferably human PON1. It will be appreciated that due to structural conservation shared between PON1 and other members of this protein family (i.e., PON2 and PON3), compounds of the present invention may serve as inhibitors of these proteins as well.

The method of this aspect of the present invention is effected by constructing a model using a set of atomic structural coordinates defining a three-dimensional atomic structure of a crystallized PON1 and computationally screening a plurality of compounds for a compound capable of specifically binding the active site of the model, to thereby identify the PON1 inhibitor.

Typically, obtaining the set of atomic coordinates which define the three dimensional structure of an enzyme (e.g., PON1) can be effected using various approaches which are well known in the art. Preferably used, is X-ray crystallography which can be effected as described in Examples 6 of the Examples section, which follows.

Structural data obtained is preferably recorded on a computer readable medium so as to enable data manipulation and construction of computational models. As used herein, "computer readable medium" refers to any medium which can be read and accessed directly by a computer. Such media include, but are not limited to, magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. Selection and use of appropriate storage media is well within the capabilities of one of ordinary skill in the art.

As used herein, "recorded" refers to a process of storing information on computer readable medium.

It will be appreciated that a number of data storage devices can be used for creating a computer readable medium having recorded thereon the structural data of the present invention. The choice of the data storage structure is typically based on the means chosen to access the stored information. In addition, a variety of data processor programs and formats can be used to store the data information of the present invention on computer readable medium. The sequence information can be represented in a word processing text file, formatted in commercially-available software such as WordPerfect and MICROSOFT Word, or represented in the form of an ASCII file, stored in a database application, such as DB2, Sybase, Oracle, or the like.

According to preferred embodiments of this aspect of the present invention, the coordinate data used to define the structure of PON1 or a portion thereof is derived from the set of coordinates set forth in the FIG. 26.

It will be appreciated that structure models of the present invention are preferably generated by a computing platform, which generates a graphic output of the models via a display generating device such as screen or printer. The computing platform generates graphic representations of atomic structure models via a processing unit which processes structure coordinate data stored in a retrievable format in the data storage device (such as described above, see FIG. 24).

Suitable software applications, well known to those of skill in the art, which may be used by the processing unit to process structure coordinate data so as to provide a graphic output of three-dimensional structure models generated therewith via display include RIBBONS (Carson, M., 1997. Methods in Enzymology 277, 25), O (Jones, T A. et al., 1991. Acta Crystallogr A47, 110), DINO (DINO: Visualizing Structural Biology (2001) dino3d.org); and QUANTA, CHARMM, INSIGHT, SYBYL, MACROMODE, ICM, MOLMOL, RASMOL and GRASP (reviewed in Kraulis, J., 1991. Appl Crystallogr. 24, 946).

As mentioned hereinabove, once a structural model of PON1 is obtained compounds which specifically bind the active site of the model are identifiable. This is preferably effected using Rational Drug Design (RDD).

RDD is a potent means of identifying enzyme inhibitors which, for example, has notably been used to identify HIV protease (Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109), and bcr-abl tyrosine kinase inhibitors (Mauro M J. et al., 2002. J Clin Oncol. 20, 325-34) used to provide the first effective pharmacological cures for human acquired immunodeficiency syndrome (AIDS) caused by human immunodeficiency virus (HIV)), and a human cancer (chronic myeloid leukemia), respectively.

One approach to identify a putative inhibitor via rational drug design is by screening a chemical structure database. ("3D database"), using software employing "scanner" type algorithms. Such software applications utilize atomic coordinates defining the three-dimensional structure of a binding pocket of a molecule and of a chemical structure stored in the database to computationally model the "docking" of the screened chemical structure with the binding pocket so as to qualify the binding of the binding pocket with the chemical structure. Iterating this process with each of a plurality of chemical structures stored in the database therefore enables computational screening of such a plurality to identify a chemical structure potentially having a desired binding interaction with the binding pocket, and hence the putative inhibitor.

Examples of suitable chemical structure databases for identifying the inhibitor molecules of the present invention include ISIS (MDL Information Systems, San Leandro, molinfo.com), MACCS-3D (Martin, Y. C., 1992. J. Med. Chem. 35, 2145-2154), The Cambridge Structural Database (CSD; cam.ac.uk/prods/csd/csd.html), Fine Chemical Database (reviewed in Rusinko A., 1993. Chem Des Auto. News 8, 44-47), and the NCBI's Molecular Modeling DataBase: MMDB; ncbi.nlm.nih.gov/Structure/MMDB/mmdb.shtml.

Other libraries of chemicals are commercially available from, for example, Merck, GlaxoWelcome, Bristol Meyers Squib, Monsanto/Searle, Eli Lilly, Novartis and Pharmacia UpJohn.

Alternatively, identifying the inhibitor molecule can be effected using de novo rational drug design, or via modification of a known chemical structure. In such case, software comprising "builder" type algorithms utilizes a set of atomic coordinates defining a three-dimensional structure of the binding pocket and the three-dimensional structures of basic chemical building blocks to computationally assemble a putative inhibitor. Such an approach may be employed to structurally refine a putative inhibitor identified, for example, via chemical database screening as described above.

Ample guidance for performing rational drug design by utilizing software employing such "scanner" and "builder" type algorithms is available in the literature (see, for example, Halperin I. et al., 2002. Proteins 47, 409-43; Gohlke H. and Klebe G., 2001. Curr Opin Struct Biol. 11, 231-5; Zeng J., 2000. Comb Chem High Throughput Screen. 3, 355-62; and RACHEL: Theory of drug design, newdrugdesign.com/Rachel_Theory.htm#Software). Additional guidance is provided hereinbelow and in the Examples section which follows.

Criteria employed by software programs used in rational drug design to qualify the binding of screened chemical structures with binding pockets include gap space, hydrogen bonding, electrostatic interactions, van der Waals forces, hydrophilicity/hydrophobicity, etc. Generally, the greater the contact area between the screened molecule and the binding region of the PON1, the lower the steric hindrance, the lower the "gap space", the greater the number of hydrogen bonds, and the greater the sum total of the van der Waals forces between the screened molecule and the substrate docking site of the PON1 protein, the greater will be the capacity of the screened molecule to bind with the active site of PON1.

The "gap space" refers to unoccupied space between the van der Waals surface of a screened molecule positioned within a binding pocket and the surface of the binding pocket defined by amino acid residues in the binding pocket. Gap space may be identified, for example, using an algorithm based on a series of cubic grids surrounding the docked molecule.

Contact area between compounds may be directly calculated from the coordinates of the compounds in docked conformation using the MS program (Connolly M L., 1983. Science 221, 709-713).

Suitable software employing "scanner" type algorithms include, for example, docking software such as GRAM, DOCK, or AUTODOCK (reviewed in Dunbrack et al., 1997. Folding and Design 2, 27), AFFINITY software of the INSIGHTII package (Molecular Simulations Inc., 1996, San Diego, Calif.), GRID (Goodford P J., 1985. "A Computational Procedure for Determining Energetically Favorable Binding Sites on Biologically Important Macromolecules", J. Med. Chem. 28, 849-857; GRID is available from Oxford University, Oxford, UK), and MCSS (Miranker A. and Karplus M., 1991. "Functionality Maps of Binding Sites: A Multiple Copy Simultaneous Search Method", Proteins: Structure Function and Genetics 11, 29-34; MCSS is available from Molecular Simulations, Burlington, Mass.).

The AUTODOCK program (Goodsell D S. and Olson A J., 1990. Proteins: Struct Funct Genet. 8, 195-202; available from Scripps Research Institute, La Jolla, Calif.) helps in docking screened molecules to binding pockets in a flexible manner using a Monte Carlo simulated annealing approach. The procedure enables a search without bias introduced by the researcher which can influence orientation and conformation of a screened molecule in the targeted binding pocket.

The DOCK program (Kuntz I D. et al., 1982. J Mol Biol. 161, 269-288; available from University of California, San Francisco), is based on a description of the negative image of a space-filling representation of the binding pocket, and includes a force field for energy evaluation, limited conformational flexibility and consideration of hydrophobicity in the energy evaluation.

Modeling or docking may be followed by energy minimization with standard molecular mechanics force fields or dynamics with programs such as CHARMM (Brooks B R. et al., 1983. J Comp Chem. 4, 187-217) or AMBER (Weiner S J. et al., 1984. J Am Chem Soc. 106, 765-784).

As used herein, "minimization of energy" means achieving an atomic geometry of a chemical structure via systematic alteration such that any further minor perturbation of the atomic geometry would cause the total energy of the system, as measured by a molecular mechanics force-field, to increase. Minimization and molecular mechanics force fields are well understood in computational chemistry (for example, refer to Burkert U. and Allinger N L., "Molecular Mechanics", ACS Monograph 177, pp. 59-78, American Chemical Society, Washington, D.C. (1982)).

Programs employing "builder" type algorithms include LEGEND (Nishibata Y. and Itai A., 1991. Tetrahedron 47, 8985; available from Molecular Simulations, Burlington, Mass.), LEAPFROG (Tripos Associates, St. Louis, Mo.), CAVEAT (Bartlett, P A. et al., 1989. Special Pub Royal Chem Soc. 78, 182-196; available from University of California, Berkeley), HOOK (Molecular Simulations, Burlington, Mass.), and LUDI (Bohm H J., 1992. J. Comp Aid Molec Design 6, 61-78; available from Biosym Technologies, San Diego, Calif. See Examples section which follows).

The CAVEAT program suggests possible binding molecules based on desired bond vectors. The HOOK program proposes docking sites by using multiple copies of functional groups in simultaneous searches. LUDI is a program based on fragments rather than on descriptors which proposes somewhat larger fragments as possible matches with a binding pocket and scores its hits based on geometric criteria taken from the Cambridge Structural Database (CSD), the Protein Data Bank (PDB) and on criteria based on binding data. LUDI may be advantageously employed to calculate the inhibition constant of a docked chemical structure. Inhibition constants (Ki values) of compounds in the final docking positions can be evaluated using LUDI software.

During or following rational drug design, docking of an intermediate chemical structure or of the putative inhibitor with the binding pocket may be visualized via structural models, such as three-dimensional models thereof displayed on a computer screen, so as to advantageously allow user intervention during the rational drug design to optimize a chemical structure.

Software programs useful for displaying such three-dimensional structural models, include RIBBONS (Carson, M., 1997. Methods in Enzymology 277, 25), O (Jones, T A. et al., 1991. Acta Crystallogr. A47, 110), DINO (DINO: Visualizing Structural Biology (2001) http://www.dino3d.org); and QUANTA, INSIGHT, SYBYL, MACROMODE, ICM, MOLMOL, RASMOL and GRASP (reviewed in Kraulis, J., 1991. Appl Crystallogr. 24, 946).

Other molecular modeling techniques may also be employed in accordance with this invention (for example, refer to: Cohen N C. et al, 1990. "Molecular Modeling Software and Methods for Medicinal Chemistry", J. Med. Chem. 33, :883-894; Navia M. A. and Murcko M. A., 1992. "The Use of Structural Information in Drug Design", Current Opinions in Structural Biology 2, 202-210). For example, where the structures of test compounds are known, a model of the test compound may be superimposed over the model of the structure of the invention. Numerous methods and techniques which are well known in the art can be used for performing this step (for example, refer to: Farmer P. S., "Drug Design", Ariens E J. (ed.), Vol. 10, pp 119-143 (Academic Press, New York, 1980); U.S. Pat. No. 5,331,573; U.S. Pat. No. 5,500,807; Verlinde C., 1994. Structure 2, 577-587; and Kuntz I D., 1992. Science 257, 1078-108).

The polynucleotides, polypeptides and/or compounds of the present invention, collectively termed agents, can be used to treat a PON-associated disease or condition in a subject in need thereof.

As used herein the phrase "PON-associated disease or condition" refers to a disease or a condition which may be treated by upregulating at least one PON activity in a subject (e.g., phosphotriesterase, phospholipase A2 like activities). Examples of such diseases or conditions include, but are not limited to, hyperlipidemia, atherosclerosis (see U.S. Pat. No. 6,521,226), neurological diseases (e.g., Alzheimer's disease, neurofibromatosis, Huntington's disease, depression, amyotrophic lateral sclerosis, multiple sclerosis, stroke, Parkinson's disease, or multi-infarct dementia, see U.S. Pat. No. 6,573,049), cancer (e.g., caused by carcinogenic lactones, see also U.S. Pat. No. 6,242,186), oxidative stress, sepsis (see U.S. Pat. No. 6,573,370), restenoses and intoxication by agents (i.e., endogenous or exogenous agents) which may be hydrolyzed and thereby inactivated by PONs, such as organophosphate poisoning (see U.S. Pat. Appl. Pub. No. 20020151068).

As used herein the term "treating" refers to preventing, curing, reversing, attenuating, alleviating, minimizing, suppressing or halting the deleterious effects of a PON associated condition or disease.

As used herein the phrase "subject in need thereof" refers to an organism, which may benefit from upregulation in PON activity.

The method is effected by administering to the subject a therapeutically effective amount of the agent of the present invention.

The agent can be provided to the subject per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compound preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979). Alternatively, the physiologically acceptable carrier may be HDL particles, HDL-like particles, and/or reconstituted HDL particles, to which PON enzymes are linked (see U.S. Pat. Nos. 5,128,318, 5,652,339 and 6,514,523).

Herein the term "excipient" refers to an inert substance added to a pharmaceutical composition to further facilitate administration of an active ingredient. Examples, without limitation, of excipients include calcium carbonate calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. The preferred route of administration is presently oral.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models (e.g., obese models such as disclosed by Bayli's J Pharmacol Exp Ther. 2003; and models for atherosclerosis such as described by Brousseau J Lipid Res. 1999 40(3):365-75) and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be effected over a short period of time (i.e., several days to several weeks) or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the polypeptides of the present invention can also be expressed from a nucleic acid construct administered to the subject employing any suitable mode of administration, described hereinabove (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

As mentioned hereinabove, to enable cellular expression of the polynucleotides of the present invention, the nucleic acid construct of the present invention includes at least one cis acting regulatory element, such as a promoter.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the trasgene is transcribed from CMV promoter. Vectors derived from Mo-MuLV are also included such as pBabe, where the transgene will be transcribed from the 5' LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Due to their hydrolytic activities (e.g., lacton and lipid hydrolysis), agents of the present invention may also be used to coat the surface of medical devices, such as for the treatment of artery narrowing caused by fatty deposits (plaque) on the walls of the arteries. Such a modality of treatment combines mechanical and pharmacological solutions. Also such coating is desired whenever the activity of the device is hampered by the accumulation of biomaterial therein or bio-incompatability, leading to foci formation and inflammation (e.g., in-stent restenosis).

As used herein the phrase "a medical device" refers to a device having surfaces which contact human or animal bodily tissue and/or fluids in the course of its operation. Examples of biomedical devices include, but are not limited to, extracorporeal devices for use in surgery such as blood oxygenators, blood pumps, blood sensors, tubing used to carry blood and the like which contact blood which is then returned to the subject; endoprostheses which are implanted in blood contact in a human or animal body such as vascular grafts, stents, pacemaker leads, heart valves, and the like that are implanted in blood vessels or in the heart; and devices for temporary intravascular use such as catheters, guide wires, and the like which are placed into the blood vessels or the heart for purposes of monitoring or repair.

Specific examples of medical devices which can be used in accordance with the present invention, include, but are not limited to, vascular grafts, aortic grafts, arterial, venous, or vascular tubing, vascular stents, dialysis membranes, tubing or connectors, blood oxygenator tubing or membranes, ultrafiltration membranes, intraaortic balloons, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind A number of approaches are known in the art for attaching proteins to the surface of a biomedical device. These approaches typically include the use of coupling agents such as glutaraldehyde, cyanogens bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to substrate surfaces. For example, covalent attachment of biomolecules using water soluble carbodiimides is described by Hoffman et al., "Covalent Binding of Biomolecules to Radiation-Grafted Hydrogels on Inert Polymer Surfaces," Trans. Am. Soc. Artif. Intern. Organs, 18, 10-18 (1972); and Ito et al., "Materials for Enhancing Cell Adhesion by Immobilization of Cell-Adhesive Peptide," J. Biomed. Mat. Res., 25, 1325-1337 (1991). U.S. Pat. No. 6,617,142 discloses methods for forming a coating of immobilized biomolecule on a surface of a medical device to impart improved biocompatibility for contacting tissue and bodily fluids.

Agents of the present invention may be immobilized to the surface of the medical device or released therefrom, either constitutively or upon induction.

To improve therapeutic efficacy, treatment with the agents of the present invention can be combined with pre-established clinical modalities. Thus, for example, treatment of organophosphate poisoning using the agents of the present invention can be combined with the administration of carbamates, antimuscarnics, reactivators and anticonvulsants.

As mentioned hereinabove, the agents of the present invention can be used for decontamination and detoxification of PON-susceptible toxic agents. Thus, for example, stockpiles of toxic agents (e.g., organophosphates, pesticides and volatile organic compounds) can be hydrolyzed using the agents of the present invention [DeFrank (1991) Applications of Enzyme Biotechnology ed. J W Kelly, T O Baldwin p: 165-80, Mazur (1946) J. Biol. Chem. 164:271-89]. Such treatments may be often optimized by UV-ozonation [Kearney (1986) J. Agric. Food Chem. 34:702-6]. Trangenic organisms (e.g., bacteria) expressing PONs of the present invention can be grown on OP toxins, for bioremediation of contaminated regions [Walker (2002) Biotechnol. Bioeng. 78:715-21; Shimazu (2001) Biotechnol. Bioeng. 76:318-24; Munnecke (1974) Appl. Microbiol. 28: 212-17]. These PONs are preferably cell-surface expressed to avoid substrate diffusion through the cell wall or membrane [Hong (1998) Bioremediation J. 2:145-57; Richins (1997) Nat. Biotechnol. 15:984-87; Kaneva (1998) Biotechnol. Prog. 14:275-78; Kim (2002) Biotechnol. Prog. 18:429-36; Zhang (1999) Biotechnol. Bioeng. 64:221-31; Kim (1997) Biotech. Lett. 19:1067-71 Mulchandani (1999) Biotechnol. Bioeng. 63:216-23; Wang (2002) Appl. Environ. Microbiol. 68:1684-89]. To improve water solubility of purified enzymes, micro-emulsions to solubilize and concentrate the hydrophobic compounds. PONs can also be incorporated in fire fighting foams, which can effectively decontaminate large surface without solvents and toxic solutions. Toxic vapors may be hydrolyzed using solid lyophilized PONs in gas phase bioreactors [Russell (1994) Chemtech 24:23-31; Komives (1994) Biotechnol. Bioeng. 43:946-59; Lejeune (1998) Nature 395:27-28; Lejeune (1999) Biotechnol. Bioeng. 62:659-65; Cheng (1998) Ann. NY Acad. Sci. 864:253-58].

Immobolized agents of the present invention are also of valuable use in detexification and as protective barriers [see Russell (2003) Annu. Rev. Biomed. 5:1-27 and references therein]. For example such agents can be adsorbed in protective clothing, however, measures are taken to employ effective immobilization methods which allow for the preparation of immobilized enzymes which retain most activity, high operational stability in its working environment and high storage stability. Methods of immobilization include the attachment of the enzyme on glass-beads via an azide-coupling method, adsorption onto trityl agarose, covalent attachment using glutaraldehyde onto nylon supports, immobilization of bacterially expressed enzymes onto cotton. Recent advances in materials synthesis using enzymes allows the preparation of a variety of bioplastics (e.g., polyurethanes and foams thereof, sol-gel, silicone) and enzyme-polymer composites for use as reactive monoliths, foams, fibers, wipes, and coatings. These polymers involve the incorporation (usually covalent) of the enzyme directly into the polymer. The enzyme may participate in the reaction and via the reactive functionalities on the enzyme surface, form multiple covalent attachments with the polymer. This ensures retention and stability of the polymeric material.

The agents of the present invention may also be incorporated in cleaning solutions (such as for cleaning pesticide-treated foods). These enzyme-based detergents also known as 'green chemicals' may find a wide range of applications in laundry, dishwashing, textile and other such industries. Cleaning compositions of the present invention include the active agents of the present invention as well as cleaning adjunct materials, preferably compatible with the enzyme action. The term "cleaning adjunct materials", as used herein, refers to a liquid, solid or gaseous material selected for the particular type of cleaning composition desired and the form of the product (e.g., liquid; granule; powder; bar; paste; spray; tablet; gel; foam composition), which materials are also preferably compatible with the hydrolytic enzyme used in the composition. Granular compositions can also be in "compact" form and the liquid compositions can also be in a "concentrated" form.

The specific selection of cleaning adjunct materials are readily made by considering the surface, item or fabric to be cleaned, and the desired form of the composition for the cleaning conditions during use (e.g., through the wash detergent use). The term "compatible", as used herein, means the cleaning composition materials do not reduce the hydrolytic activity of the enzyme to such an extent that the enzyme is not effective as desired during normal use situations. Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents dispersants, suds suppressors, dyes, perfumes, colorants, filler salts, hydrotropes, photoactivators, fluorescers, fabric conditioners, hydrolyzable surfactants, perservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments and pH control agents as described in U.S. Pat. Nos. 5,705,464, 5,710,115, 5,698,504, 5,695,679, 5,686,014, 5,646,101 and 6,610,642. Specific cleaning composition materials are exemplified in detail hereinafter.

If the cleaning adjunct materials are not compatible with the enzyme(s) in the cleaning compositions, then suitable methods of keeping the cleaning adjunct materials and the enzyme(s) separate (not in contact with each other) until combination of the two components is appropriate can be used. Suitable methods can be any method known in the art, such as gelcaps, encapulation, tablets, physical separation, etc.

Preferably an effective amount of one or more enzymes described above are included in compositions useful for cleaning a variety of surfaces in need of toxic agent removal. Such cleaning compositions include detergent compositions for cleaning hard surfaces, unlimited in form (e.g., liquid and granular); detergent compositions for cleaning fabrics, unlimited in form (e.g., granular, liquid and bar formulations); and dishwashing compositions (unlimited in form and including both granular and liquid automatic dishwashing).

As used herein, "effective amount of enzyme" refers to the quantity of enzymes described hereinbefore necessary to achieve the enzymatic activity necessary in the specific cleaning composition. Such effective amounts are readily ascertained by one of ordinary skill in the art and is based on many factors, such as the particular enzyme used, the cleaning application, the specific composition of the cleaning composition, and whether a liquid or dry (e.g., granular, bar) composition is required, and the like. Preferably the cleaning compositions comprise from about 0.0001%, preferably from about 0.001%, more preferably from about 0.01% by weight of the cleaning compositions of one or more enzymes of the present invention, to about 10%, preferably to about 1%, more preferably to about 0.1%. Also preferably the enzyme of the present invention is present in the compositions in an amount sufficient to provide a ratio of mg of active enzyme per 100 grams of composition to ppm theoretical Available $O_2$ from any peroxyacid in the wash liquor, referred to herein as the Enzyme to Bleach ratio (E/B ratio), ranging from about 1:1 to about 20:1. Several examples of various cleaning compositions wherein the enzymes of the present invention may be employed are discussed in further detail below. Also, the cleaning compositions may include from about 1% to about 99.9% by weight of the composition of the cleaning adjunct materials.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cloning and Expression of Wild-Type PON1 Genes in, *E. coli*

Materials and Experimental Procedures

Cloning of PON1 genes—The plasmid pGex-6p-2 containing the hPON1 gene ((Reddy et al., 2001) kindly provided by Srinivasa T. Reddy, UCLA) was used as a template for PCR amplification with a back primer (pET20-hPON1-bc; Table 1, below) that introduces an NcoI restriction site at the ATG initiation codon, and a forward primer (pET20-hPON1-fo, Table 1, below) annealing downstream to the NotI site. The resulting fragment was digested and cloned into pET20b and pET32b (Novagen,) using the NcoI and NotI sites. For cloning into pET43b, pET43-hPON1-bc (Table 1, below) was used as a back primer annealing downstream to the ATG initiation codon and appending an SpeI restriction. For cloning to pMAL (NEB), a back primer appending an EcoRI site (pMAL-hPON1-bc, Table 1, below), and a forward primer (pMAL-hPON1-fo, Table 1, below) annealing to the hPON1 gene upstream to the stop codon and appending an additional stop codon and a pstI site, were used.

The genes for mouse PON1 (mPON1, GenBank Accession No. NM_011134) and Rat PON1 (RatPON1, GenBank Accession No. XM_342639) were directly amplified by PCR from liver cDNA (CLONTECH) with a back primer pET32-mPON1-bc and pET32-RatPON1(+8)-bc (appending the first 8 amino acids from the mPON1 gene sequence, see Table 1, below), respectively, to introduce an NcoI restriction site at the ATG initiation codon, and forward primers pET32-mPON1-fo and pET32-RatPON1-fo (Table 1, below) to introduce a NotI restriction site downstream to a stop codon.

The gene for Rabbit PON1 (RabPON1, GenBank Accession No. AF220943) was cloned from rabbit cDNA. The total mRNA of a fresh liver of a Rabbit (New-Zealand) was extracted using an RNeasy kit (Beit Haemek) and used as a template for the RT reaction with hexamer random primer and oligo dT (Superscript II, Stratagene). The rabbit PON1 gene was amplified from this cDNA with a back primer (pET32-RabPON1-bc, Table 1) introducing an NcoI site and a forward primer (pET32-RabPON1-fo, Table 1) with a NotI site downstream to the stop codon. The resulting DNA fragments were digested and cloned into pET32b(+) vector (containing Trx and an His tag as a fusion protein) to generate the pET32b-hPON1, pET32b-mPON1, pET32b-RatPON1 and pET32b-RabPON1 constructs.

TABLE 1

| | | |
|---|---|---|
| pET20-hPON1-bc | SEQ ID NO:1 | 5 CGACGAAACCATGGCGAAGCTGATTGCG 3 |
| pET20-hPON1-fo | SEQ ID NO:2 | 5 CCGGGAGCTGCATGTGTCAGAGG 3 |
| pET43-hPON1-bc | SEQ ID NO:3 | 5'TCAATCCGACTAGTGGTTCTGGTATGGCGAAGCTG ATTGCG3' |
| PMAL-hPON1-bc | SEQ ID NO:4 | 5'CTGTCAAGGAATTCATGGCGAAGCTGATTGCG3' |
| PMAL-hPON1-fo | SEQ ID NO:5 | 5'GTCCCGGGCTGCAGTTATTAGAGCTCACAGTAAAG A3' |
| pET32-mPON1-bc | SEQ ID NO:6 | 5'GGACAAGGCCATGGCGAAGCTGCTAGCACTCACC3' |
| pET32-RatPON1(+8)-bc | SEQ ID NO:7 | 5'CGACAAGGCCATGGCGAAGCTGCTAGCACTCACC CTCGTGGGA CTGGTGTTGGCACTTTAGAG3' |
| pET32-mPON1-fo | SEQ ID NO:8 | 5'GCTCGAGTGCGGCCGCTTACAGATCACAGTAAAG AGCTTTGTGG3' |
| pET32-RatPON1-fo | SEQ ID NO:9 | 5'GCTCGAGTGCGGCCGCTTACAGGTAACAACAAAG AGCTCTGTGG3' |
| Hexamer-primer | SEQ ID NO:10 | 5'NNNNNN3' |
| Oligo dT | SEQ ID NO:11 | 5'T(20)VN 3' |
| pET32-RabPON1-bc | SEQ ID NO:12 | 5'CGACAAGGCCATGGCTAAACTGACAGCGCTC3' |
| pET32-RabPON1-fo | SEQ ID NO:13 | 5'GCTCGAGTGCGGCCGCTTAATTGGCCTGTGAGAGC TCACAG3' |
| pET32-Seq-bc | SEQ ID NO:14 | 5'CGCGGTTCTGGTATGAAAGAAACCGG3' |
| T7-term-Fo | SEQ ID NO:15 | 5'CCCGTTTAGAGGCCCCAAGGGG3' |
| Nes-shuf-fo | SEQ ID NO:16 | 5'-GGCAGCCAACTCAGCTTCC-3' |
| Nes-shuf-bc | SEQ ID NO:17 | 5'-CGAACGCCAGCACATGG-3' |

Results

Initial attempts to express recombinant PON1 were effected in *E. coli* using the human gene (GenBank Accession No. NM_000446). The gene was sub-cloned into different vectors to express the protein under different promoters (i.e., T7 or tac) and fused to different proteins [bacterial signal peptide, thioredoxin (trx), Nus (Novagen), glutathione S-transferase (GST) or maltose binding protein (MBP)]. Different *E. coli* strains—BL21, BL21 (DE3), Origami B (DE3) (Novagen), RIL (DE3) (Stratagene), were used at different growth temperatures (i.e., 20-37° C.) and under different induction conditions (i.e., 0-1 mM IPTG).

Figure 2A:
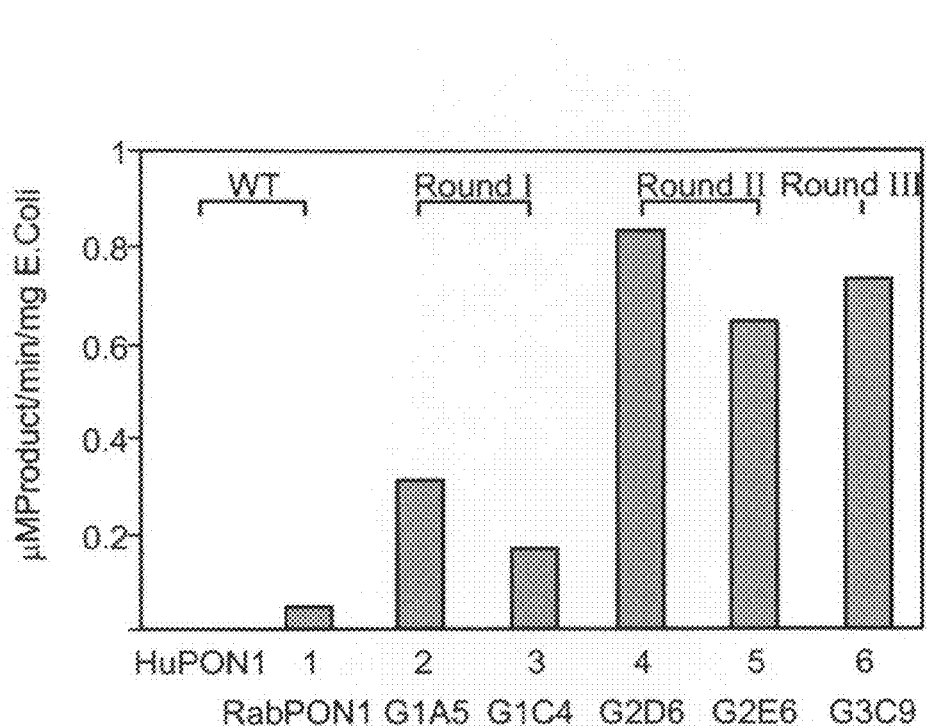
FIG. 2a is a histogram depicting paraoxonase activity of PON1 variants in crude $E.$ $coli$ lysates calculated per mg of $E.$ $coli$ cells. Activity is shown for the wild-type hPON1 and RabPON1, G1A5 and G1C4 variants from first round of evolution, G2D6 and G2E6 of the second round and G3C9 from the third round of evolution (i.e., without protein tags)
Figure 2B:
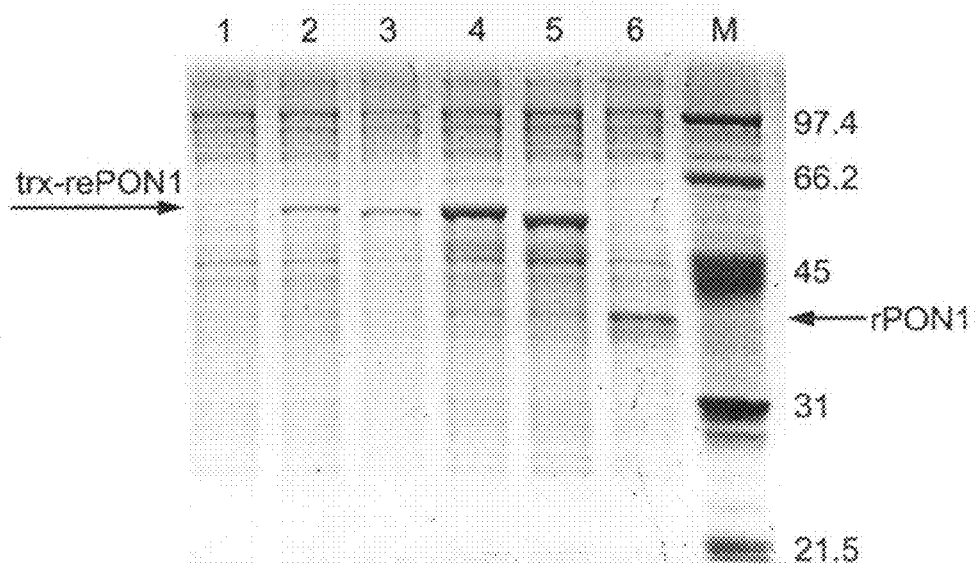
FIG. 2b is a photograph depicting SDS-PAGE (12%) analysis of the crude cell lysates of FIG. 2a. Lane 1 shows a crude lysate expression of the RabPON1 in pET32b, Lanes 2-5 show crude lysate expression of variants G1A5 G1C4 from first round of evolution and G2D6, G2E6 from second round of evolution (all in pET32b), respectively. Lane 6 shows crude lysate expression of G3C9 in modified pET32 with no protein tags.

Paraoxonase activity in the crude cell lysates served as a test for the amount of active hPON1. Although, under many conditions, large amounts of full size protein could be detected in the form of inclusion bodies, none of the above-described constructs and conditions produced detectable amounts of active hPON1. However, expression of the rabbit PON1 fused to thioredoxin (Trx-rPON1; FIG. 2) and under the T7 promoter (pET32 vector) in Origami B (DE3) cells resulted in very low paraoxonase activity (FIG. 2a). As is shown in FIG. 2b, thioredoxin was the only tag capable to solubilize rabbit PON1 when fused thereto. The ability of thioredoxin to partially solubilize rabbit PON1 was is in accordance with a recently published assessment of fusion proteins (Hammarstrom et al., 2002).

Example 2

Directed Evolution of Soluble PON1 Variants

Once conditions, under which high amounts of PON1 were expressed to form inclusion bodies in equilibrium with low amount of soluble and active PON1, were at hand (see Example 1, above), these served as a starting point for the directed evolution of highly soluble recombinant PON1 mutants.

Family DNA shuffling—The PON1 genes, hPON1, mPON1, RatPON1 and RabPON1 were shuffled using established protocols (Abecassis et al., 2000; Crameri et al., 1998; Stemmer, 1994). A forward primer (T7-term-Fo, Table 1, above) and a reverse primer (pET32-Seq-bc, Table 1, above) were used to individually amplify the various PON1 genes from the respective pET32b(+) plasmid, using ExTaq (Takara). Equal amounts of the four DNA fragments were purified, mixed together and subjected to DNase I digestion (Bovine pancrease, Sigma). A 50 µl digestion contained ~10 µg of DNA and 0.1 unit of DnaseI in 0.1 M Tris-HCl (pH 7.5) containing 10 mM manganese chloride. Following 3.5, 5 and 7 minutes at 20° C., aliquots of 17 µl were removed into 5 µl of 0.25 M EDTA and immediately heated to 90° C. for 10 minutes. The digest was separated on 2% agarose gel and fragments from 50-125 bp were extracted and purified using QIAEX II gel extraction kit (QIAGEN). Fragments were reassembled in a 50 µl reaction containing ~0.5 µg of DNA, dNTPs (0.2 mM each) and 2.5 units of ExTaq polymerase (Takara). Cycling was according to the following protocol (Abecassis et al., 2000): 94° C., 2 min; 35 cycles of (94° C., 30 seconds; 65° C., 90 seconds; 62° C., 90 seconds; 59° C., 90 seconds; 56° C., 90 seconds; 53° C., 90 seconds; 50° C., 90 seconds; 47° C., 90 seconds; 44° C., 90 seconds; 41° C., 90 seconds; 72° C., 2 minutes); 72° C., 7 minutes; and 15° C. for 5-10 hours.

To amplify the full-length genes, 0.01 µl of the reassembly reaction mixture was used as a template for a nested PCR reaction using forward and reverse primers (Nes-shuf-fo and Nes-shuf-bc respectively, Table 1, above). The assembled and PCR-amplified library was cloned to pET32b(+) vector using the NcoI/NotI sites and transformed to DH5α cells. >5×10$^4$ individual colonies were combined, grown and the plasmid DNA comprising this first generation (G1) library extracted with a maxiprep (Nucleobond AX).

Screening Procedures (esterase activity assay and paraoxonase activity assay)—The G1 library, abotained as described hereinabove, was transformed to origami B (DE3) cells and plated on LB agar plates supplemented with Amp (100 µg/ml), Kanamycin (15 µg/ml) and 1 mM CaCl$_2$. Colonies were grown overnight (O/N) at 37° C., replicated with velvet cloth and incubated at 37° C. for another 9 hours. The plates were screened for esterase activity by covering them with a layer soft agar (0.5%) in activity buffer (50 mM Tris-HCl pH 8, 1 mM CaCl$_2$) supplemented with 0.3 mM 2-naphtylacetate and 1.3 mg/ml of Fast Red (Sigma) (Khalameyzer et al., 1999; Ziomek et al., 1990). Colonies that turned bright red were picked from the replica plate into 500 µl of LB media with Amp (100 µg/ml), Kanamycin (15 µg/ml) and 1 mM CaCl$_2$, in a 96 deep-well plate, and grown O/N in a shaking incubator at 30° C. The following operations were performed in 96-well plates using a Precesion2000 liquid handling robot linked to a microtitre plate reader (Bio-Tek). 50 µl of the O/N culture were removed to a new microtiter plate and kept at 4° C. and the remaining volume spun down (3220 g for 10 min). The cell pellet was resuspended in 300 µl of Bug-buster (Novagen) supplemented with 1 mM CaCl$_2$ and allowed to shake for 15 min at room temperature. The plates were spun down at 3220 g for 15 min and 50-100 µl aliquots of lysates were re-plated. 100 µl of paraoxon in activity buffer (to a final concentration of 0.25 mM) were added to 100 µl lysate, and p-nitrophenol release was monitored at 405 nm. Esterase activity was measured by adding 150 µl of 2-naphtylacetate (to a final concentration of 0.25 mM) to 50 µl of lysate, and the release of 2-naphtol was monitored at 320 nm. About 20 of the best clones according to kinetic assays were spread and grown on agar plates as above. Three isolated colonies were picked from each clone to LB media and grown O/N at 30° C. The culture was lysed and enzymatic activity was measured as above. Plasmid DNA was extracted from the highest activity clones and used as a template for PCR amplification and reshuffling using the same protocol applied to prepare the G1 library.

Results

The present inventors used a directed evolution and screening approaches to generate soluble PON1 which retains catalytic function with both carboxy-esters and paraoxon.

DNA Shuffling—DNA shuffling of families of homologues genes has proven a powerful technique for the directed evolution of enzymes with specific functions (Abecassis et al., 2000; Crameri et al., 1998; Joern et al., 2002). This technique generates genetic diversity by recombination, thereby combining mutations from preselected functional genes. Such libraries are usually generated by random fragmentation of a pool of related genes, followed by reassembly of the fragments in a self-priming polymerase reaction (Stemmer, 1994).

For these reasons, four different PON1 genes (human, mouse, rat and rabbit) were cloned and shuffled to generate a gene library (G1 library) that was used for screening for functional PON1 expression. The library was generated using the procedure of Stemmer et al (Stemmer, 1994) with minor modifications (Abecassis et al., 2000) and analyzed by DNA sequencing.

Figure 1:
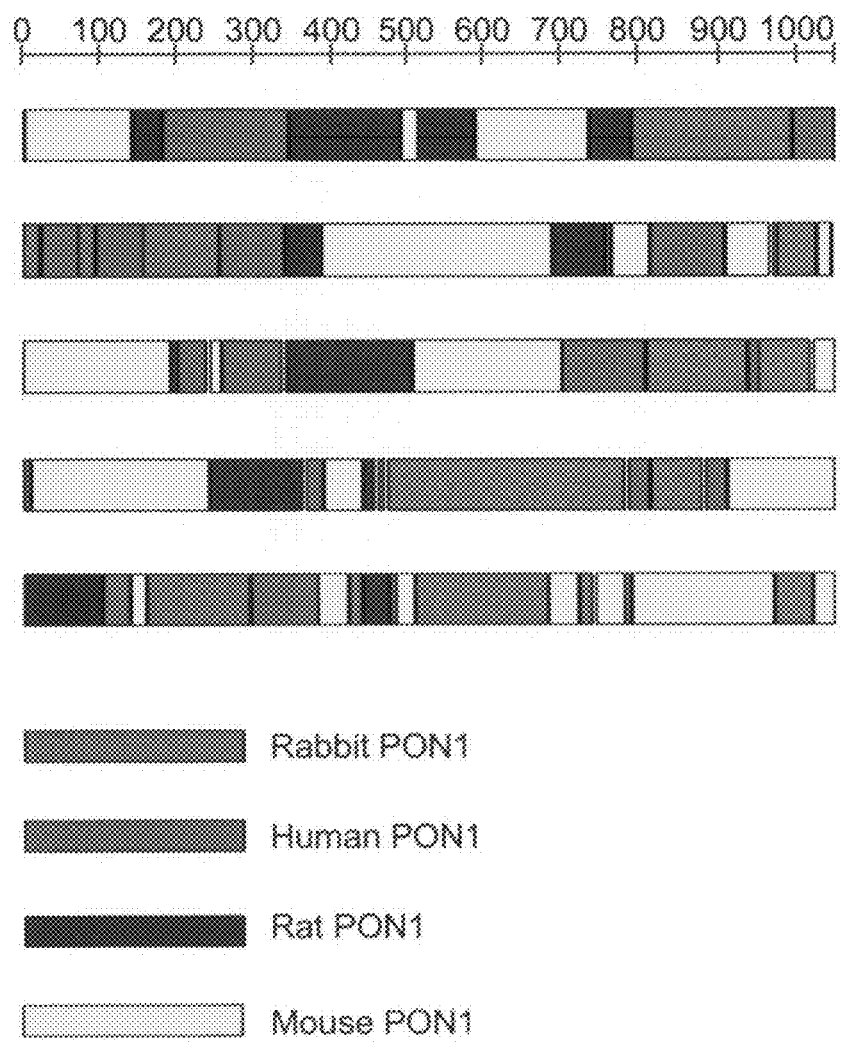
FIG. 1 is a schematic representation of the DNA sequence of five unselected clones from the family shuffling of the PON1 wild-type genes (i.e., G1 library). Different colors are assigned to each parental gene as follows: red, hPON1; yellow, mPON1; blue, RatPON1; green, RabPON1. Complete identity regions between the library clones and each of the four parental genes were followed to the point where a nucleotide, or a stretch of nucleotides, from another parental gene could be identified, allowing the identification of crossover points between parental genes.

Ten randomly chosen clones were analyzed and found to contain full-length open reading frames with no deletions insertions or stop codons. The distribution of the individual parental genes in the G1 library was close to even (mouse: 36.2%, rat: 18%, human: 19.1%, rabbit: 26.7%). In average, a crossover every 78.3 bp (13.6 crossovers per gene), was identified (see FIG. 1). The high number of crossovers and nearly even parental gene distribution in the library allowed for efficient screen of the sequence space of the four parental genes (Crameri et al., 1998).

Figure 6:
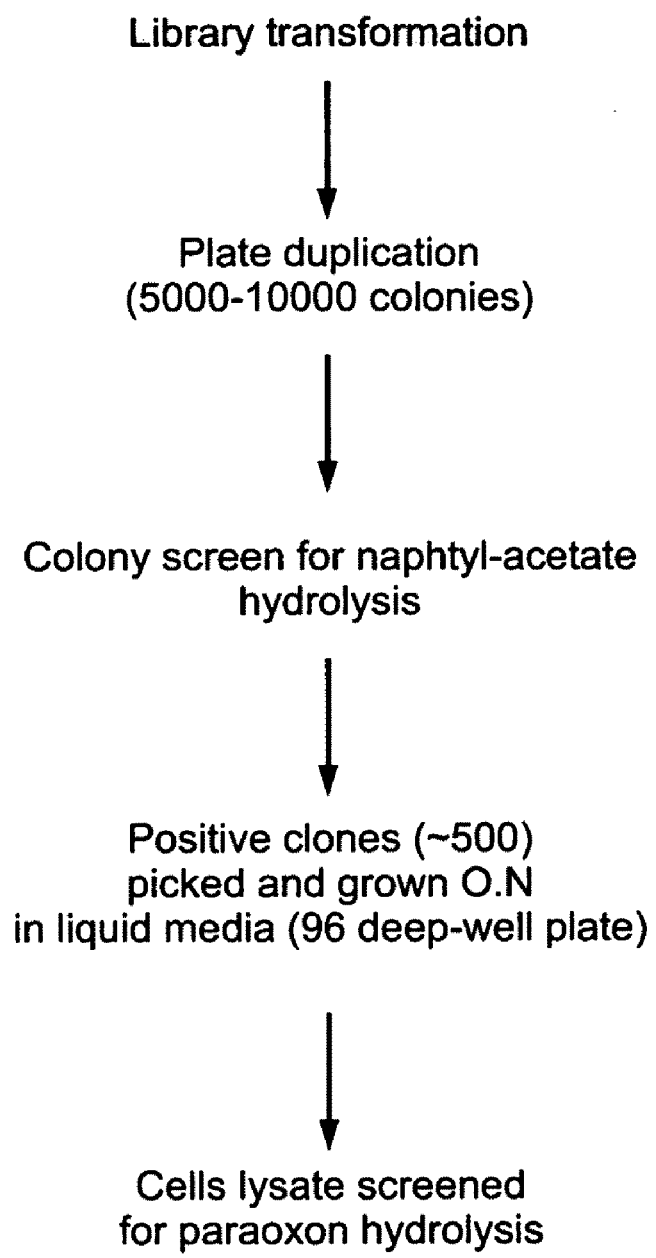
FIG. 6 is a flow chart depicting the steps of directed evolution and screening for soluble PON variants with desired spectrum of activities.

Directed evolution of soluble and active PON1 variants— The G1 library was recloned to an expression vector and transformed to Origami B (DE3) cells. Screening was first performed on agar colonies for esterase activity using 2-naphtylacetate and an azo dye (e.g., Fast Red) that reacts with the released naphtol to generate a red insoluble product (Khalameyzer et al., 1999; Ziomek et al., 1990) (FIG. 6). Positive clones were picked from a replica plate and grown for expression. Cells were lysed and then assayed spectrophotometrically for the hydrolysis of paraoxon as well as 2-naphtylacetate. Colony screening of ~10$^4$ different colonies generated ~500 colonies in the first screen. Out of these 500 colonies, about 50 clones with significantly improved paraoxonase and esterase activity (relative to wild-type RabPON1) were observed in the second screen.

The ratio of esterase activity relative to the paraoxonase activity (i.e., 588 in the wild-type hPON1 purified from serum and ~250 for all the various directly-evolved PON1 variants; Table 2, below) was used as a marker for selecting clones that maintained the catalytic properties and specificities of wild-type PON1 but had increased amounts of soluble, active protein. The twenty best clones were sub-cloned and assayed to verify their activity. Enzymatic activity and SDS-PAGE analysis both indicated an increase in solubility of the PON1 with the best clones from the first generation (G1A5, G1C4) exhibiting a 3-6 fold increase in soluble protein (FIGS. 2a-b). Plasmid DNA isolated from the 20 best clones was used as template for PCR amplification of the active PON1 genes and DNA re-shuffling. The resulting gene-library (G2) was cloned and screened as above.

Figure 3:
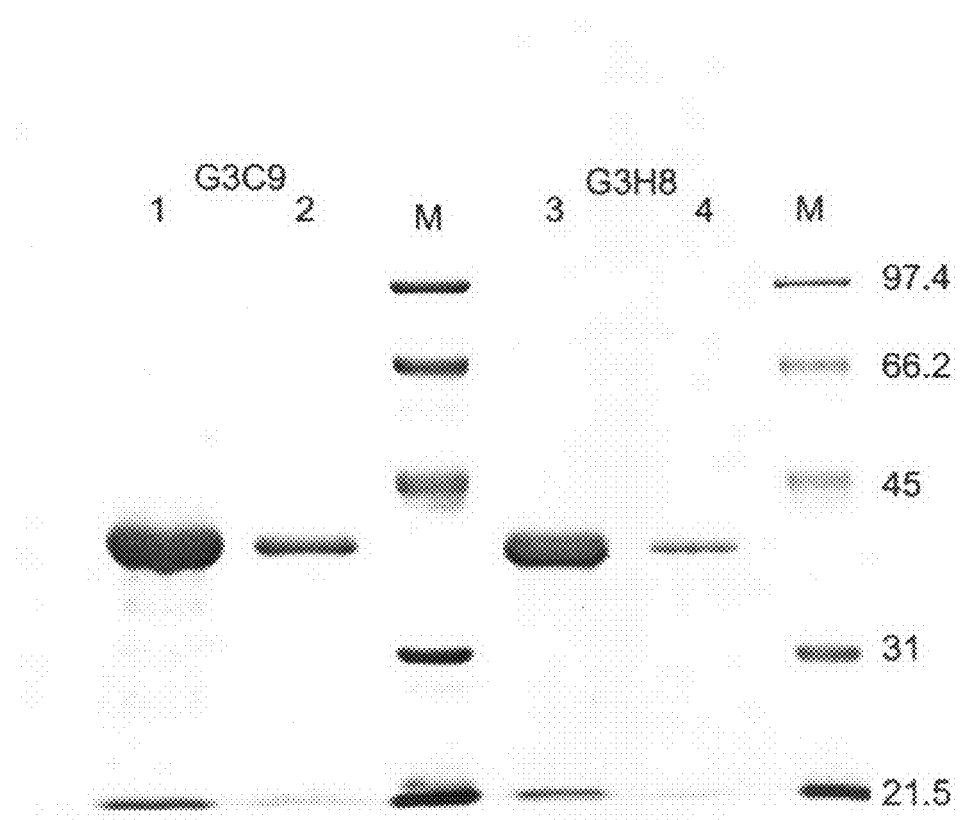
FIG. 3 is a photograph depicting SDS-PAGE (12%) analysis of purified rPON1 variants G3C9 and G3H8 from the third round of evolution. The protein is expressed with no tags in a modified pET32b vector. Lanes 1 and 2 are purified G3C9 and lanes 3 and 4 are purified G3H8.

Screening of the second-round library (G2) generated at least 20 new clones with an increase in enzymatic activity of up to 3 fold relative to the best clone from the G1 library (G1A5). The best clone from the G2 library (G2D6) exhibited over 16-fold increase in activity relative to RabPON1. Analysis of the crude lysates by SDS-PAGE indicated that the improved activity resulted from improved solubility of the PON1 variants and not a change in specific activity (FIGS. 2a-b, Table 2, below). The amount of soluble active PON1 protein purified of the G2D6 and G2E6 clones exceeded 14 mg per liter of cell culture (Table 2, below).

these clones (G3H8 and G3C9; FIGS. 2a-b and 3) were expressed and purified to homogeneity with high yield (~12 mg per litre culture).

Example 3

Characterization of Directly Evolved PON1 Variants

Sequence analysis of the directly evolved PON1 variants generated as described above was effected as is described herein below.

Materials and Experimental Procedures

Expression and purification of the directly-evolved PON1 variants. Origami B (DE3) cells were transformed with plasmid DNA isolated from selected variants. Single colonies were used to inoculate 5 ml of LB media supplemented with Amp (100 µg/ml), Kanamycin (15 µg/ml) and Calcium chloride (1 mM) and the resulting cultures were grown O/N at 30° C. Cells were harvested by centrifugation and resuspended in 60 ml of activity buffer supplemented with 1 µl of Pepstatin A, 0.1 mM DTT and 0.03% of n-dodecyl-β-D-maltopyranoside ($C_{12}$-maltoside). The cells were disrupted by sonication and the suspension was gently shaken at room temperature for 2 hours. Cell debris was removed by centrifugation and ammonium sulfate was added to 50% saturation (w/v). The resulting precipitate was dissolved in activity buffer and dialysed against the same buffer. Ni-NTA resin (5 ml; Qiagen) was added to the lysate and the mixture gently shaken at 4° C. for three hours and then loaded on a column. The resin was rinsed with activity buffer containing increasing concentrations of imidazole (10-25 mM) and the enzyme eluted at 125 mM of imidazole. Fractions with the highest paraoxonase activity

TABLE 2

| Clone/ SEQ ID NO: | $k_{cat}$ (PheAc) sec$^{-1}$ | $K_M$(PheAc) mM | $k_{cat}$(Paraoxon) sec$^{-1}$ | $K_M$(Paraoxon) mM | Ratio of $k_{cat}/K_M$ PheAc/ Paraoxon | Yield of purified enzyme (mg/L culture) |
|---|---|---|---|---|---|---|
| G1A5/25 | 833 | 0.39 | 1.16 | 0.085 | 157.9 | 2.2 |
| G1C4/26 | 552 | 0.54 | 0.54 | 0.12 | 227.1 | 2.7 |
| G1C4-20 | 238 | 0.87 | 0.25 | 0.27 | 297.3 | 5 |
| G2D6/27 | 562 | 0.32 | 0.98 | 0.10 | 179.2 | 14.4 |
| G2E6/28 | 965 | 0.43 | 0.87 | 0.089 | 229.7 | 20 |
| G3H8/29 | 1018 | 0.32 | 1.2 | 0.088 | 233.9 | 11.8 |
| G3C9/55 | 789 | 0.33 | 1.1 | 0.094 | 204.3 | 12.6 |
| hPON1[a] (w.t.)/24 | 1236 | 0.42 | 3 | 0.54 | 535 | 0 |

Figures 7A, 7B, 7C:
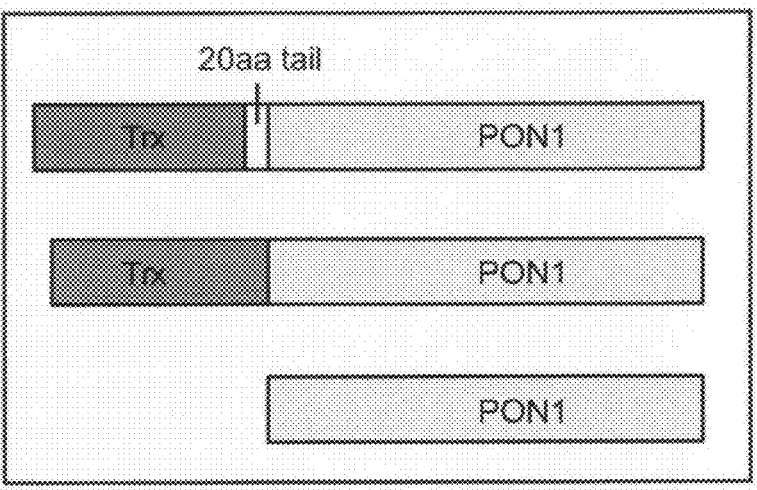
FIGS. 7a-c are schematic illustrations depicting the structure of thioredoxin fused rPON1 (trx-rPON1, FIG. 7a), thioredoxin fused to N-terminally deleted rPON1 (trx-rPON1-20, FIG. 7b) and rPON1 (FIG. 7c).

A third round of shuffling yielded the G3 library but its screening indicated no further increase in expression. The G2 library was further cloned into a truncated pET32 vector in which the fusion protein (thioredoxin) and the linker peptide carrying the His and S-tags were all deleted, leaving the intact, 355 amino acids, PON1 protein without any additions (rPON1; FIG. 7c). Screening of this library revealed similar activity levels as the library of the thioredoxin-fused PON1 from the second round of evolution, allowing the identification of at least 20 clones of highly soluble rPON1. Two of were pooled together, chromatographed on a High Trap Q column with a linear gradient of 26-33% of buffer B (20 mM Tris Hcl pH8, 1 mM $CaCl_2$, 0.03% maltoside and 1M NaCl) in buffer A (i.e., same as B without NaCl). Fractions with the highest paraoxonase activity were analyzed for purity on 12% SDS gel, pooled, dialysed against buffer A and concentrated.

For purification of rPON1 (G3H8 and G3C9; with no affinity tags) from the third round of evolution, dialysed cell lysates after ammonium sulfate precipitation were applied to a Hitrap Q column (Pharmacia) and the protein was eluted as above. Active fractions were pooled dialysed and loaded to ceramic Hydroxyapetite type 1 column (Biorad) using Biologic low-pressure chromatography system (Biorad). The protein was eluted with 0-200 mM potassium phosphate gradient in buffer A. Active fractions were pooled, dialysed against buffer A supplemented with 0.2 M NaCl, concentrated and loaded to a size exclusion column (Hi load superdex 200 26/60, pharmacia). rPON1 was eluted at ~99 kDa (calibrated by molecular weight markers). The paraoxonase active fractions were analyzed for purity on 12% SDS gel, pooled and concentrated. All various purified PON1 variants were stored for over two months at 4° C. with no apparent loss in activity.

Enzyme kinetics—Enzyme kinetic rates were measured with 0.005-1.4 µM purified PON1 and 0.01-4 µM PON3. Activity buffer at pH 8 was used with paraoxon, DEPCyC, phenyl acetate, 2Naphtyl acetate (2NA) and dihydrocoumarin; as substrates, and Hepes buffer at pH 7.3 with p-nitrophenyl acetate and L-homocysteine thiolactone (L-Hcy). In general, a range a substrate concentration was applied from $0.3 \times K_M$ up to $(2-3) \times K_M$. Product formation was monitored in 200 µl reaction volumes using 96-well microtitre plates, at 405 nm for p-nitrophenol ($\epsilon$=9100 $M^{-1}$), 408 nm for CyC ($\epsilon$=21500 $M^{-1}$), 270 nm for phenol ($\epsilon$=430 $M^{-1}$) and the hydrolysis product of dihydrocoumarin ($\epsilon$=430 $M^{-1}$), and 320 nm for 2-naphthol ($\epsilon$=860 $M^{-1}$). L-Hyc formation was monitored by detecting the free thiol group with Ellman's reagent (5,5-dithio-bis-2-nitrobenzoic acid) at 412 nm ($\epsilon$=7000 $M^{-1}$ for 5-thio-2-nitrobenzoic acid). Kinetic parameters were determined by fitting the data directly to the Michaelis-Menten model: $V_o = k_{cat}[E]_0[S]_0/([S]_0+K_M)$ using Kaleidograph. Inhibition constants were determined by fitting the data to a competitive inhibition model: $V_o = V_{max}[S]_0/([S]_0+K_M(1+[I]/K_i)$.

Results

Figures 5, 5A, 5B, 5C:
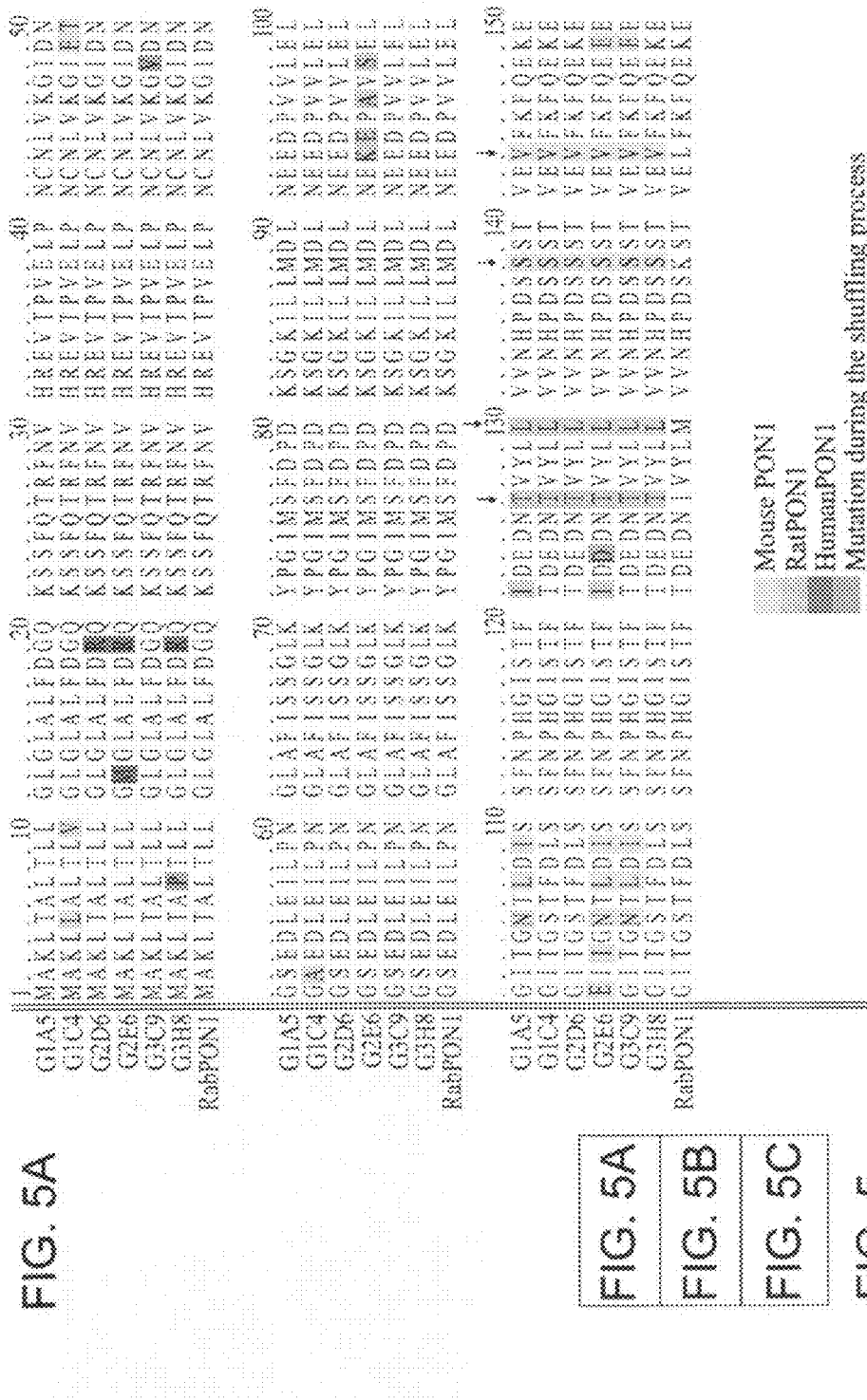
FIG. 5 is a sequence alignment of PON1 variants (G3C9. G1A5. G1C4, G2D6. G2E6, and G3H8 (SEQ ID NOs: 56-61 respectively) from different rounds of evolution aligned against the sequence of RabPON1 (SEQ ID NO: 39). Mutations in the sequence relative to the RabPON1 are colored according to their parental origin: red, hPON1; yellow, mPON1; blue, RatPON1; pink, for mutations that occurred during the shuffling and amplification processes. Conserved mutations in the directly-evolved variants are marked with an arrow.
Figure 5B:
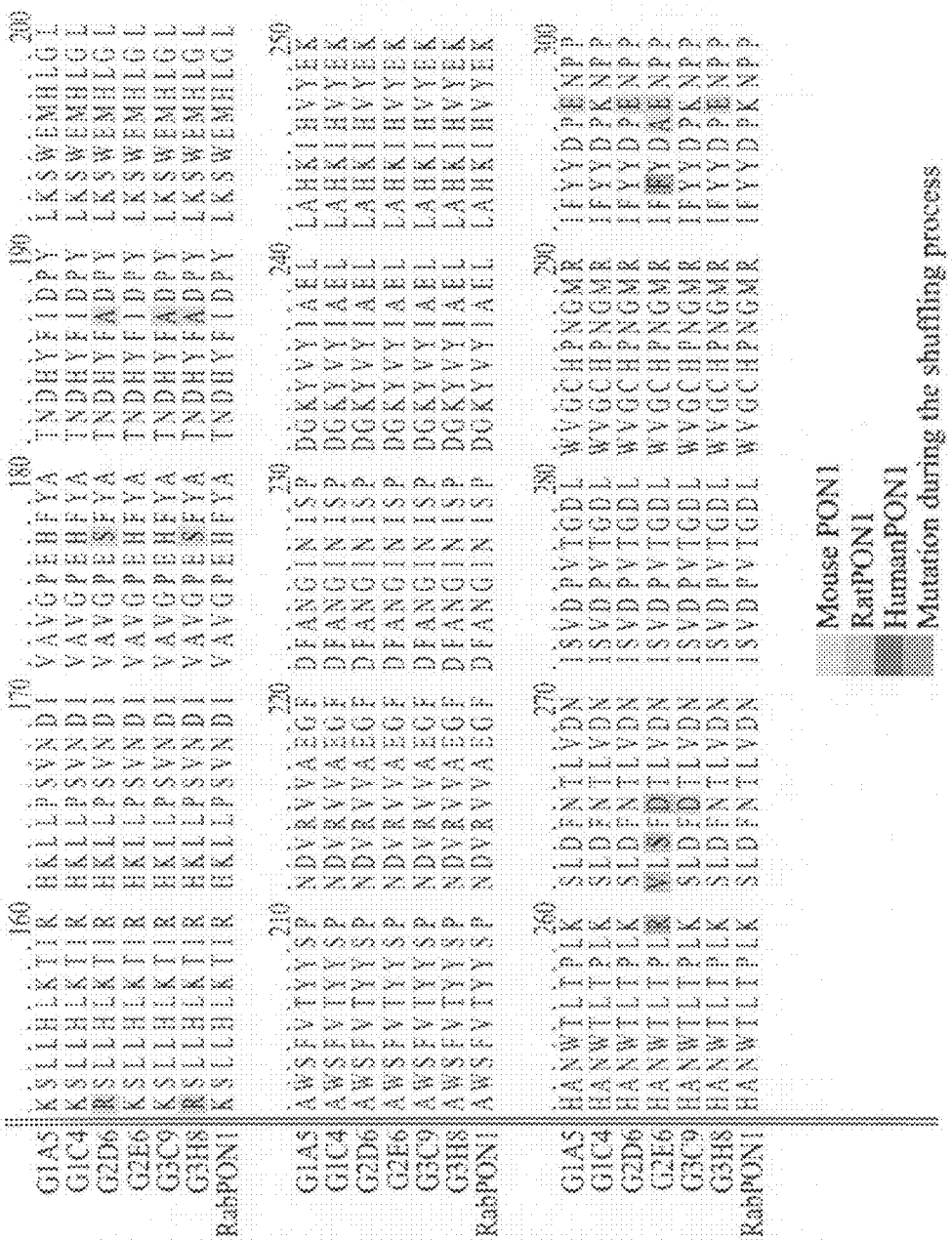
Figure 5C:
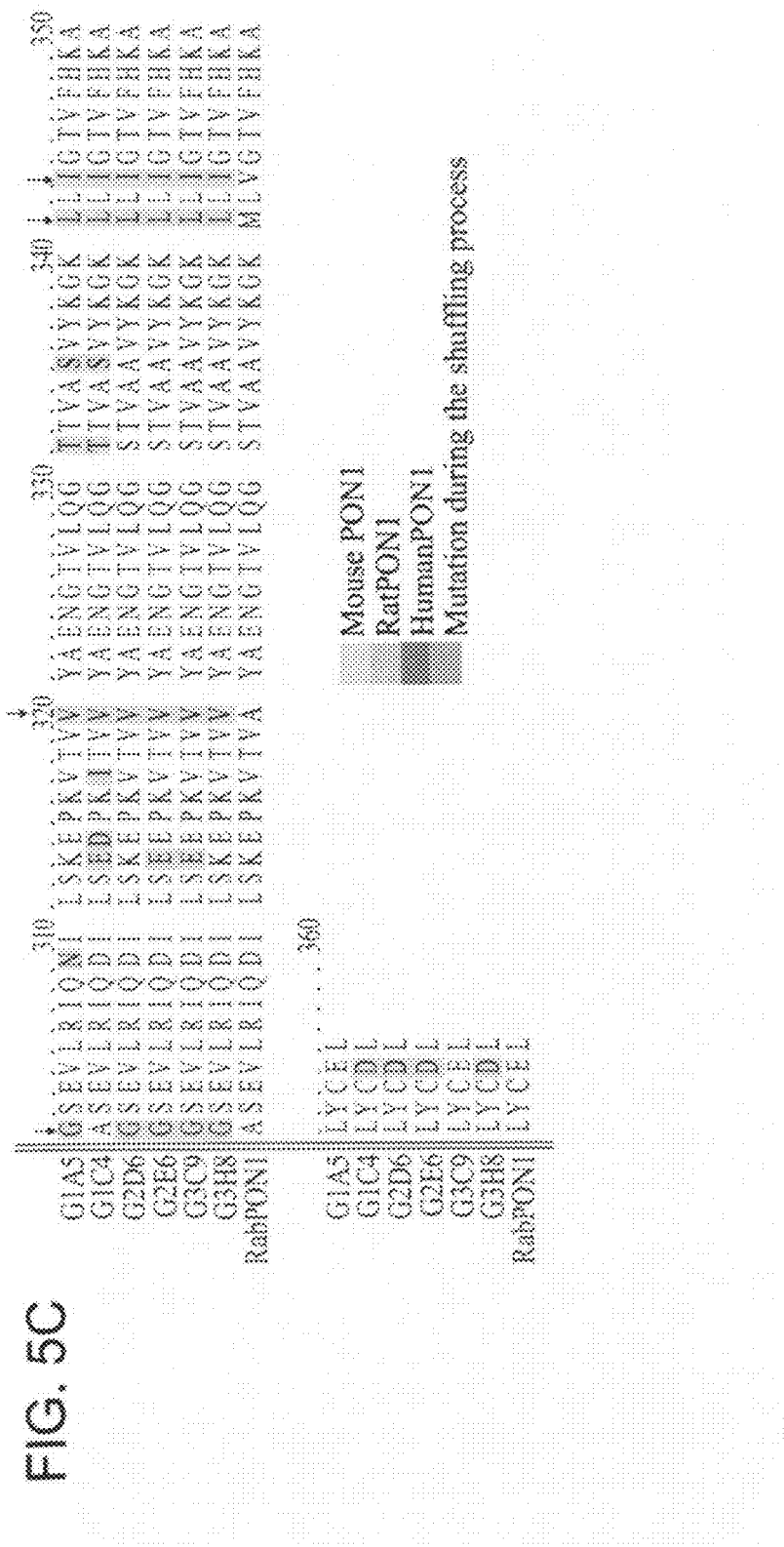

Sequence analysis—The sequences of the selected clones revealed that, as early as the first round of evolution, convergence to the RabPON1 gene has occurred with relatively small contributions from the three other parental genes (FIG. 5). This is not surprising given that the wild-type RabPON1 was the only wild-type PON1 that expressed soluble in E. coli at a measurable amount.

In all selected variants, position 192 is a lysine as in the rabbit wild-type sequence. This position is either an arginine or an Glutamine in the human R/Q PON1 isoenzymes of which the R form exhibits ~8-fold higher catalytic activity [Li (2000) Pharmacogenetics 10: 767-779]. Lysine is probably equivalent to arginine hence the resemblence of the rate parameters of the new variants to the R form of the human PON1.

Most of the mutations in the different clones analyzed (with respect to RabPON1) did not seem essential to solubility as they did not appear in all the highly-soluble variants.

Eight conserved mutations were identified, in all the selected variants located in only two regions, residues 126-142, and 301-343. The mutations in the first region are: I126T, M130L, K137S, L142V, and in the second region: A301G, A320V, M341L, V343I. Most of these mutations were fixed already at the first round of evolution (I126T, M130L, K137S, L142V, A320V, M341L, V343I; FIG. 5). Interestingly, none of the 8 conserved mutations included a drastic change. One mutation involved a change from a hydrophobic to a polar residue (I126T) and another the reverse change (A320V). But most of the mutations were in fact, from one hydrophobic amino acid into another (M130L, L142V, M341L, V343I).

The convergence of the newly-evolved PON1s towards the RabPON1 sequence may be driven by the higher stability of the wild-type RabPON1 protein (certainly with respect to hPON1) and its higher affinity to calcium. PON1s bind two calcium ions. One calcium ion is bound with higher affinity and is required for maintaining the structure; the second binds with lower affinity and is thought to be involved in catalysis (Kuo and La Du, 1998). The affinity for the first calcium is ~7 fold higher in RabPON1 relative to hPON1 ($K_d$=0.05 µM and 0.36 µM, repectively). The concentration of calcium ions in E. coli is rather low (0.3 µM) and does not exceed 0.7 µM even in the presence of high calcium concentrations in the medium (Jones et al., 1999). In the absence of calcium, hPON1 irreversibly aggregates (Kuo and La Du, 1995). The higher affinity of RabPON1 and the soluble variants that evolved from it, may have allowed them to bind calcium at sub-micromolar concentrations and stabilize the structure to prevent aggregation in the E. coli cytoplasm.

Kinetic analysis—Selected variants of the trx-rPON1 (FIG. 7a) from the first and second round of directed evolution (G1A5, G1C4, G2D6 and G2E6) and variants of rPON1 (FIG. 7c) from the third round of evolution (G3C9, G3H8), were purified to homogeneity as determined by SDS PAGE (FIG. 3).

Figure 4A:
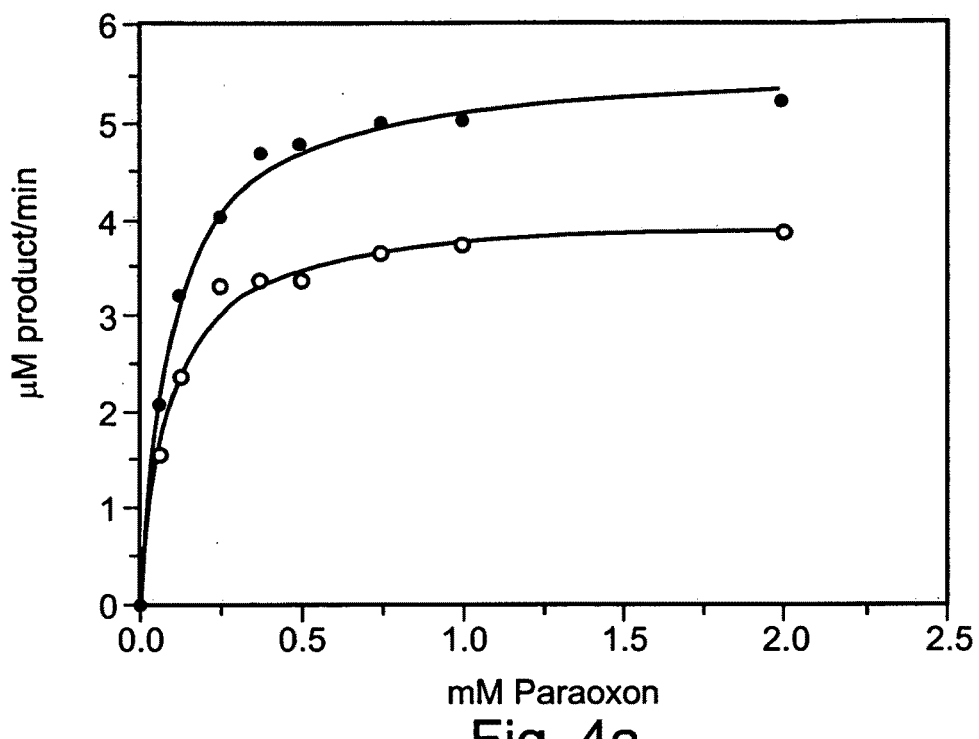
FIGS. 4a-b are graphs depicting Michaelis-Menten analysis for the paraoxon (FIG. 4a) and phenyl acetate hydrolysis (FIG. 4b) by variants G2E6 (open symbols) and G3C9 (closed symbols) from the second and third round of evolution, respectively. The rPON1 concentrations for the two variants are the same and are 0.078 μMin (FIG. 4a) and 0.0052 μMin (FIG. 4b). The kinetic parameters derived from the fit of the data to Michaelis-Menten model are listed in Table 2 below.
Figure 4B:
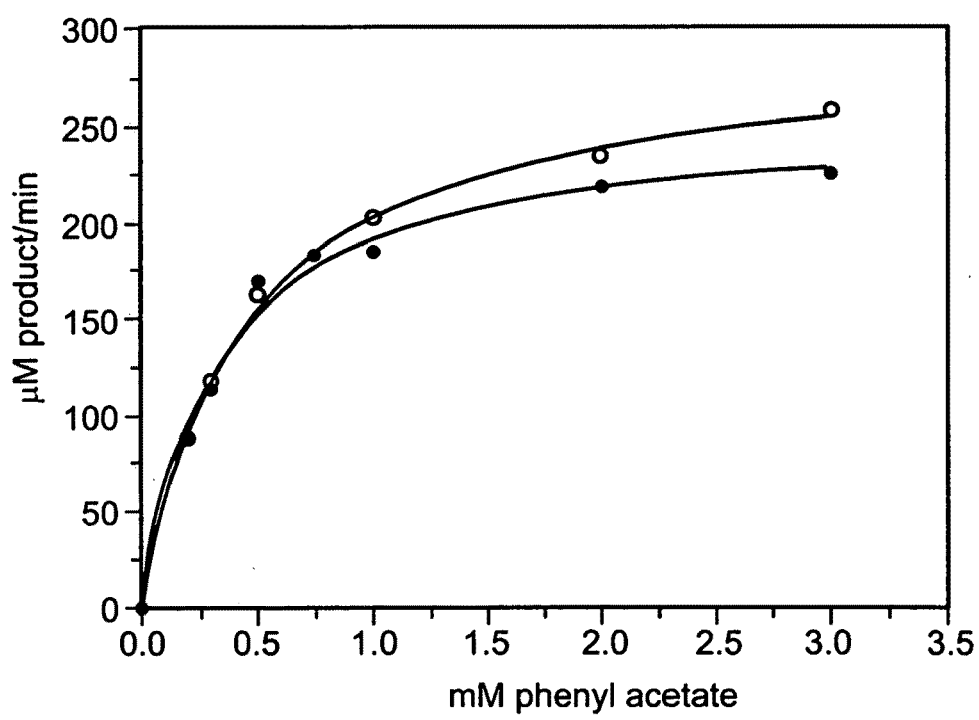

Kinetic analysis of different trx-rPON1 variants from the first and second round of evolution, with both phenyl acetate and paraoxon hydrolysis, indicated that the kinetic parameters were not significantly changed between one round to another. Variants isolated from the third round of evolution in which the enzyme was expressed without a fusion protein or any other tag (rPON1) gave similar kinetic parameters to those observed with the trx-rPON1 variants from the first and second rounds of evolution (Table 2, above, FIG. 4). It appears therefore, that the thioredoxin and tags to which the enzyme was fused in the first and second rounds did not alter its catalytic properties. Further, the kinetic parameters of the various newly evolved PON1 variants are similar to those measured with hPON1 purified from sera, although some differences were notable [e.g., the $K_M$ of the directly-evolved PON1s (0.085-0.12 mM) was significantly lower than that of hPON1 (0.54 mM)]. It should be noted, however, that the sequences of the directly-evolved PON1s appeared to be most similar to RabPON1 and not hPON1 (FIG. 5).

The kinetic parameters for RabPON1 are not reported in the literature, but comparison of the human and rabbit PON1s indicated similar substrate specificities and a very close specific activity towards phenyl acetate (Josse et al., 1999; Kuo and La Du, 1995). Such similarity is also observed between the directly-evolved PON1 derivatives from the various generations and of different constructs (trx-rPON1 vs. rPON 1, for example) and hPON1 purified from sera.

These results indicate that, following the selection pressure for a simultaneous increase in both paraoxonase and esterase activity, the evolutionary process was directed primarily towards increased solubility, and the specific activity and other catalytic properties of PON1 were not significantly altered. In each of the three rounds of the evolutionary process, variants have been identified in which the ratio of paraoxonase vs. esterase activity was significantly different than wild-type (data not shown).

The two mutated regions in the directly-evolved PON1s (amino acid 126-142, and 301-343; FIG. 5) are presumably involved in the hydrophobic packing of PON1 and its correct folding in E. coli. A recent paper described the oligomeric state of detergent-solubilized hPON1 purified from sera (Josse et al., 2002). The work highlighted the role of detergent in determining the oligomeric state of hPON1 and suggested that, in addition to the hydrophobic N-terminal leader sequence (Sorenson et al., 1999), exposed hydrophobic surfaces of hPON1 are involved in oligomerisation and aggeregation of hPON1, and its incorporation to HDL or to nonionic detergent micelles. These presumed hydrophobic surfaces may also lead to the aggregation of wild-type PON1s when expressed in E. coli. Mutations in these solvent-exposed hydrophobic surfaces may prevent misfolding and formation of high-order aggregates. These mutations, being quite subtle in their nature (see above), have probably induced minor changes in other structures and functional features of PON1 as manifested in the very similar kinetic parameters relative to wild-type PON1. In addition, analysis by gel filtration of the oligomerization state of rPON1 (C3H8, G3C9) in the presence of $C_{12}$-maltoside (0.6 mM) reveled that the protein is mostly present as a dimer, although trimers and higher aggregates could also be observed. This result is not dissimilar to the equilibrium between monomers and dimers observed with hPON1 solubilized by nonionic detergents including $C_{12}$-maltoside (Josse et al., 2002).

All wild-type PON1 posses a conserved, hydrophobic, 20 amino acid leader sequence at their N-termini. This sequence, which is not excised and is part of the mature protein, is directly involved in the binding of PON1s to HDL phospholipids (Sorenson et al., 1999). A dramatic decrease was observed upon deletion of the leader sequence of hPON1 (56 fold drop in $k_{cat}/K_M$; (Sorenson et al., 1999)). Therefore a newly-evolved clone (G1C4) without its N-terminal leader sequence was constructed (G1C4-20 N-ter amino acids; FIG. 7b). The expression levels and solubility of this clone were not decreased, and the kinetic analysis indicated only a 4-fold decrease in its catalytic activity (in terms of $k_{cat}/K_M$) for both paraoxon and phenyl acetate hydrolysis (Table 2, above). The different effect of the leader sequence on C4 vs. hPON1 could be due to differences between hPON1 and RabPON1 (no data is available regarding the effect of the leader sequence on wild-type RabPON1) and to the increased solubility of the newly-evolved PON1s. In any case, the present results suggest that the leader sequence is not directly involved in forming the active site of PON1s, nor in determining the protein's conformation. Rather, deletion of the leader sequence in PON1 affects catalysis indirectly, probably via a change in its oligomeric state or solubilization.

It is generally assumed that two out of the three cysteine residues of PON1s (Cys 42 and Cys 353) form a disulphide bond, and that formation of this bond is crucial for the correct folding and activity of rPON1 (Kuo and La Du, 1995). The formation of disulfide bonds is often hindered by the reducing environments of E. coli cytoplasm. Therefore the Origami B (DE3) bacterial strain was used in which the reduction by thioredoxin and glutathione is impaired and disulfide bond formation is therefore facilitated (Bessette et al., 1999).

The results presented herein also indicate that glycosilation of PON1 is not contributing or affecting its enzymatic function. This conclusion stems from the fact that the newly-evolved PON1s that were expressed in E. coli where no glycosylation occurs, posses kinetic parameters that are very close to wild-type PON1s (see above and Table 2). This is in agreement with the findings that mutagenesis at two putative glycosylation sites of hPON1 (N252 and N323) had no effect on its catalytic function (Josse et al., 1999).

Example 4

Homocysteine Thiolactonase Activity of rPON1 and Exclusion of Multiple Sites of Hydrolytic Activity Materials and Experimental Procedures Enzyme kinetics for L-HcyT hydrlysis—Rates for L-HcyT hydrlysis were measured with 1.4 μM purified PON1 in a Hepes buffer at pH 7.3 supplemented with 1 mM of $CaCl_2$. The L-HcyT concentration used was between 0.1-10 mM the L-Hyc formation was monitored by detecting the free thiol group with Ellman's reagent (5,5-dithio-bis-2-nitrobenzoic acid) at 412 nm ($\epsilon 7000$ $M^{-1}$ for 5-thio-2-nitrobenzoic acid). The competitive inhibitor 2-hydroxyquinoline was used at concentrations between 0-0.25 mM and used to inhibit Phenyl acetate, Paraoxon and L-HcyT hydrlysis at fixed substrates concentration (0.2 mM for Phenyl acetate, 0.25 mM for Paraoxon and 1.5 mM for L-HcyT). Kinetic parameters were determined by fitting the data directly to the Michaelis-Menten model: $V_o = k_{cat}[E]_0[S]_0/([S]_0 + K_M)$ using Kaleidograph. Inhibition constants were determined by fitting the data to a competitive inhibition model: $V_o = V_{max}[S]_0/([S]_0 + K_M(1+[I]/K_i))$.

Results

Figure 8A:
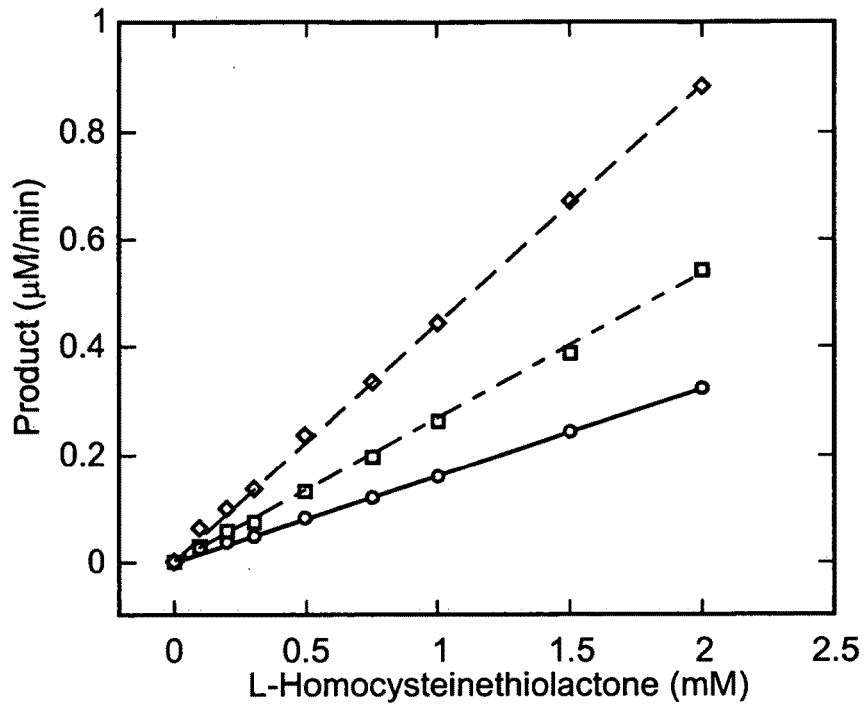
FIGS. 8a-b are steady-state plots for L-homocysteine thiolactone (L-Hcy) hydrolysis by trx-RabPON1 (FIG. 8a) and rePON1 (G3H8, expressed without fusion proteins, FIG. 8b). Diamonds denote a 1.42 μM concentration of trx-RabPON1; Squares denote an 0.6 μM concentration of trx-RabPON1; Circles denote the absence of enzyme. The concentration of rePON1 (G3H8) in FIG. 8b is 1.2 μM. Data in FIG. 8b was fitted to Michaelis Menten equation and the $K_M$ is estimated to be ~19 mM.
Figure 8B:
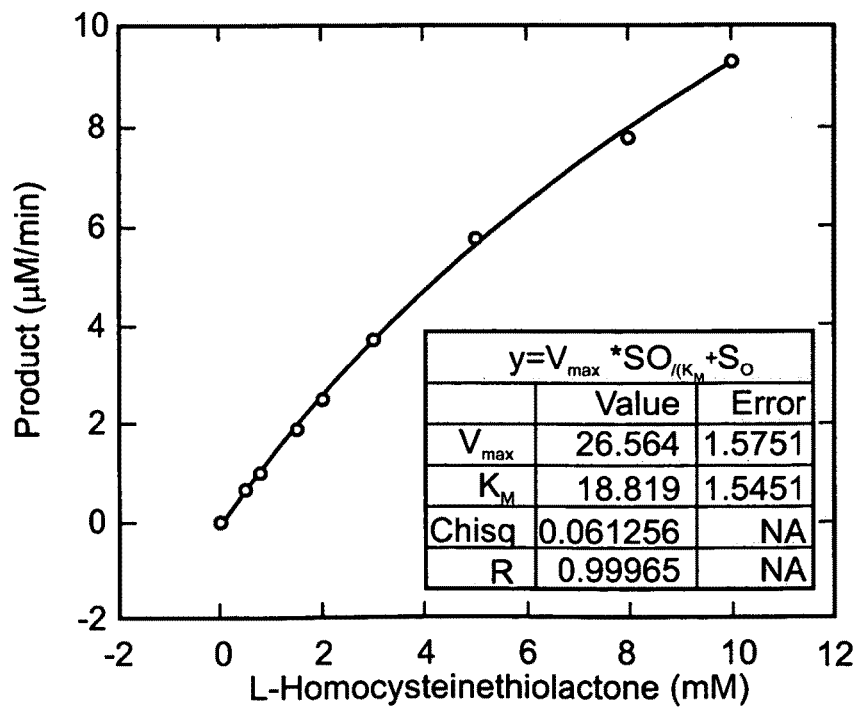

Recently it has been reported that PON1 can hydrolyze L-HcyT, which is a major risk factor in atherosclerosis [Jakubowski (2000) J. Biol. Chem. 275:3957-3962; Davies (1996) Nat. Genet. 14:334-336]. For this reason, the ability of trx-rRabPON1 and the newly evolved variants to hydrolyze L-HcyT was addressed (i.e., G1A5 and G3H8]. As is shown in FIGS. 8a-b and in Table 3, below, the $K_M$ measured for L-HcyT hydrolysis (~19 mM) was in good agreement with the $K_M$ of serum HuPON1-[23 mM, Jakubowski (2000) Supra]. These results establish the ability of the newly evolved variants to catalyze the hydrolysis of multiple substrates.

TABLE 3

| Variant[a]/ SEQ ID NO: | 2-Naphthyl acetate | | | Dihydrocoumarin | | | L-HcyT |
|---|---|---|---|---|---|---|---|
| | $k_{cat}$ (sec$^{-1}$) | $K_M$ (mM) | $k_{cat}/K_M$ (M$^{-1}$ sec$^{-1}$) | $k_{cat}$ (sec$^{-1}$) | $K_M$ (mM) | $k_{cat}/K_M$ (M$^{-1}$ sec$^{-1}$) | $k_{cat}/K_M$ (M$^{-1}$ sec$^{-1}$) |
| G1A5[a]/25 | 14 | 0.08 | 1.7 * 10$^5$ | 295 | 0.12 | 2.5 * 10$^6$ | 12.2 |
| G3H8[b]/29 | 20 | 0.11 | 1.8 * 10$^5$ | 234 | 0.076 | 3.1 * 10$^6$ | 11.6 |

[a]G1A5 was expressed fused to thioredoxin through S- and His-peptide linkers.
[b]G3H8 was expressed as the unmodified 355 aa PON1 protein without the fusion tags or protein.

Figure 9A:
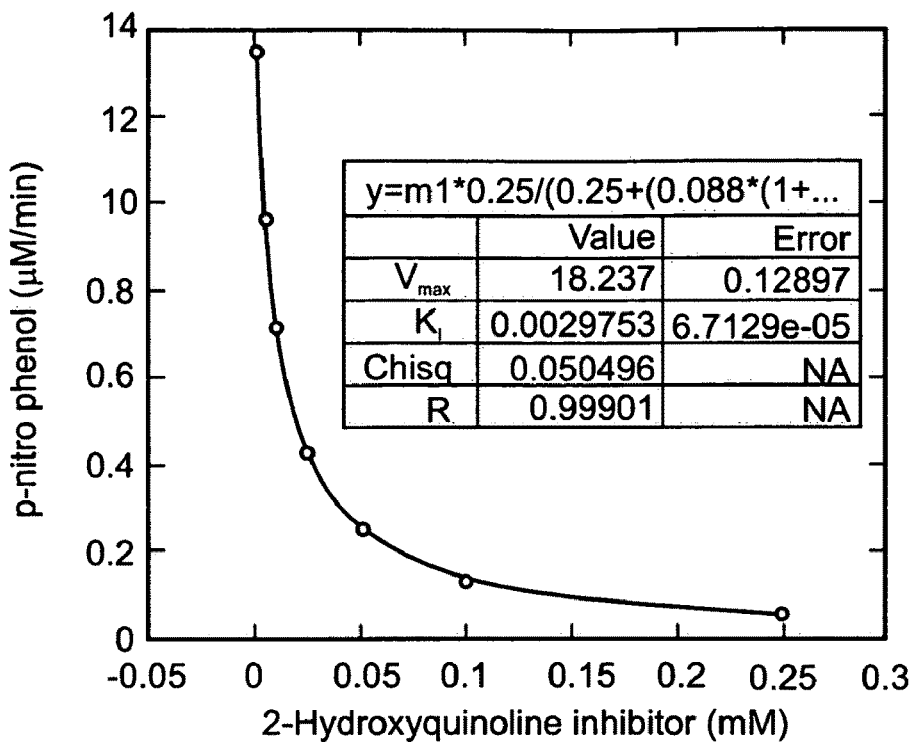
FIGS. 9a-b are plots depicting competitive inhibition of the hydrolysis of paraoxon (FIG. 9a) by 2-hydroxyquinoline and of the hydrolysis of L-Hcy (FIG. 9b) by rePON1 (G3H8, expressed without fusion proteins). Substrate concentrations were 0.25 mM for paraoxon and 1.5 mM for L-Hcy. Data was fitted to the competitive inhibition model $V_o=V_{max}[S]_0/([S]_0+K_M(1+[I]/K_i))$. Enzyme concentrations for paraoxon and L-Hcy hydrolysis were 0.625 µM and 1.9 µM respectively.
Figure 9B:
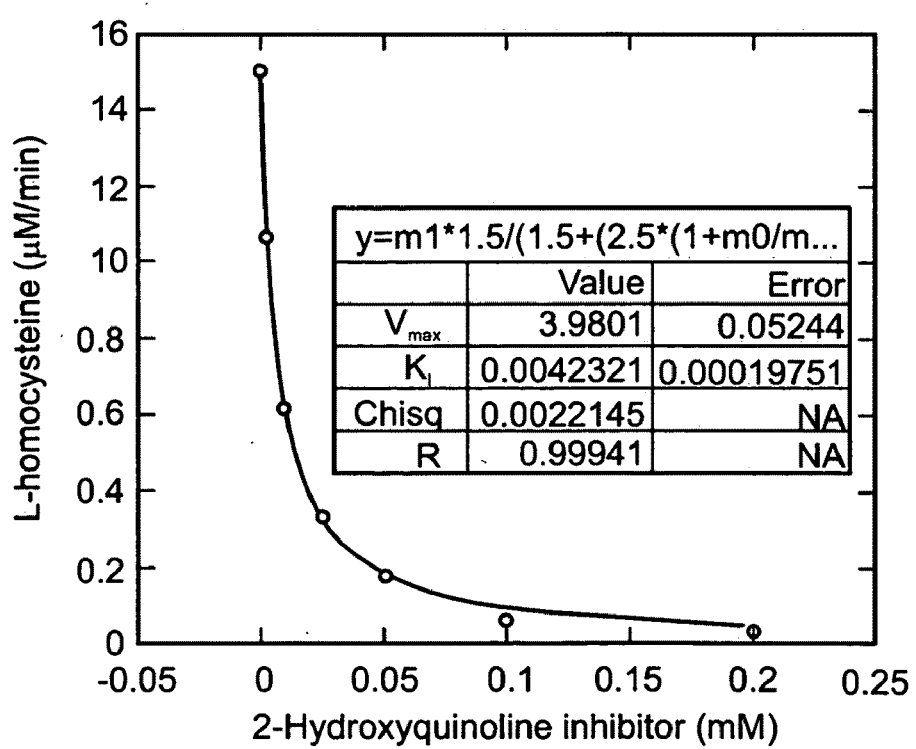

To test whether all these activities are mediated by a single catalytic site, the competitive inhibitor, 2-hydroxyquinoline, was used on clone G3H8 [Billecke (2000) Drug Metab. Dispos. 28:1335-1342]. Despite the vast differences in $K_{cat}$ and $K_M$ values, the inhibition constants for phenyl-acetate, paraxon and L-HcyT hydrolysis were found to be 3-11 μM (see Table 4, below and FIGS. 9a-b). These Values are in accordance with an inhibition constant of ~5 μM which was measured for hydrolysis of phenylacetate by serum huPON1 [Billecke (2000) Supra]. The close similarity of the inhibition constants serves as a strong indication that all three substrates are hydrolyzed at the same active site.

TABLE 4

| Substrate | $k_{cat}/K_M$ (M$^{-1}$sec$^{-1}$) | Inhibition constant ($K_i$) μM |
|---|---|---|
| Phenyl Acetate | 3.2 * 10$^6$ | 11 ± 1.0 (~5)[a] |
| Paraoxon | 1.4 * 10$^4$ | 3 ± 0.06 |
| L-Homocysteinthiolactone | 11.6 | 4.2 ± 0.2 |

[a]$K_i$ for 2-hydroxyquinoline inhibition of phenyl acetate hydrolysis by HuPON1 purified from serum[11].

Example 5

Recombinant Expression and Direct Evolution of PON3

Relative to PON1, little is known about PON3. Because of low amounts in the serum (i.e., ~50-fold lower than PON1), PON3 was only recently purified and characterized [Draganov (2000) J. Biol. Chem. 275:33435-33442; Reddy (2001) Arterioscler. Thromb. Vasc. Biol. 21:542-547] and it was not expressed in heterologous expression systems. The specific kinetic parameters of serum PON3, have not been determined, though relative activities of RabPON3 are available [Draganov (2000) supra]. For these reasons, recopmbinant PON# of various organisms was expressed in a bacterial expression system.

Materials and Experimental Procedures

Cloning of PON3 genes—The plasmid pGex-6p-2 containing the HuPON3 (GenBank Accession No. NM_000940) gene (Reddy et al., 2001) was provided by Srinivasa T. (Reddy, UCLA). This gene was used as a template for PCR amplification with a back primer (pET32-hPON3-bc, Table 5, below) and a forward primer (pGex-seq-fo, Table 5, below). The gene for MoPON3 was amplified from mouse liver cDNA (Clontech) using back primer (pET32-mPON3-bc, Table 5, below) and a forward primer (pET32-mPON3-fo, Table 5, below). RabPON3 (GenBank Accession No. AF220944) was amplified from fresh liver of New Zealand rabbits using back primer (pET32-RabPON3-bc, Table 5, below) and a forward primer (pET32-RabPON3-fo, Table 5, below). All genes were cloned into PET32b(+) (Novagen). Primers used for amplifications are listed in Table 5 below.

Construction of PON3 libraries by DNA shuffling—see Example 2, above.

Screening procedures—see Example 2, above.

Characterization of the evolved PON3 variants including purification and kinetic analysis—see Example 3, above.

Results

Recombinant expression and activities of PON3—The present inventors were able to express reasonable levels (4-6 mg/lit) of soluble and active PON3 genes when fused to thioredoxin. Serum-purified and *E. coli* expressed RabPON3s (SEQ ID NO: 41) show the same pattern of specificity with the lactone substrate, dihydrocoumarin, and the ester substrates phenyl and naphtyl acetate (see Table 6, below).

TABLE 6

| Substrate | Trx-reRabPON3 $k_{cat}/K_M$ (M$^{-1}$sec$^{-1}$) | Ratio to PA for trx-rRabPON3 | Ratio to Phenyl acetate for RabPON3 (Draganov et al)[14] |
|---|---|---|---|
| Phenyl Acetate | 278.8 | 1 | 1 |
| 2-Naphthyl acetate | 3128 | 11.2 | 4.6 |
| Dihydrocoumarin | 67901 | 243.5 | 220 |
| PNPA[a] | 331 | 1.2 | — |
| Paraoxon | 0.73 | 0.0026 | — |
| L-Hcy[b] | 0.09 | 0.0003 | — |

[a]PNPA-p-nitrophenyl acetate.
[b]L-HcyT-L-Homocysteinethiolactone.

Interestingly, very weak paraoxonase activity was observed with both mouse and rabbit PON3 (SEQ ID NOs: 42 and 41, respectively). Activity was very low (i.e., <0.1% of that of PON1) and exhibited a prolonged lag (~30 min) in onset (i.e., hysteresis). These findings indicate that the enzymatic properties of RabPON3 are not significantly altered on fusion to thioredoxin and expression in *E. coli*, and the detailed kinetic parameters obtained herein (see Table 7 below) are in general relevant to wild-type PON3s.

Directed evolution of PON3 variants—Wild-type PON3s exhibit 100- to 1,000-fold lower rates of ester and phosphotriester hydrolysis than PON1, although lactonase activities of the two enzymes are similar [Draganov (2000) supra, Reddy (2001) supra]. Their sequences exhibit 65% similarity at the amino acid level. In order to determine how far the two

TABLE 5

| Primer | SEQ ID NO: | Sequence |
|---|---|---|
| pGex-Seq-fo | 18 | 5CCGGGAGCTGCATGTGTCAGAGG 3 |
| pET32-hPON3-bc | 19 | 5CGACAAGGCCATGGGGAAGCTCGTGGC3 |
| pET32-mPON3-fo | 20 | 5GCTCGAGTGCGGCCGCTTACAGATCACAGTAAAGAGCTTTGTGG3 |
| pET32-mPON3-bc | 21 | 5CGACAAGGCCATGGGGGACCTCGTGGC3 |
| pET32-RabPON3-fo | 22 | 5GCTCGAGTGCGGCCGCTTATTAGAGTTCACAGTACAAGGCTTTCTGG3 |
| pET32-RabPON3-fo | 23 | 5CGACAAGGCCATGGCGAAGCTCCTGCTGC3 | enzymes had diverged and whether, under directed selection pressure, they might re-converge to exhibit, similar, if not identical, phenotypes, PON3 genes were subjected to directed evolution through DNA shuffling. Following three rounds of shuffling and screening of wild-type PON3 genes, a number of clones were obtained with increased rates of both ester and phosphotriester hydrolysis. Comparison of selected variants from three rounds of evolution (see Table 7, below) indicated that the evolutionary process was directed primarily toward an increase in the catalytic efficiency of PON3.

Figure 10:
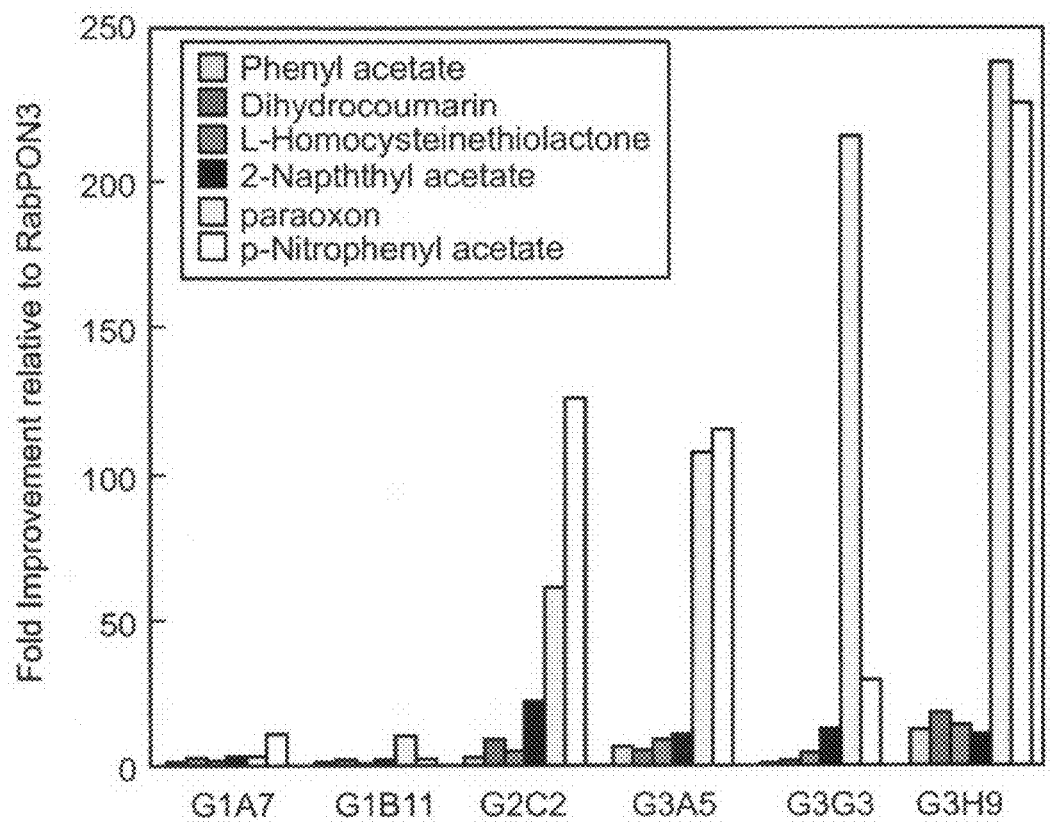
FIG. 10 is a histogram depicting improvement in catalytic specificity ($K_{cat}/K_M$) toward various substrates of variants of trx-rPON3 from different rounds of evolution as compared to wild-type trx-RabPON3. G1A7 and G1B11 are first generation variants; G2C2 is a second-generation variant; and G3A5, G3G3 and G3H9 are third generation variants. The kinetic parameters are presented in Table 7-8, below.

PON3. Following the third round of evolution, three clones were isolated (i.e., G3A5, G3G3 and G3H9), which exhibited an overall improvement of up to 240-fold in paraoxonase activity. Thus, although wild-type PON3s exhibit almost no paraoxonase activity, shuffled variants of the same genes exhibit paraoxonase activity which is only 60 fold lower than that of PON1. However, no further improvement in 2NA activity was observed with these clones (see FIG. 10 and Table 7 above). A 4- to 7-fold fold increase in the expression

TABLE 7

| Variant*/SEQ ID NO: | Paraxon hydrolysis | | | 2NA hydrolysis | | |
|---|---|---|---|---|---|---|
| | $K_{cat}$, $S^{-1}$ | $K_M$, mM | $K_{cat}/K_M^§$, $M^{-1}S^{-1}$ | $K_{cat}$, $S^{-1}$ | $K_M$, mM | $K_{cat}/K_M^§$, $M^{-1}S^{-1}$ |
| RabPON3/41, 30 | 0.001 | 1.3 | 0.73 (1) | 0.66 | 0.211 | $3.1 \cdot 10^3$ (1) |
| MoPON3/42, 32 | 0.0008 | 1.4 | 0.58 | 2.12 | 0.5 | $4.2 \cdot 10^3$ |
| G1A7/43, 49 | 0.007 | 2.5 | 2.9 (4) | 1.9 | 0.16 | $1.2 \cdot 10^4$ (3.7) |
| G1B11/44, 50 | 0.009 | 1.1 | 7.6 (10.4) | 2 | 0.18 | $1.1 \cdot 10^4$ (3.5) |
| G2C2/45/51 | 0.036 | 0.8 | 45 (62) | 18.8 | 0.26 | $7.2 \cdot 10^4$ (23) |
| G3A5/46, 52 | 0.04 | 0.51 | 78.3 (107) | ND | ND | $3.5 \cdot 10^4$ (11) |
| G3G3/47, 53 | 0.11 | 10.75 | 156.6 (215) | 26.25 | 0.65 | $4.0 \cdot 10^4$ (13) |
| G3H9/48, 54 | 0.14 | 0.8 | 175 (240) | ND | ND | $3.5 \cdot 10^4$ (11) |

*All variants described above are trx-rPON3 variants, expressed fused to thioredoxin by S and 6xHis tags.
ND—not determined.
§Noted in parenthesis is the fold improvement relative to trx-RabPON3.

As seen in Table 7, above, following the first round of evolution, a mild improvement in catalytic efficiency was observed (i.e., variants G1A7 and G1B11). Following the second round of evolution, one clone was isolated (G2C2) that exhibited 62- and 23-fold higher activity for paraxon and 2NA hydrolysis, respectively as compared to wild type Rab-level of PON3s was also observed following three rounds of evolution (see Table 8, below). Like PON1, the newly evolved PON3 could be expressed and purified, by adding a C-terminal 6xHis tag (rPON3 variant G3H9), without the thioredoxin fusion protein (and its catalytic parameters were similar to those of trx-rPON3.

TABLE 8

| Clone[a,b]/ SEQ ID NO: | PNPA[c] $k_{cat}/K_M$ ($M^{-1}sec^{-1}$) | Dihydrocoumarin[c] $k_{cat}/K_M$ ($M^{-1}sec^{-1}$) | PA[c] $k_{cat}/K_M$ ($M^{-1}sec^{-1}$) | L-Hcy[c] $k_{cat}/K_M$ ($M^{-1}sec^{-1}$) | Yeild[c] (mg/L) |
|---|---|---|---|---|---|
| RabPON3/ 30, 41 | $3.3 * 10^2$ | $6.8 * 10^4$ | $2.8 * 10^2$ | 0.09 | 5.84 |
| MPON3/32, 42 | $1.3 * 10^2$ | $7.1 * 10^4$ | $3.5 * 10^2$ | 0.16 | 3.45 |
| G1A7/ 43, 49 | $4.2 * 10^3$ (12.6) | $2.5 * 10^5$ (3.6) | $3.4 * 10^2$ (1.2) | 0.15 (1.7) | 28.8 (4.9) |
| G1B11/44, 50 | $1.1 * 10^3$ (3.5) | $1.3 * 10^5$ (1.9) | $1.3 * 10^2$ (0.5) | 0.08 (0.9) | 20.8 (3.6) |
| G2C2/ 45, 51 | $4.2 * 10^4$ (126) | $6.9 * 10^5$ (10.1) | $1.1 * 10^3$ (3.9) | 0.54 (6.0) | 28.2 (4.8) |
| G3A5 46, 52 | $3.8 * 10^4$ (116) | $4.0 * 10^5$ (5.8) | $2.1 * 10^3$ (7.5) | 0.86 (9.5) | 20.3 (3.5) |
| G3G3/ 47, 53 | $1.0 * 10^4$ (30.7) | $2.0 * 10^5$ (2.9) | $5.5 * 10^2$ (2.0) | 0.48 (5.3) | 21.5 (3.7) |
| G3H9/ 48, 54 | $7.5 * 10^4$ (227) | $1.3 * 10^6$ (19.2) | $3.6 * 10^3$ (12.9) | 1.3 (14.4) | 37.8 (6.5) |

[a]All PON3 proteins were expressed fused to thioredoxin through S- and His- linker peptides.
[b]G1, G2 and G3 designate clones isolated after the first, second and third round of evolution, respectively.
[c]The numbers in parentheses show the fold improvement relative to trx-RabPON3.

Kinetic parameters for other ester and lactone substrates (Table 8, above) revealed that the improvements in the catalytic efficiency can be divided into two groups. For the first group, which included 2NA, phenylacetate, dihydrocoumarin and L-HcyT, the increase in $K_{cat}/K_M$ values for the third-generation variants was 2- to 20-fold relative to the wild-type, trx-rRabPON3. The second group included, paraxon and p-nitrophenylacetate, for which the third-generation variants exhibited $K_{cat}/K_M$ values up to 240-fold higher than wild-type PON3 (see FIG. 10). Thus, the activity toward p-nitrophenylacetate co-evolved with that of paraxon, whereas all the other substrates showed a much milder improvement. It is appreciated that this does not indicate the existence of two catalytic sites or subsites, rather the common feature of p-nitrophenylacetate and paraxon is the p-nitrophenol-leaving group. The co-evolution of the two substrates suggests that hydrolysis of both carboxy- and phospho-esters occur by means of the same mechanism and at the same site.

Figure 11A:
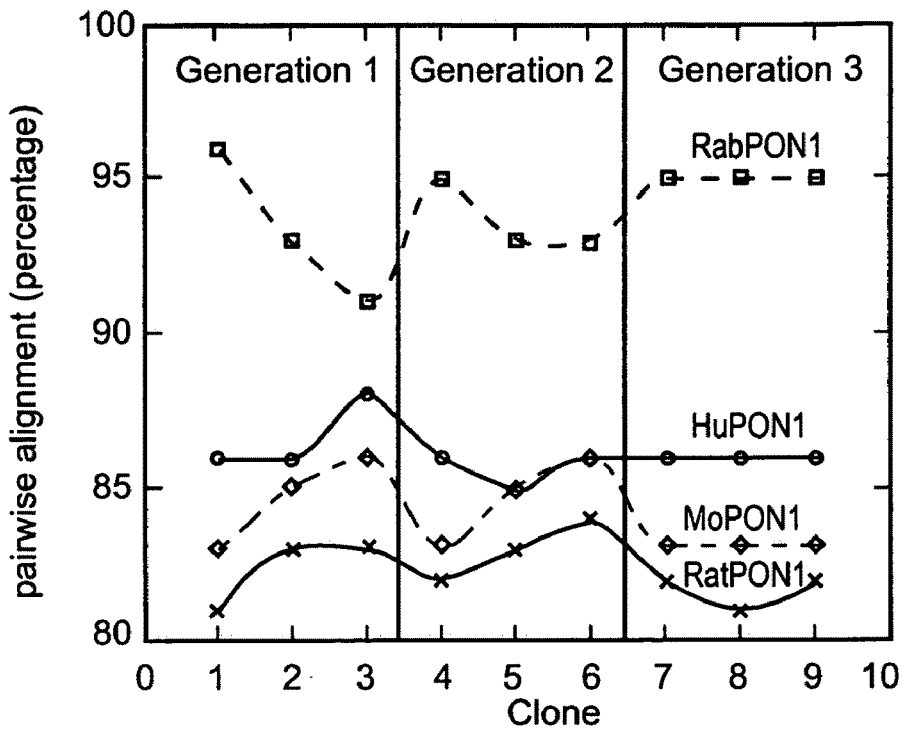
FIG. 11a-b are graphs depicting nucleic acid sequence alignments of selected clones from three rounds of evolution with their parental genes.
Figure 11B:
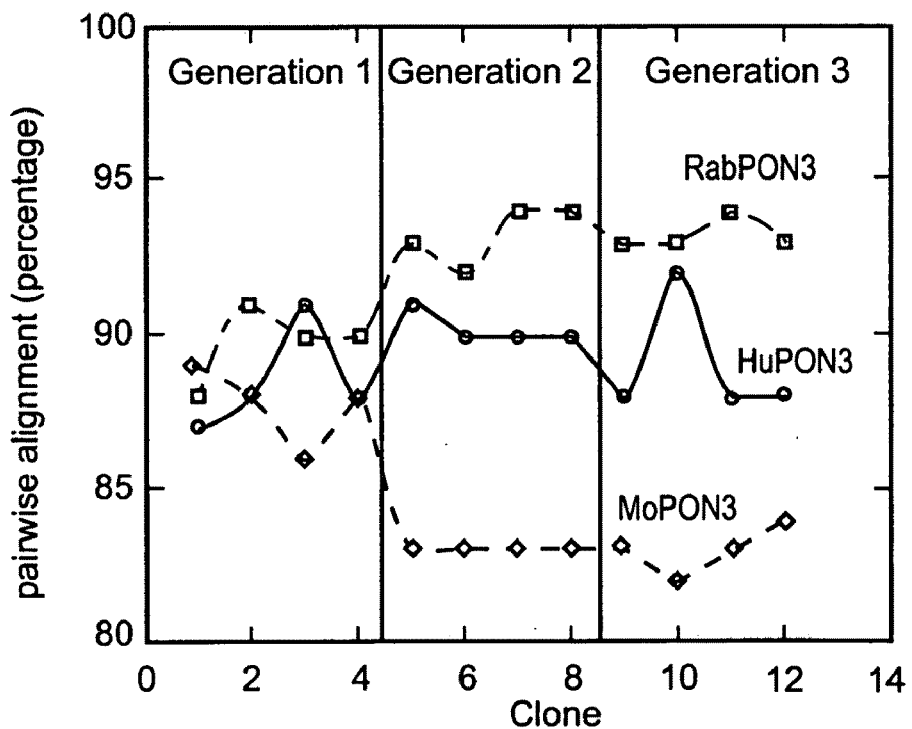

Sequence analysis of the selected rPON3 variants indicates that the parental genes are evenly represented in variants of the first round of evolution (FIG. 11b). Alignment of variants from the second and third rounds of evolution revealed that, although the sequence similarity between the selected clones is very low, the RabPON3 gene is mildly over-represented relative to the HuPON3 and MoPON3 genes. These subtle patterns of convergence in the sequences of the selected PON3 are in contrast to the clear convergence of the PON1 newly evolved variants (see FIG. 5 and FIG. 11a).

Example 5

Newly Evolved OP-Selective rPON1 Variants rPON1 variants presented in Example 3 above, were used as the starting point for evolution of PON1 variants with improved paraoxonase or esterase activity.

Experimental Procedures

Mutagenesis—Error-prone PCR libraries were derived from highly soluble rePON1 variant G3C9 gene using wobble-base PCR essentially as described [Zaccolo (1996) J. Mol. Biol. 255:589-603]. Briefly, the reG3C9 gene was PCR-amplified from a plasmid template using standard conditions, except that the nucleotide analog 6-(2-deoxy-d-ribofuranosyl)-3,4-dihydro-8H-pyrimidino-[4,5-c][1,2]oxazin-7-one-triphosphate (dPTP) was added at either 1/8 (25 μM) or 1/16 (12.5 μM) the concentration of the other four dNTPs (200 μM). In a separate reaction, 8-oxo-2'-deoxoguanosine (8-oxo-dGTP) was added at 200 μM. PCRs were performed for either 5 or 5, 10 and 15 cycles with dPTP and 8-oxo-dGTP, respectively, resulting in 5 different libraries. The PCR-amplified libraries were recloned into pET32-tr and plasmids comprising libraries were prepared as described above. The average number of synonymous mutations per gene was 5-10 for the dPTP and 3-8 for the 8-oxo-dGTP libraries, respectively.

Synthesis of 7-O-Diethylphosphoryl-(3-cyano-7-hydroxycuomarin) (DEPCyC)—Triethylamine (0.6 ml, 4.3 mmol) was added to a suspension of 3-cyano-7-hydroxycoumarin (Indofine, N.J.; 562 mg, 3 mmol) in dichloromethane (50 ml) containing diethylphosphorochloridate (0.61 ml, 4.2 mmol). The mixture was stirred for 3 h at room temperature, by which time the insoluble 3-cyano-7-hydroxycoumarin had almost completely disappeared. TLC on silica (solvent: 5% methanol in dichloromethane) indicated the disappearance of the fluorescent starting material (Rf<0.1) and a non-fluorescent product with Rf≈0.7. The reaction mixture was diluted with dichloromethane (100 ml) and extracted twice with 0.5N HCl, once with 0.1M $NaHCO_3$ and finally with brine acidified with HCl. The reaction mixture was dried over $Na_2SO_4$, the organic solvent evaporated, and the product purified by chromatography on silica using the same solvent system as for TLC. Recrystallization in dichloromethane-ether gave a white crystalline solid (650 mg; 68% yield). $^1H$ NMR ($CDCl_3$): 8.22 (s, 1H), 7.57 (d, J=8Hz, 1H), 7.27 (m, 1H), 7.25 (d, J=5.5Hz), 4.28 (m, 4H), 1.36 (m, 6H).

Results

Gene libraries of the highly soluble rPON1 variant, G3C9, were prepared by random mutagenesis using the wobble-base PCR method with either dPTP or 8-oxo-dGTP nucleoside analogs [Zaccolo (1996) J. Mol. Biol. 255:589-603]. The number of mutations per gene was adjusted by varying the concentration of dNTP analogs and the number of PCR cycles. Five libraries were generated: two dPTP libraries with 98% transitions, an average of 5-14 mutations per gene, and 20% to 6% residual activity in the pools of genes, respectively; and three 8-oxo-dGTP libraries with an average of 85% transversions, 3-10 mutations per gene, and 13% to 7% residual activity. In addition to the plate screen for 2NA hydrolysis described above, the libraries were directly screened on agar plates, negating the use of replication, for the hydrolysis of a newly synthesized fluorogenic OP substrate, DEPCyC [see FIG. 25]. DEPCyC is a close homologue of the insecticide, coumaphos, previously used for the directed evolution of a bacterial phosphotriesterase [Harcourt (2002) Lett. Appl. Microbiol. 34:263-268; Yang (2003) Protein Eng. 16:135-145]. The substrate exhibits higher fluorescence at a more convenient wavelength (408 nm). Screening of ~$10^3$ to $10^4$ colonies from each library with 2NA yielded variants with mildly improved activity against OP substrates. The best variants were re-shuffled and screened directly with DEPCyC, yielding a highly improved variant, reG3C9.49 that carried four mutations: G19R, S193P, N287D and V346A. The V346A mutation appeared in other improved variant, suggesting its primary role in the enhancement of DEPCyC-hydrolyzing activity.

Figure 12B:
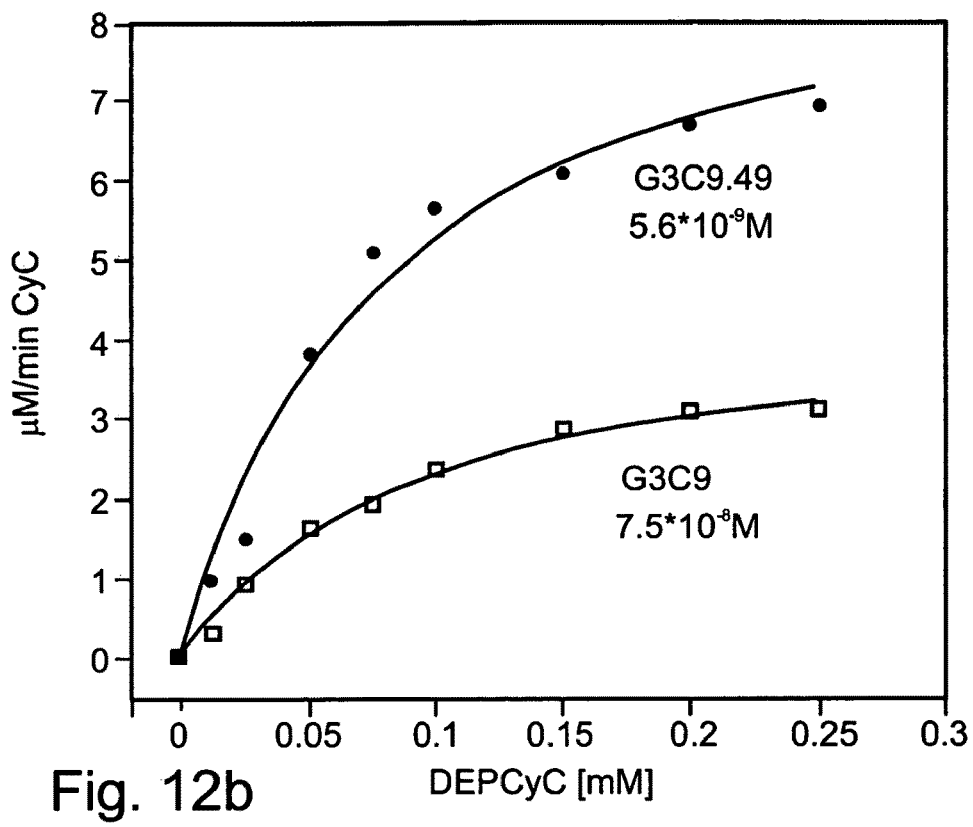

The first generation 8-oxo-dGTP libraries were also screened directly with DEPCyC to yield another highly improved variant, reG3C9.10, which contained two mutations, L69V and E218D. The two clones were purified and analyzed as described in FIGS. 12a-b and in Table 9, below.

TABLE 9

| Variant*/SEQ ID NO: | DEPCyC hydrolysis[§] | | | Phenylacetate hydrolysis | | | Selectivity factor $K_{cat}/K_M$ (DEPCyC)/ $K_{cat}/K_M$(PA) |
|---|---|---|---|---|---|---|---|
| | $K_{cat}$, $S^{-1}$ | $K_M$, mM | $K_{cat}/K_M$, $M^{-1}S^{-1}$ | $K_{cat}$, $S^{-1}$ | $K_M$, mM | $K_{cat}/K_M$, $M^{-1}S^{-1}$ | |
| G3C9/55, 56 | 0.8 | 0.07 | $1.1 \cdot 10^4$ | 789 | 0.33 | $2.4 \cdot 10^6$ | 0.0046 |
| G3C9.10/62, 63 | 25.7 | 0.05 | $4.8 \cdot 10^5$ | 39.6 | 0.76 | $5.2 \cdot 10^4$ | 9.2 |
| G3C9.49/64, 65 | 28.1 | 0.08 | $3.6 \cdot 10^5$ | 12.4 | 0.3 | $4.1 \cdot 10^4$ | 8.8 |

Figure 12B:
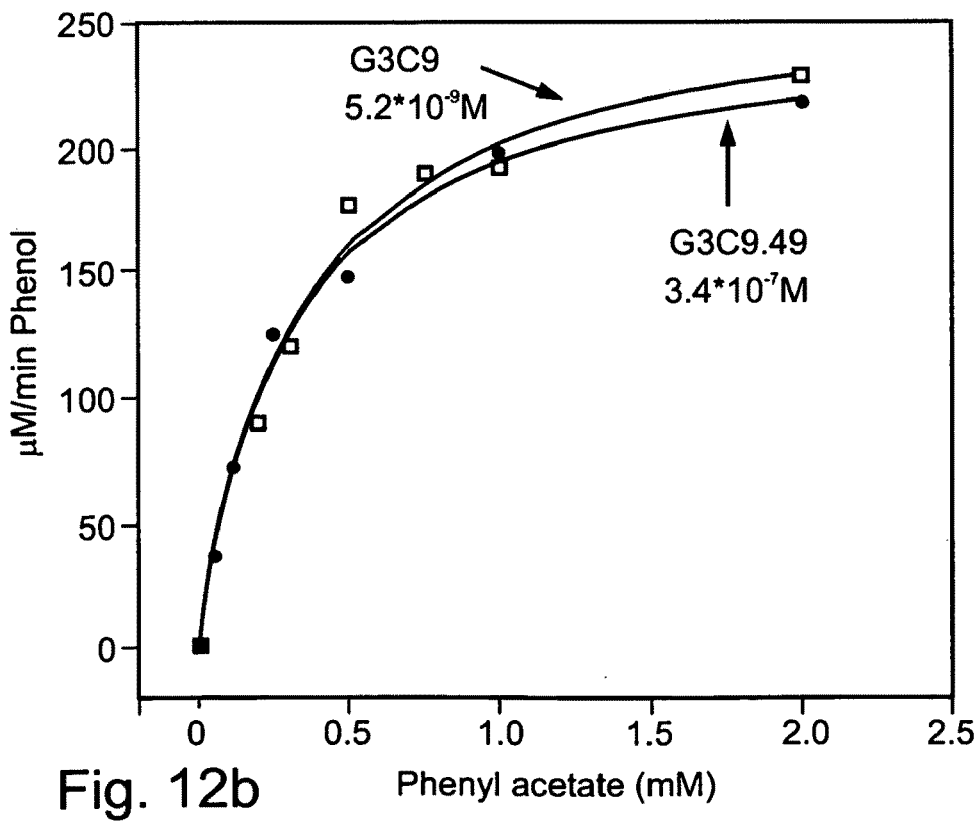

*All rPON1 variants above include the unmodified 355-aa PON1 protein without any additions.
[§]see FIG. 12.

The mutations affected the specific activity toward DEP-CyC and phenylacetate, whereas the expression level of the two selected variants was not altered. Both variants exhibited a ~40 fold increase in catalytic proficiency ($K_{cat}/K_M$) toward DEPCyC compared with wild-type PON1 and its recombinant variant G3C, and a simultaneous 50-fold reduction in catalytic proficiency toward phenylacetate. The change in catalytic efficiencies, resulted primarily from changes in Kcat values for both substrates. Both variants showed a similarly reduced activity with other esters (e.g., 2NA) and mildly improved activity with another OP substrate (paraxon).

Thus, in contrast to wild type PON1 which is essentially an esterase with very weak phosphotriesterase activity, the directly evolved variants were converted into a phosphotriesterase with weak esterase activity. Noteworthy are the subtle nature of mutations, which led to the shift in specificity and the fact that mutations at two different locations (i.e., V346A in rG3C9.49 vs. L69V in E218D in rG3C9.10) produce the same shift.

Example 6

Crystallization and Structure Elucidation of PON1

Previous attempts to determine the structure of PON1 relied on limited amounts of serum-purified proteins and led to the crystallization of a protein that co-purified with it [A. Fokine et al., Acta Crystallogr D Biol Crystallogr 59, 2083 (2003)]. Human PON1 is rather unstable, and tends to aggregate in the absence of detergents [D. Josse et al., J Biol Chem 277, 33386 (2002)]. For these reasons, soluble recombinant PON1 variants generated according to the teachings of the present invention (see Examples 1-3 above) were used for performing detailed evolutionary, mechanistic and structural studies of PON enzymes.

Materials and Experimental Procedures

Expression and purification of native rePON1-G2E6 and its SeMet derivative—rePON1-G2E6 was expressed in fusion with thioredoxin (Trx) and purified essentially as described above. During the course of the purification and crystallization attempts it was noticed that during storage, the linker between the Trx and rePON1 was spontaneously cleaved and the crystals were comprised of intact rePON1. The origins of this cleavage are still under investigation. It was observed in all rePON1 variants, and could even be mediated by PON1 itself. Subsequent crystallizations were set up with the cleaved and purified rePON1 as described below. Following purification of the Trx fusion by Ni-NTA and ion exchange, the protein was incubated at 25° C. for ten days. The cleavage was monitored by 10% SDS gel and mass spectrometry. The cleaved protein was concentrated and applied to HiLoad 26/60/Superdex 200 (preperative grade, Pharmacia). Fractions from the main peak were analyzed by 10% SDS gel, and enzymatic activity, pooled, and concentrated to 10 mg/ml. Sodium azide was added to a concentration of 0.02%. Mass spectrometry indicated a mass of 40223±201 Da. N-terminal Edman sequencing gave the following sequence: $H_2N$-DDDKAM. Both data are consistent with cleavage of the linker 5 amino acids (expected mass spec 40108Da) before the methionine residue that comprised PON1's first amino acid.

The SeMet labeled rePON1-G2E6 was obtained as follows: pET 32b plasmid containing rePON1-G2E6 (see Example 1) was freshly transformed to B834(DE3) cells and plated on an LB agar plates supplemented with Ampicilin. Colonies from three agar plates were scraped and rinsed (by resuspention and centrifugation) with M9 salt solution supplemented with 2 mM $MgSO_4$, 0.4% Glucose, 25 μg/ml $FeSO_4$, 40 μg/ml of each of the 20 natural amino acid except L-methionine, 40 μg/ml of Seleno-L-Methionine, 1 μg/ml of vitamins (Riboflavin, Niacinamide, Pyridoxine monohydrochloride and Thiamine) and 100 μg/ml of Ampicilin. Typically, 1 L of M9 minimal media with the above supplements was inoculated with 5 ml of rinsed E. coli colonies and grown at 30° C. to $OD^{600\ nm}$ of 0.7. Cultures were then transferred to 20° C. and IPTG added to 0.5 mM. Growth was continued for another 36 hours at 20° C. after which, cells were harvested, lysed and purified as above. Mass spectrometry indicated the incorporation of six SeMets per rePON1 including the Trx tag. Purification, cleavage of the Trx fusion, and isolation of rePON1 were performed as above.

Crystallization, data collection and structure refinement—Crystallization: The rePON1 crystals were grown using the crystallization Douglas Instruments robot IMPAX 1-5 microbatch method. Native crystals grew in 3 days from an optimization grid varying the protein concentration from 1.1 to 4.5 mg/ml and the mother liquor (20% PEG 3350, 0.2M $NaH_2PO_4$) from 50 to 62.5% concentration. The drops consisted of 0.3 μL protein and 0.3 μL mother liquor. The crystals were cryoprotected with a gradient of 5%-15% glycerol. The SeMet protein crystals were grown in an optimization grid, varying the protein concentration from 1.1 to 5.5 mg/ml and the mother liquor (0.17M $NH_4Ac$, 0.085M citrate buffer pH 5.6, 25.5% PEG 4000, 15% glycerol) from 25 to 45% concentration.

Data collection: 3 X-ray datasets were collected from the SeMet protein crystal at 100K at Se peak wavelength (0.9794 Å) in order to increase the redundancy and accuracy of the Se anomalous signal while monitoring the extent of radiation damage. A data set of the native crystal was collected at a wavelength of 0.9796 Å. Data were collected on beamline ID14-4 at the European Synchrotron Radiation Facility (ESRF) and processed with XDS [Kabsch (1993)]. Data collection statistics are given in Table 10, below.

Molecular replacement (MR): Although PON1 bears no sequence similarity to any other protein sequence, it was suggested that it may have a 6-beta propeller conformation. As a consequence, we attempted to solve its structure by MR using the structure of 3-carboxy-cis, cis-muconate lactonizing enzyme (PDB-code 1 jof) as a search template. A weak but still significant MR peak was found by the maximum likelihood program PHASER [Storoni (2004)]. Although this did not result in structure solution, it did help in selecting the correct space group ($P4_32_12$).

Structure solution and refinement: 3 Se sites were located on the basis of the anomalous difference using SHELXD after local scaling using XPREP [Uson (1999)]. SHELXE confirmed the correct space group and solvent content. Good experimental SIRAS (single isomorphous replacement anomalous scattering) phases were obtained using the program SHARP [Fortelle (1997)] while refining 3 Se sites against the 2.2 Å native and 2.6 Å Se SAD data, resulting in an overall figure of merit (FOM) of 0.11/0.06 for the acentric/centric reflections respectively. The isomorphous difference phasing power was very low (0.22 overall) due to the lack of isomorphism between the native and SeMet data sets, however, the anomalous phasing power for the SeMet SAD data set was good to at least 4 Å (0.74 overall). Phases were improved by applying solvent-flipping density modification using SOLOMON [Abrahams (1996)] as directed by SHARP using a 63% solvent content giving an overall FOM of 0.88. An automated tracing program ARP/wARP [Perrakis (1999)], using native amplitudes to 2.2 Å, coupled with experimental phase-restraints resulted in an automatic tracing of ca. 95% of the chain. Manual model completion was performed using program O [Jones (1999)] iterated with refinement using REFMAC [Murshudov (1999)]. The refinement and model statistics are listed in Table 10, below.

Results rPON1 variants exhibiting enzymatic properties essentially identical to those of wild-type (wt) PON1, and similar biological activities in inhibiting LDL oxidation and mediating macrophage cholesterol efflux were used for crystallization.

An interesting correlation was observed between solubility and degree of evolution towards bacterial expression, and the tendency to crystallize. Variants from the $1^{st}$ round of evolution (e.g., variants G1A5 and G1C4, see Example 1-4, above) aggregated, and none crystallized. The $2^{nd}$-generation variants (obtained by shuffling of the $1^{st}$ generation variants and screening for highest expression levels) did not aggregate, and at least one (G2E6) gave stable and well diffracting crystals. rPON1-G2E6 exhibits 91% homology to wt rabbit PON1 with the vast majority of variations deriving from human, mouse, or rat wt PON1. Rabbit and human PON1s are also highly homologous in sequence (86%) and function. Sequence variations between rPON1-G2E6 and rabbit and human PON1 are in regions that do not affect their active sites and overall structures (see FIGS. 13-14a-b.).

Table 14, below, lists amino acid changes in G2E6 relative to Rabbit PON1.

The refined 2.2 Å crystal structure of rPON1 (R-factor 18.5%; R-free 21.7%) contains one molecule per asymmetric unit. It was solved by single isomorphous replacement anomalous scattering (SIRAS) from data collected on crystals of the native protein and the selenomethionine (SeMet) protein at 2.6 Å resolution (Table 10, below). The structure shows all residues except N-terminal residues 1-15 and a surface loop (72-79). Two calcium atoms, a phosphate ion, and 115 water molecules are also seen.

TABLE 10

Part A: Data collection

| | Native[a] | SeMet protein[b] |
|---|---|---|
| Wavelength (Å) | 0.9796 | 0.9794 |
| Unit cell (Å) | 98.44, 139.17 | 98.49, 139.56 |
| Space group | $P4_32_12$ | $P4_32_12$ |
| Resolution range (Å) | 20-2.2 | 30-2.6 |
| Number of unique reflections | 35,312 | 39,473 |
| Completeness (%)[c] | 99.7 (97.9) | 97.8 (97.7) |
| I/σ(I)[c] | 12.7 (2.7) | 13.7 (4.2) |
| $R_{sym}$(I) (%)[c] | 8.6 (66.1) | 10.4 (51.0) |

Part B: Refinement and model statistics[d]

| | |
|---|---|
| Resolution range (Å) | 20-2.2 |
| Number of reflections | 33,505 |

TABLE 14

| Group | Mutations[a,b] | Origin[c,d] | Location and nature[e] |
|---|---|---|---|
| I | T126, L130, S138, V143, G301, V320, L341, I343 | wild type Human, Mouse, Rat, PON1c | hydrophobic core; conserved residues among all soluble PON variants. |
| II | M12, K93, E94, A96, S98, E101, I103, N105, L107, I109, I121, E149, V261, S263, D265, F293, A296, E297, E313, D354. | wild type Human, Mouse, Rat, PON1c | protein surface; non-conserved between different soluble PON1 variants. |
| III | R19, D123, R260 | Mutationd | protein surface |

[a]The rePON1-G2E6 sequence was aligned to the Rabbit PON1 protein sequence using ClustaWI. Amino acid identities are to rePON1-G2E6 sequence.
[b]positions highlighted in red were also found to be mutated in the directed evolution of PON1 for catalytic specialization (see Table 2 and article text

| Group | Mutationsa, b | Originc, d | Location and naturee |
|---|---|---|---|
| I | T126, L130, S138, V143, G301, V320, L341, I343 | wild type Human, Mouse, Rat, PON1c | hydrophobic core; conserved residues among all soluble PON variants. |
| II | M12, K93, E94, A96, S98, E101, I103, N105, L107, I109, I121, E149, V261, S263, D265, F293, A296, E297, E313, D354. | wild type Human, Mouse, Rat, PON1c | protein surface; non-conserved between different soluble PON1 variants. |
| III | R19, D123, R260 | Mutationd | protein surface |

Figure 14A:
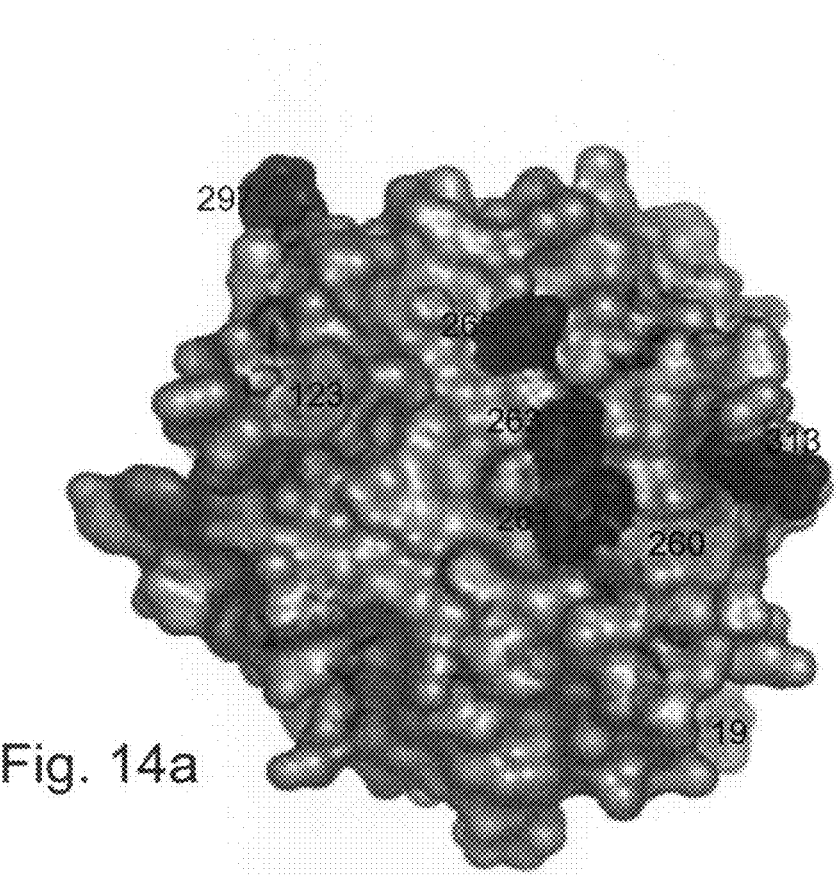
FIGS. 14a-b are schematic illustrations depicting-two surface representations of the side of the β-propeller—one rotated 180° relative to the other. The amino acid variations between rPON1 variant G2E6 and wt RabPON1 are marked: In red are amino acids that originate from Human, Mouse and Rat PON1 and are conserved among all the E. coli expressed rPON1 variants (Table 14, below, group I). In blue—amino acids that originate from Human, Mouse and Rat PON1 and are not conserved among soluble rPON1 variants (Table 14, below, group II). In green—amino acids that were mutated during the DNA shuffling process. (Table 14, below, group III).
Figure 14B:
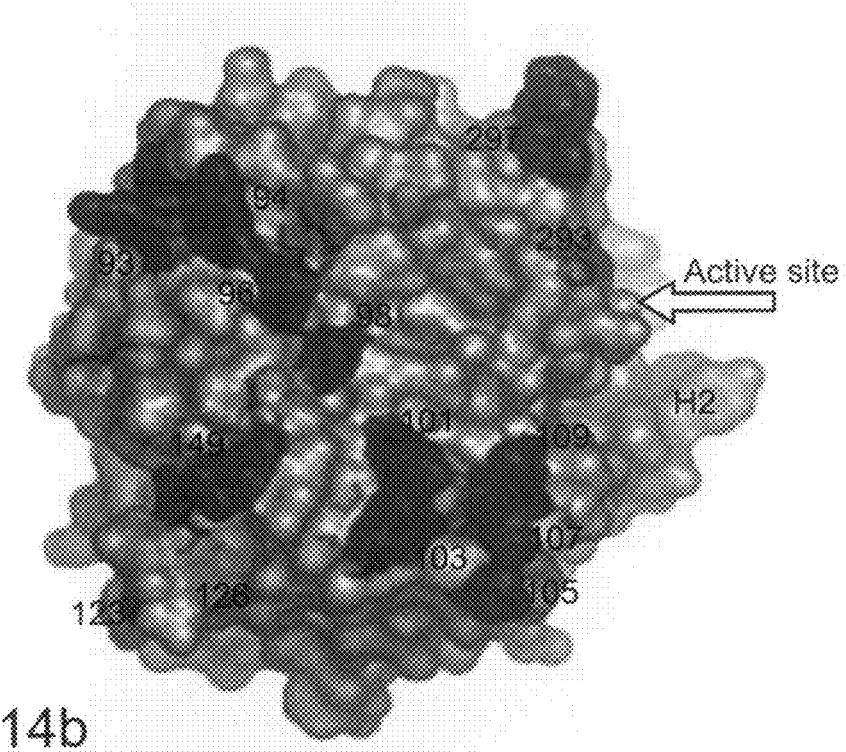

[a]The rePON1-G2E6 sequence was aligned to the Rabbit PON1 protein sequence using ClustaWI. Amino acid identities are to rePON1-G2E6 sequence.
[b]positions highlighted in red were also found to be mutated in the directed evolution of PON1 for catalytic specialization (see Table 2 and article text for additional information).
[c]Positions identical to Human, Mouse and Rat PON1 sequence.
[d]Mutations that occurred during the shuffling process.
[e]The precise locations of these amino acids on PON1's structure are shown in FIG. 14a-b. for additional information).
[c]Positions identical to Human, Mouse and Rat PON1 sequence.
[d]Mutations that occurred during the shuffling process.
[e]The precise locations of these amino acids on PON1's structure are shown in FIG. 14a-b.

TABLE 10-continued

| | |
|---|---|
| R-factor: work, free (%) | 18.5, 21.7 |
| Average B-factors (Å$^2$) | 347.6 |
| RMSD from ideal values: | |
| Bond length (Å) | 0.028 |
| Bond angle (°) | 2.02 |
| Dihedral angles (°) | 28.7 |
| Improper torsion angles (°) | 2.06 |
| Estimated coordinate error: | |
| Low resolution cutoff (Å) | 5.0 |
| ESD from Luzzati plot (Å) | 0.32 |
| ESD from SIGMAA (Å) | 0.34 |
| Ramachandran outliers (%)$^e$ | 3.9 |

$^a$The structure was determined for rePON1 variant G2E6 (sequence is given in FIG. 13). rePON1-G2E6 was expressed and purified in fusion with thioredoxin (via a linker containing a 6His tag) [A. Aharoni et al., Proc. Natl. Acad. Sci. USA 101, 482 (2004)]. The Trx tag was cleaved, leaving rePON1's intact sequence plus 4 amino acids from the linker peptide. The purified protein was crystallized using the Douglas Instruments robot IMPAX 1-5 microbatch method.
$^b$The SeMet rePON1-G2E6 was expressed, purified and crystallized as above, but from a different mother liquor. Details for the native and SeMet protein are provided in the Supplementary experimental section.
$^c$Data for the outer shell given in parentheses.

Figure 15B:
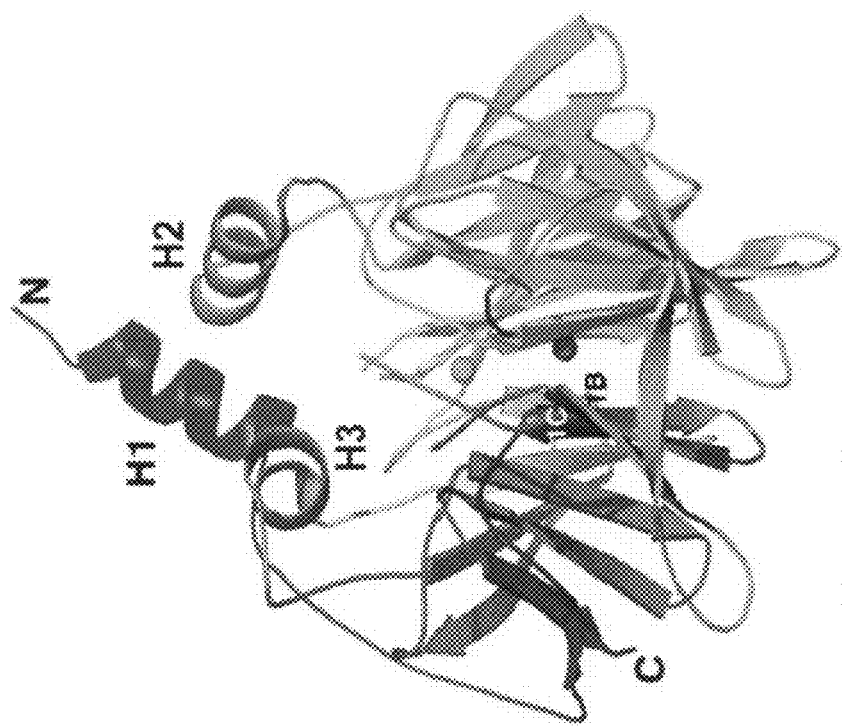
FIGS. 15a-b are schematic representations depicting the overall structure of PON1.
Figure 15A:
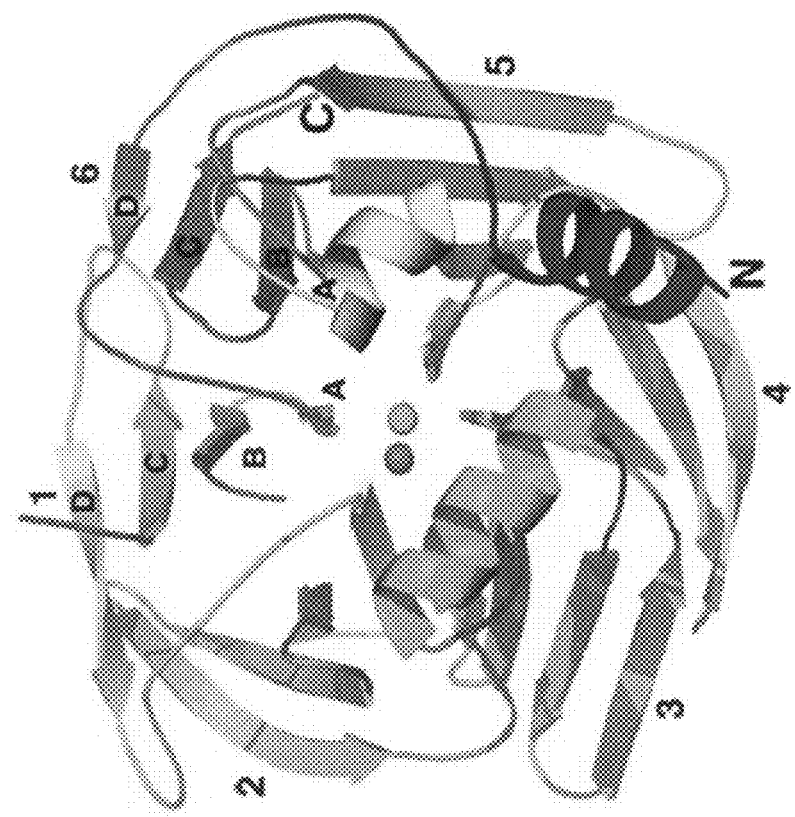

The overall architecture of PON1—PON1 adopts the fold of a 6-bladed β-propeller, with each blade containing 4 strands (FIGS. 15a-b). The 'velcro' closure characteristic of this fold is between the fourth strand of blade 6 (6D) coming from the N-terminus, and the third strand of blade 6 (6C) that comprises the C-terminus of the protein. This consensus interaction [Z. Jawad, M. Paoli, Structure 10, 447 (2002)] is complemented by a disulphide bridge between Cys42 (strand 6D) and Cys353 (strand 6C). This covalent closure of the N- and C-termini is rarely seen in β-propellers with more than four blades, but is conserved throughout the PON family (see below).

Figure 16:
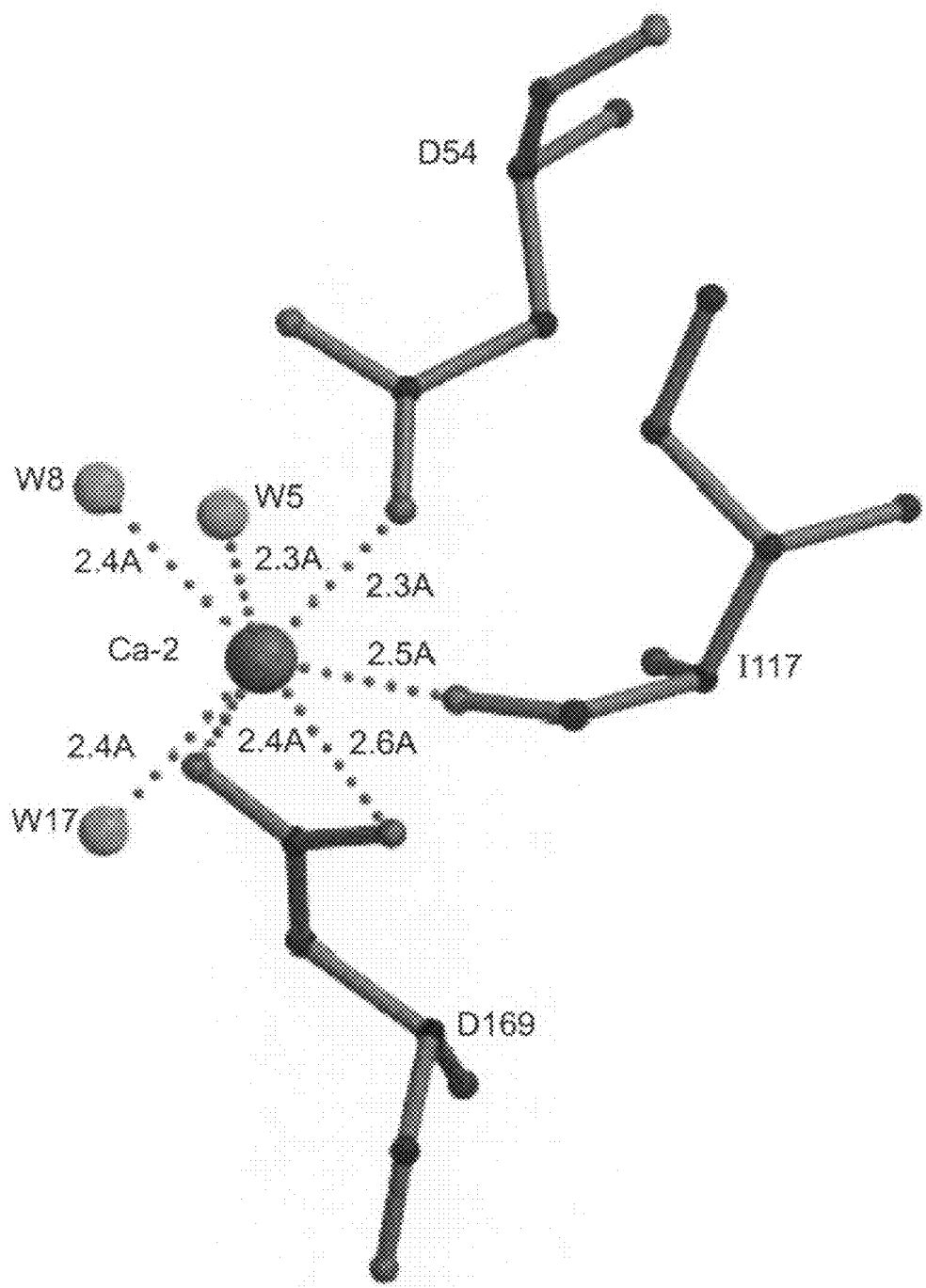
FIG. 16 is a view of the binding site for the inner calcium (Ca-2) in crystallized PON1.

Two calcium ions, 7.4 Å apart, were seen in the central tunnel of the propeller: one at the top (Ca-1) and one in the central section (Ca-2). Ca-2 is most probably a 'structural calcium' whose dissociation leads to irreversible denaturation [C. L. Kuo, B. N. La Du, Drug Metab Dispos 26, 653 (1998)]. It appears to be ligated to three protein residues (the carboxylate oxygens of Asp54 and Asp169 and the backbone carbonyl of Ile117) and three water molecules (FIG. 16).

Ca-1 is assigned as the 'catalytic calcium' [Kuo (1998) Supra]. It appears to interact with five protein residues (the side-chain oxygens of Asn224, Asn270, Asn168, Asp269 and Glu53), 2.2-2.5 Å away.

Figure 17:
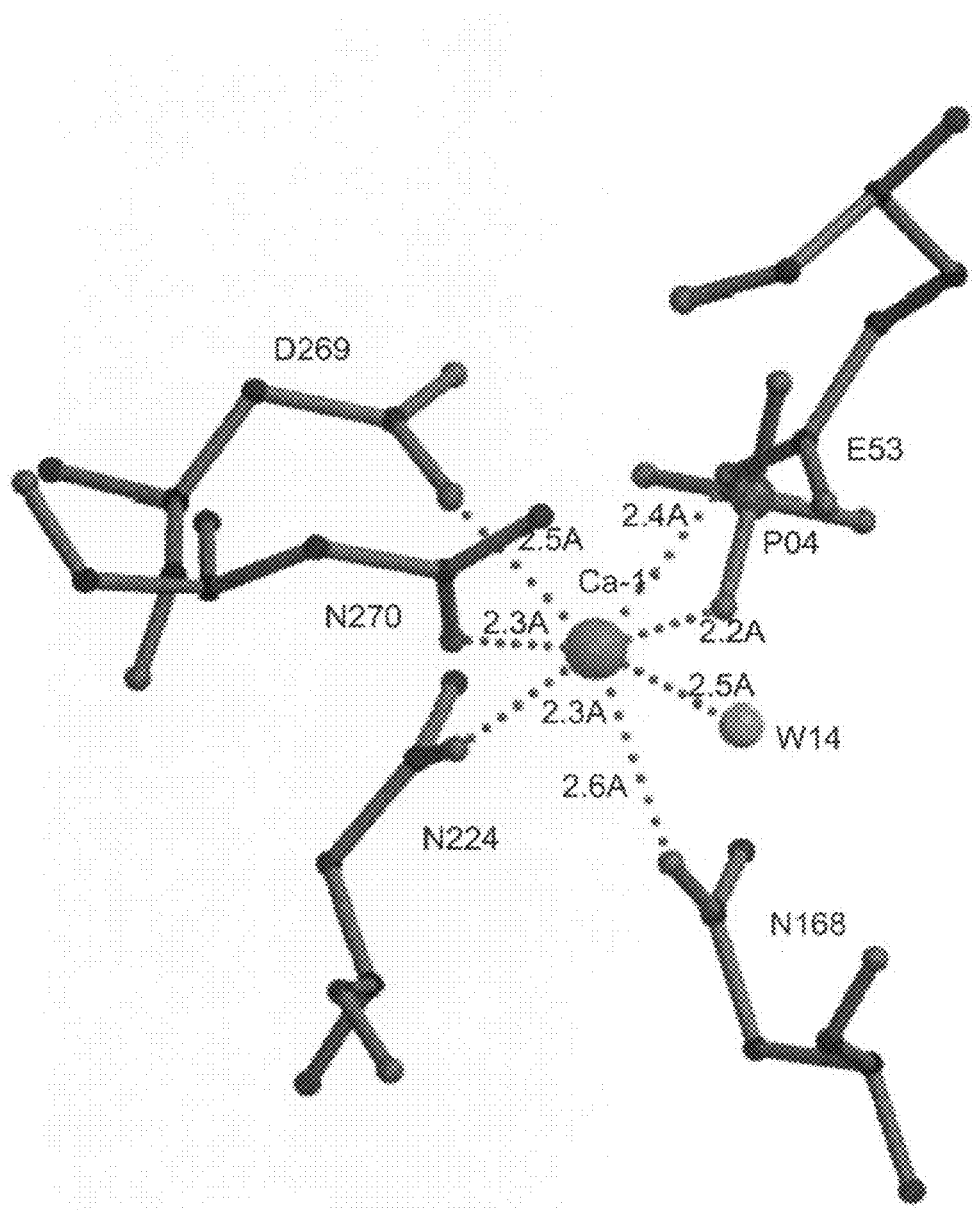
FIG. 17 is a view of the binding site for the upper calcium (Ca-1) in crystallized PON1.

Two other potential ligands are a water molecule (2.5 Å away in the direction of Ca-2), and one of the oxygens of a phosphate ion (see FIG. 17). PON1's two calcium ions exhibit markedly different affinities [C. L. Kuo, B. N. La Du, Drug Metab Dispos 23, 935 (1995)]. Ca-1's ligation is more extensive than Ca-2's. However, two of Ca-1's ligating residues (Asn224, Asp269) exhibited distorted dihedral angles. This, and the higher solvent accessibility of Ca-1, indicate that Ca-2 is the higher affinity calcium.

As is shown in FIGS. 15a-b, PON1's structure resembles Loligo Volgaris DFPase [Scharff (2001) Supra]. Both are 6-bladed propellers with two calcium atoms in their central tunnel. They also share functional homology, since both exhibit phosphotriesterase activity, although PON1 is primarily an esterase or lactonase. However, there is no clear sequence homology between them (BLAST E-score>>3.6) although more sensitive algorithms indicate weak but significant similarity [A. Fokine et al., Acta Crystallogr D Biol Crystallogr 59, 2083 (2003)]. This is not surprising: low sequence homology is a distinct characteristic of β-propellers [H. Jakubowski, J Biol Chem 275, 3957 (2000)]. DFPase, for example, exhibits no sequence homology to other 6-blade β-propellers [E. I. Scharff, J. Koepke, G. Fritzsch, C. Lucke, H. Ruterjans, Structure 9, 493 (2001)]. Closer inspection reveals that PON1 and DFPase differ significantly in their overall architecture, active-site structure and mechanism. Most distinctly, PON1 possesses a unique addition in the form of an active-site canopy defined by helices H2 and H3 and the loops connecting them to the β-propeller scaffold. This addition provides PON with an uncharacteristically closed active site as β-propellers, including DFPase, generally exhibit uncovered active sites defined only by loops that connect the β-strands. This addition seems to play a critical role in PON1's function, both in defining the active-site architecture and sequestering it from solvent, and in anchoring PON1 to the HDL particle. It is notable that the LDL receptor which, like PON1, is involved in prevention of atherosclerosis and in cholesterol efflux or homeostasis, contains a 6-bladed β-propeller domain [G. Rudenko et al., Science 298, 2353 (2002); H. Jeon et al., Nature Struct Biology 8, 499 (2001)].

Detergent-solubilized PON1 forms dimers and higher oligomers [D. Josse et al., J Biol Chem 277, 33386 (2002)], but there is only one molecule per asymmetric unit, and very few contacts between symmetry-related molecules. It could be that crystallization favours a monomeric form. But it seems more likely that oligomerization of PON1 is a consequence of its anchoring to detergent micelles in a mode similar to its anchoring to HDL.

PON1 expressed in animal cells is glycosylated [D. I. Draganov, B. N. La Du, Nau Schm Arch Pharmacol (2003)]. Glycosylation is not essential for the hydrolytic activities of PONs [A. Aharoni et al., Proc. Natl. Acad. Sci. USA 101, 482 (2004); D. Josse et al., Biochemistry 38, 2816 (1999)] but may be important in increasing their solubility and stability, or in preventing non-specific binding to cell membranes, as proposed for other HDL-associated enzymes [A. Jonas, Biochim Biophys Acta-Mol Cell Biol Lipids 1529, 245 (2000)]. There are four potential N-glycosylation sites on PON1 (NX(S/T) sites). Two (Asn227 and Asn270) are in the central tunnel of the propeller, and are largely inaccessible to solvent. Asn253 and Asn324 are located on surface loops, and are most probably, as previously proposed [D. Josse et al., Biochemistry 38, 2816 (1999)], PON1's glycosylation sites.

Directed evolution of an array of specialized variants reveals the location and structure of PON1's active site— Site-directed mutagenesis is routinely used to identify residues in active site residues. This approach suffers, however, from a well-recognized drawback. Loss of activity does not necessarily indicate direct involvement of a particular amino acid in the protein's function since mutations often disrupt the overall structure. Indeed, whereas certain residues identified by site-directed mutagenesis as being essential for PON1's activity [D. Josse et al., Biochemistry 38, 2816 (1999); D. Josse et al., J Appl Toxicol 21, S7 (2001); D. Josse, W. H. Xie, P. Masson, L. M. Schopfer, O. Lockridge, Chem. Biol. Interact. 120, 79 (1999)] are related to its active site (e.g., Glu53 that ligates Ca-1, His115 and His134), others are not (e.g., Glu54 that ligates the structural calcium (Ca-2) and Trp281 that is far from the active site). In contrast, mutations identified following directed evolution towards a modified function are inevitably relevant to activity, and involve residues located within, or in the vicinity of, the active site. Indeed, the amino acids identified by the directed evolution process described above led to the unambiguous identification of PON1's active site, and provided key insights as to how the substrate selectivity of the PON family members evolved in nature.

As is mentioned herein above (see Example 5), the newly-evolved PON1 variants clearly define a set of amino acids the alteration of which dramatically shifts PON1's reactivity and substrate selectivity (see Table 11, below).

walls, as are the side-chain methylenes of Lys192. In human PON1, this position is normally arginine, but a commonly observed polymorphism to glutamine (192Q) results in ~10-fold decrease in paraoxonase activity and higher susceptibil-

TABLE 11

|  |  |  |  | Esterase activity[e] | |
| --- | --- | --- | --- | --- | --- |
|  |  | Phosphotriesterase activity[b,c] | Lactonase activity[d] | short chain ester | long chain esters |
|  | Variant[a] rPON1 (wt-like activity) | 3.5 * 10$^3$ | 1.4 * 10$^2$ | 3.0 * 10$^4$ | 1.7 * 10$^2$ |
|  | Directly-evolved variants with 'specialized' substrate selectivities | | | | |
| ID/SEQ ID NO: | Mutations[f] | | | | |
| 7PC/ 66, 67 | V346A | 1.3 * 10$^4$ (3.7)[b] | 5.0 * 10$^1$ (0.36) | 1.4 * 10$^3$ (0.05) | 1.4 * 10$^1$ (0.08) |
| 4PC/ 68, 69 | L69V, S193P, V346A | 5.7 * 10$^4$ (16.3) | 0.9 (0.006) | 4.4 * 10$^2$ (0.015) | n.d |
| 1HT/ 70, 71 | I291L, T332A, G339E | 6.0 * 10$^2$ (0.17) | 3.0 * 10$^3$ (25.9) | 8.6 * 10$^3$ (0.3) | n.d. |
| 2AC/ 72, 73 | F292S, V346M V30A, E249K | 1.1 * 10$^2$ (0.03) | 6.4 (0.04) | 6.0 * 10$^5$ (20) | 7.0 * 10$^2$ (4.1) |
| 7HY/ 74, 75 | F292V, Y293D, I109M | 4.1 * 10$^1$ (0.01) | 4.1 (0.03) | 1.2 * 10$^5$ (4.0) | 8.0 * 10$^3$ (47) |
| 4HY/ 76, 77 | I74L, F292L K84Q, I343M | 5.3 * 10$^1$ (0.015) | 5.9 (0.04) | 5.2 * 10$^4$ (1.7) | 6.5 * 10$^3$ (38) |

Figure 13:
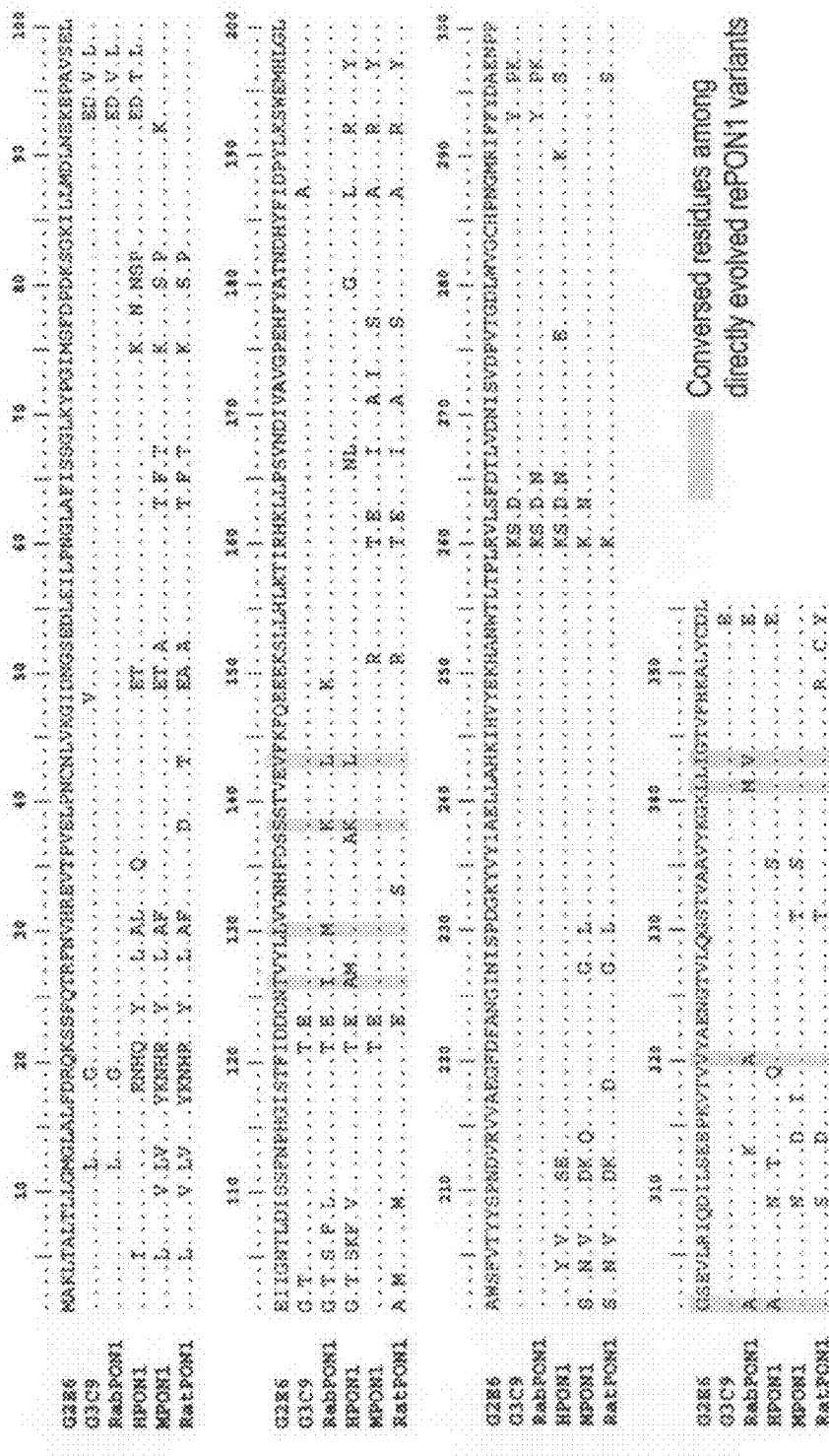
FIG. 13 is a multiple sequence alignment of human (H) (SEQ ID NO: 36), rat (SEQ ID NO: 39), mouse (M) (SEQ ID NO: 38) and rabbit (Rab) PON1 (SEQ ID NO: 39), and rPON1 variants G2E6 and G3C9 (SEQ ID NOs: 60 and 56 respectively).

[a]rPON1 variant G3C9 was used as the starting point for directed evolution. It exhibits a sequence almost identical to those of wt rabbit PON1 and rPON1 variant G2E6, whose 3D-structure was determined (91% homology; FIG. 13), and the same enzymatic parameters.
[b]All activities were determined at 0.1 mM substrate, and are expressed as µmoles of product released per minute per mg enzyme. In parentheses are the activities of the new variants relative to wt PON1's activity for the same substrate.
[c]Phosphotriesterase activity was screened, and subsequently quantified, with the fluorogenic OP substrate, 7-O-diethylphosphoryl-3-cyano-7-hydroxycoumarin as described [A. Aharoni et al., Proc. Natl. Acad. Sci. USA 101, 482 (2004)].
[d]Libraries were initially screened with 2NA, and positive clones picked from replica plates and grown in 96-well plates as described [A. Aharoni et al., Proc. Natl. Acad. Sci. USA 101, 482 (2004)]. The crude cell lysates and purified proteins were assayed for hydrolysis of γ-butyrothiolactone using DTNB (5,5-dithio-bis-2-nitrobenzoic acid) for detection of product (absorbance at 412 nm).
[e]Esterase activity was screened with the fluorogenic substrate, 7-acetoxycoumarin (for short-chain esterase activity) or with 2-naphthyl octanoate (for long-chain esterase activity) using fast red for the detection of 2-naphthol [A. Aharoni et al., Proc. Natl. Acad. Sci. USA 101, 482 (2004)]. Colonies exhibiting the highest activity were grown in 96-well plates, and the crude cell lysate assayed spectrophotometrically at 365 nm, for hydrolysis of 7-acetoxycoumarin, and at 320 nm with 2-naphthyl laurate. The activity of the variants described above was determined with the same substrates and assays.
[f]Mutations are given in relation to the sequence of the wt-like variant G3C9. In bold are positions found to be mutated in all the highest-activity variants for a given substrate. Typically, the same mutations could be individually identified in the sequence of selected variants from the 1$^{st}$ and 2$^{nd}$ rounds of evolution, and appear together in the 3$^{rd}$ generation variants. Mutations that appear in only one selected variant, but not in others selected for the same substrate, and/or do not appear in the 1$^{st}$ and 2$^{nd}$ round of evolution, are noted in regular print.

These shifts involve not only an increase of 16-46-fold in activity towards the substrate for which each particular variant was evolved, but also a drastic decrease in activity on substrates which had not been selected for (6-167-fold). Overall, shifts in substrate selectivity of up to 4,600-fold were observed (e.g., variant 7HY that exhibits, relative to wt PON1, 46-fold higher long-chain esterase activity and 100-fold lower phosphotriesterase activity). Some of the new variants, which were all derived from PON1, represent substrate and reaction selectivities that are closer to PON2 or PON3. For example, variants 2AC and 1HT exhibit ~20-fold higher esterase and lactonase activity relative to PON1 and 5-30-fold weaker phosphotriesterase activity.

The positions identified by directed evolution all appear in the same region at the top of the β-propeller and thereby clearly mark the entrance to and walls of PON1's active site (FIGS. 18a-b). The Cα and phenyl side-chain of Phe292, the entire side-chain of Ile291, and the carbonyl oxygens of both these residues, all line the cavity. At the bottom of the cavity lies the methyl side chain of Thr332. The phenyl ring of Phe293 is part of the active-site perimeter. All these residues seem to affect the esterase and lactonase activities of PON1. Another subset of residues was identified in the variants specialized for OP hydrolysis.

The side-chains of Leu69 and Val346, and Cα and the side-chain methylene of Ser193, are part of the active-site ity to atherosclerosis [D. I. Draganov, B. N. La Du, Nau Schm Arch Pharmacol (2003)]. Given the drastic effects that changes in other active-site residues have on PON1's substrate selectivity, the human 192Q variant may indeed exhibit significantly reduced activities with PON1's physiological substrates, resulting in increased susceptibility to atherosclerosis.

Other residues lining the cavity, which did not mutate during directed evolution, include the side chains of Met196, Phe222, and Leu240, and Glu53 (the carboxylate of which interacts with Ca-1 at the bottom of the cavity). The perimeter is defined by several residues that are ~15-20 Å from the deepest point of the cavity, including Tyr190, His 197, Phe293 and Tyr294. The top of the active site is partly covered, e.g., by the phenyl ring of Phe347 and the backbones of Lys70 and Tyr71. The latter form the end of a loop that is disordered and hence not seen in the structure. This loop may be part of an active-site lid, since mutations in residue 74 were also observed that led to changes in substrate selectivity (e.g., variant 4HY, Table 11).

The catalytic mechanism of PON1—At the very bottom of the active-site cavity just described, lies the upper calcium (Ca-1), and a phosphate ion which was present in the mother liquor (FIG. 18b). One of the phosphate's oxygens is only 2.2 Å from Ca-1. This phosphate ion may be bound in a mode similar to the intermediates in the hydrolytic reactions catalyzed by PON. One of its negatively-charged oxygens, that closest to Ca-1, may mimic the oxyanionic moiety of these intermediates stabilized by the positively-charged calcium. This type of 'oxyanion hole' is seen in secreted phospholipases A2 (PLA2s) [K. Sekar et al., Biochemistry 36, 3104 (1997)] and has also been suggested for DFPase. Two other phosphate oxygens may be mimicking the attacking hydroxyl ion and the oxygen of the alkoxy or phenoxy leaving groups of ester and lactone substrates.

Figure 19:
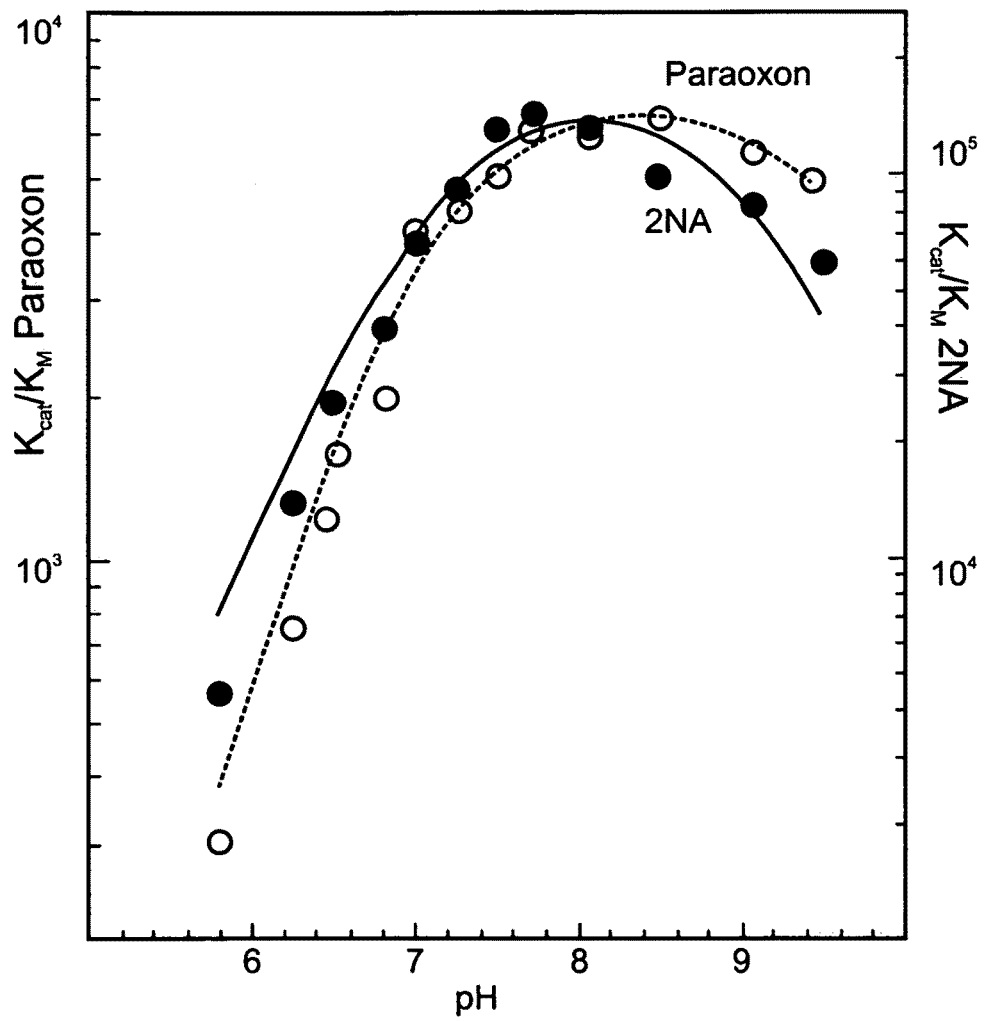
FIG. 19 is a graph depicting pH-rate profiles of PON1. $k_{cat}$ and $K_M$ values were determined for rPON1-G2E6 with 2 naphthyl acetate (2NA) and paraoxon [A. Aharoni et al., Proc. Natl. Acad. Sci. USA 101, 482 (2004)] at pH 5.6-9.5. $k_{cat}/K_M$ values for each pH value ($(k_{cat}/K_M)^H$) were fitted to a 'bell-shaped' model using the equation: $(k_{cat}/K_M)^H=(k_{cat}/K_M)^{max}/[(10^{-pH}/10^{-pKa1})+(10^{-pKa2}/10^{-pH})+1]$; where $(k_{cat}/K_M)^{max}$ is the pH-independent (or plateau value) of $k_{cat}/K_M$, and $pK_a^1$ and $pK_a^2$, are the $pK_a$ values for the acidic and basic groups, respectively. The fit gave the following values for paraoxon: $(k_{cat}/K_M)^{max}=7016$ $M^{-1}s^{-1}$, $pK_a^1=7.06$ and $pK_a^2=9.78$; for 2NA: $(k_{cat}/K_M)^{max}=1.67\times10^5$ $M^{-1}s^{-1}$, $pK_a^1=7.15$ and $pK_a^2=9.03$. Kinetic parameters were obtained from 3-5 independent measurements averaged with standard deviations of 2-23%. Buffers used: MES (pH 5.6-6.5) and bis-tris propane (pH 6.5-9.4) at 0.1M, plus 1 mM $CaCl_2$; the ionic strength was adjusted to 0.2M with NaCl.

To help elucidate PON1's mechanism, the pH-rate profile thereof was determined with two typical substrates: an ester (2-naphthyl acetate, 2NA, FIG. 19) and a phosphotriester (paraoxon). Both profiles exhibit a bell-shaped curve. The minor basic shoulder fits a pKa of 9.8 (paraoxon) or 9.0 (2NA), probably reflecting the deprotonation of a basic side-chain that affects the active site but is not directly involved in catalysis. The fully pronounced acidic shoulder, with a pKa of ~7.1, may be ascribed to a His imidazole involved in a base-catalyzed, rate-determining step. In hydrolytic enzymes, His often serves as a base, deprotonating a water molecule and generating the attacking hydroxide ion that produces hydrolysis. In secreted PLA2, the attacking hydroxide is generated by a His-Asp dyad, in which the imidazole acts as a base to deprotonate a water molecule, and the Asp carboxylate increases the imidazole's basicity via a proton-shuttle mechanism. The closest His nitrogen in PLA2 is 6.3 Å from the catalytic calcium, and two water molecules are involved: one attacking the substrate (after deprotonation), and another 'catalytic water' that mediates between the attacking water and the His base [Sekar (1997) Supra]. The DFPase active site also contains a His-Glu dyad with a His nitrogen 7.2 Å from the catalytic calcium [Scharff (2001) Supra].

Figure 20:
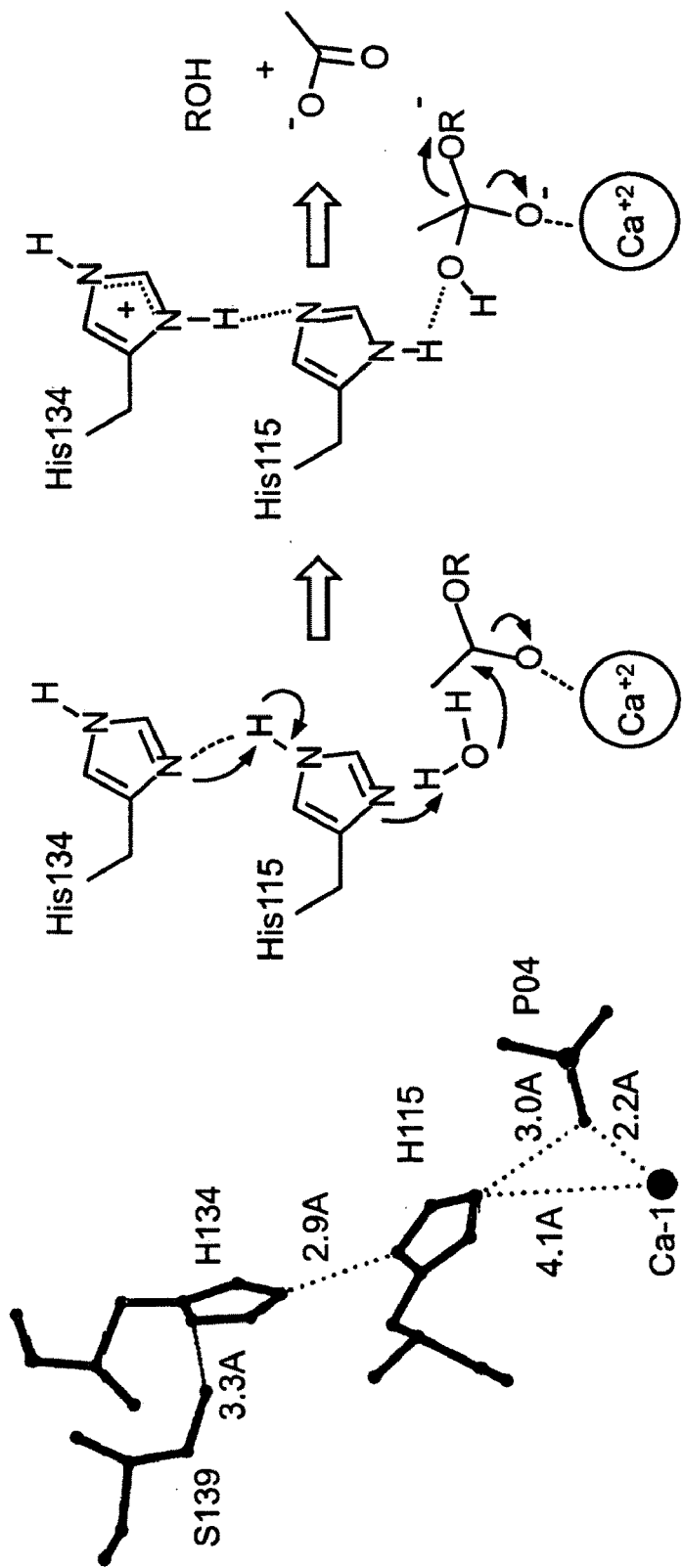
FIGS. 20a-b are proposed catalytic site and mechanism of action of PON1 enzyme.
Figure 21:
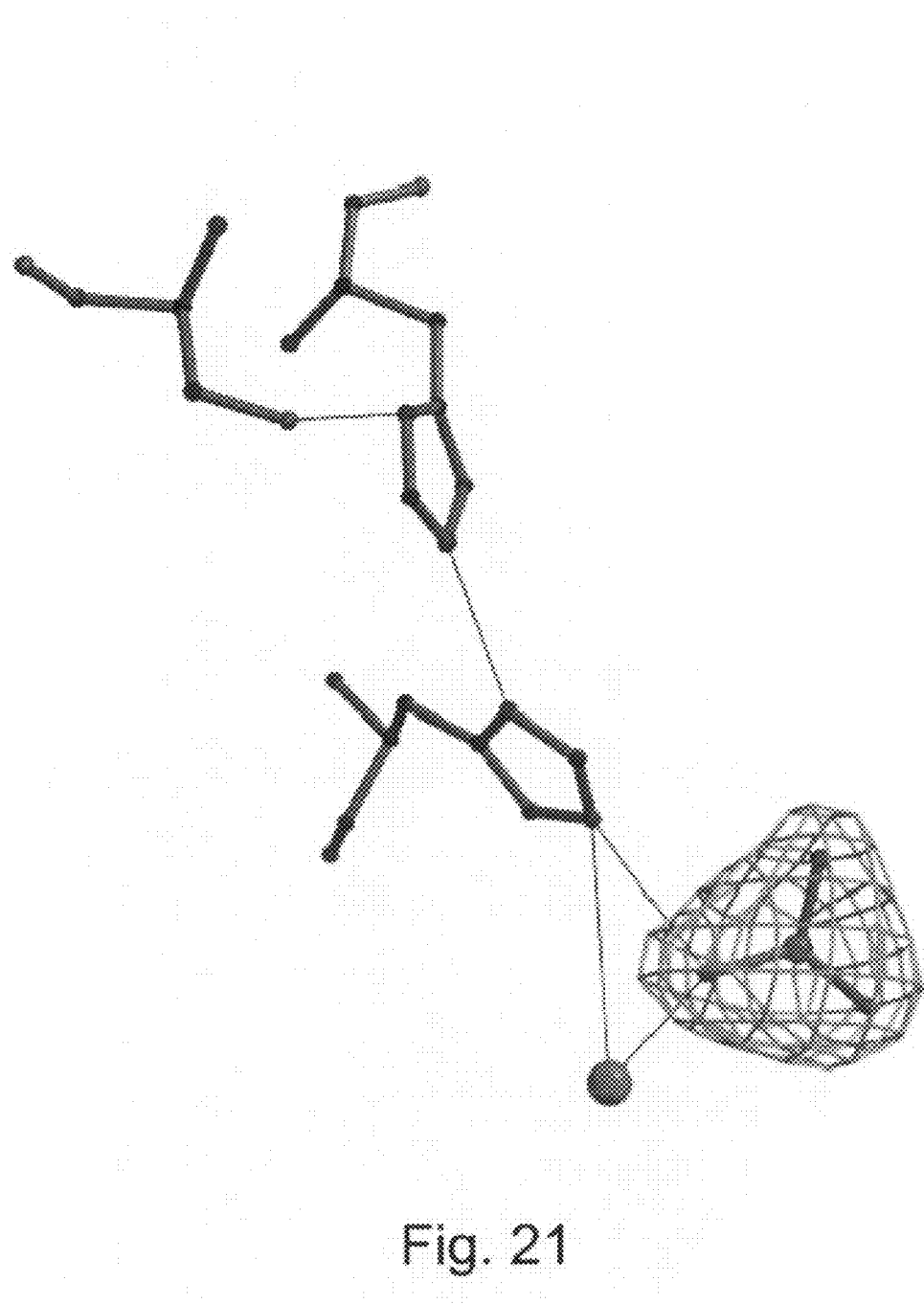
FIG. 21 is an Fo-Fc OMIT map of the phosphate ion at 4ó. Crystallization mother liquor of the native rPON1 contained $0.2M$ $NaH_2PO_4$. The electron density map of the SeMet protein, which was crystallized with no phosphate, showed no peak at this location. The presence of the phosphate was verified by atomic absorption measurements after dialysis against 20 mM Tris pH 8 buffer that did not contain phosphate ions, using the ICP instrument, Spectroflame Modula E (Specto, Kleve, Germany). The Instrument was first calibrated against various pre-mix metal ions standards (Merck) at concentration of 1 ppm and the allowed maximal variation was ±5%. The amount of phosphate found was 0.72 mole per 1 mole of rPON1-G2E6.

Interestingly PON1 adopted a similar mechanism—namely a His-Glu/Asp dyad acting as base on a two-water-molecule cascade. PON1's active site contains a His-Glu/Asp dyad (Asp183, His184), with the Asp183 carboxylate oxygen apparently H-bonded to one of His184's nitrogens. However, His184's nitrogens are 10.8 Å and 12 Å from Ca-1, and the His184Asn mutant of human PON1 is active [Josse (1999) Supra]. Another such dyad in PON1's active site is His285-Asp269. Yet Asp269 ligates Ca-1, and His285 is ~8 Å from Ca-1 and ~5 Å from the nearest phosphate oxygen. A His-His dyad was identified near both Ca-1 and the phosphate ion (FIG. 20-21). It is suggested that His115 (the closer nitrogen of which is only 4.1 Å from Ca-1) acts as a general-base to deprotonate a single water molecule and generate the attacking hydroxide, while His134 acts in a proton shuttle mechanism to increase His115's basicity. His134 appears to make a second H-bond to Ser139-Oγ that may stabilize the dyad and further increase its basicity. Interestingly, His115 adopts distorted dihedral angles—a phenomenon observed in catalytic residues of many enzymes. In strong support of the proposed mechanism are the His115Gln mutation, that resulted in a dramatic decrease (~2×10$^4$ fold) in activity, and His134Gln, that resulted in a milder, yet significant decrease (6-150 fold; Table 12, below).

TABLE 12

| Variant | Phenyl acetate[a] (Units) (fold decrease) | Paraoxon[a] (Units) (fold decrease) |
|---|---|---|
| WT | 1.5 * 10$^6$ (1) | 3.8 * 10$^3$ (1) |
| H134Q | 9.5 * 10$^3$ (154) | 6.1 * 10$^2$ (6.2) |
| H115Q | 42 (35,100) | 0.22 (17,270) |
| C283A | 8.7 * 10$^5$ (1.7) | 1.9 * 10$^3$ (2) |
| C283S[b] | — | — |

[a]Activities for phenyl acetate and paraoxon hydrolyses were determined at 0.2 mM and 0.1 mM, respectively, and are given in units (μmoles product/minute/mg enzyme). The decrease in activity of the mutants relative to 'wt' rPON1-G2E6 are given in parenthesis.
[b]The C283S mutant did not express in *E. coli*, neither as soluble protein nor in inclusion bodies. It is presumably misfolded and proteolytically digested.

It will be appreciated that, the mechanism proposed above has not been observed before, although its key elements are seen in DFPase and PLA2. Catalysis of both C—O and P—O hydrolyses at one site is unusual but not unprecedented [Bencharit, C. L. Morton, Y. Xue, P. M. Potter, M. R. Redinbo, Nature Struct Biol 10, 349 (2003); C. B. Millard, O. Lockridge, C. A. Broomfield, Biochemistry 37, 237 (1998)]. The structure, the directed evolution results, the pH-rate profiles, and previous biochemical data (see Draganov and Examples 1-5) show that both these activities take place at the same site. At this stage, however, a possibility remains that certain PON1 activities (e.g., as homocysteine thiolactonase) make use of a different subset of residues of this site, including His285, whose side chain also points towards both the center of the cavity and the phosphate ion. In addition, nucleophilic catalysis by His115 cannot yet be ruled out, although there is currently no evidence to support catalysis via an acyl- or phosphoryl-enzyme intermediate.

The 3D-structure does provide a hint regarding the origins of PON1's remarkably wide substrate range. The transition states, intermediates and leaving groups of the various substrates (phenoxy, alkoxy, etc.) are obviously very different. Yet hydrophobicity is common to all of PON1s effective substrates. The hydrophobicity and depth of PON1's active site explain this preference, and account for the fact that PON1's substrates, whether poor or effective, generally exhibit similar $K_M$ values (0.1-0.5 mM) but dramatically different $k_{cat}$ values. Homocysteine thiolactone is perhaps the only poor PON substrate with a notably high $K_M$ (~20 mM) (8, 13). It is also the only charged substrate. Thus, PON1's multi-specificity is driven primarily by non-specific hydrophobic forces, as observed with other enzymes that possess deep hydrophobic active sites [e.g., acetylcholinesterase; H. M. Greenblatt, H. Dvir, I. Silman, J. L. Sussman, *J Mol Neurosci* 20, 369 (2003)]. The mutations that led to up to 4,600-fold changes in PON1's substrate selectivity also affect the $k_{cat}$ values, whereas $K_M$ values remain essentially unchanged. Yet the structure makes it clear that the active-site chemistry of these mutants is identical to the wt. The results presented herein thus indicate that, poor as well as effective substrates, bind at the active site with similar affinity; yet the mode of binding differs, as the poor substrates are inadequately positioned relative to Ca-1 and to the catalytic base. The mutations reshape the active site walls and perimeter, thereby improving the positioning of certain substrates (and of their respective catalytic intermediates and transition states) and worsening that of others. As discussed below, reshaping of the active site walls is also the driving force behind the divergence of various PON sub-families.

Structural and evolutionary analysis of the PON family members—The 3D structure of PON1 provides key insights as to how the substrate and reaction selectivity of different PONs is determined, and how they diverged towards different activities. Further insights are provided into the possible effects of various SNPs on PON's activity and stability.

Figure 22:
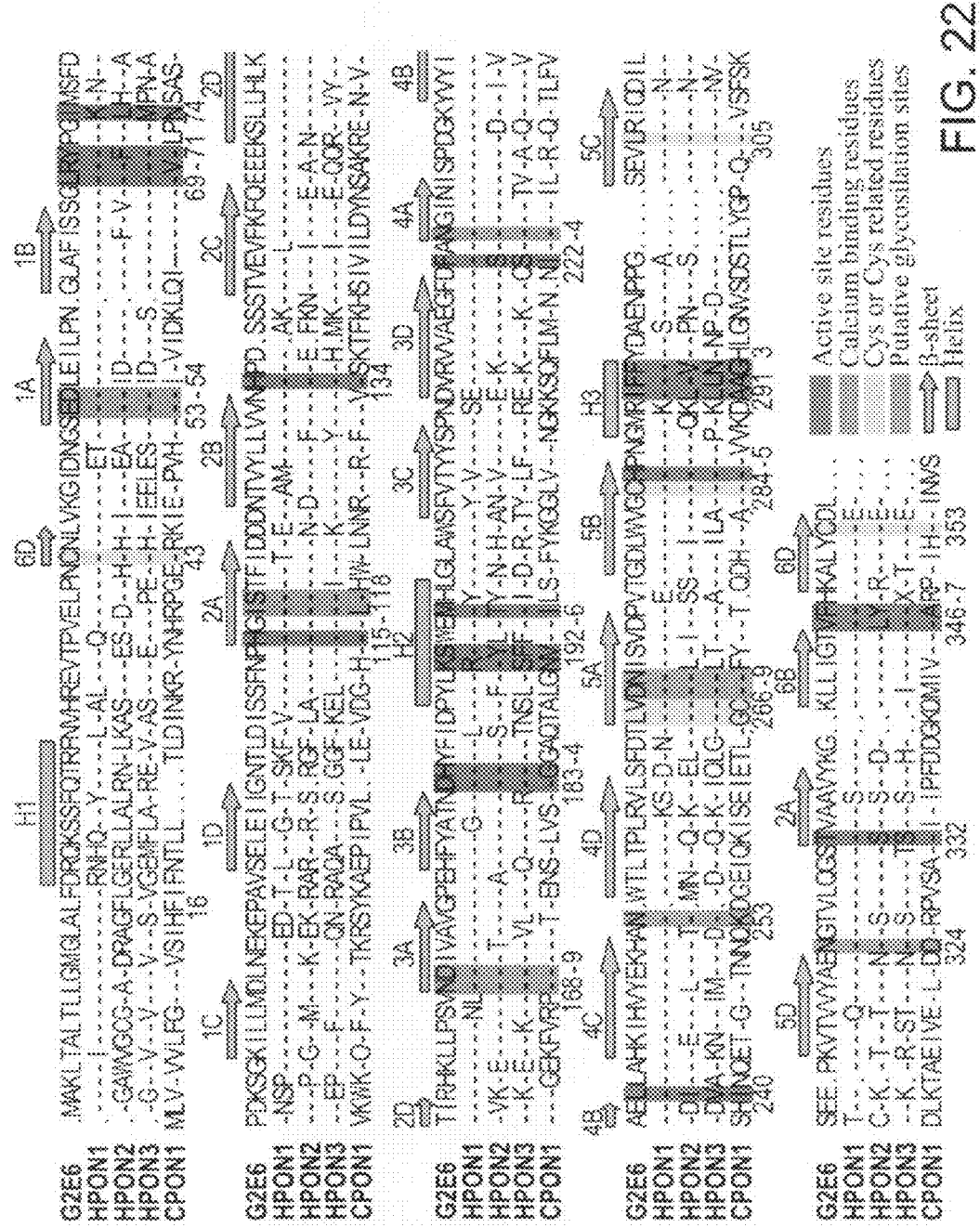
FIG. 22 is a sequence alignment of representative members of the PON family. Shown are human PON1, PON2 and PON3 (with an 'H' prefix) (SEQ ID NOs: 36, 40 and 88 respectively), *C. elegans* PON1 (CPON1) (SEQ ID NO: 89), and rPON1 variant G2E6 (SEQ ID NO: 60), the structure of which was solved.

The key elements of the PON catalytic site are highly conserved; these include the residues that ligate Ca-1, neighboring residues that are in H-bond contact with the latter, and the catalytic histidines (see FIG. 22). The different PON sub-families therefore diverged while maintaining their overall active-site structure and catalytic machinery. However, their substrate and reaction selectivities changed dramatically. The present results show how PONs readily adopt new selectivities. PON1 variants evolved in the laboratory show patterns reminiscent of PON2 or PON3 (e.g., variants 1HT and 2AC, with high lactonase and esterase activity and low phosphotriesterase activity). These results define a set of sixteen residues that comprise the walls and perimeter of the PON active site, and thereby govern substrate selectivity (Table 13, below).

TABLE 13

| Sub-family | | | | Newly-evolved PON1s | |
|---|---|---|---|---|---|
| Position | PON1 | PON2 | PON3 | Residue | Selectivity |
| 69 | L | L | L | V/I | PTE[a] |
| 74[b] | I | L | M | L/M | lactonase/esterase |
| 75[b] | K/M | K/H | P | | |
| 76[b] | S | S | N/A | | |
| 78[b] | N/D | A | A | | |
| 190 | Y | F/I | L/V/F | | |
| 192 | K/R | K/M | S/A/V | | human R/Q SNP |
| 193 | S | Y/F | F/L | P | PTE[a] |
| 196 | M | M/T | M | | |
| 222 | F | S | S | | |
| 240 | L | I | V | | |
| 291 | I | L/V | L | L | lactonase |
| 292 | F | F/Y | L | L/V/S | esterase |
| 293 | F/Y | V/Y/I | N/I | D | lipase-like[c] |
| 332 | T | S | S/T | A | lactonase |
| 346 | V | L/V | I/V | A | PTE[a] |

[a]PTE = phosphotriesterase. Note that the PTE activity of these mutants is much higher than that of wt PON1 which is the best PTE amongst all PONs (Table 11).
[b]Residues 74-79 belong to the selectivity-determining residues which differ between the PON subfamilies (FIG. 22) but are conserved within them. These residues are part of a mobile loop, which also contains residue 74, is not seen in the structure but is part of the active site.
[c]Lipase-like activity refers to esters of long-chain carboxylic acids (Table 11).

Variants exhibiting patterns of activities that have not yet been identified in natural PONs, carry mutations at the same positions, but to amino acids other than those observed in wt PONs (e.g., 4PC, with higher phosphotriesterase activity than wt PON1 and dramatically lower esterase activity; Table 13, above). At some stage in evolution, changes in the selectivity-determining residues (Table 13, above) led to divergence of the individual PON sub-families, each of which is highly conserved with respect to these residues. It may be that each of the sub-families evolved, and is evolutionarily preserved, for a different substrate of key physiological importance, yet the identities of these substrates remain obscure.

There are also residues outside the active site that vary from one subfamily to another, yet are conserved within each family. Most seem to be related to the β-propeller scaffold, but some may be linked to function. A clear example is Asn253, which is one of the two presumed glycosylation sites of PON1, and thus is within an NX(S/T) consensus sequence. This site is abolished in PON2 and PON3 due to a change in the third position, from Thr to Asn or Asp (FIG. 22). Other residues, or clusters of residues, appear to be specific for each sub-family (e.g., in the region of 20-50). These may be linked to non-hydrolytic roles of PONs, in particular in relation to atherosclerosis, and to their localization (e.g., PON1 and PON3 are exclusively localized in the liver and HDL, whereas PON2 is found in many tissues).

As is the case for the catalytic machinery, the residues maintaining the hydrophobic core of the β-propeller, its central tunnel, the two calciums, and the 'velcro' closure, are also highly conserved (FIG. 22). Residue 55 falls into this category (Leu/Ile in all PONs, Leu in PON1s) except for the human polymorphism of Met55. Residue 55's conservation is clear, given its neighboring residues (Glu53 and Asp54 that ligate Ca-1 and Ca-2), and its role in packing the propeller's central tunnel at the interface between blade 1 and 6. A mutation of Leu to Met may significantly affect PON1's stability and account for the lower enzymatic activity [I. Leviev, S. Deakin, R. W. James, J Lipid Res 42, 528 (2001).]. Cys284 (strand 5B) is another example. It is in a highly conserved stretch (283-287) that includes active-site His285. It is packed against four highly-conserved residues from the adjacent strands: Leu267 and Val268 (strand 5A) and Leu305 and the methylenes of Glu303's side-chain (strand 5C). Mutation of Cys284 is, therefore, likely to destabilize the core structure, thus indirectly affecting function. Although mutation of Cys284 has no significant effect on PON1's hydrolytic activity [R. C. Sorenson et al., Proc Natl Acad Sci USA 92, 7187 (1995)], Cys284 mutants of rPON1 were found to be poorly expressed and relatively unstable (Table 12, above). As the 3D structure reveals that Cys284 has no solvent accessibility, this residue is less likely to serve in alternative functions of PON1 related to atherosclerosis [M. Aviram et al., Arterioscler Thromb Vasc Biol 18, 1617 (1998)].

Some remote PON family members, found in bacteria and fungi, exhibit functional and, presumably, structural resemblance to mammalian PONs [M. Kobayashi, M. Shinohara, C. Sakoh, M. Kataoka, S. Shimizu, Proc Natl Acad Sci USA 95, 12787 (1998)]. Nature has also recruited the PON scaffold for completely different tasks. An interesting example is the C. elegans MEC-6 protein, shown to be part of the degenerin channel that mediates mechanotransduction [D. S. Chelur et al., Nature 420, 669 (2002).]. The present analysis, based on the PON1 structure, suggests that MEC-6 maintains the key structural elements of PON (most notably, the Cys42-Cys353 disulphide bridge, and two of the three residues that ligate the structural calcium). The hydrolytic site, however, including the residues that ligate Ca-1 and the His-dyad, were mutated away.

PON1s structure suggests a mode of anchoring of PON1 to HDL—PON1 and PON3 are synthesized in the liver, and secreted into the blood, where they specifically associate with HDL. HDL mediates reverse transport of cholesterol from peripheral cells and limits LDL oxidation by the activity of HDL-associated enzymes such as platelet-activating factor acetylhydrolase (PAF-AH), PON1 and PON3 [S. Lund-Katz, L. J. Liu, S. T. Thuahnai, M. C. Phillips, Frontiers in Bioscience 8, D1044 (2003); M. Navab et al., Curr Opin Lipidology 9, 449 (1998)]. HDL is a particle of ~10 nm diameter, composed primarily of membrane components (phospholipids, cholesterol and cholesterol esters), and apolipoprotein A-I (apoA-I), the amphipathic helices of which are thought to wrap around the particle's membrane-like bilayer in a belt-wise manner [J. P. Segrest, S. C. Harvey, V. Zannis, Trends Cardiovasc Med 10, 246 (2000)]. Several other proteins are associated with HDL, including lecithin:cholesterol acyl transferase (LCAT) (24), but their mode of binding to HDL is still under investigation. PON1 is the first HDL-associated protein the 3D-structure of which becomes known.

PON1 retains its hydrophobic N-terminus, which resembles a signal peptide, and is thought to be involved in anchoring of PON1 to HDL [R. C. Sorenson et al., Arterioscler Thromb Vasc Biol 19, 2214 (1999)]. Most of the N-terminus is disordered and invisible in the crystal structure, yet the hydrophilic part of it that extends beyond the signal peptide (residues 19-28) adopts a helical structure (H1). The entire sequence of the N-terminus is compatible with a transmembrane helix, yet following a secondary structure prediction, only residues 7-18 were found to be part of H1 (FIG. 23). Helix H2, adjacent to H1, shows a clear amphipathic nature. Its hydrophobic face points unexpectedly to the solvent, as do several residues from the two loops that connect H2 to the propeller scaffold. Helices H1 and H2 form, therefore, two adjacent hydrophobic patches that clearly provide a potential membrane-binding surface (FIG. 23). The interface with HDL was further defined by a characteristic 'aromatic belt' rich in Trp and Tyr side chains, and a Lys side chain on H1 (38). Notably, the glycosylation sites point away from the interface (FIG. 23).

It has also been suggested that PON1 interacts specifically with apoA-I, and that these interactions modulate its activity [M. N. Oda, J. K. Bielicki, T. Berger, T. M. Forte, Biochemistry 40, 1710 (2001)]. This hypothesis is supported by the striking proximity of PON1's HDL-anchoring region to its active site. In fact, the proposed HDL-anchoring region is part of an active-site lid, and several of the selectivity-determining residues are on amphipathic helix H2 and on the loops linked to H1 (FIG. 23). If the postulated mode of HDL-anchoring is correct, it may support the notion of interfacial activation, whereby HDL-anchoring modifies PON1's active site. This mode is present in both lipases [K. Sekar et al., Biochemistry 36, 3104 (1997)] and LCAT [A. Jonas, Biochim Biophys Acta-Mol Cell Biol Lipids 1529, 245 (2000)] for both of which interfacial activation leads to dramatically higher activity towards lipid substrates. The structure of PON1 presented here should direct further research aimed at elucidating PON1's mode of binding to HDL and its effect on the enzyme's activities, as well as the precise physiological roles of these activities.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CYTED

Abecassis, V., Pompon, D. and Truan, G. (2000) High efficiency family shuffling based on multi-step PCR and in vivo DNA recombination in yeast: statistical and functional analysis of a combinatorial library between human cytochrome P450 1A1 and 1A2. Nucleic Acids Res, 28, e88.

Ahmed, Z., Ravandi, A., Maguire, G. F., Emili, A., Draganov, D., La Du, B. N., Kuksis, A. and Connelly, P. W. (2001) Apolipoprotein A-I promotes the formation of phosphatidylcholine core aldehydes that are hydrolyzed by paraoxonase (PON-1) during high density lipoprotein oxidation with a peroxynitrite donor. Journal of Biological Chemistry, 276, 24473-24481.

Aviram, M., Rosenblat, M., Bisgaier, C. L., Newton, R. S., Primo-Parmo, S. L. and La Du, B. N. (1998) Paraoxonase inhibits high-density lipoprotein oxidation and preserves its functions. A possible peroxidative role for paraoxonase. J Clin Invest, 101, 1581-1590.

Bessette, P., Aslund, F., Beckwith, J. and Georgiou, G. (1999) Efficient folding of proteins with multiple disulfide bonds in the Escherichia coli cytoplasm. Proc Natl Acad Sci USA, 96, 13703-13708.

Billecke, S., Draganov, D., Counsell, R., Stetson, P., Watson, C., Hsu, C. and La Du, B. N. (2000) Further characterization of human serum paraoxonase (PON1) lactonase activity. Faseb Journal, 14, 74.

Billeclke, S., Draganov, D., Counsell, R., Stetson, P., Watson, C. and La Du, B. N. (2000) Human serum paraoxonase (PON1) isozymes Q and R hydrolyze lactones and cyclic carbonate esters. Drug Metabolism and Disposition, 28, 1335-1342.

Brushia, R. J., Forte, T. M., Oda, M. N., La Du, B. and Bielicki, J. K. (2001) Baculovirus-mediated expression and purification of human serum paraoxonase 1A. J Lipid Res, 42, 951-958.

Crameri, A., Raillard, S. A., Bermudez, E. and Stemmer, W. P. (1998) DNA shuffling of a family of genes from diverse species accelerates directed evolution. Nature, 391, 288-291.

Davies, H. G., Richter, R. J., Keifer, M., Broomfield, C. A., Sowalla, J. and Furlong, C. E. (1996) The effect of the human serum paraoxonase polymorphism is reversed with diazoxon, soman and sarin. Nat Genet, 14, 334 336.

Georgiou, G. (2000) Analysis of large libraries of protein mutants using flow cytometry. Adv Protein Chem, 55, 293-315.

Griffiths, A. D. and Tawfik, D. S. (2000) Man-made enzymes—from design to in vitro compartmentalisation. Curr Opin Biotechnol, 11, 338-353.

Hammarstrom, M., Hellgren, N., van Den Berg, S., Berglund, H. and Hard, T. (2002) Rapid screening for improved solubility of small human proteins produced as fusion proteins in Escherichia coli. Protein Sci, 11, 313-321.

Jakubowski, H. (2000) Calcium-dependent human serum homocysteine thiolactone hydrolase. A protective mechanism against protein N-homocysteinylation. J Biol Chem, 275, 3957-3962.

Joern, J. M., Meinhold, P. and Arnold, F. H. (2002) Analysis of shuffled gene libraries. J Mol Biol, 316, 643-656.

Jones, H. E., Holland, I. B., Baker, H. L. and Campbell, A. K. (1999) Slow changes in cytosolic free Ca2+ in Escherichia coli highlight two putative influx mechanisms in response to changes in extracellular calcium. Cell Calcium, 25, 265-274.

Josse, D., Ebel, C., Stroebel, D., Fontaine, A., Borges, F., Echalier, A., Baud, D., Renault, F., le Maire, M., Chabrieres, E. and Masson, P. (2002) Oligomeric states of the detergent-solubilized human serum paraoxonase (PON1). Journal of Biological Chemistry, 277, 33386-33397.

Josse, D., Xie, W. H., Renault, F., Rochu, D., Schopfer, L. M., Masson, P. and Lockridge, O. (1999) Identification of residues essential for human paraoxonase (PON1) arylesterase/organophosphatase activities. *Biochemistry,* 38, 2816-2825.

Khalameyzer, V., Fischer, I., Bornscheuer, U. and Altenbuchner, J. (1999) Screening, nucleotide sequence, and biochemical characterization of an esterase from *Pseudomonas fluorescens* with high activity towards lactones. *Appl Environ Microbiol,* 65, 477-482.

Kuo, C. L. and La Du, B. N. (1995) Comparison of purified human and rabbit serum paraoxonases. *Drug Metab Dispos,* 23, 935-944.

Kuo, C. L. and La Du, B. N. (1998) Calcium binding by human and rabbit serum paraoxonases. Structural stability and enzymatic activity. *Drug Metab Dispos,* 26, 653-660.

Mackness, M. I., Mackness, B., Durrington, P. N., Connelly, P. W. and Hegele, R. A. (1996) Paraoxonase: biochemistry, genetics and relationship to plasma lipoproteins. *Curr Opin Lipidol,* 7, 69-76.

Marathe, G., Zimmerman, G. and McIntyre, T. (2002) PAF acetylhydrolase, and not paraoxonase-1, is the oxidized phospholipid hydrolase of high density lipoprotein particles. *J Biol Chem,* In Press.

Maxwell, K. L., Mittermaier, A. K., Forman-Kay, J. D. and Davidson, A. R. (1999) A simple in vivo assay for increased protein solubility. *Protein Sci,* 8, 1908-1911.

Petrounia, I. P. and Arnold, F. H. (2000) Designed evolution of enzymatic properties. *Curr Opin Biotechnol,* 11, 325-330.

Reddy, S. T., Wadleigh, D. J., Grijalva, V., Ng, C., Hama, S., Gangopadhyay, A., Shih, D. M., Lusis, A. J., Navab, M. and Fogelman, A. M. (2001) Human paraoxonase-3 is an HDL-associated enzyme with biological activity similar to paraoxonase-1 protein but is not regulated by oxidized lipids. *Arteriosclerosis Thrombosis and Vascular Biology,* 21, 542-547.

Rodrigo, L., Mackness, B., Durrington, P. N., Hernandez, A. and Mackness, M. I. (2001) Hydrolysis of platelet-activating factor by human serum paraoxonase. *Biochemical Journal,* 354, 1-7.

Shih, D. M., Gu, L. J., Xia, Y. R., Navab, M., Li, W. F., Hama, S., Castellani, L. W., Furlong, C. E., Costa, L. G., Fogelman, A. M. and Lusis, A. J. (1998) Mice lacking serum paraoxonase are susceptible to organophosphate toxicity and atherosclerosis. *Nature,* 394, 284-287.

Smolen, A., Eckerson, H., Gan, K., Hailat, N. and La Du, B. (1991) Characteristics of the genetically determined allozymic forms of human serum paraoxonase/arylesterase. *Drug Metab Dispos,* 19, 107-112.

Sorenson, R. C., Bisgaier, C. L., Aviram, M., Hsu, C., Billecke, S. and La Du, B. N. (1999) Human serum paraoxonase/arylesterase's retained hydrophobic N-terminal leader sequence associates with HDLs by binding phospholipids—Apolipoprotein A-I stabilizes activity. *Arteriosclerosis Thrombosis and Vascular Biology,* 19, 2214-2225.

Stemmer, W. P. (1994) DNA shuffling by random fragmentation and reassembly: in vitro recombination for molecular evolution. *Proc Natl Acad Sci USA,* 91, 10747-10751.

Sun, L., Petrounia, I. P., Yagasaki, M., Bandara, G. and Arnold, F. H. (2001) Expression and stabilization of galactose oxidase in *Escherichia coli* by directed evolution. *Protein Eng,* 14, 699-704.

Waldo, G. S. (2003) Genetic screens and directed evolution for protein solubility. *Curr Opin Chem biol,* 7, 33-38.

Waldo, G. S., Standish, B. M., Berendzen, J. and Terwilliger, T. C. (1999) Rapid protein-folding assay using green fluorescent protein. *Nat Biotechnol,* 17, 691-695.

Yang, J. K., Park, M. S., Waldo, G. S. and Suh, S. W. (2003) Directed evolution approach to a structural genomics project: Rv2002 from Mycobacteriumtuberculosis. *Proc Natl Acad Sci USA,* 100, 455-460.

Ziomek, C. A., Lepire, M. L. and Torres, I. (1990) A highly fluorescent simultaneous azo dye technique for demonstration of nonspecific alkaline phosphatase activity. *J Histochem Cytochem,* 38, 437-442.

Kabsch, W. *J. Appl. Cryst.* 26, 795-800, (1993).

Storoni, L. C., McCoy, A. J. and Read, R., *Acta Crystallog. D* (in press).

Uson, I. And Sheldrick, G. M., *Curr. Opin. Struct. Biol.,* 9, 643-648 (1999).

Fortelle, E. and Bricogne, G., *Methods Enzymol.,* 276, 472-494 (1997).

Abrahams, J. P. and Leslie, A. G., *Acta Ctystallog. D.,* 52, 30-42 (1996).

Perrakis, A., Morris, R. and Lamzin, V. S., *Nature Struct. Biol.,* 6, 458-463 (1999).

Jones, T. A., Zou, J. Y., Cowan, S. W. and Kjeldgaard, M., *Acta Crystallogr. A.,* 47, 110-119 (1991).

Murshudov, G. N., Vagin, A. A., Lebedev, A., Wilson, K. S. and Dodson, E. J., *Acta Crystallogr. D.,* 55, 247-255 (1999).

---

What is claimed is:

1. An isolated polypeptide comprising the amino acid sequence of SEQ ID NO: 56.

2. A pharmaceutical composition comprising the isolated polypeptide of claim 1 and a pharmaceutically accepted carrier.

* * * * *